US012435088B2

(12) United States Patent
Tan et al.

(10) Patent No.: US 12,435,088 B2
(45) Date of Patent: Oct. 7, 2025

(54) SALICYL-ADENOSINEMONOSULFAMATE ANALOGS AND USES THEREOF

(71) Applicants: Memorial Sloan-Kettering Cancer Center, New York, NY (US); Research Foundation of the City University of New York, New York, NY (US); The Johns Hopkins University, Baltimore, MD (US)

(72) Inventors: Derek Shieh Tan, New York, NY (US); Lisa Charlotte Standke, New York, NY (US); Luis Edmundo Nereo Quadri, New York, NY (US); Glennon Valere Bythrow, Chicago, IL (US); William Ramses Bishai, Baltimore, MD (US); Shichun Lun, Ellicott City, MD (US)

(73) Assignees: Memorial Sloan-Kettering Cancer Center, New York, NY (US); Research Foundation of the City University of New York, New York, NY (US); The Johns Hopkins University, Baltimore, MD (US)

( * ) Notice: Subject to any disclaimer, the term of this patent is extended or adjusted under 35 U.S.C. 154(b) by 1050 days.

(21) Appl. No.: 17/416,976

(22) PCT Filed: Dec. 20, 2019

(86) PCT No.: PCT/US2019/068107

§ 371 (c)(1),
(2) Date: Jun. 21, 2021

(87) PCT Pub. No.: WO2020/132603

PCT Pub. Date: Jun. 25, 2020

(65) Prior Publication Data

US 2022/0162209 A1 May 26, 2022

Related U.S. Application Data

(60) Provisional application No. 62/784,323, filed on Dec. 21, 2018.

(51) Int. Cl.
*C07D 473/30* (2006.01)
*C07D 473/18* (2006.01)

(52) U.S. Cl.
CPC ......... *C07D 473/30* (2013.01); *C07D 473/18* (2013.01)

(58) Field of Classification Search
CPC ............................ C07D 473/30; C07D 473/18
See application file for complete search history.

(56) References Cited

U.S. PATENT DOCUMENTS

| | | | |
|---|---|---|---|
| 6,730,767 | B2 | 5/2004 | Salamone et al. |
| 6,989,430 | B2 | 1/2006 | Salamone et al. |
| 7,816,326 | B2 | 10/2010 | Velazquez et al. |
| 7,989,430 | B2 | 8/2011 | Aldrich et al. |
| 8,067,379 | B2 | 11/2011 | Bennett et al. |
| 8,461,128 | B2 | 6/2013 | Tan et al. |
| 8,946,188 | B2 | 2/2015 | Tan et al. |
| 10,874,686 | B2 | 12/2020 | Tan et al. |
| 2006/0189636 | A1 | 8/2006 | Critchley et al. |
| 2007/0042968 | A1 | 2/2007 | Bennett et al. |
| 2018/0243328 | A1 | 8/2018 | Wu et al. |
| 2018/0273573 | A1 | 9/2018 | Tan et al. |
| 2019/0038656 | A1 | 2/2019 | Tan et al. |
| 2022/0235088 | A1 | 7/2022 | Tan et al. |

FOREIGN PATENT DOCUMENTS

| | | | |
|---|---|---|---|
| EP | 0433898 | A2 | 6/1991 |
| WO | WO 2006/113615 | A2 | 10/2006 |
| WO | WO 2007/067559 | A2 | 6/2007 |
| WO | WO 2017/059411 | A1 | 4/2017 |
| WO | WO 2017/059446 | A1 | 4/2017 |

OTHER PUBLICATIONS

Giegrich, H., et al. Nucleosides & Nucleotides, 17(9-11), 1987-1996 (1998). (Year: 1998).*

Extended European Search Report for EP 16852815.6 mailed on May 10, 2019.

International Search Report and Written Opinion for PCT/US2016/055136 mailed on Jan. 6, 2017.

International Preliminary Report on Patentability for PCT/US2016/055136 mailed on Apr. 12, 2018.

(Continued)

*Primary Examiner* — Joseph K McKane
*Assistant Examiner* — Quincy McKoy
(74) *Attorney, Agent, or Firm* — Wolf, Greenfield & Sacks, P.C.

(57) ABSTRACT

Provided herein are compounds of Formula (I), and pharmaceutically acceptable salts or tautomers thereof. Also provided are pharmaceutical compositions, kits, and methods involving the inventive compounds for the treatment and/or prevention of an infectious disease (e.g., bacterial infection (e.g., *Mycobacterium* infection (e.g., tuberculosis)). (I)

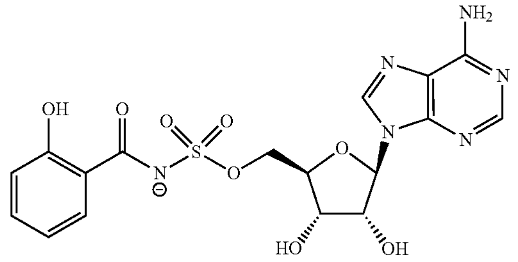

Salicyl-AMS (1)

20 Claims, 13 Drawing Sheets

Specification includes a Sequence Listing.

(56) References Cited

OTHER PUBLICATIONS

International Search Report and Written Opinion for PCT/US2016/055200 mailed on Feb. 17, 2017.
International Preliminary Report on Patentability for PCT/US2016/055200 mailed on Apr. 12, 2018.
International Search Report and Written Opinion for PCT/US2019/068107, mailed on Jun. 3, 2020.
International Preliminary Report on Patentability for PCT/US2019/068107, mailed on Jul. 1, 2021.
International Search Report and Written Opinion for PCT/US2020/017140, mailed on May 5, 2020.
International Preliminary Report on Patentability for PCT/US2020/017140, mailed on Aug. 19, 2021.
[No Author Listed], A Scientific Roadmap for Antibiotic Discovery; A sustained and robust pipeline of new antibacterial drugs and therapies is critical to preserve public health. Pew. May 11, 2016. Accessible at https://www.pewtrusts.org/en/research-and-analysis/reports/2016/05/a-scientific-roadmap-for-antibiotic-discovery.47 pages.
Ackerley et al., Substrate specificity of the nonribosomal peptide synthetase PvdD from Pseudomonas aeruginosa. J Bacteriol. May 2003;185(9):2848-55.
Akerley et al., A genome-scale analysis for identification of genes required for growth or survival of Haemophilus influenzae. Proc Natl Acad Sci U S A. Jan. 22, 2002;99(2):966-71. doi: 10.1073/pnas.012602299.
Alipanah et al., Adherence interventions and outcomes of tuberculosis treatment: A systematic review and meta-analysis of trials and observational studies. PLoS Med. Jul. 3, 2018;15(7):e1002595. doi: 10.1371/journal.pmed.1002595.
Andersson et al., The *Mycobacterium tuberculosis* very-long-chain fatty acyl-CoA synthetase: structural basis for housing lipid substrates longer than the enzyme. Structure. Jun. 6, 2012;20(6):1062-70. doi: 10.1016/j.str.2012.03.012. Epub May 3, 2012.
Arora et al., Mechanistic and functional insights into fatty acid activation in Mycobacterium tuberculosis. Nat Chem Biol. Mar. 2009;5(3):166-73. doi: 10.1038/nchembio.143. Epub Feb. 1, 2009.
Bandarian et al., Domain alternation switches B(12)-dependent methionine synthase to the activation conformation. Nat Struct Biol. Jan. 2002;9(1):53-6.
Bardaweel et al., Synthesis and evaluation of potential inhibitors of human and *Escherichia coli* histidine triad nucleotide binding proteins. Bioorg Med Chem Lett. Jan. 1, 2012;22(1):558-60. doi:10.1016/j.bmcl.2011.10.082. Epub Oct. 31, 2011.
Barry et al., Drug sensitivity and environmental adaptation of mycobacterial cell wall components. Trends Microbiol. Jul. 1996;4(7):275-81. doi: 10.1016/0966-842x(96)10031-7.
Bisseret et al., Synthesis of a 2-indolylphosphonamide derivative with inhibitory activity against yersiniabactin biosynthesis. Tetrahedron Lett. Aug. 27, 2007;48(35):6080-6083. doi: 10.1016/j.tetlet.2007.06.150.
Branchini et al., Synthesis of an N-acyl sulfamate analog of luciferyl-AMP: a stable and potent inhibitor of firefly luciferase. Bioorg Med Chem Lett. Sep. 1, 2005;15(17):3860-4.
Brown et al., Antibacterial drug discovery in the resistance era. Nature. Jan. 21, 2016;529(7586):336-43. doi: 10.1038/nature17042.
Bythrow et al., Kinetic Analyses of the Siderophore Biosynthesis Inhibitor Salicyl-AMS and Analogues as MbtA Inhibitors and Antimycobacterial Agents. Biochemistry. Feb. 12, 2019;58(6):833-847 and Supplemental Information. doi: 10.1021/acs.biochem.8b01153. Epub Jan. 10, 2019. 57 pages.
Calfee et al., Interference with Pseudomonas quinolone signal synthesis inhibits virulence factor expression by Pseudomonas aeruginosa. Proc Natl Acad Sci U S A. Sep. 25, 2001;98(20):11633-7.
Callahan et al., Nanomolar inhibition of the enterobactin biosynthesis enzyme, EntE: synthesis, substituent effects, and additivity. Bioorg Med Chem Lett. Jul. 15, 2006;16(14):3802-5. doi: 10.1016/j.bmcl.2006.04.024. Epub May 5, 2006.
Castro-Pichel et al., A facile synthesis of ascamycin and related analogues. Tetrahedron. 1987; 43(2);383-389.
Centers for Disease Control, Antibiotic Resistance Threats in the United States. 2013. 144 pages.
Chan et al., In vitro postantibiotic effects of rifapentine, isoniazid, and moxifloxacin against Mycobacterium tuberculosis. Antimicrob Agents Chemother. Jan. 2004;48(1):340-3. doi: 10.1128/AAC.48.1.340-343.2004.
Charifson et al., Acidic and basic drugs in medicinal chemistry: a perspective. J Med Chem. Dec. 11, 2014;57(23):9701-17. doi: 10.1021/jm501000a. Epub Sep. 18, 2014.
Chavadi et al., Mutational and phylogenetic analyses of the mycobacterial mbt gene cluster. J Bacteriol. Nov. 2011;193(21):5905-13. doi: 10.1128/JB.05811-11. Epub Aug. 26, 2011.
Chen et al., Crystal structure of the thioesterification conformation of Bacillus subtilis o-succinylbenzoyl-CoA synthetase reveals a distinct substrate-binding mode. J Biol Chem. Jul. 21, 2017;292(29):12296-12310. doi: 10.1074/jbc.M117.790410. Epub May 30, 2017.
Chen et al., Mechanistic Insights from the Crystal Structure of Bacillus subtilis o-Succinylbenzoyl-CoA Synthetase Complexed with the Adenylate Intermediate. Biochemistry. Dec. 6, 2016;55(48):6685-6695. doi: 10.1021/acs.biochem.6b00889. Epub Nov. 28, 2016.
Chen et al., OGEE v2: an update of the online gene essentiality database with special focus on differentially essential genes in human cancer cell lines. Nucleic Acids Res. Jan. 4, 2017;45(D1):D940-D944. doi: 10.1093/nar/gkw1013. Epub Oct. 30, 2016.
Chen et al., Structural Basis for the ATP-dependent Configuration of Adenylation Active Site in Bacillus subtilis o-Succinylbenzoyl-CoA Synthetase. J Biol Chem. Sep. 25, 2015;290(39):23971-83. doi: 10.1074/jbc.M115.676304. Epub Aug. 14, 2015.
Ciulli et al., Inhibition of *Mycobacterium tuberculosis* pantothenate synthetase by analogues of the reaction intermediate. Chembiochem. Nov. 3, 2008;9(16):2606-11. doi: 10.1002/cbic.200800437.
Coleman et al., Pseudomonas aeruginosa PqsA is an anthranilate-coenzyme A ligase. J Bacteriol. Feb. 2008;190(4):1247-55. Epub Dec. 14, 2007.
Conti et al., Crystal structure of firefly luciferase throws light on a superfamily of adenylate-forming enzymes. Structure. Mar. 15, 1996;4(3):287-98. doi: 10.1016/s0969-2126(96)00033-0.
Danziger, Vitamin K-dependent proteins, warfarin, and vascular calcification. Clin J Am Soc Nephrol. Sep. 2008;3(5):1504-10. doi: 10.2215/CJN.00770208. Epub May 21, 2008.
Davis et al., Design, synthesis, and biological evaluation of ?-hydroxyacyl-AMS inhibitors of amino acid adenylation enzymes. Bioorg Med Chem Lett. Nov. 1, 2016;26(21):5340-5345. doi: 10.1016/j.bmcl.2016.09.027. Epub Sep. 16, 2016.
Davis et al., General platform for systematic quantitative evaluation of small-molecule permeability in bacteria. ACS Chem Biol. Nov. 21, 2014;9(11):2535-44. doi: 10.1021/cb5003015. Epub Sep. 8, 2014.
Dawadi et al., Conformationally Constrained Cinnolinone Nucleoside Analogues as Siderophore Biosynthesis Inhibitors for Tuberculosis. ACS Med Chem Lett. Mar. 16, 2018;9(4):386-391. doi: 10.1021/acsmedchemlett.8b00090.
Dawadi et al., Synthesis and pharmacological evaluation of nucleoside prodrugs designed to target siderophore biosynthesis in Mycobacterium tuberculosis. Bioorg Med Chem. Mar. 15, 2016;24(6):1314-21. doi: 10.1016/j.bmc.2016.02.002. Epub Feb. 3, 2016.
De Voss et al., Iron acquisition and metabolism by mycobacteria. J Bacteriol. Aug. 1999;181(15):4443-51. doi: 10.1128/JB.181.15.4443-4451.1999.
De Voss et al., The salicylate-derived mycobactin siderophores of *Mycobacterium tuberculosis* are essential for growth in macrophages. Proc Natl Acad Sci U S A. Feb. 1, 2000;97(3):1252-7. doi: 10.1073/pnas.97.3.1252.
Dhiman et al., Menaquinone synthesis is critical for maintaining mycobacterial viability during exponential growth and recovery from non-replicating persistence. Mol Microbiol. Apr. 2009;72(1):85-97. doi: 10.1111/j.1365-2958.2009.06625.x. Epub Feb. 11, 2009.
Drake et al., Biochemical and structural characterization of bisubstrate inhibitors of BasE, the self-standing nonribosomal peptide synthetase

(56) References Cited

OTHER PUBLICATIONS adenylate-forming enzyme of acinetobactin synthesis. Biochemistry. Nov. 2, 2010;49(43):9292-305. doi: 10.1021/bi101226n.
Duckworth et al., Adenylating enzymes in *Mycobacterium tuberculosis* as drug targets. Curr Top Med Chem. 2012;12(7):766-96. doi: 10.2174/156802612799984571. Author Manuscript. 78 pages.
Emsley et al., Coot: model-building tools for molecular graphics. Acta Crystallogr D Biol Crystallogr. Dec. 2004;60(Pt 12 Pt 1):2126-32. doi: 10.1107/S0907444904019158. Epub Nov. 26, 2004.
Engelhart et al., Synthesis of chromone, quinolone, and benzoxazinone sulfonamide nucleosides as conformationally constrained inhibitors of adenylating enzymes required for siderophore biosynthesis. J Org Chem. Aug. 2, 2013;78(15):7470-81. doi: 10.1021/jo400976f. Epub Jul. 12, 2013.
Eschgfäller et al., Synthesis and biodistribution of a short nonionic oligonucleotide analogue in mouse with a potential to mimic peptides. J Med Chem. Jan. 29, 1998;41(3):276-83. doi: 10.1021/jm9705380.
Evans et al., How good are my data and what is the resolution? Acta Crystallogr D Biol Crystallogr. Jul. 2013;69(Pt 7):1204-14. doi: 10.1107/S0907444913000061. Epub Jun. 13, 2013.
Evans et al., Stereoselective Synthesis, Docking, and Biological Evaluation of Difluoroindanediol-Based MenE Inhibitors as Antibiotics. Org Lett. Dec. 16, 2016;18(24):6384-6387. doi: 10.1021/acs.orglett.6b03272. Epub Dec. 1, 2016.
Evans et al., Structure-Based Design, Synthesis, and Biological Evaluation of Non-Acyl Sulfamate Inhibitors of the Adenylate-Forming Enzyme MenE. Biochemistry. Apr. 9, 2019;58(14):1918-1930. doi: 10.1021/acs.biochem.9b00003. Epub Mar. 26, 2019.
Fang et al., Succinylphosphonate esters are competitive inhibitors of MenD that show active-site discrimination between homologous alpha-ketoglutarate-decarboxylating enzymes. Biochemistry. Mar. 30, 2010;49(12):2672-9. doi: 10.1021/bi901432d.
Fang et al., Using substrate analogues to probe the kinetic mechanism and active site of *Escherichia coli* MenD. Biochemistry. Oct. 11, 2011;50(40):8712-21. doi: 10.1021/bi201202n. Epub Sep. 19, 2011.
Felczak et al., Cofactor-type inhibitors of inosine monophosphate dehydrogenase via modular approach: targeting the pyrophosphate binding sub-domain. Bioorg Med Chem. Mar. 1, 2011;19(5):1594-605. doi: 10.1016/j.bmc.2011.01.042. Epub Jan. 27, 2011.
Ferreras et al., Mycobacterial phenolic glycolipid virulence factor biosynthesis: mechanism and small-molecule inhibition of polyketide chain initiation. Chem Biol. Jan. 2008;15(1):51-61. Epub Dec. 27, 2007.
Ferreras et al., Small-molecule inhibition of siderophore biosynthesis in *Mycobacterium tuberculosis* and Yersinia pestis. Nat Chem Biol. Jun. 2005;1(1):29-32. Epub May 24, 2005.
Finking et al., Aminoacyl adenylate substrate analogues for the inhibition of adenylation domains of nonribosomal peptide synthetases. Chembiochem. Sep. 5, 2003;4(9):903-6.
Furt et al., A bimodular oxidoreductase mediates the specific reduction of phylloquinone (vitamin K?) in chloroplasts. Plant J. Oct. 2010;64(1):38-46. doi: 10.1111/j.1365-313X.2010.04305.x. Epub Aug. 23, 2010.
Gehring et al., The nonribosomal peptide synthetase HMWP2 forms a thiazoline ring during biogenesis of yersiniabactin, an iron-chelating virulence factor of Yersinia pestis. Biochemistry. Aug. 18, 1998;37(33):11637-50. doi: 10.1021/bi9812571. Erratum in: Biochemistry Dec. 1, 1998;37(48):17104.
Gulick et al., The 1.75 A crystal structure of acetyl-CoA synthetase bound to adenosine-5'-propylphosphate and coenzyme A. Biochemistry. Mar. 18, 2003;42(10):2866-73. doi: 10.1021/bi0271603.
Gulick, Conformational Dynamics in the Acyl-CoA Synthetases, Adenylation Domains of Non-ribosomal Peptide Synthetases, and Firefly Luciferase. ACS Chem Biol. Oct. 16, 2009;4(10):811-27. doi: 10.1021/cb900156h.
Hisanaga et al., Structural basis of the substrate-specific two-step catalysis of long chain fatty acyl-CoA synthetase dimer. J Biol Chem. Jul. 23, 2004;279(30):31717-26. doi: 10.1074/jbc.M400100200. Epub May 15, 2004.
Ilangovan et al., Structural basis for native agonist and synthetic inhibitor recognition by the Pseudomonas aeruginosa quorum sensing regulator PqsR (MvfR). PLoS Pathog. 2013;9(7):e1003508. doi: 10.1371/journal.ppat. 1003508. Epub Jul. 25, 2013.
Isono et al., Ascamycin and dealanylascamycin, nucleoside antibiotics from *Streptomyces* sp. J Antibiot (Tokyo). Jun. 1984;37(6):670-2.
Jiang et al., Identification and characterization of (1R,6R)-2-succinyl-6-hydroxy-2,4-cyclohexadiene-1-carboxylate synthase in the menaquinone biosynthesis of Escherichia coli. Biochemistry. Mar. 18, 2008;47(11):3426-34. doi: 10.1021/bi7023755. Epub Feb. 20, 2008.
Kabsch, XDS. Acta Crystallogr D Biol Crystallogr. Feb. 2010;66(Pt 2):125-32. doi: 10.1107/S0907444909047337. Epub Jan. 22, 2010.
Kasper et al., Chemical Inhibition of Kynureninase Reduces Pseudomonas aeruginosa Quorum Sensing and Virulence Factor Expression. ACS Chem Biol. Apr. 15, 2016;11(4):1106-17. doi: 10.1021/acschembio.5b01082. Epub Feb. 10, 2016.
Khan et al., Double-hexahistidine tag with high-affinity binding for protein immobilization, purification, and detection on ni-nitrilotriacetic acid surfaces. Anal Chem. May 1, 2006;78(9):3072-9. doi: 10.1021/ac0601841.
Kobayashi et al., Essential Bacillus subtilis genes. Proc Natl Acad Sci U S A. Apr. 15, 2003;100(8):4678-83. doi: 10.1073/pnas. 0730515100. Epub Apr. 7, 2003.
Koroniak et al., Synthesis and characterization of an N-acylsulfonamide inhibitor of human asparagine synthetase. Org Lett. Jun. 12, 2003;5(12):2033-6.
Krajczyk et al., 2-Aryl-8-aza-3-deazaadenosine analogues of 5'-O-[N- (salicyl)sulfamoyl]adenosine: Nucleoside antibiotics that block siderophore biosynthesis in *Mycobacterium tuberculosis*. Bioorg Med Chem. Jul. 15, 2016;24(14):3133-43. doi: 10.1016/j.bmc.2016. 05.037. Epub May 20, 2016.
Kulka et al., Growth of *Mycobacterium tuberculosis* Biofilms. J Visual Exp. 2012;60:e3820.
Kurosu et al., Vitamin K2 in electron transport system: are enzymes involved in vitamin K2 biosynthesis promising drug targets? Molecules. Mar. 10, 2010;15(3):1531-53. doi: 10.3390/molecules15031531.
Kwon et al., Menaquinone (vitamin K2) biosynthesis: overexpression, purification, and properties of o-succinylbenzoyl-coenzyme A synthetase from *Escherichia coli*. J Bacteriol. Dec. 1996;178(23):6778-81. doi: 10.1128/jb.178.23.6778-6781.1996.
Labello et al., Quantitative three dimensional structure linear interaction energy model of 5'- O-[N-(salicyl)sulfamoyl]adenosine and the aryl acid adenylating enzyme MbtA. J Med Chem. Nov. 27, 2008;51(22):7154-60. doi: 10.1021/jm800668u.
Lee et al., High-throughput T7 Lic vector for introducing C-terminal poly-histidine tags with variable lengths without extra sequences. Protein Expr Purif. Jan. 2009;63(1):58-61. doi: 10.1016/j.pep.2008. 09.005. Epub Sep. 14, 2008.
Lewis, Platforms for antibiotic discovery. Nat Rev Drug Discov. May 2013;12(5):371-87. doi: 10.1038/nrd3975.
Li et al., CoA Adducts of 4-Oxo-4-Phenylbut-2-enoates: Inhibitors of MenB from the *M. tuberculosis*Menaquinone Biosynthesis Pathway. ACS Med Chem Lett. Nov. 10, 2011;2(11):818-823. doi: 10.1021/ml200141e.
Li et al., Multitarget drug discovery for tuberculosis and other infectious diseases. J Med Chem. Apr. 10, 2014;57(7):3126-39. doi: 10.1021/jm500131s. Epub Apr. 1, 2014.
Li et al., Synthesis and SAR studies of 1,4-benzoxazine MenB inhibitors: novel antibacterial agents against *Mycobacterium tuberculosis*. Bioorg Med Chem Lett. Nov. 1, 2010;20(21):6306-9. doi: 10.1016/j.bmcl.2010.08.076. Epub Aug. 21, 2010.
Liu et al., Structures of Mycobacterium tuberculosis FadD10 protein reveal a new type of adenylate-forming enzyme. J Biol Chem. Jun. 21, 2013;288(25):18473-83. doi: 10.1074/jbc.M113.466912. Epub Apr. 26, 2013. Erratum in: J Biol Chem. Aug. 9, 2013;288(32):23435.
Lu et al., Designed semisynthetic protein inhibitors of Ub/Ub1 E1 activating enzymes.J Am Chem Soc. Feb. 17, 2010;132(6):1748-9. doi: 10.1021/ja9088549.

(56) References Cited

OTHER PUBLICATIONS

Lu et al., Mechanism-based inhibitors of MenE, an acyl-CoA synthetase involved in bacterial menaquinone biosynthesis. Bioorg Med Chem Lett. Nov. 15, 2008;18(22):5963-6. doi: 10.1016/j.bmcl.2008.07.130. Epub Aug. 12, 2008.
Lu et al., Stable analogues of OSB-AMP: potent inhibitors of MenE, the o-succinylbenzoate-CoA synthetase from bacterial menaquinone biosynthesis. Chembiochem. Jan. 2, 2012;13(1):129-36. doi: 10.1002/cbic.201100585. Epub Nov. 23, 2011.
Ma et al., Correlations between Shine-Dalgarno sequences and gene features such as predicted expression levels and operon structures. J Bacteriol. Oct. 2002;184(20):5733-45. doi: 10.1128/JB.184.20.5733-5745.2002.
Madigan et al., Lipidomic analysis links mycobactin synthase K to iron uptake and virulence in *M. tuberculosis*. PLoS Pathog. Mar. 27, 2015;11(3):e1004792. doi: 10.1371/journal.ppat.1004792.
Matarlo et al., Mechanism of MenE inhibition by acyl-adenylate analogues and discovery of novel antibacterial agents. Biochemistry. Oct. 27, 2015;54(42):6514-6524. doi: 10.1021/acs.biochem.5b00966. Epub Oct. 15, 2015.
May et al., Crystal structure of DhbE, an archetype for aryl acid activating domains of modular nonribosomal peptide synthetases. Proc Natl Acad Sci U S A. Sep. 17, 2002;99(19):12120-5. doi: 10.1073/pnas.182156699. Epub Sep. 9, 2002.
McClerren et al., A slow, tight-binding inhibitor of the zinc-dependent deacetylase LpxC of lipid A biosynthesis with antibiotic activity comparable to ciprofloxacin. Biochemistry. Dec. 20, 2005;44(50):16574-83. doi: 10.1021/bi0518186.
Meganathan et al., Menaquinone (vitamin K2) biosynthesis: conversion of o-succinylbenzoic acid to 1,4-dihydroxy-2-naphthoic acid by *Mycobacterium phlei* enzymes. J Bacteriol. Oct. 1979;140(1):92-8. doi: 10.1128/jb.140.1.92-98.1979.
Miethke et al., Inhibition of aryl acid adenylation domains involved in bacterial siderophore synthesis. FEBS J. Jan. 2006;273(2):409-19.
Migron et al., A facile synthesis of α,α,ω,ω-tetrahalo-α,ω-dicarboxylic esters. Tetrahedron. 1987;43(2):361-364.
Morton et al., The structure of nucleocidin. 3. (A new structure). J Am Chem Soc. Mar. 12, 1969;91(6):1535-7.
Nahid et al., Official American Thoracic Society/Centers for Disease Control and Prevention/Infectious Diseases Society of America Clinical Practice Guidelines: Treatment of Drug-Susceptible Tuberculosis. Clin Infect Dis. Oct. 1, 2016;63(7):e147-e195. doi: 10.1093/cid/ciw376. Epub Aug. 10, 2016.
Nakagawa et al., Identification of UBIAD1 as a novel human menaquinone-4 biosynthetic enzyme. Nature. Nov. 4, 2010;468(7320):117-21. doi: 10.1038/nature09464. Epub Oct. 17, 2010.
Nakatsu et al., Structural basis for the spectral difference in luciferase bioluminescence. Nature. Mar. 16, 2006;440(7082):372-6. doi: 10.1038/nature04542.
Nelson et al., Synthesis and Pharmacokinetic Evaluation of Siderophore Biosynthesis Inhibitors for *Mycobacterium tuberculosis*. J Med Chem. Jul. 23, 2015;58(14):5459-75. doi: 10.1021/acs.jmedchem.5b00391. Epub Jul. 9, 2015.
Neres et al., Inhibition of siderophore biosynthesis in *Mycobacterium tuberculosis* with nucleoside bisubstrate analogues: structure-activity relationships of the nucleobase domain of 5'- O-[N-(salicyl)sulfamoyl]adenosine. J Med Chem. Sep. 11, 2008;51(17):5349-70. doi: 10.1021/jm800567v. Epub Aug. 9, 2008.
Parish et al., Use of a flexible cassette method to generate a double unmarked *Mycobacterium tuberculosis* tlyA plcABC mutant by gene replacement. Microbiology (Reading). Aug. 2000;146 ( Pt 8):1969-1975. doi: 10.1099/00221287-146-8-1969.
Patskovsky et al., 3IPL. Crystal Structure Of o-succinylbenzoic acid-CoA ligase FROM *Staphylococcus aureus* subsp. aureus Mu50. Rcsb Pdb. Aug. 17, 2009. doi: 10.2210/pdb3IPL/pdb. 4 pages.
Qiao et al., 5'-O-[(N-acyl)sulfamoyl]adenosines as antitubercular agents that inhibit MbtA: an adenylation enzyme required for siderophore biosynthesis of the mycobactins. J Med Chem. Nov. 29, 2007;50(24):6080-94. Epub Oct. 30, 2007.
Qiao et al., A mechanism-based aryl carrier protein/thiolation domain affinity probe. J Am Chem Soc. May 23, 2007;129(20):6350-1. Epub May 1, 2007.
Quadri et al., Assembly of the Pseudomonas aeruginosa nonribosomal peptide siderophore pyochelin: In vitro reconstitution of aryl-4, 2-bisthiazoline synthetase activity from PchD, PchE, and PchF. Biochemistry. Nov. 9, 1999;38(45):14941-54. doi: 10.1021/bi991787c.
Quadri et al., Identification of a Mycobacterium tuberculosis gene cluster encoding the biosynthetic enzymes for assembly of the virulence-conferring siderophore mycobactin. Chem Biol. Nov. 1998;5(11):631-45. doi: 10.1016/s1074-5521(98)90291-5.
Quadri, Strategic paradigm shifts in the antimicrobial drug discovery process of the 21st century. Infect Disord Drug Targets. Sep. 2007;7(3):230-7. doi: 10.2174/187152607782110040.
Ratledge et al., The occurrence of carboxymycobactin, the siderophore of pathogenic mycobacteria, as a second extracellular siderophore in *Mycobacterium smegmatis*. Microbiology (Reading). Aug. 1996;142 ( Pt 8):2207-12. doi: 10.1099/13500872-142-8-2207.
Ratledge, Iron, mycobacteria and tuberculosis. Tuberculosis (Edinb). 2004;84(1-2):110-30. doi: 10.1016/j.tube.2003.08.012.
Reddy et al., Disruption of mycobactin biosynthesis leads to attenuation of *Mycobacterium tuberculosis* for growth and virulence. J Infect Dis. Oct. 15, 2013;208(8):1255-65. doi: 10.1093/infdis/jit250. Epub Jun. 20, 2013.
Reger et al., Biochemical and crystallographic analysis of substrate binding and conformational changes in acetyl-CoA synthetase. Biochemistry. Jun. 5, 2007;46(22):6536-46. doi: 10.1021/bi6026506. Epub May 12, 2007.
Richter et al., Predictive compound accumulation rules yield a broad-spectrum antibiotic. Nature. May 18, 2017;545(7654):299-304. doi: 10.1038/nature22308. Epub May 10, 2017.
Rodriguez et al., Identification of an ABC transporter required for iron acquisition and virulence in *Mycobacterium tuberculosis*. J Bacteriol. Jan. 2006;188(2):424-30. doi: 10.1128/JB.188.2.424-430.2006.
Sassetti et al., Genes required for mycobacterial growth defined by high density mutagenesis. Mol Microbiol. Apr. 2003;48(1):77-84. doi: 10.1046/j.1365-2958.2003.03425.x.
Schüttelkopf et al., PRODRG: a tool for high-throughput crystallography of protein-ligand complexes. Acta Crystallogr D Biol Crystallogr. Aug. 2004;60(Pt 8):1355-63. doi: 10.1107/S0907444904011679. Epub Jul. 21, 2004.
Sharman et al., Isolation, purification and structure of exochelin MS, the extracellular siderophore from *Mycobacterium smegmatis*. Biochem J. Jan. 1, 1995;305 ( Pt 1)(Pt 1):187-96. doi: 10.1042/bj3050187.
Sikora et al., Kinetic and inhibition studies of dihydroxybenzoate-AMP ligase from *Escherichia coli*. Biochemistry. May 4, 2010;49(17):3648-57. doi: 10.1021/bi100350c.
Soares Da Costa et al., Selective inhibition of biotin protein ligase from *Staphylococcus aureus*. J Biol Chem. May 18, 2012;287(21):17823-17832. doi: 10.1074/jbc.M112.356576. Epub Mar. 21, 2012.
Somu et al., Antitubercular nucleosides that inhibit siderophore biosynthesis: SAR of the glycosyl domain. J Med Chem. Dec. 28, 2006;49(26):7623-35. doi: 10.1021/jm061068d.
Somu et al., Rationally designed nucleoside antibiotics that inhibit siderophore biosynthesis of *Mycobacterium tuberculosis*. J Med Chem. Jan. 12, 2006;49(1):31-4.
Stachelhaus et al., The specificity-conferring code of adenylation domains in nonribosomal peptide synthetases. Chem Biol. Aug. 1999;6(8):493-505. doi: 10.1016/S1074-5521(99)80082-9.
Stirrett et al., Small molecules with structural similarities to siderophores as novel antimicrobials against *Mycobacterium tuberculosis* and Yersinia pestis. Bioorg Med Chem Lett. Apr. 15, 2008;18(8):2662-8. doi: 10.1016/j.bmcl.2008.03.025. Epub Mar. 18, 2008.
Stubbings et al., Assessment of a microplate method for determining the post-antibiotic effect in *Staphylococcus aureus* and *Escherichia coli*. J Antimicrob Chemother. Jul. 2004;54(1):139-43. doi: 10.1093/jac/dkh275. Epub May 18, 2004.

(56) References Cited

OTHER PUBLICATIONS

Sundlov et al., Structural and functional investigation of the intermolecular interaction between NRPS adenylation and carrier protein domains. Chem Biol. Feb. 24, 2012;19(2):188-98. doi: 10.1016/j.chembiol.2011.11.013.
Tian et al., Bacillus anthracis o-succinylbenzoyl-CoA synthetase: reaction kinetics and a novel inhibitor mimicking its reaction intermediate Biochemistry. Nov. 25, 2008;47(47):12434-47. doi: 10.1021/bi801311d.
Tonge, Drug-Target Kinetics in Drug Discovery. ACS Chem Neurosci. Jan. 17, 2018;9(1):29-39. doi: 10.1021/acschemneuro.7b00185. Epub Jul. 14, 2017.
Tufariello et al., Separable roles for Mycobacterium tuberculosis ESX-3 effectors in iron acquisition and virulence. Proc Natl Acad Sci U S A. Jan. 19, 2016;113(3):E348-57. doi: 10.1073/pnas.1523321113. Epub Jan. 4, 2016.
Ueda et al., X-ray crystallographic conformational study of 5'-O-[N-(L-alanyl)-sulfamoyl]adenosine, a substrate analogue for alanyl-tRNA synthetase. Biochim Biophys Acta. Oct. 25, 1991;1080(2):126-34.
Vandelaer et al., Reaching Every District (RED) approach: a way to improve immunization performance. Bulletin of the World Health Organization. Mar. 2008;86(30:A-F.
Vannada et al., Design, synthesis, and biological evaluation of beta-ketosulfonamide adenylation inhibitors as potential antitubercular agents. Org Lett. Oct. 12, 2006;8(21):4707-10. doi: 10.1021/010617289.
Varma et al., Physicochemical determinants of human renal clearance. J Med Chem. Aug. 13, 2009;52(15):4844-52. doi: 10.1021/jm900403j.
Vergnolle et al., Post-translational Acetylation of MbtA Modulates Mycobacterial Siderophore Biosynthesis. J Biol Chem. Oct. 14, 2016;291(42):22315-22326. doi: 10.1074/jbc.M116.744532. Epub Aug. 26, 2016.
Waller et al., The Structure of Nucleocidin. I. J. Am. Chem. Soc., 1957, 79 (4), pp. 1011-1012 DOI: 10.1021/ja01561a076.
Wells et al., Discovery of a siderophore export system essential for virulence of *Mycobacterium tuberculosis*. PLoS Pathog. Jan. 2013;9(1):e1003120. doi: 10.1371/journal.ppat.1003120. Epub Jan. 31, 2013.
World Health Organization, Antimicrobial Resistance: Global Report on Surveillance. 2014. Accessible at https://apps.who.int/iris/handle/10665/112642. 256 pages.
World Health Organization, Global Tuberculosis Report. 2017. 147 pages.
Yoshimura et al., Diffusion of beta-lactam antibiotics through the porin channels of *Escherichia coli* K-12. Antimicrob Agents Chemother. Jan. 1985;27(1):84-92. doi: 10.1128/AAC.27.1.84.
Yu et al., Analysis of the exochelin locus in *Mycobacterium smegmatis*: biosynthesis genes have homology with genes of the peptide synthetase family. J Bacteriol. Sep. 1998;180(17):4676-85. doi: 10.1128/JB.180.17.4676-4685.1998.
Zhang et al., Engineering the substrate specificity of the DhbE adenylation domain by yeast cell surface display. Chem Biol. Jan. 24, 2013;20(1):92-101. doi:10.1016/j.chembiol.2012.10.020.
Zhu et al., Exochelin genes in *Mycobacterium smegmatis*: identification of an ABC transporter and two non-ribosomal peptide synthetase genes. Mol Microbiol. Jul. 1998;29(2):629-39. doi: 10.1046/j.1365-2958.1998.00961.x.
Extended European Search Report for EP 20752529.6 mailed on Nov. 7, 2022.
Awofeso, Anti-tuberculosis medication side-effects constitute major factor for poor adherence to tuberculosis treatment. Bull World Health Organ. Mar. 2008;86(3):B-D. doi: 10.2471/blt.07.043802. 6 pages.
Begley et al., Cofactor Biosynthesis: A Mechanistic Perspective. Biosynthesis: Topics in Current Chemistry. 1998(195):93-142. doi: 10.1007/3-540-69542-7_3.
Copeland, Evaluation of Enzyme Inhibitors in Drug Discovery: A Guide for Medicinal Chemists and Pharmacologists, Second Edition. Mar. 8, 2013. John Wiley & Sons, Inc. pp. 245-285.
Craig, Antimicrobial Pharmacodynamics in Theory and Clinical Practice. 2nd ed. Sep. 19, 2019. CRC Press. New York, NY. pp 1-22.
Dowd et al., The mechanism of action of vitamin K. Annu Rev Nutr. 1995;15:419-40. doi: 10.1146/annurev.nu.15.070195.002223.
Ferreras et al., Chemical scaffolds with structural similarities to siderophores of nonribosomal peptide-polyketide origin as novel antimicrobials against *Mycobacterium tuberculosis* and Yersinia pestis. Bioorg Med Chem Lett. Nov. 1, 2011;21(21):6533-7. doi: 10.1016/j.bmcl.2011.08.052. Epub Aug. 26, 2011. Author Manuscript. 15 pages.
Fiss et al., Identification of genes involved in the sequestration of iron in mycobacteria: the ferric exochelin biosynthetic and uptake pathways. Mol Microbiol. Nov. 1994;14(3):557-69. doi: 10.1111/j.1365-2958.1994.tb02189.x.
Kurosu et al., MenA is a promising drug target for developing novel lead molecules to combat *Mycobacterium tuberculosis*. Med Chem. Mar. 2009;5(2):197-207. doi: 10.2174/157340609787582882. Author Manuscript. 20 pages.
Lun et al., Pharmacokinetic and in vivo efficacy studies of the mycobactin biosynthesis inhibitor salicyl-AMS in mice. Antimicrob Agents Chemother. Oct. 2013;57(10):5138-40. doi: 10.1128/AAC.00918-13. Epub Jul. 15, 2013.
Mackenzie, et al., The post-antibiotic effect. J Antimicrob Chemother. Oct. 1993;32(4):519-37. doi: 10.1093/jac/32.4.519.
Meganathan et al., Biosynthesis of Menaquinone (Vitamin K2) and Ubiquinone (Coenzyme Q). EcoSal Plus. Aug. 2009;3(2):10.1128/ecosalplus.3.6.3.3. doi: 10.1128/ecosalplus.3.6.3.3. Author Manuscript. 37 pages.
Meganathan et al., Biosynthesis of menaquinone (vitamin K2) and ubiquinone (coenzyme Q): a perspective on enzymatic mechanisms. Vitam Horm. 2001;61:173-218. doi: 10.1016/s0083-6729(01)61006-9.
Meneghetti et al., Iron Acquisition Pathways as Targets for Antitubercular Drugs. Curr Med Chem. 2016;23(35):4009-4026. doi: 10.2174/0929867323666160607223747.
Mohan et al., Complete Genome Sequences of a *Mycobacterium smegmatis* Laboratory Strain (MC2 155) and Isoniazid-Resistant (4XR1/R2) Mutant Strains. Genome Announc. Jan./Feb. 2015;3(1):e01520-14. 2 pages.
Monfeli et al., Targeting iron acquisition by *Mycobacterium tuberculosis*. Infect Disord Drug Targets. Sep. 2007;7(3):213-20. doi: 10.2174/187152607782110031.
Morrison et al., The behavior and significance of slow-binding enzyme inhibitors. Adv Enzymol Relat Areas Mol Biol. 1988;61:201-301. doi: 10.1002/9780470123072.ch5.
Murshudov et al., Refinement of macromolecular structures by the maximum-likelihood method. Acta Crystallogr D Biol Crystallogr. May 1, 1997;53(Pt 3):240-55. doi: 10.1107/S0907444996012255.
Paudel, Menaquinone as a potential target of antibacterial agents. Drug Discov Ther. 2016;10(3):123-8. doi: 10.5582/ddt.2016.01041.
Pulaganti et al., Molecular modeling and docking studies of O-succinylbenzoate synthase of *M. tuberculosis*—a potential target for antituberculosis drug design. Appl Biochem Biotechnol. Feb. 2014;172(3):1407-32. doi: 10.1007/s12010-013-0569-4. Epub Nov. 9, 2013.
Quadri et al., Tuberculosis and the Tubercle Bacillus. 2005:341-357. ASM Press, Washington DC.
Snapper et al., Isolation and characterization of efficient plasmid transformation mutants of *Mycobacterium smegmatis*. Mol Microbiol. Nov. 1990;4(11):1911-9. doi: 10.1111/j.1365-2958.1990.tb02040.x.
Vagin et al., Molecular replacement with MOLREP. Acta Crystallogr D Biol Crystallogr. Jan. 2010;66(Pt 1):22-5. doi: 10.1107/S0907444909042589. Epub Dec. 21, 2009.
Partial Supplementary European Search Report for EP 19899257.0 mailed on Dec. 20, 2022.
Extended European Search Report for EP 19899257.0 mailed on Mar. 22, 2023.

* cited by examiner

Salicyl-AMS (1)

Salicyl-AMP

AMS

SEQUENCE LISTING

```
<160> NUMBER OF SEQ ID NOS: 25

<210> SEQ ID NO 1
<211> LENGTH: 565
<212> TYPE: PRT
<213> ORGANISM: Artificial Sequence
<220> FEATURE:
<223> OTHER INFORMATION: Synthetic polypeptide

<400> SEQUENCE: 1

Met Pro Pro Lys Ala Ala Asp Gly Arg Arg Pro Ser Pro Asp Gly Gly
1               5                   10                  15

Leu Gly Gly Phe Val Pro Phe Pro Ala Asp Arg Ala Ala Ser Tyr Arg
            20                  25                  30

Ala Ala Gly Tyr Trp Ser Gly Arg Thr Leu Asp Thr Val Leu Ser Asp
        35                  40                  45

Ala Ala Arg Arg Trp Pro Asp Arg Leu Ala Val Ala Asp Ala Gly Asp
    50                  55                  60

Arg Pro Gly His Gly Gly Leu Ser Tyr Ala Glu Leu Asp Gln Arg Ala
65                  70                  75                  80

Asp Arg Ala Ala Ala Ala Leu His Gly Leu Gly Ile Thr Pro Gly Asp
                85                  90                  95

Arg Val Leu Leu Gln Leu Pro Asn Gly Cys Gln Phe Ala Val Ala Leu
            100                 105                 110

Phe Ala Leu Leu Arg Ala Gly Ala Ile Pro Val Met Cys Leu Pro Gly
        115                 120                 125

His Arg Ala Ala Glu Leu Gly His Phe Ala Ala Val Ser Ala Ala Thr
    130                 135                 140

Gly Leu Val Val Ala Asp Val Ala Ser Gly Phe Asp Tyr Arg Pro Met
145                 150                 155                 160

Ala Arg Glu Leu Val Ala Asp His Pro Thr Leu Arg His Val Ile Val
                165                 170                 175

Asp Gly Asp Pro Gly Pro Phe Val Ser Trp Ala Gln Leu Cys Ala Gln
            180                 185                 190

Ala Gly Thr Gly Ser Pro Ala Pro Pro Ala Asp Pro Gly Ser Pro Ala
        195                 200                 205

Leu Leu Leu Val Ser Gly Gly Thr Thr Gly Met Pro Lys Leu Ile Pro
    210                 215                 220

Arg Thr His Asp Asp Tyr Val Phe Asn Ala Thr Ala Ser Ala Ala Leu
225                 230                 235                 240

Cys Arg Leu Ser Ala Asp Asp Val Tyr Leu Val Val Leu Ala Ala Gly
                245                 250                 255

His Asn Phe Pro Leu Ala Cys Pro Gly Leu Leu Gly Ala Met Thr Val
            260                 265                 270
```

```
Gly Ala Thr Ala Val Phe Ala Pro Asp Pro Ser Pro Glu Ala Ala Phe
        275                 280                 285

Ala Ala Ile Glu Arg His Gly Val Thr Val Thr Ala Leu Val Pro Ala
    290                 295                 300

Leu Ala Lys Leu Trp Ala Gln Ser Cys Glu Trp Glu Pro Val Thr Pro
305                 310                 315                 320

Lys Ser Leu Arg Leu Leu Gln Val Gly Gly Ser Lys Leu Glu Pro Glu
                325                 330                 335

Asp Ala Arg Arg Val Arg Thr Ala Leu Thr Pro Gly Leu Gln Gln Val
            340                 345                 350

Phe Gly Met Ala Glu Gly Leu Leu Asn Phe Thr Arg Ile Gly Asp Pro
        355                 360                 365

Pro Glu Val Val Glu His Thr Gln Gly Arg Pro Leu Cys Pro Ala Asp
    370                 375                 380

Glu Leu Arg Ile Val Asn Ala Asp Gly Glu Pro Val Gly Pro Gly Glu
385                 390                 395                 400

Glu Gly Glu Leu Leu Val Arg Gly Pro Tyr Thr Leu Asn Gly Tyr Phe
                405                 410                 415

Ala Ala Glu Arg Asp Asn Glu Arg Cys Phe Asp Pro Asp Gly Phe Tyr
            420                 425                 430

Arg Ser Gly Asp Leu Val Arg Arg Arg Asp Asp Gly Asn Leu Val Val
        435                 440                 445

Thr Gly Arg Val Lys Asp Val Ile Cys Arg Ala Gly Glu Thr Ile Ala
    450                 455                 460

Ala Ser Asp Leu Glu Glu Gln Leu Leu Ser His Pro Ala Ile Phe Ser
465                 470                 475                 480

Ala Ala Ala Val Gly Leu Pro Asp Gln Tyr Leu Gly Glu Lys Ile Cys
                485                 490                 495

Ala Ala Val Val Phe Ala Gly Ala Pro Ile Thr Leu Ala Glu Leu Asn
            500                 505                 510

Gly Tyr Leu Asp Arg Arg Gly Val Ala Ala His Thr Arg Pro Asp Gln
        515                 520                 525

Leu Val Ala Met Pro Ala Leu Pro Thr Thr Pro Ile Gly Lys Ile Asp
    530                 535                 540

Lys Arg Ala Ile Val Arg Gln Leu Gly Ile Ala Thr Gly Pro Val Thr
545                 550                 555                 560

Thr Gln Arg Cys His
                565


<210> SEQ ID NO 2
<211> LENGTH: 517
<212> TYPE: PRT
<213> ORGANISM: Artificial Sequence
<220> FEATURE:
<223> OTHER INFORMATION: Synthetic polypeptide

<400> SEQUENCE: 2

Met Ser Thr Leu Ala Asn Leu Thr Glu Val Leu Phe Arg Leu Asp Phe
1               5                   10                  15

Asp Pro Asp Thr Ala Val Tyr His Tyr Arg Gly Gln Thr Leu Ser Arg
            20                  25                  30

Leu Gln Cys Arg Thr Tyr Ile Leu Ser Gln Ala Ser Gln Leu Ala Arg
        35                  40                  45

Leu Leu Lys Pro Gly Asp Arg Val Val Leu Ala Leu Asn Asp Ser Pro
    50                  55                  60
```

-continued

```
Ser Leu Ala Cys Leu Phe Leu Ala Cys Ile Ala Val Gly Ala Ile Pro
65                  70                  75                  80

Ala Val Ile Asn Pro Lys Ser Arg Glu Gln Ala Leu Ala Asp Ile Ala
                85                  90                  95

Ala Asp Cys Gln Ala Ser Leu Val Val Arg Glu Ala Asp Ala Pro Ser
            100                 105                 110

Leu Ser Gly Pro Leu Ala Pro Leu Thr Leu Arg Ala Ala Ala Gly Arg
        115                 120                 125

Pro Leu Leu Asp Asp Phe Ser Leu Asp Ala Leu Val Gly Pro Ala Asp
    130                 135                 140

Leu Asp Trp Ser Ala Phe His Arg Gln Asp Pro Ala Ala Ala Cys Phe
145                 150                 155                 160

Leu Gln Tyr Thr Ser Gly Ser Thr Gly Ala Pro Lys Gly Val Met His
                165                 170                 175

Ser Leu Arg Asn Thr Leu Gly Phe Cys Arg Ala Phe Ala Thr Glu Leu
            180                 185                 190

Leu Ala Leu Gln Ala Gly Asp Arg Leu Tyr Ser Ile Pro Lys Met Phe
        195                 200                 205

Phe Gly Tyr Gly Met Gly Asn Ser Leu Phe Phe Pro Trp Phe Ser Gly
    210                 215                 220

Ala Ser Ala Leu Leu Asp Asp Thr Trp Pro Ser Pro Glu Arg Val Leu
225                 230                 235                 240

Glu Asn Leu Val Ala Phe Arg Pro Arg Val Leu Phe Gly Val Pro Ala
                245                 250                 255

Ile Tyr Ala Ser Leu Arg Pro Gln Ala Arg Glu Leu Leu Ser Ser Val
            260                 265                 270

Arg Leu Ala Phe Ser Ala Gly Ser Pro Leu Pro Arg Gly Glu Phe Glu
        275                 280                 285

Phe Trp Ala Ala His Gly Leu Glu Ile Cys Asp Gly Ile Gly Ala Thr
    290                 295                 300

Glu Val Gly His Val Phe Leu Ala Asn Arg Pro Gly Gln Ala Arg Ala
305                 310                 315                 320

Asp Ser Thr Gly Leu Pro Leu Pro Gly Tyr Glu Cys Arg Leu Val Asp
                325                 330                 335

Arg Glu Gly His Thr Ile Glu Glu Ala Gly Arg Gln Gly Val Leu Leu
            340                 345                 350

Val Arg Gly Pro Gly Leu Ser Pro Gly Tyr Trp Arg Ala Ser Glu Glu
        355                 360                 365

Gln Gln Ala Arg Phe Ala Gly Gly Trp Tyr Arg Thr Gly Asp Leu Phe
    370                 375                 380

Glu Arg Asp Glu Ser Gly Ala Tyr Arg His Cys Gly Arg Glu Asp Asp
385                 390                 395                 400

Leu Phe Lys Val Asn Gly Arg Trp Val Val Pro Thr Gln Val Glu Gln
                405                 410                 415

Ala Ile Cys Arg His Leu Pro Glu Val Ser Glu Ala Val Leu Val Pro
            420                 425                 430

Thr Cys Arg Leu His Asp Gly Leu Arg Pro Thr Leu Phe Val Thr Leu
        435                 440                 445

Ala Thr Pro Leu Asp Asp Asn Gln Ile Leu Leu Ala Gln Arg Ile Asp
    450                 455                 460

Gln His Leu Ala Glu Gln Ile Pro Ser His Met Leu Pro Ser Gln Leu
465                 470                 475                 480
```

-continued

His Val Leu Pro Ala Leu Pro Arg Asn Asp Asn Gly Lys Leu Ala Arg
485 490 495

Ala Glu Leu Arg His Leu Ala Asp Thr Leu Tyr His Asp Asn Leu Pro
500 505 510

Glu Glu Arg Ala Cys
515

<210> SEQ ID NO 3
<211> LENGTH: 1770
<212> TYPE: DNA
<213> ORGANISM: Artificial Sequence
<220> FEATURE:
<223> OTHER INFORMATION: Synthetic polynucleotide

<400> SEQUENCE: 3
atgggcagca gccatcatca tcatcatcat catcatcatc acagcagcgg cctggtgccg 60
cgcggcagcc atatgccgcc gaaagcggcg gatggtcgtc gtccgagccc ggatggtggt 120
ctgggtggtt ttgtgccgtt cccggcggat cgtgcggcga gctaccgtgc ggcgggttat 180
tggagcggcc gtaccctgga caccgtgctg agcgatgcgg cgcgtcgttg gccggatcgt 240
ctggcggttg cggatgcggg tgatcgtccg ggccacggtg gcctgagcta cgcggaactg 300
gaccagcgtg cggatcgtgc tgcggcggcg ctgcacggtc tgggtatcac cccgggcgat 360
cgtgtgctgc tgcagctgcc gaacggttgc caattcgcgg ttgcgctgtt tgcgctgctg 420
cgtgcgggtg cgattccggt gatgtgcctg ccgggtcatc gtgcggcgga actgggtcac 480
tttgcggcgg tgagcgcggc gaccggcctg gtggttgcgg atgttgcgag cggttttgat 540
tatcgtccga tggcgcgtga gctggttgcg gaccacccga ccctgcgtca cgtgatcgtt 600
gacggtgatc cgggtccgtt tgttagctgg gcgcagctgt gcgcgcaagc gggcaccggc 660
agcccggctc cgccggcgga cccgggcagc ccggcgctgc tgctggttag cggtggcacc 720
accggtatgc cgaagctgat tccgcgtacc cacgacgatt atgtgtttaa cgcgaccgcg 780
agcgcggcgc tgtgccgtct gagcgcggac gatgtttatc tggtggttct ggcggcgggt 840
cacaactttc cgctggcgtg cccgggtctg ctgggtgcga tgaccgtggg tgcgaccgcg 900
gtttttgcgc cggacccgag cccggaggcg gcgtttgcgg cgattgaacg tcacggtgtt 960
accgttaccg cgctggtgcc ggcgctggcg aaactgtggg cgcagagctg cgagtgggaa 1020
ccggtgaccc cgaagagcct gcgtctgctg caagttggtg gcagcaaact ggagccggaa 1080
gatgcgcgtc gtgtgcgtac cgcgctgacc ccgggcctgc agcaagtttt cggtatggcg 1140
gaaggcctgc tgaactttac ccgtatcggt gacccgccgg aagtggttga acacacccaa 1200
ggtcgtccgc tgtgcccggc ggacgagctg cgtattgtga acgcggatgg tgaaccggtt 1260
ggtccgggcg aggaaggtga actgctggtg cgtggcccgt acaccctgaa cggttatttc 1320
gcggcggagc gtgacaacga acgttgcttc gacccggatg gtttttaccg tagcggcgat 1380
ctggttcgtc gtcgtgacga tggcaacctg gtggttaccg gtcgtgtgaa ggacgttatc 1440
tgccgtgcgg gtgaaaccat tgcggcgagc gatctggagg aacagctgct gagccatccg 1500
gcgattttca gcgctgcggc ggttggcctg ccggaccaat acctgggtga aaaaatctgc 1560
gcggcggtgg tttttgcggg tgcgccgatt accctggcgg agctgaacgg ctatctggac 1620
cgtcgtggtg tggcggcgca cacccgtccg gatcaactgg ttgcgatgcc ggcgctgccg 1680
accaccccga tcggcaagat tgataaacgt gcgattgttc gtcaactggg tattgcgacc 1740
ggcccggtta ccacccaacg ctgccactaa 1770

<210> SEQ ID NO 4
<211> LENGTH: 589
<212> TYPE: PRT
<213> ORGANISM: Artificial Sequence
<220> FEATURE:
<223> OTHER INFORMATION: Synthetic polypeptide

<400> SEQUENCE: 4

```
Met Gly Ser Ser His His His His His His His His His His Ser Ser
1               5                   10                  15

Gly Leu Val Pro Arg Gly Ser His Met Pro Pro Lys Ala Ala Asp Gly
            20                  25                  30

Arg Arg Pro Ser Pro Asp Gly Gly Leu Gly Gly Phe Val Pro Phe Pro
        35                  40                  45

Ala Asp Arg Ala Ala Ser Tyr Arg Ala Ala Gly Tyr Trp Ser Gly Arg
    50                  55                  60

Thr Leu Asp Thr Val Leu Ser Asp Ala Ala Arg Arg Trp Pro Asp Arg
65                  70                  75                  80

Leu Ala Val Ala Asp Ala Gly Asp Arg Pro Gly His Gly Gly Leu Ser
                85                  90                  95

Tyr Ala Glu Leu Asp Gln Arg Ala Asp Arg Ala Ala Ala Ala Leu His
            100                 105                 110

Gly Leu Gly Ile Thr Pro Gly Asp Arg Val Leu Leu Gln Leu Pro Asn
        115                 120                 125

Gly Cys Gln Phe Ala Val Ala Leu Phe Ala Leu Leu Arg Ala Gly Ala
    130                 135                 140

Ile Pro Val Met Cys Leu Pro Gly His Arg Ala Ala Glu Leu Gly His
145                 150                 155                 160

Phe Ala Ala Val Ser Ala Ala Thr Gly Leu Val Val Ala Asp Val Ala
                165                 170                 175

Ser Gly Phe Asp Tyr Arg Pro Met Ala Arg Glu Leu Val Ala Asp His
            180                 185                 190

Pro Thr Leu Arg His Val Ile Val Asp Gly Asp Pro Gly Pro Phe Val
        195                 200                 205

Ser Trp Ala Gln Leu Cys Ala Gln Ala Gly Thr Gly Ser Pro Ala Pro
    210                 215                 220

Pro Ala Asp Pro Gly Ser Pro Ala Leu Leu Leu Val Ser Gly Gly Thr
225                 230                 235                 240

Thr Gly Met Pro Lys Leu Ile Pro Arg Thr His Asp Asp Tyr Val Phe
                245                 250                 255

Asn Ala Thr Ala Ser Ala Ala Leu Cys Arg Leu Ser Ala Asp Asp Val
            260                 265                 270

Tyr Leu Val Val Leu Ala Ala Gly His Asn Phe Pro Leu Ala Cys Pro
        275                 280                 285

Gly Leu Leu Gly Ala Met Thr Val Gly Ala Thr Ala Val Phe Ala Pro
    290                 295                 300

Asp Pro Ser Pro Glu Ala Ala Phe Ala Ala Ile Glu Arg His Gly Val
305                 310                 315                 320

Thr Val Thr Ala Leu Val Pro Ala Leu Ala Lys Leu Trp Ala Gln Ser
                325                 330                 335

Cys Glu Trp Glu Pro Val Thr Pro Lys Ser Leu Arg Leu Leu Gln Val
            340                 345                 350

Gly Gly Ser Lys Leu Glu Pro Glu Asp Ala Arg Arg Val Arg Thr Ala
        355                 360                 365
```

-continued

Leu Thr Pro Gly Leu Gln Gln Val Phe Gly Met Ala Glu Gly Leu Leu
370 375 380

Asn Phe Thr Arg Ile Gly Asp Pro Pro Glu Val Val Glu His Thr Gln
385 390 395 400

Gly Arg Pro Leu Cys Pro Ala Asp Glu Leu Arg Ile Val Asn Ala Asp
405 410 415

Gly Glu Pro Val Gly Pro Gly Glu Glu Gly Glu Leu Leu Val Arg Gly
420 425 430

Pro Tyr Thr Leu Asn Gly Tyr Phe Ala Ala Glu Arg Asp Asn Glu Arg
435 440 445

Cys Phe Asp Pro Asp Gly Phe Tyr Arg Ser Gly Asp Leu Val Arg Arg
450 455 460

Arg Asp Asp Gly Asn Leu Val Val Thr Gly Arg Val Lys Asp Val Ile
465 470 475 480

Cys Arg Ala Gly Glu Thr Ile Ala Ala Ser Asp Leu Glu Glu Gln Leu
485 490 495

Leu Ser His Pro Ala Ile Phe Ser Ala Ala Ala Val Gly Leu Pro Asp
500 505 510

Gln Tyr Leu Gly Glu Lys Ile Cys Ala Ala Val Val Phe Ala Gly Ala
515 520 525

Pro Ile Thr Leu Ala Glu Leu Asn Gly Tyr Leu Asp Arg Arg Gly Val
530 535 540

Ala Ala His Thr Arg Pro Asp Gln Leu Val Ala Met Pro Ala Leu Pro
545 550 555 560

Thr Thr Pro Ile Gly Lys Ile Asp Lys Arg Ala Ile Val Arg Gln Leu
565 570 575

Gly Ile Ala Thr Gly Pro Val Thr Thr Gln Arg Cys His
580 585

<210> SEQ ID NO 5
<211> LENGTH: 7523
<212> TYPE: PRT
<213> ORGANISM: Artificial Sequence
<220> FEATURE:
<223> OTHER INFORMATION: Synthetic polypeptide

<400> SEQUENCE: 5

Met Thr Ala Asp Ser Leu Asp Ile Ala Glu Leu Leu Glu Leu Trp Asn
1 5 10 15

Asn His Ser Thr Pro Glu Arg Thr Ser Thr Val Pro Thr Leu Phe Ala
20 25 30

Ala Gln Cys Ala Leu Thr Pro Asp Glu Val Ala Val Val Asp Gly Glu
35 40 45

Arg Arg Leu Thr Tyr Arg His Leu Glu Thr His Val Ala Gln Leu Ala
50 55 60

His Ala Val Arg Val Ala Ala Gly Glu Gly Pro Glu Pro Ile Val Ala
65 70 75 80

Ile Gly Val Pro Arg Ser Ala Glu Met Val Val Cys Val Leu Ala Ala
85 90 95

Met Met Ala Gly Val Ala Phe Val Pro Leu Asp Pro Ser Trp Pro Ala
100 105 110

His Arg Arg Arg Gln Val Leu Ala Asp Ser Gly Ala Val Ala Thr Phe
115 120 125

Ile Thr Arg Glu Asp Glu Ser Asp Trp Gly Val Pro Gly Leu Arg Val
130 135 140

-continued

```
Asp Leu Gly Ala Trp Gln Phe Thr Ala Glu Ser Pro Val Leu Pro Gln
145                 150                 155                 160

Ala Asp Val His Pro Ala Gln Leu Ala Tyr Val Ile Phe Thr Ser Gly
                165                 170                 175

Ser Thr Gly Lys Pro Lys Gly Ala Met Ile Arg His Asp Ala Ile Ala
            180                 185                 190

Glu Arg Leu Gln Trp Gln Arg Asp His Ile Leu His Phe Gly Lys His
        195                 200                 205

Asp His Thr Asp Ala Ser Leu Phe Lys Ala Pro Leu Ser Phe Asp Ile
    210                 215                 220

Ser Val Asn Glu Ile Leu Leu Pro Leu Val Ser Gly Gly Arg Val Val
225                 230                 235                 240

Val Ala Val Pro Asp Gly Glu Lys Asp Pro Glu Tyr Leu Leu Glu Leu
                245                 250                 255

Ile Arg Thr Glu Gln Val Thr Phe Val Tyr Leu Val Ser Ser Met Leu
            260                 265                 270

Asp Thr Leu Leu Glu Leu Asp Arg Leu Ala Thr Ala Asp Gly Ala Pro
        275                 280                 285

Ser Ser Leu Ala Ser Leu Arg His Val Trp Cys Gly Gly Glu Val Leu
    290                 295                 300

Thr Pro Gly Leu Phe Ala Arg Phe Arg Lys Gln Leu Thr Thr Thr Leu
305                 310                 315                 320

Tyr His Gly Tyr Gly Pro Ala Glu Ala Thr Ile Gly Val Ser His Val
                325                 330                 335

Ile Tyr Arg Asp Thr Ala Glu Arg Ile Ala Thr Ser Ile Gly Arg Pro
            340                 345                 350

Asn Pro His Thr Gln Leu Tyr Val Leu Asp Glu Tyr Leu Arg Pro Val
        355                 360                 365

Pro Pro Gly Val Gly Gly Glu Leu Tyr Ala Ala Gly Phe Leu Leu Gly
    370                 375                 380

Arg Gly Tyr Val Asn Ala Pro Ser Leu Thr Ala Ser Arg Phe Val Ala
385                 390                 395                 400

Asn Pro Phe Asp Gly Asn Gly Ser Arg Met Tyr Arg Thr Gly Asp Leu
                405                 410                 415

Ala Arg Trp Thr Glu Asp Gly Ser Leu Glu Phe Leu Gly Arg Ala Asp
            420                 425                 430

Asn Gln Val Lys Ile Gly Gly Arg Arg Val Glu Leu Glu Glu Ile Glu
        435                 440                 445

Ser Gln Leu Ala Asp His Pro Ala Val Arg His Ala Val Val Asp Val
    450                 455                 460

His Arg Gln Gly Gly Ala Asp Val Leu Val Gly Tyr Leu Val Ala Ala
465                 470                 475                 480

Asp Gly Val Arg Asn Asp Ala Ala Trp His Ala Glu Val Ala Asp Trp
                485                 490                 495

Ala Arg Thr Arg Leu Pro Glu Tyr Met Val Pro Lys Ala Phe Val Ala
            500                 505                 510

Leu Asp Gln Val Pro Leu Thr Ala Asn Gly Lys Thr Asp Arg Arg Ala
        515                 520                 525

Leu Pro Ala Pro Asp Leu Glu Arg Ser Gly Thr Val Lys Pro Pro Arg
    530                 535                 540

Thr Pro Arg Glu Thr Val Leu Cys Gln Val Phe Ala Asp Ala Leu Asp
545                 550                 555                 560

Ile Asp Ala Val Gly Val Asp Glu Asp Phe Phe Ala Leu Gly Gly Asp
```

```
                565                 570                 575

Ser Ile Val Ala Ile Arg Val Val Ser Arg Leu Arg Ala Ala Gly Tyr
            580                 585                 590

Thr Leu Arg Pro Arg Asp Met Phe Ala His Arg Thr Val Glu Ala Leu
        595                 600                 605

Ala Pro Leu Leu Gly Asp Ser Asp Val Arg Asp Thr Gly Pro Ala Val
    610                 615                 620

Asp Pro Thr Gly Ala Ala Thr Pro Thr Pro Ile Leu Arg Trp Leu Asp
625                 630                 635                 640

Glu Val Gly Thr Ala Gly Ser Val Leu Asn Gly Phe His Gln Gly Met
                645                 650                 655

Ser Leu Val Thr Pro Ala Asp Ala Asp Glu Asn Thr Leu Arg Ala Ala
            660                 665                 670

Ile Ala Ala Thr Val Arg Arg His His Val Leu Trp Ala Pro Pro Gly
        675                 680                 685

Arg Thr Ala Ser Asp Ile Asp Ile Pro Gly Thr Pro Pro Glu Thr Arg
    690                 695                 700

Leu Leu Ile Ala Asp Ala Ser Asp Gly Ile Pro Ala Gln Ala Glu Lys
705                 710                 715                 720

Val Ala Arg Gln Leu Val Ser Leu Leu Asp Thr Ala Arg Ile Ala Phe
                725                 730                 735

Gly Trp Ile Arg Arg Pro Ala Ala Pro Gly Arg Leu Val Val Ile Ala
            740                 745                 750

Asp His Thr Val Ile Asp Gly Val Ser Leu Arg Ile Leu Ala Glu Asp
        755                 760                 765

Ile Ala Thr Ala Tyr Gly Leu Ile Ala Glu Gly Arg Ala Val Glu Leu
    770                 775                 780

Pro Thr Pro His Thr Ser Trp Arg Ala Trp Ala Gln Arg Leu Ala Asp
785                 790                 795                 800

Thr Ala Ala Ala Gly Gly Phe Asp Ala Asp Leu Glu His Trp Gln Gln
                805                 810                 815

Val Cys Ala Thr Thr Glu Thr Pro Trp Gly Asp Arg Ala Leu Asp Pro
            820                 825                 830

Ala Ile Asp Thr Val Ala Thr Glu Ser Arg Leu Thr Val Glu Leu Pro
        835                 840                 845

Ser Ala Val Thr Asp Ala Ile Leu Thr Thr Val Pro Asp Arg Ile His
    850                 855                 860

Gly His Val Asn Asp Ala Leu Val Ala Ala Leu Tyr Leu Ala Leu Arg
865                 870                 875                 880

Arg Trp Leu His Thr Arg Gly Val Gly Ala Asp Thr Leu Leu Val Glu
                885                 890                 895

Met Glu Gly His Gly Arg Glu Gly His Leu Val Asp Ser Asp Thr Ala
            900                 905                 910

Gly Leu Asp Leu Ser Asn Thr Val Gly Trp Phe Thr Thr Leu Tyr Pro
        915                 920                 925

Val Ala Leu Arg Asp Ala Glu Phe Asp Trp Gln Ala Ala Val Ser Gly
    930                 935                 940

Gly Pro Gln Leu Gly Ala Ala Val Arg Ser Val Lys Asp Gln Leu Arg
945                 950                 955                 960

Ser Val Pro Ser His Gly Phe Ser Tyr Gly Ala Leu Arg Tyr Leu Arg
                965                 970                 975

Asp Gly Thr Ser Gly Leu Glu Ala Ala Pro Gln Val Leu Phe Asn Tyr
            980                 985                 990
```

-continued

Leu Gly Arg Phe Gly Thr Ala Asp Arg Pro Trp Ala Leu Ala Asn Asp
995 1000 1005

Thr Thr Ala Val Leu Glu Asp Arg Asp Pro Gly Met Pro Leu Pro
1010 1015 1020

Arg Leu Leu Glu Val Asn Ala Glu Ala Val Thr Thr Ala Asp Gly
1025 1030 1035

Ser Val Leu Arg Ala Thr Phe Ser Trp Pro Ala His Ala Val Ala
1040 1045 1050

Glu Val Asp Val Arg Thr Leu Ala Gly Met Trp Thr Asp Leu Leu
1055 1060 1065

Thr Ala Ile Ala Ser Ser Asp Asp Val Arg Gly His Ser Ala Ser
1070 1075 1080

Asp Phe Asp Arg Val Ser Val Thr Ala Asp Asp Val Ala Glu Leu
1085 1090 1095

Glu Arg Arg Tyr Pro Gly Leu Thr Asp Leu Leu Pro Leu Thr Pro
1100 1105 1110

Thr Gln Gln Gly Ile Tyr Phe His Ser Thr Phe Ser Arg Asp Arg
1115 1120 1125

Asp Pro Tyr Val Val Gln Gln Ile Val Asp Ile Thr Gly Pro Leu
1130 1135 1140

Asp Thr Glu Arg Phe Gln Arg Ala Thr Glu Ser Val Ala Ala Arg
1145 1150 1155

His Arg Ala Leu Gly Ala Val Phe Thr Thr Leu Ser Asp Gly Thr
1160 1165 1170

Pro Val Ala Val His Ala Ala Thr Val Ala Pro Asp Phe Asp Val
1175 1180 1185

Leu Asp Ala Arg His Ala Ala Asp Pro Ser Thr Val Val Ala Gln
1190 1195 1200

Arg Ala Arg Trp Glu Arg Glu Arg Arg Phe Asp Leu Ala Ala Ala
1205 1210 1215

Pro Leu Thr Arg Tyr Thr Leu Val Arg Arg Arg Asp Asp Leu His
1220 1225 1230

Thr Met Ile Glu Thr Val His His Ile Val Ala Asp Gly Trp Ser
1235 1240 1245

Val Pro Ile Val Leu Asp Asp Leu Leu Thr Ala Tyr Ala Gly Asp
1250 1255 1260

Asp Phe Asp Gly Pro Ala Pro Glu Phe Ala Arg Phe Val Asp Trp
1265 1270 1275

Leu Glu Gln Arg Asp Thr Asp Ser Asp Arg Ala Ala Trp Ala Pro
1280 1285 1290

Ala Leu Glu Asp Ile Thr Glu Pro Thr Arg Leu Ala Ala Ala Asp
1295 1300 1305

Gly Ala Arg Gly Arg Thr Thr Gly Ser Gly Phe Gly Thr Arg Thr
1310 1315 1320

Val Thr Leu Gln Ser Arg Ser Ala Val Ala Asp Ala Ala Asn Gly
1325 1330 1335

Ala Ala Val Thr Val Gly Thr Leu Leu His Thr Ala Trp Gly Leu
1340 1345 1350

Ala Leu Gly Arg Leu Thr Gly Arg Asp Asp Val Val Phe Gly Thr
1355 1360 1365

Val Val Ser Gly Arg Gly Ala Asp Val His Gly Ile Glu Ser Met
1370 1375 1380

-continued

```
Val Gly Leu Leu Val Asn Thr Val Pro Val Arg Val Ala Trp Ser
    1385                1390                1395

Ala Asp Asp Thr Gly Ala Asp Val Ala Gly Arg Leu Ala Ala Val
    1400                1405                1410

Glu Ser Thr Leu Leu Glu His His His Leu Pro Leu Thr Glu Ala
    1415                1420                1425

His Arg Leu Ala Gly Val Gly Glu Leu Phe Asp Thr Leu Val Val
    1430                1435                1440

Ile Glu Asn Leu Gly Ala Thr Thr His Thr Arg Gly Asp Leu Thr
    1445                1450                1455

Leu Gly Asp Ile Gly Val Ile Glu Ala Pro His Tyr Pro Leu Thr
    1460                1465                1470

Leu Met Ile Ser Val Arg Asp Thr Ile Thr Val Thr Val Thr Asn
    1475                1480                1485

Asp Arg Glu His Val Ser Asp Val Leu Ala Asp Thr Ala Val Ala
    1490                1495                1500

Ala Phe Thr Glu Val Leu Thr Ala Leu Thr Ala Asp Pro Gly Val
    1505                1510                1515

Ser Pro Gly Asp Ile Ala Leu Pro Ala Pro Gln Ala Thr Ala Pro
    1520                1525                1530

Pro Thr Gln Ala Pro Gln Thr Val Thr Asp Leu Ile Ala Ala Ala
    1535                1540                1545

Ile Ala Glu His Arg Asp Asp Ile Ala Leu Val Val Gly Glu Thr
    1550                1555                1560

Glu Trp Thr Tyr Gly Gln Leu Gly Ala Arg Ala Gly Glu Leu Ala
    1565                1570                1575

Ala Ala Leu Ala Glu Ala Gly Val Arg Arg Gly Asp Ile Val Ala
    1580                1585                1590

Leu Ala Thr Ala Arg Ser Ala Asp Leu Val Ala Ala Ile Trp Ala
    1595                1600                1605

Ile Ile Ala Ala Gly Ala Ala Tyr Leu Pro Val Asp Leu Ala Tyr
    1610                1615                1620

Pro Arg Thr Arg Ile Glu Tyr Met Leu Arg His Ala Arg Pro Thr
    1625                1630                1635

Ala Val Ile Ala Asp Gly Val Gly Ala His Val Val Ser Gly Ala
    1640                1645                1650

Leu Pro Ala Asp Thr Ile Val Val Ser Thr Thr Ala Thr His Ala
    1655                1660                1665

Ala Val Pro Phe Thr Pro Val Pro Val Asp Gly Ala Asp Ala Val
    1670                1675                1680

Ser Val Leu Tyr Thr Ser Gly Ser Thr Gly Glu Pro Lys Ala Val
    1685                1690                1695

Val Gly Thr His Ala Ala Leu Ala Asn Arg Leu Ala Trp Ala Val
    1700                1705                1710

Glu Ala Trp Pro Ala Ala Thr Arg Ile Ala Lys Ser Pro Leu Ser
    1715                1720                1725

Phe Ile Asp Gly Thr Thr Glu Leu Leu Ala Gly Leu Ala Ala Gly
    1730                1735                1740

Ala Arg Thr Val Leu Ala Gly Asp Glu Thr Ala Arg Asp Gly Arg
    1745                1750                1755

Arg Leu Ala Gln Leu Val Ala Ala His Gly Val Glu Gln Leu Leu
    1760                1765                1770

Ala Val Pro Ser Leu Ala Ala Val Leu Ala Asp Glu Arg Thr Glu
```

-continued

```
    1775                1780                1785

Asp Val  Ala Glu Leu Asn Arg  Trp Ile Val Ser Gly  Glu Ala Leu
    1790                1795                1800

Glu Pro  Arg His Leu His Ala  Leu Arg Thr Ala Cys  Pro Thr Ala
    1805                1810                1815

Glu Ile  Val Asn Ser Tyr Gly  Ser Ser Glu Val Ala  Gly Asp Val
    1820                1825                1830

Leu Ala  Gly Val Gln Asp Asp  Ala Gly Ile Thr Leu  Gly Ala Ala
    1835                1840                1845

Val Pro  Gly Ala Gly Ile Arg  Ile Leu Asp Ser Arg  Leu Arg Gln
    1850                1855                1860

Leu Pro  Ala Gly Val Ile Gly  Glu Ile Tyr Val Thr  Gly Gly Gln
    1865                1870                1875

Leu Ala  Arg Gly Tyr Leu Gly  Arg Pro Gly Gln Thr  Ala Thr Arg
    1880                1885                1890

Phe Val  Ala Ala Pro Gly Gly  Glu Arg Met Tyr Arg  Thr Gly Asp
    1895                1900                1905

Leu Gly  Ala Leu Leu Pro Gly  Gly Arg Val Val Phe  Ala Gly Arg
    1910                1915                1920

Ala Asp  Asp Gln Leu Lys Ile  Asn Gly His Arg Val  Glu Pro Gly
    1925                1930                1935

Glu Ile  Glu Ser Val Leu Ala  Arg Gln Pro Gly Val  Arg Glu Ala
    1940                1945                1950

Ala Val  Ile Gly Thr Gly Thr  Gln Leu Ala Ala Phe  Val Val Leu
    1955                1960                1965

Glu Ser  Asp Ala Pro Gly Ala  Gly Asp Leu Leu Thr  Ala Val Ser
    1970                1975                1980

Ala Glu  Leu Pro Gly His Leu  Val Pro Ser Ser Leu  Arg Pro Val
    1985                1990                1995

Asp Ala  Ile Pro Leu Leu Pro  Asn Gly Lys Arg Asp  Asn Asn Ala
    2000                2005                2010

Leu Arg  Ser Leu Leu Val Pro  Gly Glu Ser Thr Gly  Thr Ala Pro
    2015                2020                2025

Thr Asn  Asp Val Glu Arg Ala  Val Leu Asp Val Met  Thr Gly Val
    2030                2035                2040

Leu Gly  Arg Asp Pro Leu Gly  Ala Asp Asp Asp Phe  Phe Ala Val
    2045                2050                2055

Gly Gly  Asp Ser Ile Ser Ala  Ile Arg Val Thr Ser  Arg Leu Ala
    2060                2065                2070

Arg Ala  Gly Tyr His Ile Ala  Thr Glu Asp Val Phe  Arg Gly Arg
    2075                2080                2085

Thr Ala  Ala Gly Val Ala Ala  Leu Val Asp Thr Val  Glu Ser Leu
    2090                2095                2100

Ala His  Asp Ala Ala Ile Glu  Pro Phe Ala Thr Val  Arg Leu Ser
    2105                2110                2115

Pro Gln  Thr Ile Asp Arg Ile  Arg Glu Ser Gly Gln  Val Glu Asp
    2120                2125                2130

Ile Trp  Ala Met Ser Pro Leu  Gln Leu Gly Val Tyr  Tyr Gln Ser
    2135                2140                2145

Thr Leu  Ala Asp Ala Gly Pro  Thr Tyr Ile Ala Gln  Asn Val Phe
    2150                2155                2160

Glu Phe  Asp Arg Arg Ile Asp  Val Asp Ala Met Arg  Arg Ala Phe
    2165                2170                2175
```

```
Thr Ala  Leu Leu Arg Arg His  Pro Gln Leu Arg Ala  Gly Phe Arg
    2180                 2185                 2190

Thr Val  Glu His Ala Glu Pro  Glu Pro Ala Pro Asp  Ala Thr Pro
    2195                 2200                 2205

Val Val  Gln Val Val Val Thr  Asp Pro Pro Ser Asp  Leu Thr Val
    2210                 2215                 2220

Val Asp  Leu Thr Asp Gln Asp  Asp Pro Ala Ala Ala  Gln His Ile
    2225                 2230                 2235

Val Asp  Thr Asp Arg Thr Ala  Pro Phe Asp Val Ala  Thr Pro Pro
    2240                 2245                 2250

Leu Leu  Arg Leu Thr Val Ile  Arg Leu Pro Gly Gly  Arg Asp Arg
    2255                 2260                 2265

Met Leu  Phe Thr Tyr His Phe  Leu Leu Phe Asp Gly  Trp Ser Arg
    2270                 2275                 2280

Glu Leu  Val Leu Arg Asp Leu  Phe Ala Leu Tyr Asp  Ser Asp Ala
    2285                 2290                 2295

Gln His  Gly Ala Ile Ala Pro  His Gly Asp Leu Val  Val Arg His
    2300                 2305                 2310

Leu Gln  Trp Leu Ala Thr Asp  Gly Asp Pro Gln Ala  Ser Gly Ala
    2315                 2320                 2325

Arg Asp  Ala Trp Arg Asp Leu  Leu Ala Gly Leu Thr  Glu Pro Thr
    2330                 2335                 2340

Leu Ala  Ser Gly Val Ser Pro  Asp His Pro Asp Ala  Arg Pro Gly
    2345                 2350                 2355

Thr Glu  Pro Gly Arg Ile Val  Val Arg Val Pro Glu  Asp Val Thr
    2360                 2365                 2370

Thr Gln  Leu His Thr Cys Ala  Thr Ala His Gly Ala  Thr Leu Asn
    2375                 2380                 2385

Ser Val  Val Thr Ala Ala Val  Ala Leu Val Thr Gly  Tyr His Ala
    2390                 2395                 2400

Gly Thr  Thr Asp Val Val Ile  Gly Thr Thr Val Ala  Gly Arg Pro
    2405                 2410                 2415

Gly His  Leu Val Gly Ile Asp  Glu Thr Ile Gly Leu  Phe Leu Asn
    2420                 2425                 2430

Thr Val  Pro Val Arg Val Asp  Met Ser Pro Thr Arg  Ser Val Ala
    2435                 2440                 2445

Ala Ala  Met Ala Ser Ile Gly  Glu Gln Arg Val Ala  Met Met Arg
    2450                 2455                 2460

His Asp  His Leu Gly Leu Gly  Gln Ile Gln Arg Ala  Ala Gly Asp
    2465                 2470                 2475

Ser Gly  Ser Ala Leu Phe Asp  Ser Leu Leu Val Leu  Gln Asn Phe
    2480                 2485                 2490

Leu Asp  Asp Asp Thr Phe Thr  Asp Leu Glu Ser Arg  His Gly Ile
    2495                 2500                 2505

Val Asp  Val Ser Tyr His Asp  Thr Thr His Phe Pro  Leu Thr Trp
    2510                 2515                 2520

Val Leu  Thr Pro Gly Arg Glu  Leu Ala Ile Lys Leu  Glu His Arg
    2525                 2530                 2535

Val Val  Asp Asp Ala Arg Ala  Thr Glu Met Val Glu  Gln Leu Val
    2540                 2545                 2550

Thr Val  Leu Arg Thr Ile Ala  Ala Glu Pro Asp Thr  Ala Val Gly
    2555                 2560                 2565
```

-continued

Ala Val Asp Leu Ile Gly Ala Asp Arg Arg Ala Gln Leu Glu Arg
2570 2575 2580

Arg Trp Ser Ser Thr Glu Arg Pro Leu Glu Pro Val Thr Ile Ala
2585 2590 2595

Glu Leu Leu Ala Arg Arg Ala Glu Gln Asn Pro Asp Asp Val Ala
2600 2605 2610

Leu Val Phe Gly Ala Gln Ser Val Thr Tyr Arg Glu Phe Asp Asp
2615 2620 2625

Arg Val Ser Gln Phe Ala Arg His Leu Arg Ala Arg Gly Ala Ala
2630 2635 2640

Pro Glu Thr Phe Val Ala Leu Ala Leu Pro Arg Ser Ile Asp Met
2645 2650 2655

Val Val Ala Leu Phe Ala Val Leu Arg Ala Gly Ala Ala Tyr Leu
2660 2665 2670

Pro Leu Glu Leu Asp Leu Pro Ile Asp Arg Leu Arg Thr Ile Ile
2675 2680 2685

Asp Asn Ala Glu Pro Val Leu Leu Val Thr Thr Thr Asp Arg Thr
2690 2695 2700

Glu Leu Ile Gly His Ala Arg Ala Arg Gly Ala Asp Val Ile Ala
2705 2710 2715

Leu Asp Asp Ala Glu Thr Ala Ala Thr Leu Ala Asp Thr Pro Ala
2720 2725 2730

His Pro Leu Thr Ala Gly Glu Leu Gly Ala Phe Ala Ser Asp Ser
2735 2740 2745

Thr Arg Leu Asn His Pro Ala Tyr Leu Ile Tyr Thr Ser Gly Ser
2750 2755 2760

Thr Gly Arg Pro Lys Gly Val Leu Thr Gly Tyr Ala Gly Leu Thr
2765 2770 2775

Asn Met Tyr Phe Asn His Arg Glu Ala Ile Phe Ala Pro Thr Val
2780 2785 2790

Ala Arg Ala Gly Ser Ala Glu Gln Leu Arg Ile Ala His Thr Val
2795 2800 2805

Ser Phe Ser Phe Asp Met Ser Trp Glu Glu Leu Phe Trp Leu Val
2810 2815 2820

Glu Gly His Gln Val His Val Cys Asp Glu Glu Leu Arg Arg Asp
2825 2830 2835

Ala Pro Ala Leu Val Ala Tyr Cys His Arg His Arg Ile Asp Val
2840 2845 2850

Ile Asn Val Thr Pro Thr Tyr Ala His His Leu Phe Asp Ala Gly
2855 2860 2865

Leu Leu Asp Asp Gly Ala His Thr Pro Pro Leu Val Leu Leu Gly
2870 2875 2880

Gly Glu Ala Val Gly Asp Gly Val Trp Ser Ala Leu Arg Asp His
2885 2890 2895

Pro Asp Ser Ala Gly Tyr Asn Leu Tyr Gly Pro Thr Glu Tyr Thr
2900 2905 2910

Ile Asn Thr Leu Gly Gly Gly Thr Asp Asp Ser Asp Thr Pro Thr
2915 2920 2925

Val Gly Gln Pro Ile Trp Asn Thr Arg Gly Tyr Ile Leu Asp Ala
2930 2935 2940

Ala Leu Arg Pro Val Pro Asp Gly Ala Val Gly Glu Leu Tyr Ile
2945 2950 2955

Ala Gly Thr Gly Leu Ala Leu Gly Tyr His Arg Arg Ala Gly Leu

-continued

```
    2960                2965                2970

Thr Ala  Ala Thr Met Val Ala  Asp Pro Tyr Val Pro  Gly Gly Arg
    2975                2980                2985

Met Tyr  Arg Thr Gly Asp Leu  Val Arg Arg Arg Pro  Gly Ser Ala
    2990                2995                3000

Glu Leu  Leu Asp Tyr Leu Gly  Arg Val Asp Asp Gln  Val Lys Ile
    3005                3010                3015

Arg Gly  Tyr Arg Val Glu Leu  Gly Glu Ile Glu Ser  Val Leu Thr
    3020                3025                3030

Arg Ala  Asp Gly Val Ala Arg  Cys Ala Val Val Ala  Arg Ala Thr
    3035                3040                3045

Gly Ala  Asn Pro Pro Val Lys  Thr Leu Ala Ala Tyr  Val Ile Pro
    3050                3055                3060

Asp Arg  Trp Pro Ala Glu Asp  Ala Ala Phe Ile Thr  Gly Leu Arg
    3065                3070                3075

Asp His  Leu Ala Arg Val Leu  Pro Gly Tyr Met Val  Pro Thr Arg
    3080                3085                3090

Tyr Gly  Ile Val Asp Thr Leu  Pro Leu Thr Ile Asn  Gly Lys Leu
    3095                3100                3105

Asp Val  Ala Ala Leu Pro Glu  Pro Ile Ala Ala Thr  Ser Gly Thr
    3110                3115                3120

Gly Arg  Thr Pro Arg Thr Asp  Arg Glu Ala Thr Leu  Leu Glu Ile
    3125                3130                3135

Val Ala  Ser Val Leu Gly Ile  Asp Gly Ile Gly Val  Asp Asp Asp
    3140                3145                3150

Phe Phe  Thr Leu Gly Gly Asp  Ser Ile Ser Ser Ile  Ser Val Cys
    3155                3160                3165

Gly Arg  Ala Arg Lys Ala Gly  Leu Asn Ile Thr Pro  Arg Asp Val
    3170                3175                3180

Phe Arg  Arg Arg Thr Ile Ala  Ala Leu Ala Ala Ser  Ala Asp Thr
    3185                3190                3195

Thr Gln  Thr Pro Glu Ser Gly  Pro Asp Thr Gly Thr  Gly Ala Ile
    3200                3205                3210

Thr Ala  Thr Pro Met Leu Ala  Glu Thr Ala Gln Ala  Asn Thr Pro
    3215                3220                3225

Leu Thr  Asn Phe Tyr Gln Ala  Met Val Leu Ala Thr  Pro Ala Gly
    3230                3235                3240

Ile Thr  Ala His Glu Val Gln  Arg Val Leu Gln Thr  Val Val Asp
    3245                3250                3255

Ala His  Ala Met Leu Arg Ala  Arg Leu Val Thr Thr  Ala Thr Gly
    3260                3265                3270

Trp Thr  Leu Thr Val Pro Asp  Gln Thr Ala Ala Ile  Gly Leu Thr
    3275                3280                3285

Val Arg  Ser Gly Ala Leu Thr  Ser Asp Cys Val Glu  Ala Glu Lys
    3290                3295                3300

Ala Ala  Ala Ala Ala Glu Leu  Asp Pro Arg Ala Gly  Asn Met Val
    3305                3310                3315

Arg Ala  Val Trp Phe Asp Ala  Pro Glu Ala Ser Gly  Gln Leu Leu
    3320                3325                3330

Leu Val  Ile His His Leu Val  Ile Asp Gly Val Ser  Trp Arg Ile
    3335                3340                3345

Leu Ser  Glu Asp Leu Ser Arg  Ala Trp Asn Asp Leu  Ala Ala Gly
    3350                3355                3360
```

-continued

Arg Asp Val Ala Ala Asp Ala Val Pro Thr Ser Phe His Thr Trp
3365 3370 3375

Ala Asn Ala Leu Ala Gln Arg Thr Phe Asp Asp Glu Ser Glu Tyr
3380 3385 3390

Trp Ala Asp Val Leu Ala Thr Pro Asp Pro Asp Leu Gly Ser Arg
3395 3400 3405

Pro Pro Asp Pro Ala Ile Asp Thr Ala Asp Thr Val Arg Ser His
3410 3415 3420

Glu Val Thr Leu Ala Ser Asp Val Thr Glu Ala Leu Leu Thr Ser
3425 3430 3435

Val Pro Ala Ala Met His Gly Gly Val Asn Asp Val Leu Leu Thr
3440 3445 3450

Gly Leu Ala Val Ala Leu Ala Gln Trp Arg Ala Asp Arg Gly His
3455 3460 3465

Ser Gln Asn Thr Ala Ala Val Ile Ser Leu Glu Gly His Gly Arg
3470 3475 3480

Glu Ser Asp Leu Val Ala Ala Asp Leu Asp Leu Ser Arg Thr Val
3485 3490 3495

Gly Trp Phe Thr Ser Ile Tyr Pro Val Arg Ile Asp Pro Gly Pro
3500 3505 3510

Leu Glu Trp Asp Thr Val Arg Ser Ala Gly Ala Glu Leu Ala Ala
3515 3520 3525

Ala Ala Lys Ala Val Lys Glu Gln Leu Arg Ala Val Pro Asn Arg
3530 3535 3540

Gly Leu Gly Tyr Gly Val Leu Arg His Leu His Gly Ala Leu Asp
3545 3550 3555

Gly Thr Pro Pro Gln Ile Leu Phe Asn Tyr Leu Gly Arg Phe Thr
3560 3565 3570

Gly Gly Ser Gly Asn Asp Trp Arg Pro Val Ala Gly Ile Gly Ala
3575 3580 3585

Leu Thr Glu Gly Val Asp Pro Ser Asn Pro Ala Met Ser Leu Glu
3590 3595 3600

Ile Asn Ala Leu Ala Glu Glu Arg Pro Asp Gly Thr Val Leu Ser
3605 3610 3615

Met Thr Leu Ala Trp Pro Gly Gly Leu Leu Asp Ala Asp Asp Val
3620 3625 3630

Ser Glu Leu Gly Ser Met Trp Ala Asp Val Leu Val Ala Leu Thr
3635 3640 3645

Arg Cys Asp Ala Leu Arg Gly His Thr Pro Ser Asp Phe Gly Leu
3650 3655 3660

Val Thr Val Ser Gln Asp Asp Ile Asp Gly Trp Asp Arg Leu Gly
3665 3670 3675

Glu Val Glu Glu Val Leu Pro Leu Leu Pro Leu Gln Glu Gly Met
3680 3685 3690

Tyr Phe His Ser Met Phe Gly Asp Pro Ala Thr Asp Thr Tyr Arg
3695 3700 3705

Val Gln Gln Ile Ala Gln Leu Ser Gly Pro Val Asp Pro Glu Val
3710 3715 3720

Leu Arg Thr Ser Leu Thr Val Val Met Arg Arg His Gln Ala Leu
3725 3730 3735

Arg Ala Ser Phe Asn Glu Leu Thr Asp Gly Arg Val Ala Gln Val
3740 3745 3750

-continued

```
Ile Trp  Ser Asp Val Pro Val  Gln Leu Thr Val Val  Asp Thr Asp
    3755                 3760                 3765

Asp Leu  Glu Ser Ile Ala Ala  Glu Glu Leu Ala Arg  Pro Phe Asn
    3770                 3775                 3780

Leu Ala  Glu Ala Pro Leu Val  Arg Tyr Met Leu Val  Arg Leu Gly
    3785                 3790                 3795

Asp Asp  Asp His Arg Leu Val  Gln Thr Met His His  Ile Ile Ala
    3800                 3805                 3810

Asp Gly  Trp Ser Tyr Pro Val  Leu Phe Gly Asp Ile  Val Asp His
    3815                 3820                 3825

Tyr Asn  Ala Ala Ile Gly Val  Gly Ser Ala Pro Gln  Pro Ile Thr
    3830                 3835                 3840

Val Thr  Leu Arg Asp His Ile  Glu Thr Val Thr Asp  Arg Asp Arg
    3845                 3850                 3855

Gly Ala  Ala Arg Gln Ala Trp  Glu Gln Ala Leu Ala  Gly Ala Glu
    3860                 3865                 3870

Pro Thr  Ala Leu Val Pro Arg  Pro Asp Gly Ala Pro  Val Gly Glu
    3875                 3880                 3885

His Arg  Ser Val Val Arg Arg  Leu Asp Ser Ala Arg  Thr Ala Ala
    3890                 3895                 3900

Val Gly  Arg Ala Ala Arg Val  His Gly Val Thr Val  Gly Thr Val
    3905                 3910                 3915

Leu His  Gly Ala Trp Gly Leu  Met Leu Gly Arg Leu  Leu Gly Arg
    3920                 3925                 3930

Asn Arg  Val Val Phe Gly Ser  Thr Val Ser Gly Arg  Gly Gly Asp
    3935                 3940                 3945

Leu Ala  Gly Thr Glu Ser Ile  Val Gly Leu Leu Ile  Asn Thr Ile
    3950                 3955                 3960

Pro Val  Pro Met Ser Trp Glu  Pro His Ala Thr Leu  Ala Ser Ala
    3965                 3970                 3975

Leu Ile  Asp Leu Gln Asp Gln  Gln Ser Ala Leu Leu  Asp Ala Gln
    3980                 3985                 3990

Gln Met  Gly Leu Ala Glu Leu  Ala Arg Leu Ala Gly  Val Arg Glu
    3995                 4000                 4005

Phe Phe  Asp Thr Met Val Ile  Val Glu Asn Phe Pro  Ser Thr Ser
    4010                 4015                 4020

Ser Ala  Glu His Thr Asp Pro  Arg Ala Val Ala Phe  Arg Gly Phe
    4025                 4030                 4035

Thr Gly  Thr Asp Ser Pro His  Tyr Pro Val Ser Phe  Val Ala Tyr
    4040                 4045                 4050

Ala Asp  Asp Gln Leu Thr Val  Glu Ile Lys Tyr Asp  Ala Gly Val
    4055                 4060                 4065

Val Thr  Pro Glu Gln Ala Glu  Arg Tyr Ala Glu Arg  Val Glu Arg
    4070                 4075                 4080

Ile Leu  Thr Ala Phe Ala Glu  Thr Pro Asp Leu Pro  Val Ser Arg
    4085                 4090                 4095

Ile Asp  Leu Arg Thr Asn Ala  Glu Arg Gln Phe Thr  Ala Gly His
    4100                 4105                 4110

Ala Ser  Arg Pro Gly Pro Gly  Arg Thr Leu Gly Ala  Ser Phe Ala
    4115                 4120                 4125

Glu Val  Ala Ala Thr Tyr Pro  Asp Ala Val Ala Val  Ser Cys Gly
    4130                 4135                 4140

Asp Thr  Arg Leu Thr Tyr Arg  Glu Leu Asp Asp Arg  Ala Ala Ala
```

-continued

```
    4145                4150                4155

Val Ala  Ala Thr Leu Ala Glu  Arg Gly Val Gly Ala  Glu Ser Arg
    4160                4165                4170

Val Ala  Ile Ala Leu Pro Arg  Ser Ala Asp Leu Ile  Val Ala Val
    4175                4180                4185

Leu Ala  Val Ile Lys Ala Gly  Gly Thr Tyr Val Pro  Ile Asp Ile
    4190                4195                4200

Gly Ala  Pro Ala Ala Arg Val  Gln His Ile Leu Ala  Asp Ser Ala
    4205                4210                4215

Pro Val  Cys Leu Leu Thr Asp  Thr Ala Glu Arg Phe  Thr Gly Val
    4220                4225                4230

Pro His  Val Ile Leu Ala Glu  Ala Ala Gln Asn Pro  Ala Arg Pro
    4235                4240                4245

Gln Ala  Pro Thr Val Ser Pro  Asp His Ala Ala Tyr  Val Ile Tyr
    4250                4255                4260

Thr Ser  Gly Ser Thr Gly Val  Pro Lys Gly Val Glu  Val Thr His
    4265                4270                4275

Arg Asn  Val Ala Ala Leu Phe  Ala Gly Thr Thr Ser  Gly Leu Tyr
    4280                4285                4290

Asp Phe  Gly Pro Asp Asp Val  Trp Thr Met Phe His  Ser Ala Ala
    4295                4300                4305

Phe Asp  Phe Ser Val Trp Glu  Leu Trp Gly Pro Leu  Leu His Gly
    4310                4315                4320

Gly Arg  Leu Val Val Val Glu  His Asp Val Ala Arg  Asp Pro Glu
    4325                4330                4335

Arg Phe  Val Asp Leu Leu Ala  Arg Glu Arg Val Thr  Val Leu Asn
    4340                4345                4350

Gln Thr  Pro Ser Ala Phe Tyr  Pro Leu Leu Glu Ala  Asp Ala Arg
    4355                4360                4365

Leu Arg  Arg Gln Leu Ala Leu  Arg Tyr Val Ile Phe  Gly Gly Glu
    4370                4375                4380

Ala Leu  Asp Val Arg Arg Leu  Ala Pro Trp Tyr Ala  Asn His Glu
    4385                4390                4395

Ser His  Ser Pro Arg Leu Val  Asn Met Tyr Gly Ile  Thr Glu Thr
    4400                4405                4410

Cys Val  His Val Ser His Arg  Ala Leu Asp Thr Ala  Asp Thr Gly
    4415                4420                4425

Ala Ala  Gly Ser Val Ile Gly  Gly Pro Leu Pro Gly  Leu Arg Ile
    4430                4435                4440

His Leu  Leu Asp Asn Asn Leu  Gln Pro Val Pro Ala  Gly Val Val
    4445                4450                4455

Gly Glu  Met Tyr Ile Ala Gly  Gly Gln Val Ala Arg  Gly Tyr Thr
    4460                4465                4470

Gly Arg  Pro Gly Leu Thr Ala  Thr Arg Phe Val Ala  Asn Pro Phe
    4475                4480                4485

Asp Gly  Ala Gly Glu Arg Leu  Tyr Arg Ser Gly Asp  Leu Ala Met
    4490                4495                4500

Trp Thr  Asp Ala Gly Glu Leu  Val Tyr Leu Gly Arg  Ser Asp Ala
    4505                4510                4515

Gln Val  Lys Val Arg Gly Tyr  Arg Ile Glu Leu Gly  Glu Val Glu
    4520                4525                4530

Ala Ala  Leu Val Thr Leu Pro  Gly Val Thr Asn Ala  Ala Ala Asp
    4535                4540                4545
```

-continued

```
Val Arg His Asp Asp Thr Gly Arg Ala Arg Leu Ile Gly Tyr Val
    4550                4555                4560

Val Gly Asp Ala Leu Asp Ile Gly Ala Leu Arg Ser Thr Leu Ala
    4565                4570                4575

Glu Arg Leu Pro Asp Tyr Met Val Pro Ser Val Leu Leu Arg Leu
    4580                4585                4590

Asp Val Leu Pro Leu Thr Val Asn Gly Lys Leu Asp Arg Ala Ala
    4595                4600                4605

Leu Pro Asp Pro Glu Pro Val Glu Gln Ala Pro Ala Pro Val Ala
    4610                4615                4620

Gly Thr Gly Thr Ala Ser Leu Leu Ala Gly Leu Cys Thr Glu Ile
    4625                4630                4635

Leu Gly Thr Thr Val Gly Val Glu Asp Asp Phe Phe Thr Ala Gly
    4640                4645                4650

Gly Asp Ser Ile Ile Ala Ile Gln Leu Val Asn Arg Ala Arg Arg
    4655                4660                4665

Glu Gly Val Arg Ile Thr Pro Gln Gln Val Phe Val His Arg Thr
    4670                4675                4680

Pro Ala Ala Leu Ala Ser Val Leu Asp Thr Gly Ser Val Ala Ala
    4685                4690                4695

Pro Asp Ala Thr Pro Asp Glu Asp Ala Gly Pro Asp Leu Gly Glu
    4700                4705                4710

Val Met Leu Thr Pro Ile Val Gln Arg Leu Ala Glu Leu Gly Gly
    4715                4720                4725

Thr Val Thr Arg Phe Asn Gln Ser Glu Leu Leu Arg Thr Pro Ala
    4730                4735                4740

Gly Ala Thr Val Ala Arg Leu Glu Thr Ala Ile Asn Ala Val Ile
    4745                4750                4755

Ala Arg His Asp Ala Leu Arg Ile Arg Leu His Arg Pro Ala Pro
    4760                4765                4770

Met Leu Trp Ser Leu Glu Thr Thr Ala Ala Ala Pro Val Ser Ile
    4775                4780                4785

Thr Arg Ile Asp Ala His Gly Phe Asp Asp Glu Gln Leu Arg Thr
    4790                4795                4800

Val Ile Ala Thr Glu Ser Asp Ala Ala Ala Asp Arg Leu Asp Pro
    4805                4810                4815

Glu Asn Gly Val Val Val Val Ala Val Trp Phe Asp Arg Gly Thr
    4820                4825                4830

Asp Thr Gln Gly Arg Leu Leu Leu Val Val His His Leu Ala Val
    4835                4840                4845

Asp Gly Val Ser Trp Arg Ile Leu Leu Asp Asp Leu Ala Glu Ala
    4850                4855                4860

Tyr Arg Gln Ala Leu Ser Gly Gln Arg Val Ala Pro Ala Pro Val
    4865                4870                4875

Thr Thr Ser Leu Arg Gln Tyr Ala Arg Thr Val Asn Glu Asn Ala
    4880                4885                4890

Gln His Ser Ser Arg Leu Thr Glu Phe Glu His Trp Thr Glu Val
    4895                4900                4905

Leu Ala Pro Gly Gly Glu Leu Val Ala Thr Ala Asp Val Val Thr
    4910                4915                4920

Leu Thr Val Gly Ala Thr Arg Asp His Glu Ile Arg Leu Ser Thr
    4925                4930                4935
```

-continued

Glu Asp Thr Ala Pro Leu Leu Thr Thr Val Pro Ala Ala Ala Asn
4940 4945 4950

Ala Asp Val Thr Glu Thr Leu Val Ala Ala Leu His Leu Ala Val
4955 4960 4965

Ser Arg Trp Arg Ala Ala Arg Gly Glu Ala Ala Asp Ala Pro Leu
4970 4975 4980

Val Leu Ser Leu Glu Arg His Gly Arg Asp Gly Trp Pro Asp Asp
4985 4990 4995

Val Asp Leu Ser Arg Thr Val Gly Trp Phe Thr Ser Ile Ala Pro
5000 5005 5010

Val Arg Leu Pro Ala Pro Gly Glu Asp Leu Leu Asn Thr Leu Lys
5015 5020 5025

Ala Val Lys Glu Ser Leu Arg Ala Ala Pro Asp Gly Gly Leu Gly
5030 5035 5040

Phe Gly Gln Leu Arg Tyr Cys Asn Pro Arg Thr Ser Ala Val Leu
5045 5050 5055

Ala Arg Leu Gly Thr Pro Gln Leu Leu Phe Asn Tyr Leu Gly Arg
5060 5065 5070

Trp Ala Ala Asp Ala Cys Asp Asp Trp Ala Ser Ala Pro Glu Val
5075 5080 5085

Asp Ala Leu Arg Thr Glu Pro Asn Pro Asp Leu Gly Thr Pro Tyr
5090 5095 5100

Leu Val Glu Val Asn Ala Ile Cys Asp Asp Thr Val Asp Gly Pro
5105 5110 5115

Arg Leu Arg Ala Thr Leu Thr Tyr Ala Asp Gly Glu Leu Asp Glu
5120 5125 5130

Pro Ser Val Ala Glu Leu Gly Glu Leu Trp Val Ala Ala Leu Arg
5135 5140 5145

Glu Leu Gly Ser Leu Ala Thr Gly Gly Asp Ala Ala Leu Thr Pro
5150 5155 5160

Ser Asp Leu Pro Leu Val Thr Leu Thr Gln Glu His Ile Asp Arg
5165 5170 5175

Val Thr Gly Ala Val Pro Gly Asn Val Glu Thr Ile Trp Pro Leu
5180 5185 5190

Ser Pro Leu Gln Glu Gly Val Tyr Leu Gln Ala Arg Tyr Ala Thr
5195 5200 5205

Ala Ala Val Tyr Ile Val Gln Asn Val Phe Asp Phe Ala Glu Pro
5210 5215 5220

Val Asp Thr Thr Ala Leu Arg Thr Ala Tyr Ser Ala Val Met Ala
5225 5230 5235

Arg Asn Pro Val Leu Arg Ser Ala Phe Trp Ala Asp Asp Leu Pro
5240 5245 5250

Gln Pro Val Ala Ala Ile Val Ala Asp Pro Val Cys Glu Pro Arg
5255 5260 5265

Val Val Asp Leu Gly Gly Leu Pro Ala Thr Gln Val Glu Arg Arg
5270 5275 5280

Val Glu Glu Ile Thr Ala Asp Asp Arg Gln Gln Thr Phe Asp Leu
5285 5290 5295

Ala Ala Ala Pro Leu Ala Arg Met Thr Val Leu Arg Thr Pro Asp
5300 5305 5310

Arg Asp Arg Leu Ile Phe Ser Tyr His Phe Leu Leu Leu Asp Gly
5315 5320 5325

Trp Ser Arg Glu Gln Leu Leu Arg Glu Leu Phe Ala Glu Tyr Thr

```
    5330                5335                5340

Ala Ala  Arg Gly Gly Ala Val  Ala Gln Leu Pro Ala  Pro Thr Ala
    5345                5350                5355

Asp Phe  Thr Asp Tyr Leu Arg  Trp Leu Ala Arg Gln  Asp Arg Asp
    5360                5365                5370

Val Ser  Ala Arg Glu Trp Ser  Glu Ala Leu Arg Asp  Leu Glu Ala
    5375                5380                5385

Pro Thr  Leu Leu Val Pro Asp  Ala Val Gly Thr Asp  Pro Thr Leu
    5390                5395                5400

Ala Leu  Arg Leu Glu Phe Leu  Leu Ser Glu Ala Asp  Thr Ala Ala
    5405                5410                5415

Leu Thr  Ala Ala Ala Arg Ser  Ala Gly Val Thr Leu  Asn Ala Leu
    5420                5425                5430

Ile Ser  Thr Ala Leu Ala Met  Val Leu Ala Tyr Glu  Thr Gly Arg
    5435                5440                5445

Asp Asp  Val Val Phe Gly Ser  Thr Val Ala Gly Arg  Pro Thr Asp
    5450                5455                5460

Leu Asp  Gly Ile Asp Ser Val  Ile Gly Leu Phe Leu  Asn Thr Val
    5465                5470                5475

Pro Thr  Arg Val Arg Leu Ala  Pro His Arg Thr Val  Ala Asp Thr
    5480                5485                5490

Met Arg  Ala Val Gln Ser Asp  Arg Leu Arg Leu Met  Asp His Glu
    5495                5500                5505

Tyr Leu  Gly Leu Gly Asp Ile  Gln Arg Ala Val Ser  Thr Gly Gly
    5510                5515                5520

Gly Pro  Leu Phe Asp Ser Leu  Tyr Val Leu Gln Asn  Phe Leu Asp
    5525                5530                5535

Asp Asp  Thr Phe Thr Asp Met  Glu Ala Gln Tyr Gly  Ile Val Gly
    5540                5545                5550

His Asp  Ser Ile Asp Ala Ser  His Tyr Pro Leu Thr  Trp Val Ala
    5555                5560                5565

Ser Pro  Gly Arg Arg Leu Trp  Met Lys Leu Glu Tyr  Arg Pro Asp
    5570                5575                5580

Val Val  Glu Arg Asp Arg Ala  Gln Gly Leu Leu Asp  Arg Leu Arg
    5585                5590                5595

Gln Val  Leu Leu Gln Val Gly  Thr Gly Val Glu Arg  Pro Ser Ala
    5600                5605                5610

Ala Leu  Thr Leu Pro Leu Pro  Ala Glu Ala Asp His  Lys Arg Thr
    5615                5620                5625

Arg Asp  Ala Ala Thr Glu His  Asp Leu Pro His Ala  Ser Val Leu
    5630                5635                5640

Asp Leu  Leu Ala Glu Arg Ala  Val Gln Ser Gly Asp  Leu Thr Ala
    5645                5650                5655

Leu Val  Cys Gly Gly Glu Phe  Val Asp Tyr Ala Glu  Leu Leu Ala
    5660                5665                5670

Arg Val  Asn Arg Leu Ala Trp  Val Leu Arg Ser Arg  Gly Ile Gly
    5675                5680                5685

Pro Glu  Asp Thr Val Ala Leu  Ala Val Pro Arg Ser  Ile Asp Ala
    5690                5695                5700

Val Val  Ala Leu Phe Ala Val  Leu Arg Ala Gly Ala  Ala Tyr Leu
    5705                5710                5715

Pro Leu  Glu Leu Asp Tyr Pro  Asp Glu Arg Leu Ala  Val Met Leu
    5720                5725                5730
```

Gly Asp Ala Glu Pro Val Arg Val Leu Val Thr Gly Ala Thr Ala
5735 5740 5745

Gln Arg Ile Ala Arg Val Ala Ser Ala Pro Leu Thr Val Leu Asp
5750 5755 5760

Ala Pro Asp Thr Cys Asp Glu Leu Ala Arg Ala Arg Ser Asp Trp
5765 5770 5775

Asp Gly Tyr Ser Pro His Pro Asp Gln Pro Ala Tyr Val Ile Tyr
5780 5785 5790

Thr Ser Gly Ser Thr Gly Lys Pro Lys Gly Val Val Thr Pro His
5795 5800 5805

Arg Gly Leu Thr Asn Met His Leu Asn His Arg Glu Ala Ile Phe
5810 5815 5820

Ala Pro Thr Ile Ala Arg Ala His Gly Arg Arg Leu Lys Ile Ala
5825 5830 5835

His Thr Val Ser Phe Ser Phe Asp Met Ser Trp Glu Glu Leu Leu
5840 5845 5850

Trp Leu Ile Glu Gly His Glu Val His Ile Cys Asp Glu Val Leu
5855 5860 5865

Arg Arg Asp Ala Thr Ser Leu Val Arg Tyr Cys His Asp His Arg
5870 5875 5880

Ile Asp Val Ile Asn Val Thr Pro Thr Tyr Ala Ala Leu Leu Phe
5885 5890 5895

Glu Glu Gly Leu Leu Glu Gln Ala Gly His Pro Pro Val Leu Val
5900 5905 5910

Leu Leu Gly Gly Glu Ala Val Ser Thr Thr Val Trp Asn Arg Leu
5915 5920 5925

Arg Asp Ser Glu Arg Trp Tyr Gly Tyr Asn Leu Tyr Gly Pro Thr
5930 5935 5940

Glu Tyr Thr Ile Asn Thr Leu Gly Gly Gly Thr Asp Asp Ser Ala
5945 5950 5955

Thr Pro Thr Val Gly Thr Pro Ile Trp Asn Thr Arg Ala His Ile
5960 5965 5970

Leu Asp Asn Trp Leu Arg Pro Val Pro Asp Gly Val Pro Gly Glu
5975 5980 5985

Leu Tyr Ile Ala Gly Ala Gly Leu Ala Arg Gly Tyr Leu Gly Gln
5990 5995 6000

Pro Gly Leu Thr Ala Ser Arg Phe Val Ala Asn Pro Phe Glu Pro
6005 6010 6015

Gly Arg Met Tyr Arg Thr Gly Asp Leu Val Val Arg Arg Ala Asp
6020 6025 6030

Asp Asn Ile Asp Phe Leu Gly Arg Thr Asp Asp Gln Val Lys Ile
6035 6040 6045

Arg Gly Tyr Arg Val Glu Leu Gly Asp Ile Glu Ala Ala Leu Val
6050 6055 6060

Ser His Pro Gly Val Ser Gln Ala Ala Val Ile Ala Arg Pro Asp
6065 6070 6075

Thr Ala Gly Ser Ser Arg Leu Val Ala Tyr Val Val Pro Thr Thr
6080 6085 6090

Glu Asn Pro Asp Val Leu Asp Asp Leu Arg Met His Leu Thr Ala
6095 6100 6105

Thr Leu Pro Ala Tyr Met Val Pro Thr Ala Met Ala Thr Leu Thr
6110 6115 6120

```
Glu Ile  Pro Leu Thr Asp Asn  Gly Lys Leu Asp Thr  Arg Ala Leu
    6125                 6130                 6135

Pro Asp  Val Ala Pro Ile Gly  Arg His Gly Ala Gly  Arg Ala Pro
    6140                 6145                 6150

Gln Gly  Ala Val Glu Ala Thr  Leu Cys Ser Val Phe  Ala Glu Val
    6155                 6160                 6165

Leu Gly  Leu Asp Gly Pro Asp  Gly Leu Ser Val Asp  Asp Asp Phe
    6170                 6175                 6180

Phe Asp  Leu Gly Gly His Ser  Leu Leu Thr Ile Arg  Leu Ile Ser
    6185                 6190                 6195

Arg Ile  Arg Ser Glu Leu Gly  Ala Glu Leu Thr Leu  Gly Asp Val
    6200                 6205                 6210

Phe Asn  Ser Arg Thr Val Ala  Ala Leu Ala Arg His  Val Thr Ala
    6215                 6220                 6225

Asp Glu  Gly Asp Asn Arg Arg  Pro Arg Leu Val Ala  Gly Pro Arg
    6230                 6235                 6240

Pro Gln  His Ile Pro Ala Ser  Pro Ala Gln Arg Arg  Met Leu Met
    6245                 6250                 6255

Leu Asp  Arg Leu Gly Glu Thr  Gly Ser Ala Tyr Asn  Tyr Pro Leu
    6260                 6265                 6270

Val Phe  Arg Val Arg Gly Ala  Leu Asp Val Asp Ala  Leu Arg Asp
    6275                 6280                 6285

Ala Leu  Thr Ala Val Val Asp  Arg His Glu Ala Leu  Arg Thr Val
    6290                 6295                 6300

Phe Asp  Asp Arg Asp Gly Val  Tyr His Gln Arg Ile  Leu Pro Arg
    6305                 6310                 6315

Gly Thr  Gln Pro Pro Leu His  Val Ser Asp Cys Pro  Glu His Glu
    6320                 6325                 6330

Leu Ala  Thr Arg Ala Asp Ala  Leu Val Glu His Arg  Phe Asp Leu
    6335                 6340                 6345

Thr Gly  Glu Ile Pro Leu Arg  Val Asp Val Leu Arg  Ser Gly Pro
    6350                 6355                 6360

Glu Asp  His Thr Val Val Met  Leu Leu His His Ile  Ala Ile Asp
    6365                 6370                 6375

Glu Trp  Ser Asp Ala Val Phe  Leu Ala Asp Leu Asp  Ala Ala Tyr
    6380                 6385                 6390

Ala Ala  His Arg Ala Gly Thr  Ala Ala Pro Leu Pro  Glu Pro Val
    6395                 6400                 6405

Val Gln  Tyr Ala Asp His Thr  Leu Trp Gln Arg Asp  Val Leu Ala
    6410                 6415                 6420

Gln Leu  Gly Asp Arg Gln Arg  Glu Phe Trp Arg Thr  Ala Leu Ala
    6425                 6430                 6435

Gly Ala  Pro Asp Glu Leu Ala  Leu Pro Ala Asp Arg  Pro Arg Pro
    6440                 6445                 6450

Ala Arg  Pro Thr Gly Ala Gly  Gly Thr Leu Asp Val  Glu Ile Thr
    6455                 6460                 6465

Ala Glu  Thr Ala Ser Ala Leu  Arg Arg Leu Ala Ala  Asp Lys Gln
    6470                 6475                 6480

Val Ser  Met Leu Met Val Leu  His Ala Ala Val Ala  Val Leu Ile
    6485                 6490                 6495

His Arg  Leu Gly Ala Gly Asp  Asp Ile Val Val Gly  Thr Pro Val
    6500                 6505                 6510

Ala Gly  Arg Asp Asp Ala Ala  Leu Asp Asp Val Val  Gly Leu Phe
```

6515 6520 6525

Val Asn Thr Val Val Leu Arg Ala Asp Leu Ala Gly Asn Pro Thr
6530 6535 6540

Phe Thr Glu Leu Leu Asp Arg Val Arg Thr Ala Asp Leu Ala Ala
6545 6550 6555

Phe Ala His Gln Asp Leu Pro Phe Asp His Leu Val Glu Glu Leu
6560 6565 6570

Asn Pro Pro Arg Val Ala Gly Arg Asn Pro Leu Phe Asn Leu Phe
6575 6580 6585

Val Gly Tyr His Leu Arg Ser Gly Thr Asp Ser Asp Met Phe Gly
6590 6595 6600

Leu Pro Thr Glu Trp Thr Glu Pro Ala Val Ser Ala Ala Met Phe
6605 6610 6615

Asp Leu Gly Phe Thr Leu Val Asp His Gly Gly Asp Glu Ser Ala
6620 6625 6630

Ser Ile Thr Ala Glu Tyr Ala Ala Asp Leu Phe Asp Ala Ser Thr
6635 6640 6645

Val His Thr Leu Ala Arg Arg Leu Val Ala Leu Leu Asp His Val
6650 6655 6660

Val Ala Asp Ala Glu Thr Arg Ile Gly Ala Leu Asp Leu Leu Ala
6665 6670 6675

Pro Gly Glu His Asp Thr Leu Val Val Glu His Asn Ala Thr Glu
6680 6685 6690

His Pro Leu Glu Pro Ile Thr Leu Gly Ala Leu Val Ser Arg Gln
6695 6700 6705

Ala Thr Ser Thr Pro His Ala Thr Ala Leu Arg Tyr Glu Glu Ser
6710 6715 6720

Glu Leu Ser Tyr Arg Asp Leu Asp Gly Trp Ser Asp Arg Leu Ala
6725 6730 6735

Ala His Leu Ser Ala Arg Gly Ala Ala Pro Gly Thr Val Val Gly
6740 6745 6750

Val Ser Leu Pro Arg Ser Val Glu Leu Val Val Ala Leu Val Ala
6755 6760 6765

Val Ala Lys Ser Gly Ala Ala Phe Leu Pro Leu Asp Pro Glu Tyr
6770 6775 6780

Pro Arg Glu Arg Leu Glu Tyr Met Val Ser Asp Ala Arg Pro Ile
6785 6790 6795

Thr Val Leu Asp Asp Pro Asp Ala Val Arg Arg Ser Arg Gly Glu
6800 6805 6810

Pro Asp Gly Glu Leu Pro Arg Ile Asp Pro Ala Ala Trp Ala Tyr
6815 6820 6825

Val Leu Tyr Thr Ser Gly Ser Thr Gly Arg Pro Lys Gly Val Ala
6830 6835 6840

Val Ala His Ala Gly Ile Val Asn Arg Ile Ala Cys Leu Gln His
6845 6850 6855

Ala Tyr Pro Leu Gly Thr Asp Asp Arg Met Leu Val Lys Thr Pro
6860 6865 6870

Ile Ser Phe Asp Thr Ser Val Trp Glu Val Phe Trp Pro Leu Ser
6875 6880 6885

Val Gly Ala Thr Leu Val Val Ala Arg Pro Gly Gly His Arg Glu
6890 6895 6900

Pro Ala Tyr Leu Ala Ala Met Ile Ala Glu Gln Cys Val Thr Ala
6905 6910 6915

-continued

```
Val Asp Phe Val Pro Ser Met Leu Glu Val Phe Leu Asp Glu Val
    6920                6925                6930

Ala Gly Thr Cys Ala Ser Leu Thr Arg Val Thr Val Gly Gly Glu
    6935                6940                6945

Ala Leu Thr Thr Glu Leu Ala Ala Arg Phe Ala Glu Ala Phe Pro
    6950                6955                6960

Gly Val Pro Leu His Asn Leu Tyr Gly Pro Thr Glu Ala Ala Val
    6965                6970                6975

Asp Val Leu Gly Trp Thr Ala Asp Gly Gly Pro Val Ala Leu Gly
    6980                6985                6990

Val Pro Gly Trp Asn Val Arg Ala Tyr Val Leu Asp Asp Tyr Leu
    6995                7000                7005

Asn Pro Val Pro Ala Gly Ala Pro Gly Glu Leu Tyr Leu Ala Gly
    7010                7015                7020

Ile Gln Leu Ala Asp Gly Tyr Leu His Arg Gly Ala Leu Thr Ala
    7025                7030                7035

Ala Arg Phe Val Ala Ser Pro Phe Asp Gln Gly Ala Arg Met Tyr
    7040                7045                7050

Arg Thr Gly Asp Val Val Arg Trp Arg Ala Asp Gly Gln Leu Glu
    7055                7060                7065

Tyr Leu Gly Arg Ser Asp Asp Gln Ile Lys Leu Arg Gly Val Arg
    7070                7075                7080

Ile Glu Pro Gly Glu Ile Glu Thr Val Leu Ala Thr His Pro Ala
    7085                7090                7095

Val Ser Ser Val Arg Val Ile Ala Arg Gly Gly Arg Leu Met Ala
    7100                7105                7110

Tyr Tyr Val Pro Ala Gly Val Glu Ala Ser Ala Gly Glu Leu Arg
    7115                7120                7125

Asp Glu Leu Arg Glu His Ala Ala Ala Ala Leu Pro Ser His Met
    7130                7135                7140

Val Pro Ser Gly Phe Val Ala Leu Thr Glu Phe Pro Leu Thr Pro
    7145                7150                7155

Ser Gly Lys Leu Asp Arg Arg Ala Leu Pro Glu Phe Ala Gly Ala
    7160                7165                7170

Thr Ala Gly Val Pro Gly Arg Ala Pro Thr Thr Glu Arg Gln His
    7175                7180                7185

Arg Leu Cys Glu Leu Phe Ser Asp Val Leu Gly Leu Glu Val Thr
    7190                7195                7200

Gly Ile Asp Asp Asp Phe Phe Val Leu Gly Gly His Ser Leu Leu
    7205                7210                7215

Leu Val Arg Leu Ala Ala Ala Leu Arg Arg Glu Phe Ser Val Asp
    7220                7225                7230

Val Pro Val Ala Asp Leu Met Val Ser Pro Thr Val Ala Asp Ile
    7235                7240                7245

Asp Gln Arg Leu Asp Ala Ala Gly Ser Ser Val Asp Ser Leu Ala
    7250                7255                7260

Pro Val Leu Pro Phe Arg Ala Ser Gly Thr Asp Ala Pro Leu Phe
    7265                7270                7275

Cys Val His Pro Ala Ser Gly Leu Ser Trp Gln Phe Ala Gly Leu
    7280                7285                7290

Lys Arg His Leu Pro Arg Gln Ile Pro Ile Tyr Gly Leu Gln Ser
    7295                7300                7305
```

-continued

Pro Leu Phe Thr Gly Thr Pro Leu Pro Glu Ser Ile Ala Glu Leu
    7310                7315                7320

Thr Ala Arg Tyr Ala Asp Thr Ile Val Ala Val Ala Pro Ser Gly
    7325                7330                7335

Pro Val Arg Leu Leu Gly Trp Ser Phe Gly Gly Ser Met Ala Leu
    7340                7345                7350

Leu Ile Ala Gln Glu Leu Ser Arg Arg Gly Arg Glu Val Thr Phe
    7355                7360                7365

Val Gly Met Leu Asp Ala Arg Thr Asp Thr Ala Asp Pro Asn Ala
    7370                7375                7380

Gly Phe Asp Pro Glu Ala Val Leu Ala Gly Leu Leu Arg Glu Met
    7385                7390                7395

Gly Phe Gly Val Asp Pro Gln Ala Arg Met Thr Val Ala Asp Ala
    7400                7405                7410

Val Ala Leu Val Arg Asp Thr Asp Asp Ala Ile Thr Val Leu Asp
    7415                7420                7425

Asp Glu Gln Ile Ala Leu Val Ile Glu Asn Tyr Val Ala Ala Glu
    7430                7435                7440

Arg Leu Thr Ala Asp Ala Asp Tyr Gly Arg Tyr Asp Gly Asp Val
    7445                7450                7455

Phe Phe Val Asp Ala Thr Ile Leu Glu Met Asp Leu Ala Gly Val
    7460                7465                7470

Ala Ser Arg Gly Trp His Asp His Val Gly Gly Arg Leu Lys Val
    7475                7480                7485

Ala Glu Leu Asp Cys Arg His Ser Glu Leu Met Asp Ala Glu Val
    7490                7495                7500

Leu Glu Arg Leu Gly Pro Leu Ile Ala Ala Glu Leu Arg Gly Gly
    7505                7510                7515

Asp Val Ala Ser Gly
    7520

<210> SEQ ID NO 6
<211> LENGTH: 558
<212> TYPE: PRT
<213> ORGANISM: Artificial Sequence
<220> FEATURE:
<223> OTHER INFORMATION: Synthetic polypeptide

<400> SEQUENCE: 6

Met Thr Leu Thr Thr Pro His Pro Arg Pro Glu Gln Ser Glu Ser Ala
1               5                   10                  15

Ala Gln Ser Ser Leu Leu Ala Gly Phe Thr Pro Phe Pro Ala Glu Arg
            20                  25                  30

Ala Gln Ala Tyr Arg Ala Ala Gly Tyr Trp Arg Asp Gln Leu Leu Asp
        35                  40                  45

Ser Val Leu Arg Thr Ala Ala Arg Thr Trp Pro Asp His Ile Ala Val
    50                  55                  60

Ile Asp Ala Asp His Arg His Thr Tyr Ala Glu Leu Asp Arg Leu Ala
65                  70                  75                  80

Asp Arg Ala Ala Ala Gly Ile Ala Gly Leu Gly Ile Arg Pro Gly Asp
                85                  90                  95

Arg Val Leu Val Gln Leu Pro Asn Thr Ala Glu Phe Ala Val Ala Leu
            100                 105                 110

Phe Gly Leu Leu Arg Ala Gly Ala Val Pro Val Met Cys Leu Pro Gly
        115                 120                 125

-continued

```
His Arg Leu Ala Glu Leu Thr His Phe Ala Glu Val Ser Ser Ala Val
    130                 135                 140

Ala Leu Val Val Ala Asp Thr Ala Gly Gly Phe Asp His Arg Asp Leu
145                 150                 155                 160

Ala Arg Glu Leu Val Arg Ser His Pro Asp Val Arg His Val Leu Val
                165                 170                 175

Asp Gly Asp Ala Ala Glu Phe Leu Ser Trp Ala Glu Val Thr Arg Ala
            180                 185                 190

Ala Pro Gly Pro Val Pro Glu Ile Ala Pro Asp Pro Ala Ala Pro Ala
        195                 200                 205

Leu Leu Leu Val Ser Gly Gly Thr Thr Gly Ala Pro Lys Leu Ile Pro
    210                 215                 220

Arg Thr His Gln Asp Tyr Val Tyr Asn Ala Thr Ala Ser Ala Glu Leu
225                 230                 235                 240

Cys Arg Leu Thr Ala Asp Asp Val Tyr Leu Val Ala Leu Pro Ala Ala
                245                 250                 255

His Asn Phe Pro Leu Ala Cys Pro Gly Leu Leu Gly Ala Met Thr Val
            260                 265                 270

Gly Ala Thr Thr Val Phe Thr Thr Asp Pro Ser Pro Glu Ala Ala Phe
        275                 280                 285

Ala Ala Ile Asp Glu His Gly Val Thr Ala Thr Ala Leu Val Pro Ala
    290                 295                 300

Leu Ala Lys Leu Trp Ala Gln Ala Cys Ala Trp Glu Pro Leu Ala Pro
305                 310                 315                 320

Lys Thr Leu Arg Leu Leu Gln Val Gly Gly Ala Lys Leu Ala Ala Pro
                325                 330                 335

Asp Ala Ala Leu Val Arg Gly Ala Leu Thr Pro Gly Leu Gln Gln Val
            340                 345                 350

Phe Gly Met Ala Glu Gly Leu Leu Asn Tyr Thr Arg Ile Gly Asp Pro
        355                 360                 365

Pro Glu Val Leu Glu Asn Thr Gln Gly Arg Pro Leu Ser Pro Asp Asp
    370                 375                 380

Glu Ile Arg Ile Val Asp Glu Val Gly Asn Glu Val Pro Pro Gly Ala
385                 390                 395                 400

Glu Gly Glu Leu Leu Val Arg Gly Pro Tyr Thr Leu Asn Gly Tyr Phe
                405                 410                 415

Asn Ala Glu Ala Ala Asn Glu Arg Ser Phe Ser Pro Asp Gly Phe Tyr
            420                 425                 430

Arg Ser Gly Asp Arg Val Arg Arg Phe Ala Asp Gly Pro Leu Ala Gly
        435                 440                 445

Tyr Leu Glu Val Thr Gly Arg Ile Lys Asp Val Ile Val Arg Gly Gly
    450                 455                 460

Glu Asn Val Ser Ala Leu Asp Leu Glu Glu His Leu Leu Thr His Pro
465                 470                 475                 480

Ser Val Trp Ala Ala Ala Ala Val Ala Leu Pro Asp Glu Phe Leu Gly
                485                 490                 495

Glu Lys Ile Cys Ala Val Val Val Phe Asn Gly Pro Pro Val Ser Leu
            500                 505                 510

Ala Glu Leu His Ala His Leu Glu Gln Arg Gly Val Ala Ala His Ser
        515                 520                 525

Arg Pro Asp Ala Leu Val Pro Met Pro Ser Leu Pro Thr Thr Ala Val
    530                 535                 540

Gly Lys Ile Asp Lys Lys Ala Ile Val Arg Gln Leu Gly Gly
```

545 550 555

<210> SEQ ID NO 7
<211> LENGTH: 1698
<212> TYPE: DNA
<213> ORGANISM: Artificial Sequence
<220> FEATURE:
<223> OTHER INFORMATION: Synthetic polynucleotide

<400> SEQUENCE: 7
atgccaccga aggcggcaga tggccgccga cccagtcccg acggcggact gggtggcttt 60
gtaccgttcc ccgcggatcg ggccgcgtcg taccgggcgg ccggctattg gtcggggcga 120
accctggaca ccgtgctctc cgatgccgcg cggcgctggc ctgaccgcct cgcggtggcc 180
gacgccggtg atcgtcccgg ccacggcggc ctcagttacg ccgaactcga ccagcgggcc 240
gaccgggccg ccgcggcgct gcacggcctg ggcatcacgc caggcgaccg ggtactgctc 300
cagctgccaa acggctgcca gttcgcggtt gccctgttcg cgttattgcg ggcgggagcg 360
atcccagtga tgtgcctgcc cggtcaccgc gccgccgaat tgggccactt cgccgccgtc 420
agcgcggcca ccgggctggt ggtcgccgat gtggccagcg ggttcgacta tcggccgatg 480
gcgcgcgaac ttgttgccga tcaccccacc ctgcgccatg tcatcgtcga tggcgatccg 540
ggaccgttcg tgtcgtgggc gcagctgtgc gcccaggccg gcaccggttc gccggcaccg 600
ccggccgatc ccggatcgcc agcgctgctg ctggtctccg gcggcaccac tggcatgccc 660
aaactcattc cacgcaccca cgacgactac gtgttcaacg cgacggccag cgccgcactc 720
tgtcggctta gcgccgacga cgtctatctg gtggtgctgg ccgccggcca caatttcccg 780
ctggcctgcc cgggcctgct cggcgcgatg accgtcgggg ccaccgccgt gttcgccccc 840
gatcccagcc cggaggccgc cttcgccgcc atcgagcgcc acggtgtcac cgtcaccgcg 900
ttggttccgg cactggccaa actgtgggcc caatcctgtg agtgggagcc ggtgacaccg 960
aagtcactgc ggttgttgca ggttggcggg tccaagctag aacccgagga cgctcgccgg 1020
gtacgcaccg cgctcacccc gggcctgcag caggtgttcg gcatggcgga ggggctgctg 1080
aacttcaccc gcatcggcga cccacccgaa gtggtggagc acacccaggg gcggccacta 1140
tgcccggccg acgaactgcg catcgtcaac gccgatggtg agccggtggg gcccggggag 1200
gaaggcgaac tcttggtgcg cgggccctac acgctgaacg gctattttgc tgccgaacgc 1260
gacaacgagc gctgcttcga tccggacggc ttctaccgca gcggcgacct ggtccgccgc 1320
cgcgacgacg gcaatctggt ggtcaccggg cgcgtcaagg atgtcatctg ccgtgcggga 1380
gaaaccatcg ccgccagcga cctcgaagaa cagctgctga gccatccggc gatcttctcg 1440
gccgcggcgg tgggactacc tgaccagtat ctgggggaaa aaatctgcgc tgcagtcgtt 1500
ttcgctggag ctccgattac gcttgcggag ttgaacggct accttgaccg gcgtggtgtg 1560
gccgcgcata cgcgacccga ccagctggtc gcgatgccgg cgctgcccac aacgccgatc 1620
gggaagatcg acaaacgagc gatcgtccgc cagctcggca tcgcgacggg tcccgtgacg 1680
acccagcgct gccattga 1698

<210> SEQ ID NO 8
<211> LENGTH: 1778
<212> TYPE: DNA
<213> ORGANISM: Artificial Sequence
<220> FEATURE:
<223> OTHER INFORMATION: Synthetic polynucleotide

<400> SEQUENCE: 8

-continued

```
atgccgccga aagcggcgga tggtcgtcgt ccgagcccgg atggtggtct gggtggtttt     60

gtgccgttcc cggcggatcg tgcggcgagc taccgtgcgg cgggttattg gagcggccgt    120

accctggaca ccgtgctgag cgatgcggcg cgtcgttggc cggatcgtct ggcggttgcg    180

gatgcgggtg atcgtccggg ccacggtggc ctgagctacg cggaactgga ccagcgtgcg    240

gatcgtgctg cggcggcgct gcacggtctg ggtatcaccc cgggcgatcg tgtgctgctg    300

cagctgccga acggttgcca attcgcggtt gcgctgtttg cgctgctgcg tgcgggtgcg    360

attccggtga tgtgcctgcc gggtcatcgt gcggcggaac tgggtcactt tgcggcggtg    420

agcgcggcga ccggcctggt ggttgcggat gttgcgagcg gttttgatta tcgtccgatg    480

gcgcgtgagc tggttgcgga ccacccgacc ctgcgtcacg tgatcgttga cggtgatccg    540

ggtccgtttg ttagctgggc gcagctgtgc gcgcaagcgg gcaccggcag cccggctccg    600

ccggcggacc cgggcagccc ggcgctgctg ctggttagcg gcagctgtgc gcgcaagcgg    660

gcaccggcag cccggctccg ccggcggacc cgggcagccc ggcgctgctg ctggttagcg    720

gtggcaccac cggtatgccg aagctgattc cgcgtaccca cgacgattat gtgtttaacg    780

cgaccgcgag cgcggcgctg tgccgtctga gcgcggacga tgtttatctg gtggttctgg    840

cggcgggtca caactttccg ctggcgtgcc cgggtctgct gggtgcgatg accgtgggtg    900

cgaccgcggt ttttgcgccg gacccgagcc cggaggcggc gtttgcggcg attgaacgtc    960

acggtgttac cgttaccgcg ctggtgccgg cgctggcgaa actgtgggcg cagagctgcg   1020

agtgggaacc ggtgaccccg aagagcctgc gtctgctgca agttggtggc agcaaactgg   1080

agccggaaga tgcgcgtcgt gtgcgtaccg cgctgacccc gggcctgcag caagttttcg   1140

gtatggcgga aggcctgctg aactttaccc gtatcggtga cccgccggaa gtggttgaac   1200

acacccaagg tcgtccgctg tgcccggcgg acgagctgcg tattgtgaac gcggatggtg   1260

aaccggttgg tccgggcgag gaaggtgaac tgctggtgcg tggcccgtac accctgaacg   1320

gttatttcgc ggcggagcgt gacaacgaac gttgcttcga cccggatggt tttaccgta    1380

gcggcgatct ggttcgtcgt cgtgacgatg gcaacctggt ggttaccggt cgtgtgaagg   1440

acgttatctg ccgtgcgggt gaaaccattg cggggagcga tctggaggaa cagctgctga   1500

gccatccggc gattttcagc gctgcggcgg ttggcctgcc ggaccaatac ctgggtgaaa   1560

aaatctgcgc ggcggtggtt tttgcgggtg cgccgattac cctggcggag ctgaacggct   1620

atctggaccg tcgtggtgtg gcggcgcaca cccgtccgga tcaactggtt gcgatgccgg   1680

cgctgccgac cacccccgatc ggcaagattg ataaacgtgc gattgttcgt caactgggta   1740

ttgcgaccgg cccggttacc acccaacgct gccactaa                             1778
```

<210> SEQ ID NO 9
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 9

```
actttggtcg tcggattcct gctggtgcg                                   29
```

<210> SEQ ID NO 10
<211> LENGTH: 39
<212> TYPE: DNA
<213> ORGANISM: Artificial Sequence
<220> FEATURE:

<223> OTHER INFORMATION: Synthetic polynucleotide

<400> SEQUENCE: 10
ctatccagaa gccacatccg cggtcacgtg cgagcgtcc 39

<210> SEQ ID NO 11
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 11
acattggctt cgcgccatgg caccgatttt 30

<210> SEQ ID NO 12
<211> LENGTH: 39
<212> TYPE: DNA
<213> ORGANISM: Artificial Sequence
<220> FEATURE:
<223> OTHER INFORMATION: Synthetic polynucleotide

<400> SEQUENCE: 12
cacgtgaccg cggatgtggc ttctggatag tggccggaa 39

<210> SEQ ID NO 13
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 13
atcttctgaa cacgctcaag gc 22

<210> SEQ ID NO 14
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 14
aggtagttga acagcagttg cg 22

<210> SEQ ID NO 15
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 15
tagttaacga ggaaacccac atgccaccga 30

<210> SEQ ID NO 16
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 16
tagctagctc aatggcagcg ctgggtcgtc a 31

-continued

<210> SEQ ID NO 17
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 17
taccatgggc atgccgccga aagcggcgga t 31

<210> SEQ ID NO 18
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 18
taccatgggc agcagccatc atcatcatca tcacagc 37

<210> SEQ ID NO 19
<211> LENGTH: 50
<212> TYPE: DNA
<213> ORGANISM: Artificial Sequence
<220> FEATURE:
<223> OTHER INFORMATION: Synthetic polynucleotide

<400> SEQUENCE: 19
taccatgggc agcagccatc atcatcatca tcatcatcac agcagcggcc 50

<210> SEQ ID NO 20
<211> LENGTH: 56
<212> TYPE: DNA
<213> ORGANISM: Artificial Sequence
<220> FEATURE:
<223> OTHER INFORMATION: Synthetic polynucleotide

<400> SEQUENCE: 20
taccatgggc agcagccatc atcatcatca tcatcatcat catcacagca gcggcc 56

<210> SEQ ID NO 21
<211> LENGTH: 95
<212> TYPE: DNA
<213> ORGANISM: Artificial Sequence
<220> FEATURE:
<223> OTHER INFORMATION: Synthetic polynucleotide

<400> SEQUENCE: 21
taccatgggc agcagccatc atcatcatca tcacagccgt gcgtggcgtc atccgcagtt 60
tggcggtcat catcatcatc atcacagcag cggcc 95

<210> SEQ ID NO 22
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 22
ccggatcctt agtggcagcg ttg 23

<210> SEQ ID NO 23
<211> LENGTH: 62
<212> TYPE: DNA
<213> ORGANISM: Artificial Sequence
<220> FEATURE:

-continued

<223> OTHER INFORMATION: Synthetic polynucleotide

<400> SEQUENCE: 23
ccggatcctt agtggtggtg gtggtggtgc aggccgctgc tgtggcagcg ttgggtggta 60
ac 62

<210> SEQ ID NO 24
<211> LENGTH: 68
<212> TYPE: DNA
<213> ORGANISM: Artificial Sequence
<220> FEATURE:
<223> OTHER INFORMATION: Synthetic polynucleotide

<400> SEQUENCE: 24
ccggatcctt agtggtggtg gtggtggtgg tggtgcaggc cgctgctgtg gcagcgttgg 60
gtggtaac 68

<210> SEQ ID NO 25
<211> LENGTH: 74
<212> TYPE: DNA
<213> ORGANISM: Artificial Sequence
<220> FEATURE:
<223> OTHER INFORMATION: Synthetic polynucleotide

<400> SEQUENCE: 25
ccggatcctt agtggtggtg gtggtggtgg tggtggtggt gcaggccgct gctgtggcag 60
cgttgggtgg taac 74

SALICYL-ADENOSINEMONOSULFAMATE ANALOGS AND USES THEREOF

RELATED APPLICATIONS

This application is a national stage filing under 35 U.S.C. § 371 of international PCT application, PCT/US2019/08107, filed Dec. 20, 2019, which claims priority under 35 U.S.C. § 119(e) to U.S. provisional application, U.S. Ser. No. 62/784,323, filed Dec. 21, 2018, the contents of both of which are is incorporated herein by reference in their entireties.

GOVERNMENT SUPPORT

This invention was made with government support under AI118224 and CA008748 awarded by the National Institutes of Health. The government has certain rights in the invention.

BACKGROUND OF THE INVENTION

*Mycobacterium tuberculosis* (Mtb), the causative agent of tuberculosis, is a resilient, obligate bacterial pathogen with a devastating impact on global public health (Global tuberculosis report 2017. Geneva: World Health Organization (2017). License: CC BY-NCSA 3.0 IGO). The intrinsic clinical resistance of Mtb to many antimicrobial drugs is one of the challenges at the center of the problematic chemotherapy and global control of tuberculosis (Barry, C. E., et al. (1996) *Trends Microbiol.* 4, 275-281). Standard tuberculosis treatment requires prolonged chemotherapy with multiple drugs and is associated with adverse side effects and compliance challenges (Nahid, P., et al. (2016) *Clin. Infect. Dis.* 63, e147-e195; Alipanah, N., et al. (2018) *PLoS Med.* 15, e1002595). The cumbersome chemotherapy regimens against tuberculosis result in high frequency of suboptimal or incomplete drug treatment courses (Alipanah. N., et al. (2018) *PLoS Med* 15, e1002595; Awofeso, N. Bull World Health Organ. 2008 March; 86 (3):B-D), a situation that over the decades has led to the rise of tuberculosis cases produced by multidrug-resistant (MDR) and extensively drug-resistant (XDR) strains of Mtb (Global tuberculosis report 2017. Geneva: World Health Organization (2017). License: CC BY-NCSA 3.0 IGO). The rise of these strains compounds the already challenging problem of tuberculosis chemotherapy and presents a growing threat to global tuberculosis control and eradication efforts. This grim scenario underscores the need for expanding the antituberculosis drug armamentarium.

Towards this end, the first-in-class nucleoside antibiotic salicyl-AMS (5'-O—[N-salicylsulfamoyl]adenosine) (1, FIG. 1A) was developed (Ferreras, J. A., et al. (2005) *Nat. Chem. Biol.* 1, 29-32). Salicyl-AMS 1 was designed as a salicyl-AMP intermediate mimetic inhibitor of the bifunctional enzyme salicyl-AMP ligase ($MbtA_{tb}$, encoded by the gene Rv2384, FIG. 1B) (Quadri, L. E., et al. (1998) *Chem. Biol.* 5, 631-645). MbtA has no human homologues and is required for the biosynthesis of salicylic acid-derived mycobactin (MBT) siderophores, which are high-affinity $Fe^{3+}$ chelators involved in scavenging and the uptake of iron (Fe) (Quadri, L. E., et al. (2011) *J. Bacteriol.* 193, 5905-5913; Chavadi, S. S., et al. (2011) *J. Bacteriol.* 193, 5905-5913), a micronutrient essential for Mtb growth and pathogenesis (FIG. 1C) (Quadri, L. E. N., et al. (2005) *Tuberculosis and the Tubercle Bacillus*, pp 341-357, ASM Press, Washington, DC; Ratledge, C. (2004) *Tuberculosis* (*Edinb*) 84, 110-130; De Voss, J. J., et al. (1999) *J. Bacteriol.* 181, 4443-4451). The realization of the critical role of the MBT siderophore system in Mtb biology emerges from multiple studies demonstrating that Mtb mutant strains with gene knockouts in the siderophore biosynthesis and/or transport systems have impaired survival in macrophages (De Voss, J. J., et al. (2000) *Proc. Natl. Acad. Sci.* 97, 1252-1257; Rodriguez, G. M., et al. (2006) *J. Bacteriol* 188, 424-430; Reddy, P. V., et al. (2013)*J. Infect. Dis.* 208, 1255-1265) and various degrees of attenuation in guinea pig (Reddy, P. V., et al. (2013) *J. Infect. Dis.* 208, 1255-1265) and mouse (Rodriguez. G. M., et al. (2006) *J. Bacteriol.* 188, 424-430; Madigan, C. A., et al. (2015) *PLoS Pathog.* 11, e1004792; Wells, R. M., et al. (2013) *PLoS Pathog.* 9, e1003120; Tufariello, J. M., et al. (2016) *Proc. Natl. Acad. Sci.* 113, E348-357) models of tuberculosis. Thus, MBT biosynthesis is considered an attractive target for developing antituberculosis drugs with novel mechanisms of action (Quadri, L. E. (2007) *Infect. Disord Drug Targets* 7, 230-237; Meneghetti, F., et al. (2016) *Curr. Med. Chem.* 23, 4009-4026; Monfeli, R. R., et al. (2007) *Infect. Disord. Drug Targets* 7, 213-220).

Previous in vitro studies on salicyl-AMS (1) demonstrated that it is a potent, selective, tight-binding inhibitor (TBI) of $MbtA_{tb}$ as well as other salicylate adenylation enzymes from pathogenic bacteria (Ferreras, J. A., et al. (2 (05) *Nat. Chem. Biol.* 1, 29-32), including YbtE from *Yersinia pestis* (Gehring, A. M., et al. (1998) *Biochemistry* 37, 11637-11650) and PchD from *Pseudomonas aeruginosa* (Quadri, L. E., et al. (1999) *Biochemistry* 38, 14941-14954). Moreover, it has been shown that salicyl-AMS (1) inhibits the biosynthesis of MBTs in Mtb and, as expected, restricts the growth of the pathogen with much greater potency under Fe-limiting conditions (Ferreras, J. A., et al. (2005) *Nat. Chem. Biol.* 1, 29-32), in which the production of MBTs is crucial for Fe acquisition. In all, this early work provided proof of principle for the druggability of salicylate adenylation enzymes, validated pharmacological inhibition of siderophore biosynthesis as a new mechanism of antibiotic action, and established salicyl-AMS (1) as a first-in-class antibacterial lead compound for the development of antituberculosis drugs targeting siderophore biosynthesis. Subsequent studies by Aldrich and coworkers confirmed the inhibitory activity of salicyl-AMS (1) against $MbtA_{tb}$ and Mtb, demonstrated that the inhibitor is not cytotoxic against mammalian cells, and provided extensive in vitro structure-activity relationship (SAR) analysis for the inhibition of $MbtA_{tb}$ biochemical activity and Mtb growth using a wide range of salicyl-AMS analogues (Neres, J., et al. (2008) *J. Med Chem.* 51, 5349-5370; Somu, R. V., et al. (2006) *J. Med. Chem.* 49, 31-34; Somu, R. V., et al. (2006) *J. Med. Chem.* 49, 7623-7635; Vannada, J., et al. (2006) *Org. Lett.* 8, 4707-4710; Nelson, K. M., et al. (2015)*J. Med. Chem.* 58, 5459-5475; Duckworth, B. P., et al. (2012) *Curr. Top. Med. Chem.* 12, 766-796; Dawadi, S., et al. (2018) *ACS Med. Chem. Lett.* 9, 386-391; Engelhart, C. A., et al. (2013) *J Org Chem* 78, 7470-7481; Dawadi, S., et al. (2016) *Bioorg. Med. Chem. Lett.* 24, 1314-1321; Krajczyk, A., et al. (2016) *Bioorg. Med. Chem. Lett.* 24, 3133-3143).

More recently, studies were reported on the in vivo efficacy of salicyl-AMS (1) in a mouse model of tuberculosis (Lun, S., et al. (2013) *Antimicrob. Agents Chemother.* 57, 5138-5140). Importantly, this work showed that monotherapy with salicyl-AMS (1) at 5.6 or 16.7 mg/kg correlated with a significant reduction of Mtb growth in the mouse lung, thus supporting $MbtA_{tb}$ as a promising target for the development of novel antituberculosis drugs blocking siderophore biosynthesis. However, it was also observed in vivo toxicity at ≥16.7 mg/kg doses, precluding further dose escalation to improve efficacy. Thus, there is a continued need to develop new salicyl-AMS analogues with the goal of improving pharmacokinetic, efficacy, and toxicity profiles.

SUMMARY OF THE INVENTION

Reported herein is the development of new salicyl-AMS analogues containing an alkoxy group on the nucleobase. These compounds were previously believed to be inactive due to the lack of a C6-substituent hydrogen-bond donor which was thought to be required for interaction of the salicyl-AMS inhibitor with the enzyme target in the bacterial pathogen. Detailed herein is the use of C6-OR salicyl-AMS analogues as potent inhibitors of siderophore biosynthesis (e.g., inhibition of $MbtA_{tb}$ which is required for myobactin synthesis) demonstrating their propensity for use as antimicrobials such as antibacterials (e.g., for use against *Mycobacterium tuberculosis*), antifungals, antivirals, antiparasitics. Also provided herein are pharmaceutical compositions, methods of treatment and/or prevention, and kits.

In one aspect, the present disclosure provides compounds of Formula (I):

(I)

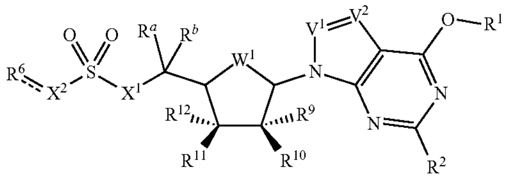

or a pharmaceutically acceptable salt or tautomer thereof, wherein $R^1$, $R^2$, $R^9$, $R^{10}$, $R^{11}$, $R^{12}$, $R^a$, $R^b$, $V^1$, $V^2$, $W^1$, $X^1$, $X^2$, and $R^6$ are as defined herein.

In another aspect, the present disclosure provides compounds of Formula (IA):

(IA)

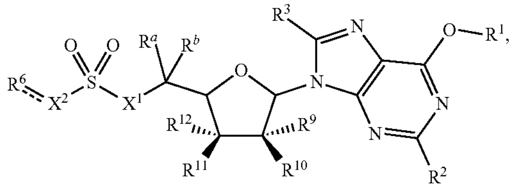

or a pharmaceutically acceptable salt or tautomer thereof, wherein $R^1$, $R^2$, $R^3$, $R^6$, $R^9$, $R^{10}$, $R^{11}$, $R^{12}$, $R^a$, $R^b$, $V^1$, $V^2$, $W^1$, $X^1$, $X^2$, and Z are as defined herein.

In another aspect, the present disclosure provides compounds of Formula (III):

(III)

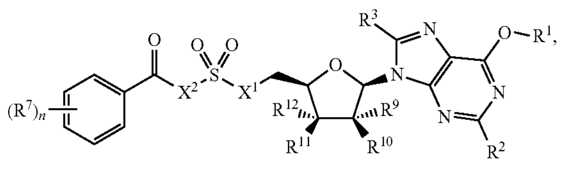

or a pharmaceutically acceptable salt, stereoisomer, or tautomer thereof, wherein $R^1$, $R^2$, $R^3$, $R^4$, $R^5$, $R^7$, $R^9$, $R^{10}$, $R^{11}$, $R^{12}$, $X^1$, $X^2$, and n are as defined herein.

In yet another aspect, the present disclosure provides compounds of Formula (IV-K):

(IV-K)

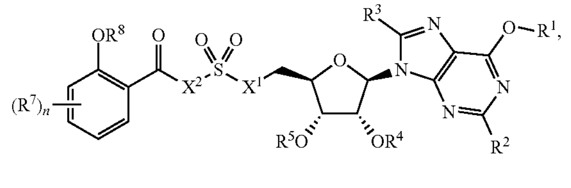

or a pharmaceutically acceptable salt, stereoisomer, or tautomer thereof, wherein $R^1$, $R^2$, $R^3$, $R^4$, $R^5$, $R^7$, $R^8$, $X^1$, $X^2$, and n is as defined herein.

As described herein, the present disclosure provides exemplary compounds including, but not limited to:

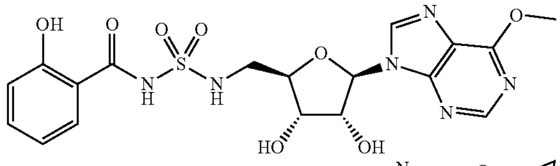

,

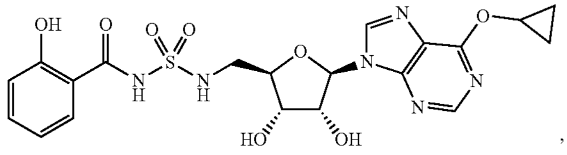

, and

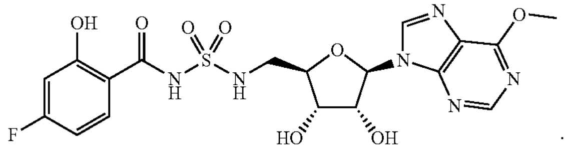

.

In another aspect, the present disclosure provides pharmaceutical compositions including a compound described herein, and optionally a pharmaceutically acceptable excipient. In certain embodiments, the pharmaceutical compositions described herein include an effective amount of a compound described herein. In certain embodiments, the pharmaceutical compositions described herein include an additional pharmaceutical agent. The pharmaceutical composition may be useful for treating and/or preventing an infectious disease. In some embodiments, the infectious disease is a bacterial infection (e.g., a gram positive bacterial infection, a gram negative bacterial infection. *Mycobacterium tuberculosis* infection). In some embodiments, the disease is a viral infection, a parasitic infection, or a fungal infection. The pharmaceutical compositions described herein may be useful for treating or preventing tuberculosis.

The present disclosure describes methods for administering to a subject in need thereof (e.g., a subject with an infection, a subject with tuberculosis) an effective amount of a compound, or a pharmaceutical composition thereof, as described herein. In certain embodiments, a method described herein further comprises administering to the subject an additional pharmaceutical agent (e.g., another antimicrobial agent).

In yet another aspect, the present disclosure provides compounds for use in the treatment or prevention of an infectious disease in a subject. In some embodiments, the present disclosure provides compounds for use in the treatment or prevention of a bacterial infection.

In another aspect, the present disclosure provides methods for treating and/or preventing a disease. Exemplary diseases which may be treated include bacterial infections (e.g., *Mycobacterium tuberculosis* infection), fungal infections, viral infections, and fungal infections. In certain embodiments, the bacterial infection may be caused by a gram positive bacteria or a gram negative bacteria. In some embodiments, the bacterial infection is tuberculosis.

Another aspect of the disclosure relates to methods of inhibiting siderophore biosynthesis or MBT biosynthesis (e.g., inhibiting $MbtA_{tb}$).

Another aspect of the disclosure relates to methods of inhibiting the biosynthesis of a virulence factor (e.g., pyocyanin).

In yet another aspect, the present disclosure provides compounds, and pharmaceutical compositions thereof, as described herein for use in any method of the disclosure.

Another aspect of the present disclosure relates to kits comprising a container with a compound, or pharmaceutical composition thereof, as described herein. The kits described herein may include a single dose or multiple doses of the compound or pharmaceutical composition. The kits may be useful in any method of the disclosure. In certain embodiments, the kit further includes instructions for using the compound or pharmaceutical composition. A kit described herein may also include information (e.g. prescribing information) as required by a regulatory agency such as the U.S. Food and Drug Administration (FDA).

In another aspect, the present disclosure provides a protein. In certain embodiments, the protein, $H_{10}MbtA^{opt}$ (SEQ ID NO: 4), may be generated via a codon-optimized nucleotide sequence of $MbtA_{tb}$ with a His10 tag. The protein may be used to identify $MbtA_{tb}$ inhibitors. The present disclosure further provides a strain of *Mycobacterium smegmatis*. In some embodiments, the strain may be used for identifying a $MbtA_{tb}$ inhibitor.

The details of certain embodiments of the invention are set forth in the Detailed Description of Certain Embodiments, as described below. Other features, objects, and advantages of the invention will be apparent from the Definitions, Examples. Figures, and Claims.

BRIEF DESCRIPTION OF THE DRAWINGS

The accompanying drawings, which constitute a part of this application, illustrate several embodiments of the invention and together with the description, serve to explain the principles of the invention.

DETAILED DESCRIPTION OF CERTAIN EMBODIMENTS

Figure 1A:
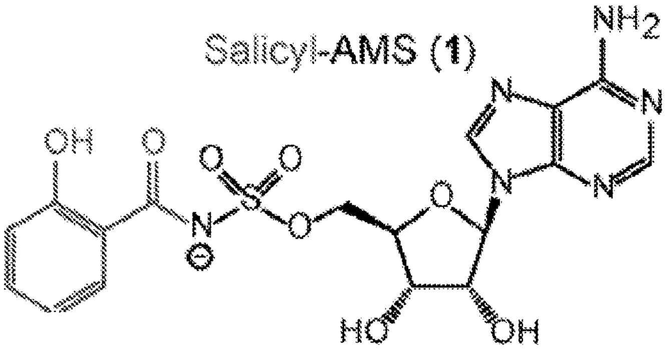
FIG. 1A shows the nucleoside antibiotic salicyl-AMS (compound 1).

Provided herein are compounds for the treatment and/or prevention of diseases including bacterial infections. The compounds may inhibit a particular enzyme (e.g., $MbtA_{tb}$) of an organism (e.g., *Mycobacterium tuberculosis*) responsible for a bacterial infection (e.g., *Mycobacterium tuberculosis* infection). Further, the compounds may treat or prevent a disease (e.g., tuberculosis) caused by a bacterial infection. The compounds may interact with an enzyme so as to inhibit the activity of the enzyme in performing key transformations in the synthesis of siderophores (e.g., salicylic acid to MBT (FIG. 1C)) or virulence factors. In some embodiments, a provided compound affects the ability of an enzyme to react with ATP, i.e., inhibits the first transformation (e.g., formation of salicyl-AMP (FIG. 1B)). In some embodiments, a provided compound inhibits the ability of an enzyme to form the final product, i.e., inhibits a second transformation (e.g., salicyl-MbtB (FIG. 1C)). In some embodiments, the compound inhibits both the first and second transformations.

Salicyl-MbtB is a precursor in the biosynthesis of mycobactin (MBT). Thus, a compound of the disclosure may inhibit MBT biosynthesis. In some embodiments, a compound provided herein inhibits MBT biosynthesis by inhibiting $MbtA_{tb}$. In some embodiments, a compound provided herein inhibits siderophore biosynthesis.

Anthranilyl-CoA is a precursor in the biosynthesis of 2-heptyl-3,4-dihydroxyquinoline (PQS) and 2-heptyl-4-hydroxyquinoline (HHQ). Thus, a compound of the disclosure may inhibit PQS and/or HHQ biosynthesis. In some embodiments, a compound provided herein inhibits PQS biosynthesis by inhibiting PqsA. In some embodiments, a compound provided herein inhibits HHQ biosynthesis by inhibiting PqsA. In some embodiments, a compound provided herein inhibits PQS and HHQ biosynthesis by inhibiting PqsA.

The present disclosure provides compounds, pharmaceutical compositions, methods of treatment, and kits useful for treating or preventing an infectious disease. In certain aspects, the infectious disease is a bacterial infection, a viral infection, a fungal infection, or a parasitic infection. In some aspects, the infectious disease is pneumonic plague, septicemic plague, bubonic plague, gastroenteritis, urinary tract infections, neonatal meningitis, hemorrhagic colitis, Crohn's disease, pneumonia, septic shock, gastrointestinal infection, necrotizing enterocolitis, or anthrax. In certain embodiments, the infectious disease is tuberculosis.

In some aspects, compounds of the present disclosure are of Formula (I):

(I)

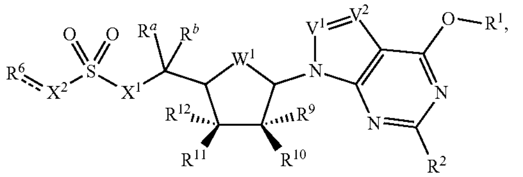

or a pharmaceutically acceptable salt or tautomer thereof, wherein:

$V^1$ is =$CR^3$— or =N—:

$V^2$ is =CH— or =N—;

$R^1$ is optionally substituted alkyl, optionally substituted heteroalkyl, optionally substituted carbocyclyl, optionally substituted heterocyclyl, optionally substituted aryl, optionally substituted heteroaryl, or optionally substituted acyl;

each or $R^2$ and $R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $—NO_2$, —CN, $—OR^e$, $—N(R^e)_2$, $—N_3$, $—SO_2H$, $—SO_3H$, $—SR^e$, $—SSR^e$, $—OC(=O)R^e$, $—OCO_2R^e$, $—OC(=O)N(R^e)_2$, $—C(=O)N(R^e)_2$, $—NC(=O)N(R^e)_2$, $—OC(=O)O(R^e)_2$, $—SO_2R^e$, $—SO_2OR^e$, $—OSO_2R^e$, $—S(=O)R^e$, or $—OS(=O)R^e$;

$W^1$ is —O—, $—CR^e_2$, $—NR^e$—, or —S—;

each of $R^9$. $R^{10}$, $R^{11}$, and $R^{12}$ is independently hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $—NO_2$, —CN, $—OR^4$, $—OR^5$, $—OR^e$, $—N(R^e)_2$, $—N_3$, $—SO_2H$, $—SO_3H$; —SH, $—SR^e$, $—SSR^e$, $—OC(=O)R^e$, $—OCO_2R^e$, $—OC(=O)N(R^e)_2$, $—C(=O)N(R^e)_2$, $—NC(=O)N(R^e)_2$, $—OC(=O)O(R^e)_2$, $—SO_2R^e$, $—SO_2OR^e$, $—OSO_2R^e$, $—S(C)R^e$, $—OS(=O)R^e$, or two occurrences of any $R^9$. $R^{10}$, $R^{11}$, and $R^{12}$ are joined to form an optionally substituted carbocyclic ring or an optionally substituted heterocyclic ring;

each of $R^4$ and $R^5$ is independently hydrogen, optionally substituted $C_{1-6}$ alkyl, optionally substituted acyl, or an oxygen protecting group, or $R^4$ and $R^5$ are joined to form an optionally substituted heterocyclic ring;

each of $R^a$ and $R^b$ is independently hydrogen, halogen, optionally substituted $C_{1-6}$ alkyl, $—OR^e$, or $—N(R^e)_2$;

$X^1$ is a bond, —O—, $—(C(R^d)_2)_q$—, or $—NR^e$—, $X^2$ is a bond, —O—, $—(C(R^d)_2)_t$—, or $—NR^e$—;

each occurrence of $R^d$ is independently hydrogen, halogen, optionally substituted $C_{1-6}$ alkyl, $—OR^e$, or $—N(R^e)_2$;

$R^6$ is of the formula:

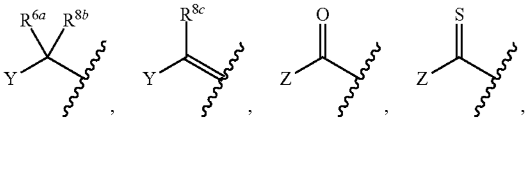

or

-continued

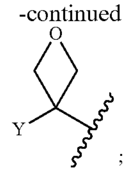

;

each of Y and Z is independently optionally substituted alkyl, optionally substituted alkenyl, optionally substituted alkynyl, optionally substituted heteroalkyl, optionally substituted heteroalkenyl, optionally substituted heteroalkynyl, optionally substituted alkoxy, optionally substituted amino, —$OR^e$, —$N(R^e)_2$, optionally substituted carbocyclyl, optionally substituted heterocyclyl, optionally substituted aryl, or optionally substituted heteroaryl;

each of $R^{6a}$, $R^{6b}$, and $R^{6c}$ is independently hydrogen, halogen, optionally substituted $C_{1-6}$ alkyl, —$OR^e$, or —$N(R^e)_2$;

each occurrence of $R^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two $R^e$ are joined to form an optionally substituted carbocyclic, an optionally substituted aryl, an optionally substituted heterocyclic or optionally substituted heteroaryl ring;

each of q and t is independently 1, 2, or 3; and

═ is a single or double bond.

In certain embodiments, the compound is of the formula:

(IA)

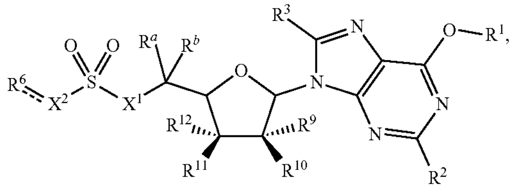

or a pharmaceutically acceptable salt or tautomer thereof.

In some embodiments, $V^1$ is =$CR^3$—. In some embodiments, $V^1$ is =CH—. In certain embodiments, $V^1$ is =N—. In some embodiments, $V^1$ is =$CR^3$— wherein $R^3$ is —F. In certain embodiments, $R^3$ is —Cl, —Br, or —F. In certain embodiments, In some embodiments, $V^1$ is =$CR^3$— wherein $R^3$ is —$OR^e$ (e.g. —OH, —OMe, —O($C_{1-6}$ alkyl)). In certain embodiments, In some embodiments, $V^1$ is =$CR^3$— wherein $R^3$ is —$N(R^e)_2$ (e.g., —$NH_2$, —$NMe_2$, —NH($C_{1-6}$ alkyl)). In certain embodiments, $V^1$ is =$CR^3$— wherein $R^3$ is optionally substituted $C_{1-6}$ alkyl. In certain embodiments, $V^1$ is =$CR^3$— wherein $R^3$ is optionally substituted methyl. In certain embodiments, $V^1$ is =$CR^3$— wherein $R^3$ is optionally substituted ethyl, propyl, or butyl.

In certain embodiments, $R^3$ is optionally substituted carbocyclyl

In certain embodiments, $R^3$ is optionally substituted aryl

In some embodiments, $V^2$ is =CH—. In certain embodiments, $V^2$ is =N—.

In some embodiments, $R^1$ is an optionally substituted $C_{1-4}$ alkyl. In certain embodiments, $R^1$ is unsubstituted methyl. In some embodiments, $R^1$ is unsubstituted ethyl. In some embodiments, $R^1$ is unsubstituted propyl. In certain embodiments, $R^1$ is unsubstituted isopropyl. In some embodiments, $R^1$ is unsubstituted propyl. In some embodiments, $R^1$ is unsubstituted butyl, sec-butyl, iso-butyl, or tert-butyl. In certain embodiments, $R^1$ is substituted methyl. In some embodiments, $R^1$ is substituted ethyl. In some embodiments, $R^1$ is substituted propyl. In certain embodiments, $R^1$ is substituted isopropyl. In some embodiments, $R^1$ is substituted propyl. In some embodiments, $R^1$ is substituted butyl, sec-butyl, iso-butyl, or tert-butyl. In some embodiments, $R^1$ is an optionally substituted $C_{5-8}$ alkyl. In certain embodiments, $R^1$ is a halogen-substituted alkyl (e.g., trifluoromethyl, difluoromethyl, monofluoromethyl, —$CH_2$—$CH_2$F). In certain embodiments $R^1$ is halogen. In certain embodiments, $R^1$ is an alkyl substituted with one or more instances of —$NO_2$, —CN, —$OR^e$, —$N(R^e)_2$, —$SR^e$, —C(=O)$R^e$, —C(=O)$OR^e$, or —C(=O)$NR^e$. In some embodiments, $R^1$ is —$CH_2CH_2NH_2$. In some embodiments, $R^1$ is —$CH_2CH_2OH$. In some embodiments, $R^1$ is an optionally substituted $C_{3-6}$ carbocyclyl (e.g., cyclopropyl, cyclobutyl, cyclopentyl, cyclohexyl). In some embodiments, $R^1$ is a $C_{7-14}$ carbocyclyl. In certain embodiments, $R^1$ is a monocyclic carbocyclyl. In some embodiments, $R^1$ is a bicyclic carbocyclyl. In certain embodiments, $R^1$ is an optionally substituted $C_{5-6}$ heterocyclyl (e.g., tetrahydrofuranyl, tetrahydropyranyl, pyrrolidinyl, piperidinyl, piperazinyl, morpholinyl). In some embodiments, $R^1$ is an optionally substituted $C_{7-14}$ heterocyclyl. In some embodiments, $R^1$ is an optionally substituted aryl. In certain embodiments, $R^1$ is an optionally substituted phenyl. In certain embodiments, $R^1$ is an optionally substituted naphthyl. In some embodiments, $R^1$ is optionally substituted monocyclic heteroaryl (e.g., pyridinyl, pyrimidinyl, pyrazinyl, pyrrolyl, furanyl, thiophenyl, imidaolyl). In certain embodiments, $R^1$ is optionally substituted bicyclic heteroaryl (e.g., indenyl, indolyl, quinolinyl, isoquinolinyl). In some embodiments, $R^1$ is optionally substituted acyl (e.g., formyl, acetyl, propionyl, benzoyl, acryloyl, trifluoroacetyl).

In certain embodiments, $R^2$ is hydrogen. In certain embodiments, $R^2$ is halogen. In certain embodiments, $R^2$ is —F. In certain embodiments, $R^2$ is —Cl, —Br, or —F. In certain embodiments, $R^2$ is —$NO_2$. In certain embodiments, $R^2$ is —CN. In certain embodiments, $R^2$ is —$OR^e$ (e.g. —OH, —OMe, —O($C_{1-6}$ alkyl)) In certain embodiments, $R^2$ is —$OR^e$, and $R^e$ is an oxygen protecting group. In certain embodiments, $R^2$ is —$N(R^e)_2$ (e.g., —$NH_2$, —$NMe_2$, —NH($C_{1-6}$ alkyl)). In certain embodiments, $R^2$ is —$NHR^e$, and $R^e$ is a nitrogen protecting group. In certain embodiments, $R^2$ is optionally substituted acyl (e.g., —C(=O)($R^e$), —C(=O)O($R^e$), —C(=O)NH($R^e$), —C(=O)N($R^e$)$_2$). In some embodiments, $R^2$ is —C(=O)OMe. In some embodiments, $R^2$ is —C(=O)OH.

In certain embodiments, $R^2$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^2$ is optionally substituted $C_{1-6}$ alkyl. In certain embodiments, $R^2$ is unsubstituted $C_{1-6}$ alkyl. In certain embodiments, $R^2$ is unsubstituted methyl. In certain embodiments, $R^2$ is unsubstituted ethyl, propyl, or butyl. In certain embodiments, $R^2$ is substituted methyl. In certain embodiments, $R^2$ is substituted ethyl, propyl, or butyl. In certain embodiments, $R^2$ is optionally substituted alkenyl, e.g., optionally substituted $C_{2-6}$ alkenyl. In certain embodiments, $R^2$ is vinyl, allyl, or prenyl. In certain embodiments, $R^2$ is optionally substituted alkynyl, e.g., $C_{2-6}$ alkynyl.

In certain embodiments, $R^2$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments $R^2$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^2$ is optionally substituted aryl, e.g., optionally substituted phenyl. In certain embodiments, $R^2$ is optionally substituted heteroaryl, e.g., optionally substituted 5-6 membered heteroaryl, or optionally substituted 9-10 membered bicyclic heteroaryl. In certain embodiments, $R^2$ is optionally substituted aralkyl, e.g., optionally substituted benzyl. In certain embodiments, $R^2$ is optionally substituted heteroaralkyl, e.g., methyl substituted with a 5-6-membered heteroaryl ring.

In certain embodiments, $R^2$ is

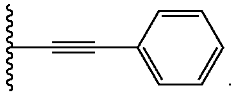 [SMILES: *C#Cc1ccccc1]

In some embodiments, $R^2$ is

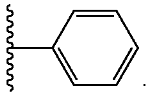

In some embodiments, $R^2$ is

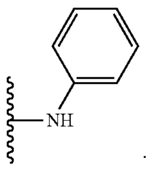 [SMILES: *Nc1ccccc1]

In certain embodiments, $R^2$ is

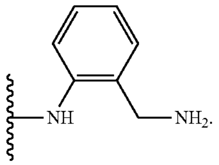 [SMILES: *Nc1ccccc1CN]

In some embodiments, $R^2$ is

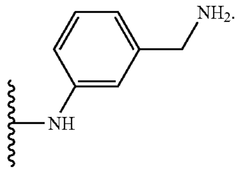 [SMILES: *Nc1cccc(CN)c1]

In certain embodiments, $R^2$ is

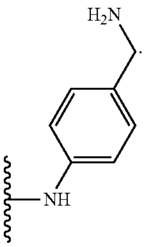 [SMILES: *Nc1ccc(CN)cc1]

In certain embodiments, $R^3$ is hydrogen. In certain embodiments, $R^3$ is halogen. In certain embodiments, $R^3$ is —F. In certain embodiments, $R^3$ is —Cl, —Br, or —F. In certain embodiments, $R^1$ is —$NO_2$. In certain embodiments, $R^3$ is —CN. In certain embodiments, $R^3$ is —$OR^e$ (e.g. —OH, —OMe, —O($C_{1-6}$ alkyl)) In certain embodiments, $R^3$ is —$OR^e$, and $R^e$ is an oxygen protecting group. In certain embodiments, $R^3$ is —$N(R^e)_2$ (e.g., —$NH_2$, —$NMe_2$, —NH($C_{1-6}$ alkyl)). In certain embodiments, $R^3$ is —$NHR^e$, and $R^e$ is a nitrogen protecting group. In certain embodiments, $R^3$ is optionally substituted acyl (e.g., —C(═O)($R^e$), —C(═O)O($R^e$), —C(═O)NH($R^e$), —C(═O)N($R^e$)$_2$). In some embodiments, $R^3$ is —C(═O)OMe. In some embodiments, $R^3$ is —C(═O)OH.

In certain embodiments, $R^3$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^3$ is optionally substituted $C_{1-6}$ alkyl. In certain embodiments, $R^3$ is unsubstituted $C_{1-6}$ alkyl. In certain embodiments, $R^3$ is unsubstituted methyl. In certain embodiments, $R^3$ is unsubstituted ethyl, propyl, or butyl. In certain embodiments, $R^3$ is unsubstituted $C_{1-6}$ alkyl. In certain embodiments, $R^3$ is substituted methyl. In certain embodiments, $R^3$ is substituted ethyl, propyl, or butyl. In certain embodiments, $R^3$ is optionally substituted alkenyl, e.g., optionally substituted $C_{2-6}$ alkenyl. In certain embodiments, $R^3$ is vinyl, allyl, or prenyl. In certain embodiments, $R^3$ is optionally substituted alkynyl, e.g., $C_{2-6}$ alkynyl.

In certain embodiments, $R^3$ is optionally substituted carbocyclyl, e.g., optionally substituted $C_{3-6}$ carbocyclyl, optionally substituted Cis carbocyclyl, optionally substituted $C_{4-5}$ carbocyclyl, or optionally substituted $C_{5-6}$ carbocyclyl. In certain embodiments $R^3$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^3$ is optionally substituted aryl, e.g., optionally substituted phenyl. In certain embodiments, $R^3$ is optionally substituted heteroaryl, e.g., optionally substituted 5-6 membered heteroaryl, or optionally substituted 9-10 membered bicyclic heteroaryl. In certain embodiments, $R^3$ is optionally substituted aralkyl, e.g., optionally substituted benzyl. In certain embodiments, $R^3$ is optionally substituted heteroaralkyl, e.g., methyl substituted with a 5-6-membered heteroaryl ring.

In some embodiments, $W^1$ is —O—. In certain embodiments, $W^1$ is —$CR^e_2$—. In certain embodiments, $W^1$ is —$CH_2$—. In certain embodiments, $W^1$ is —$CF_2$—. In some embodiments, $W^1$ is —$NR^e$—. In some embodiments, $W^1$ is —$NR^e$—, and $R^e$ is H. In some embodiments, $W^1$ is —$NR^e$—, and $R^e$ is —$CH_3$. In certain embodiments, $W^1$ is —S—.

In certain embodiments, $R^9$ is hydrogen. In certain embodiments, $R^9$ is halogen. In certain embodiments, $R^9$ is —F. In certain embodiments, $R^9$ is —Cl, —Br, or —F. In certain embodiments, $R^9$ is —$NO_2$. In certain embodiments, $R^9$ is —CN. In certain embodiments, $R^9$ is $OR^e$ (e.g. —OH, —OMe, —O($C_{1-6}$ alkyl)). In certain embodiments, $R^9$ is —OH. In certain embodiments, $R^9$ is —$OR^4$. In certain embodiments, $R^9$ is —$OR^5$. In certain embodiments, $R^9$ is —$OR^e$, and $R^e$ is an oxygen protecting group. In certain embodiments, $R^9$ is —$N(R^e)_2$ (e.g., —$NH_2$, —$NMe_2$, —NH($C_{1-6}$ alkyl)). In certain embodiments, $R^9$ is —$NHR^e$, and $R^e$ is a nitrogen protecting group. In certain embodiments, $R^9$ is optionally substituted acyl (e.g., —C(=O)($R^e$), —C(=O)O($R^e$), —C(=O)NH($R^e$), —C(=O)N($R^e$)$_2$). In some embodiments, $R^9$ is —C(=O)OMe. In some embodiments, $R^9$ is —C(=O)OH.

In certain embodiments, $R^9$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^9$ is optionally unsubstituted $C_{1-6}$ alkyl. In certain embodiments, $R^9$ is unsubstituted $C_{1-6}$ alkyl. In certain embodiments, $R^9$ is unsubstituted methyl. In certain embodiments, $R^9$ is unsubstituted ethyl, propyl, or butyl. In certain embodiments, $R^9$ is optionally substituted $C_{1-6}$ alkyl. In certain embodiments, $R^9$ is substituted methyl. In certain embodiments, $R^9$ is substituted ethyl, propyl, or butyl. In certain embodiments, $R^9$ is optionally substituted alkenyl, e.g., optionally substituted $C_{2-6}$ alkenyl. In certain embodiments, $R^9$ is vinyl, allyl, or prenyl. In certain embodiments, $R^9$ is optionally substituted alkynyl, e.g., $C_{2-6}$ alkynyl.

In certain embodiments, $R^9$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments $R^9$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^9$ is optionally substituted aryl, e.g., optionally substituted phenyl. In certain embodiments, $R^9$ is optionally substituted heteroaryl, e.g., optionally substituted 5-6 membered heteroaryl, or optionally substituted 9-10 membered bicyclic heteroaryl. In certain embodiments, $R^9$ is optionally substituted aralkyl, e.g., optionally substituted benzyl. In certain embodiments, $R^9$ is optionally substituted heteroaralkyl, e.g., methyl substituted with a 5-6-membered heteroaryl ring.

In certain embodiments, $R^{10}$ is hydrogen. In certain embodiments, $R^{10}$ is halogen. In certain embodiments, $R^{10}$ is —F. In certain embodiments, $R^{10}$ is —Cl, —Br, or —F. In certain embodiments, $R^{10}$ is —$NO_2$. In certain embodiments, $R^{10}$ is —CN. In certain embodiments, $R^{10}$ is —$OR^e$ (e.g. —OH, —OMe, —O($C_{1-6}$ alkyl)). In certain embodiments, $R^{10}$ is —OH. In certain embodiments, $R^{10}$ is —$OR^4$. In certain embodiments, $R^{10}$ is —$OR^5$. In certain embodiments, $R^{10}$ is —$OR^e$, and $R^e$ is an oxygen protecting group. In certain embodiments, $R^{10}$ is —$N(R^e)_2$ (e.g., —$NH_2$, —$NMe_2$, —NH($C_{1-6}$ alkyl)). In certain embodiments, $R^{10}$ is —$NHR^e$, and $R^e$ is a nitrogen protecting group. In certain embodiments, $R^{10}$ is optionally substituted acyl (e.g., —C(=O)($R^e$), —C(=O)O($R^e$), —C(=O)NH($R^e$), —C(=O)N($R^e$)$_2$). In some embodiments, $R^{10}$ is —C(=O)OMe. In some embodiments, $R^{10}$ is —C(=O)OH.

In certain embodiments, $R^{10}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{10}$ is unsubstituted $C_{1-6}$ alkyl. In certain embodiments, $R^{10}$ is unsubstituted methyl. In certain embodiments, $R^{10}$ is unsubstituted ethyl, propyl, or butyl. In certain embodiments, $R^{10}$ is optionally substituted $C_{1-6}$ alkyl. In certain embodiments, $R^{10}$ is substituted methyl. In certain embodiments, $R^{10}$ is substituted ethyl, propyl, or butyl. In certain embodiments, $R^{10}$ is optionally substituted alkenyl, e.g., optionally substituted $C_{2-6}$ alkenyl. In certain embodiments, $R^{10}$ is vinyl, allyl, or prenyl. In certain embodiments, $R^{10}$ is optionally substituted alkynyl, e.g., $C_{2-6}$ alkynyl.

In certain embodiments, $R^{10}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments $R^{10}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^{10}$ is optionally substituted aryl, e.g., optionally substituted phenyl. In certain embodiments, $R^{10}$ is optionally substituted heteroaryl, e.g., optionally substituted 5-6 membered heteroaryl, or optionally substituted 9-10 membered bicyclic heteroaryl. In certain embodiments, $R^{10}$ is optionally substituted aralkyl, e.g., optionally substituted benzyl. In certain embodiments, $R^{10}$ is optionally substituted heteroaralkyl, e.g., methyl substituted with a 5-6-membered heteroaryl ring.

In certain embodiments, $R^{11}$ is hydrogen. In certain embodiments, $R^{11}$ is halogen. In certain embodiments, $R^{11}$ is —F. In certain embodiments, $R^{11}$ is —Cl, —Br, or —F. In certain embodiments, $R^{11}$ is —$NO_2$. In certain embodiments, $R^{11}$ is —CN. In certain embodiments, $R^{11}$ is —$OR^4$. In certain embodiments, $R^{11}$ is —$OR^5$. In certain embodiments, $R^{11}$ is —$OR^e$ (e.g. —OH, —OMe, —O($C_{1-6}$ alkyl)). In certain embodiments, $R^{11}$ is —OH. In certain embodiments, $R^{11}$ is —$OR^e$, and $R^e$ is an oxygen protecting group. In certain embodiments, $R^{11}$ is —$N(R^e)_2$ (e.g., —$NH_2$, —$NMe_2$, —NH($C_{1-6}$ alkyl)). In certain embodiments, $R^{11}$ is —$NHR^e$, and $R^e$ is a nitrogen protecting group. In certain embodiments, $R^{11}$ is optionally substituted acyl (e.g., —C(=O)($R^e$), —C(=O)O($R^e$), —C(=O)NH($R^e$), —C(=O)N($R^e$)$_2$). In some embodiments, $R^{11}$ is —C(=O)OMe. In some embodiments, $R^{11}$ is —C(=O)OH.

In certain embodiments, $R^{11}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{11}$ is optionally substituted Cab alkyl. In certain embodiments, $R^{11}$ is substituted methyl. In certain embodiments, $R^{11}$ is substituted ethyl, propyl, or butyl. In certain embodiments, $R^{11}$ is unsubstituted $C_{1-6}$ alkyl. In certain embodiments, $R^{11}$ is unsubstituted methyl. In certain embodiments, $R^{11}$ is unsubstituted ethyl, propyl, or butyl. In certain embodiments, $R^{11}$ is optionally substituted alkenyl, e.g., optionally substituted $C_{2-6}$ alkenyl. In certain embodiments, $R^{11}$ is vinyl, allyl, or prenyl. In certain embodiments, $R^{11}$ is optionally substituted alkynyl, e.g., $C_{2-6}$ alkynyl.

In certain embodiments, $R^{11}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments $R^{11}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^{11}$ is optionally substituted aryl, e.g., optionally substituted phenyl. In certain embodiments, $R^{11}$ is optionally substituted heteroaryl, e.g., optionally substituted 5-6 membered heteroaryl, or optionally substituted 9-10 membered bicyclic heteroaryl. In certain embodiments, $R^{11}$ is optionally substituted aralkyl, e.g., optionally substituted benzyl. In certain embodiments, $R^{11}$ is optionally substituted heteroaralkyl, e.g., methyl substituted with a 5-6-membered heteroaryl ring.

In certain embodiments, $R^{12}$ is hydrogen. In certain embodiments, $R^{12}$ is halogen. In certain embodiments, $R^{12}$ is —F. In certain embodiments, $R^{12}$ is —Cl, —Br, or —F. In certain embodiments, $R^{12}$ is $—NO_2$. In certain embodiments, $R^{12}$ is —CN. In certain embodiments, $R^{12}$ is $—OR^e$ (e.g. —OH, —OMe, $—O(C_{1-6}$ alkyl)). In certain embodiments $R^{12}$ is —OH. In certain embodiments, $R^{12}$ is $—OR^4$. In certain embodiments, $R^{12}$ is $—OR^5$. In certain embodiments, $R^{12}$ is $—OR^e$, and $R^e$ is an oxygen protecting group. In certain embodiments, $R^{12}$ is $—N(R^e)_2$ (e.g., $—NH_2$, $—NMe_2$, $—NH(C_{1-6}$ alkyl)). In certain embodiments, $R^{12}$ is $—NHR^e$, and $R^e$ is a nitrogen protecting group. In certain embodiments, $R^{12}$ is optionally substituted acyl (e.g., $—C(=O)(R^e)$, $—C(=O)O(R^e)$, $—C(=O)NH(R^e)$, $—C(=O)N(R^e)_2$). In some embodiments, $R^{12}$ is —C(=O)OMe. In some embodiments, $R^{12}$ is —C(=O)OH.

In certain embodiments, $R^{12}$ is optionally substituted alkyl, e.g., optionally substituted $C_{1-6}$ alkyl, optionally substituted $C_{1-2}$ alkyl, optionally substituted $C_{2-3}$ alkyl, optionally substituted $C_{3-4}$ alkyl, optionally substituted $C_{4-5}$ alkyl, or optionally substituted $C_{5-6}$ alkyl. In certain embodiments, $R^{12}$ is optionally substituted $C_{1-6}$ alkyl. In certain embodiments, $R^{12}$ is substituted methyl. In certain embodiments, $R^{12}$ is substituted ethyl, propyl, or butyl. In certain embodiments, $R^{12}$ is unsubstituted $C_{1-6}$ alkyl. In certain embodiments, $R^{12}$ is unsubstituted methyl. In certain embodiments, $R^{12}$ is unsubstituted ethyl, propyl, or butyl. In certain embodiments, $R^{12}$ is optionally substituted alkenyl, e.g., optionally substituted $C_{2-6}$ alkenyl. In certain embodiments, $R^{12}$ is vinyl, allyl, or prenyl. In certain embodiments, $R^{12}$ is optionally substituted alkynyl, e.g., $C_{2-6}$ alkynyl.

In certain embodiments, $R^{12}$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments $R^{12}$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^{12}$ is optionally substituted aryl, e.g., optionally substituted phenyl. In certain embodiments, $R^{12}$ is optionally substituted heteroaryl, e.g., optionally substituted 5-6 membered heteroaryl, or optionally substituted 9-10 membered bicyclic heteroaryl. In certain embodiments, $R^{12}$ is optionally substituted aralkyl, e.g., optionally substituted benzyl. In certain embodiments, $R^{12}$ is optionally substituted heteroaralkyl, e.g., methyl substituted with a 5-6-membered heteroaryl ring.

In certain embodiments, two occurrences of $R^9$, $R^{10}$, $R^{11}$, and $R^{12}$ groups are joined to form an optionally substituted carbocyclic ring. In certain embodiments, two occurrences of $R^9$, $R^{10}$, $R^{11}$, and $R^{12}$ groups are joined to form an optionally substituted $C_3$-$C_6$ heterocyclyl ring (e.g., cyclopropyl, cyclobutyl, cyclopentyl, cyclohexyl). In certain embodiments, two occurrences of $R^9$, $R^{10}$, $R^{11}$, and $R^{12}$ groups are joined to form an optionally substituted heterocyclic ring. In certain embodiments, two occurrences of $R^9$, $R^{10}$, $R^{11}$, and $R^{12}$ groups are joined to form an optionally substituted $C_3$-$C_6$ heterocyclyl ring (e.g., piperidinyl, piperizinyl, morpholinyl, pyrrolidinyl).

In some embodiments, $R^9$ is $—OR^4$, $R^{10}$ is H, $R^{11}$ is $—OR^5$, and $R^{12}$ is H. In certain embodiments, $R^{10}$ is $—OR^4$, $R^9$ is H, $R^{12}$ is $—OR^5$, and $R^{11}$ is H.

As generally defined herein, each of $R^4$ and $R^5$ is independently hydrogen, optionally substituted $C_{1-6}$ alkyl, optionally substituted acyl, or an oxygen protecting group, or $R^4$ and $R^5$ are joined to form an optionally substituted heterocyclic ring. The carbon to which $R^4$ is attached may be in either the (R) or (S) configuration. The carbon to which $R^5$ is attached may be in either the (R) or (S) configuration.

In certain embodiments, at least one of $R^4$ and $R^5$ is hydrogen. In certain embodiments, at least one of $R^4$ and $R^5$ is optionally substituted $C_{1-6}$ alkyl. In certain embodiments, at least one of $R^4$ and $R^5$ is unsubstituted $C_{1-6}$ alkyl. In certain embodiments, at least one of $R^4$ and $R^5$ is methyl. In certain embodiments, at least one of $R^4$ and $R^5$ is ethyl, propyl, or butyl. In certain embodiments, at least one of $R^4$ and $R^5$ is acyl (e.g., $—C(=O)(R^e)$, $—C(=O)O(R^e)$, $—C(=O)NH(R^e)$, $—C(=O)N(R^e)_2$). In certain embodiments, at least one of $R^4$ and $R^5$ is an oxygen protecting group. In some embodiments, at least one of $R^4$ and $R^5$ is silyl (e.g., TMS, TBDMS, TIPS). In some embodiments, at least one of $R^4$ and $R^5$ is acetyl (Ac), benzyl (Bn), benzoyl (Bz), or methoxymethyl ether (MOM).

In certain embodiments, both $R^4$ and $R^5$ are hydrogen. In certain embodiments, both $R^4$ and $R^5$ are optionally substituted $C_{1-6}$ alkyl. In certain embodiments, both $R^4$ and $R^5$ are unsubstituted $C_{1-6}$ alkyl. In certain embodiments, both $R^4$ and $R^5$ are methyl. In certain embodiments, both $R^4$ and $R^5$ are ethyl, propyl, or butyl. In certain embodiments, both $R^4$ and $R^5$ are acyl (e.g., $—C(=O)(R^e)$, $—C(=O)O(R^e)$, $—C(=O)NH(R^e)$, $—C(=O)N(R^e)_2$). In certain embodiments, both $R^4$ and $R^5$ are oxygen protecting groups. In some embodiments, both $R^4$ and $R^5$ are silyl (e.g., TMS, TBDMS, TIPS). In some embodiments, both $R^4$ and $R^5$ are acetyl (Ac), benzyl (Bn), benzoyl (Bz), or methoxymethyl ether (MOM).

In certain embodiments, $R^4$ is hydrogen. In certain embodiments, $R^4$ is optionally substituted $C_{1-6}$ alkyl. In certain embodiments, $R^4$ is unsubstituted $C_{1-6}$ alkyl. In certain embodiments, $R^4$ is methyl. In certain embodiments, $R^4$ is ethyl, propyl, or butyl. In certain embodiments, $R^4$ is acyl (e.g. $—C(=O)(R^e)$, $—C(=O)O(R^e)$, $—C(=O)NH(R^e)$, $—C(=O)N(R^e)_2$). In certain embodiments, $R^4$ is an oxygen protecting group. In some embodiments, $R^4$ is silyl (e.g., TMS, TBDMS, TIPS). In some embodiments, $R^4$ is acetyl (Ac), benzyl (Bn), benzoyl (Bz), or methoxymethyl ether (MOM).

In certain embodiments, $R^5$ is hydrogen. In certain embodiments, $R^5$ is optionally substituted $C_{1-6}$ alkyl. In certain embodiments, $R^5$ is unsubstituted $C_{1-6}$ alkyl. In certain embodiments, $R^5$ is methyl. In certain embodiments, $R^5$ is ethyl, propyl, or butyl. In certain embodiments, $R^5$ is acyl (e.g., —C(═O)($R^e$), —C(═O)O($R^e$), —C(═O)NH($R^e$), —C(═O)N($R^e$)$_2$). In certain embodiments, $R^5$ is an oxygen protecting group. In some embodiments, $R^5$ is silyl (e.g., TMS, TBDMS, TIPS). In some embodiments, $R^5$ is acetyl (Ac), benzyl (Bn), benzoyl (Bz), or methoxymethyl ether (MOM).

In certain embodiments, $R^4$ and $R^5$ are joined to form an optionally substituted heterocyclic ring. In certain embodiments, $R^4$ and $R^5$ are taken together to form a cyclic acetal (e.g., —C(CH$_3$)$_2$—).

As generally defined herein, each of $R^a$ and $R^b$ is independently hydrogen, halogen, optionally substituted $C_{1-6}$ alkyl, —O$R^e$, or —N($R^e$)$_2$. The carbon to which $R^a$ and $R^b$ is attached may be in either the (R) or (S) configuration. In certain embodiments, at least one of $R^a$ and $R^b$ is hydrogen. In certain embodiments, at least one of $R^a$ and $R^b$ is halogen. In some embodiments, at least one of $R^a$ and $R^b$ is —F. In some embodiments, at least one of $R^a$ and $R^b$ is —Cl, —Br, or —I. In certain embodiments, at least one of $R^a$ and $R^b$ is optionally substituted $C_{1-6}$ alkyl. In certain embodiments, at least one of $R^a$ and $R^b$ is unsubstituted $C_{1-6}$ alkyl. In certain embodiments, at least one of $R^a$ and $R^b$ is methyl. In certain embodiments, at least one of $R^a$ and $R^b$ is ethyl, propyl, or butyl.

In certain embodiments, $R^a$ is hydrogen. In certain embodiments, $R^a$ is halogen. In some embodiments, $R^a$ is —F. In some embodiments, at least one of $R^3$ is —Cl, —Br, or —I. In certain embodiments, $R^a$ is optionally substituted $C_{1-6}$ alkyl. In certain embodiments, $R^a$ is unsubstituted $C_{1-6}$ alkyl. In certain embodiments, $R^a$ is methyl. In certain embodiments, $R^a$ is ethyl, propyl, or butyl. In certain embodiments, $R^a$ is —O$R^e$, e.g., —OH. In certain embodiments, $R^a$ is —N($R^e$)$_2$. In certain embodiments, $R^a$ is —NH$R^e$, e.g., —NH$_2$.

In certain embodiments, $R^b$ is hydrogen. In certain embodiments, $R^b$ is halogen. In some embodiments, $R^b$ is —F. In some embodiments, at least one of $R^b$ is —Cl, —Br, or —I. In certain embodiments, $R^b$ is optionally substituted $C_{1-6}$ alkyl. In certain embodiments, $R^b$ is unsubstituted $C_{1-6}$ alkyl. In certain embodiments, $R^b$ is methyl. In certain embodiments, $R^b$ is ethyl, propyl, or butyl. In certain embodiments, $R^b$ is —O$R^e$, e.g., —OH. In certain embodiments, $R^b$ is —N($R^e$)$_2$. In certain embodiments, $R^b$ is —NH$R^e$, e.g., —NH$_2$.

In certain embodiments, both $R^a$ and $R^b$ are hydrogen. In certain embodiments, both $R^a$ and $R^b$ are halogen. In some embodiments, both $R^a$ and $R^b$ are —F. In some embodiments, both $R^a$ and $R^b$ are —Cl, —Br, or —I. In certain embodiments, both $R^a$ and $R^b$ are optionally substituted $C_{1-6}$ alkyl. In certain embodiments, both $R^a$ and $R^b$ are unsubstituted $C_{1-6}$ alkyl. In certain embodiments, both $R^a$ and $R^b$ are methyl. In certain embodiments, both $R^a$ and $R^b$ are ethyl, propyl, or butyl.

As generally defined herein, $X^1$ is a bond, —O—, —(C($R^d$)$_2$)$_q$—, or —N$R^e$—. In certain embodiments, $X^1$ is a bond. In certain embodiments, $X^1$ is —O—. In certain embodiments, $X^1$ is —NH—. In certain embodiments, $X^1$ is —N$R^e$—, and $R^e$ is optionally substituted $C_{1-6}$ alkyl. In certain embodiments, $X^1$ is —N$R^e$—, and $R^e$ is unsubstituted $C_{1-6}$ alkyl. In certain embodiments, $X^1$ is —N$R^e$—, and $R^e$ is methyl. In certain embodiments, $X^1$ is —N$R^e$—, and $R^e$ is ethyl, propyl, or butyl. In certain embodiments, $X^1$ is —N$R^e$—, and $R^e$ is optionally substituted acyl (e.g., —C(═O)($R^e$), —C(═O)O($R^e$), —C(═O)NH($R^e$), —C(═O)N($R^e$)$_2$). In certain embodiments, $X^1$ is —N$R^e$—, and $R^e$ is a nitrogen protecting group. In certain embodiments, $X^1$ is —C($R^d$)$_2$. In certain embodiments, $X^1$ is —CH$_2$—. In certain embodiments, $X^1$ is —C($R^d$)$_2$—, and both $R^d$ are halogen. In certain embodiments, $X^1$ is —CF$_2$—. In certain embodiments, $X^1$ is —(CH$_2$)$_q$—, wherein q is 1, 2, or 3. In some embodiments, $X^1$ is —(CH$_2$)$_q$—, wherein q is 1. In some embodiments, $X^1$ is —(CH$_2$)$_q$—, wherein q is 2 or 3.

As generally defined herein, $X^2$ is a bond. —O—, —(C($R^d$)$_2$)$_t$—, or —N$R^e$—. As generally defined herein, $X^2$ is a bond, —O—, —(C($R^d$)$_2$)$_q$—, or —N$R^e$—. In certain embodiments, $X^2$ is a bond. In certain embodiments, $X^2$ is —O—. In certain embodiments, $X^2$ is —NH—. In certain embodiments, $X^2$ is —N$R^e$—, and $R^e$ is optionally substituted $C_{1-6}$ alkyl. In certain embodiments, $X^2$ is —N$R^e$—, and $R^e$ is unsubstituted $C_{1-6}$ alkyl. In certain embodiments, $X^2$ is —N$R^e$—, and $R^e$ is methyl. In certain embodiments, $X^2$ is —N$R^e$—, and $R^e$ is ethyl, propyl, or butyl. In certain embodiments, $X^2$ is —N$R^e$—, and $R^e$ is optionally substituted acyl (e.g., —C(═O)($R^e$), —C(═O)O($R^e$). —C(═O)NH($R^e$), —C(═O)N($R^e$)$_2$). In certain embodiments, $X^2$ is —N$R^e$—, and $R^e$ is a nitrogen protecting group. In certain embodiments, $X^2$ is —C($R^d$)$_2$. In certain embodiments, $X^2$ is —CH$_2$—. In certain embodiments, $X^2$ is —C($R^d$)$_2$—, and both $R^d$ are halogen. In certain embodiments, $X^2$ is —CF$_2$—. In certain embodiments, $X^2$ is —(CH$_2$)$_t$—, wherein t is 1, 2, or 3. In some embodiments, $X^2$ is —(CH$_2$)$_t$—, wherein t is 1. In some embodiments, $X^2$ is —(CH$_2$)$_t$—, wherein t is 2 or 3.

In some embodiments, t is 1. In certain embodiments, t is 2. In some embodiments, t is 3.

In certain embodiments, both $X^1$ and $X^2$ are bonds. In certain embodiments, both $X^1$ and $X^2$ are —O—. In certain embodiments, both $X^1$ and $X^2$ are —N$R^f$—. In certain embodiments, both $X^1$ and $X^2$ are —NH—. In certain embodiments, both $X^1$ and $X^2$ are —C($R^d$)$_2$—. In certain embodiments, $X^1$ is —(CH$_2$)$_q$—, and $X^2$ is —(CH$_2$)$_t$—, wherein each of q and t is independently 1, 2, or 3. In certain embodiments, both $X^1$ and $X^2$ are —CH$_2$—. In certain embodiments, $X^1$ is a bond, and $X^2$ is —O—. In certain embodiments, $X^1$ is a bond, and $X^2$ is —N$R^f$—. In certain embodiments, $X^1$ is a bond, and $X^2$ is —NH—. In certain embodiments, $X^1$ is a bond, and $X^2$ is —C($R^d$)$_2$—. In certain embodiments, $X^1$ is a bond, and $X^2$ is —(CH$_2$)$_t$—. In certain embodiments, $X^1$ is —O—, and $X^2$ is a bond. In certain embodiments, $X^1$ is —O—, and $X^1$ is —N$R^f$—. In certain embodiments, $X^1$ is —O—, and $X^2$ is —NH—. In certain embodiments, $X^1$ is —O—, and $X^2$ is —C($R^d$)$_2$—. In certain embodiments, $X^1$ is —O—, and $X^2$ is —CH$_2$—. In certain embodiments, $X^1$ is —O—, and $X^2$ is —(CH$_2$)$_t$—. In certain embodiments, $X^1$ is —N$R^f$—, and $X^2$ is a bond. In certain embodiments, $X^1$ is —NH—, and $X^2$ is a bond. In certain embodiments, $X^1$ is —N$R^f$—, and $X^2$ is —O—. In certain embodiments, $X^1$ is —NH—, and $X^2$ is —O—. In certain embodiments, $X^1$ is —NH—, and $X^2$ is —C($R^d$)$_2$—. In certain embodiments, $X^1$ is —N$R^f$—, and $X^2$ is —CH$_2$—. In certain embodiments, $X^1$ is —N$R^f$—, and $X^2$ is —(CH$_2$)$_t$—. In certain embodiments, $X^1$ is —NH—, and $X^2$ is —C($R^d$)$_2$—. In certain embodiments, $X^1$ is —NH—, and $X^2$ is —CH$_2$—. In certain embodiments, $X^1$ is —NH—, and $X^2$ is —(CH$_2$)$_1$—. In certain embodiments, $X^1$ is —C($R^d$)$_2$—, and $X^2$ is a bond. In certain embodiments, $X^1$ is —$C(R^d)_2$—, and $X^2$ is —$NR^f$—. In certain embodiments, $X^1$—$C(R^d)_2$—, and $X^2$ is —NH—. In certain embodiments, $X^1$ is —$C(R^d)$ and $X^2$ is —O—. In certain embodiments, $X^1$ is —$C(R^d)_2$—, and $X^2$ is —$(CH_2)$—. In certain embodiments, $X^1$ is —$CH_2$—, and $X^2$ is a bond. In certain embodiments, $X^1$ is —$CH_2$—, and $X^2$ is —$NR^f$—. In certain embodiments, $X^1$—$CH_2$—, and $X^2$ is —NH—. In certain embodiments, $X^1$ is —$CH_2$—, and $X^2$ is —O—. In certain embodiments, $X^1$ is —$(CH_2)_q$—, and $X^2$ is a bond. In certain embodiments, $X^1$ is —$(CH—)_q$—, and $X^2$ is —O—. In certain embodiments, $X^1$ is —$(CH_2)_q$—, and $X^1$ is a —$NR^f$— bond. In certain embodiments, $X^1$ is —$(CH_2)_q$—, and $X^2$ is —NH—. In certain embodiments, $X^1$ is $(CH_2)_q$—, and $X^2$ is —$C(R^d)_2$—.

In certain embodiments, q is 1. In some embodiments, q is 2. In certain embodiments, q is 3.

In certain embodiments, $R^6$ is of the formula:

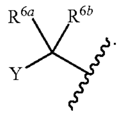

In certain embodiments, $R^6$ is of the formula:

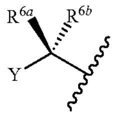 or 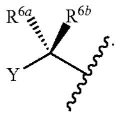

In some embodiments, $R^6$ is of the formula:

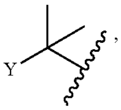, 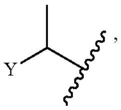, or 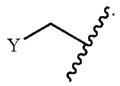

In certain embodiments, $R^6$ is of the formula:

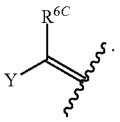

In some embodiments, $R^6$ is of the formula:

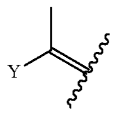 or 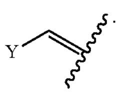

In certain embodiments, $R^6$ is of the formula:

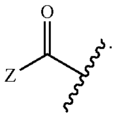

In some embodiments, $R^6$ is of the formula:

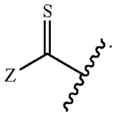

In certain embodiments, $R^6$ is of the formula:

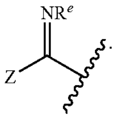

In some embodiments, $R^6$ is of the formula:

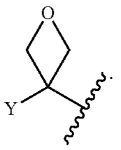

In certain embodiments, $R^6$ is of formula:

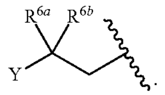

In some embodiments, $R^6$ is of formula:

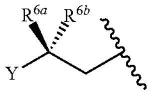 or 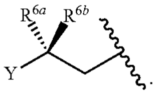

In certain embodiments, $R^6$ is of formula:

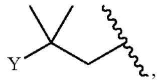, 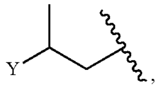, or 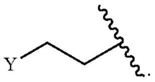

In certain embodiments, $R^6$ is of formula:

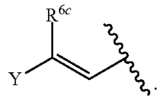

In some embodiments, $R^6$ is of formula:

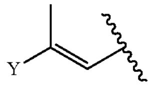

or

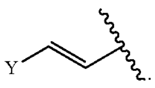

In certain embodiments, $R^6$ is of formula:

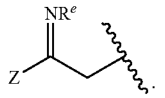

In certain embodiments, $R^6$ is of formula:

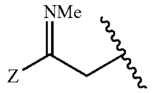

or

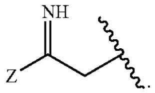

In certain embodiments, $R^6$ is of formula:

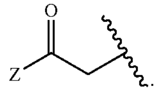

In some embodiments, $R^6$ is of formula:

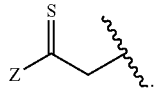

In certain embodiments, $R^6$ is of formula:

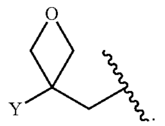

In certain embodiments, Y is optionally substituted alkyl (e.g., optionally substituted $C_{1-6}$ alkyl), optionally substituted alkenyl (e.g., optionally substituted $C_{1-6}$ alkenyl), or optionally substituted alkynyl (e.g., optionally substituted $C_{1-6}$ alkynyl). In certain embodiments, Y is optionally substituted heteroalkyl (e.g., optionally substituted $C_{1-6}$ heteroalkyl), optionally substituted heteroalkenyl (e.g., optionally substituted CLU heteroalkenyl), or optionally substituted heteroalkynyl (e.g., optionally substituted $C_{1-6}$ heteroalkynyl). In certain embodiments, Y is optionally substituted alkoxy (e.g., optionally substituted $C_{1-6}$ alkoxy), optionally substituted amino, —$OR^c$, or —$N(R^c)_2$. In certain embodiments, Y is optionally substituted carbocyclyl (e.g., optionally substituted monocyclic 3- to 7-membered carbocyclyl). In certain embodiments, Y is optionally substituted aryl (e.g., optionally substituted 6- to 14-membered aryl, e.g., optionally substituted phenyl). In certain embodiments, Y is optionally substituted heteroaryl (e.g., optionally substituted monocyclic 5- or 6-membered heteroaryl, wherein 1, 2, 3, or 4 atoms in the heteroaryl ring system are independently oxygen, nitrogen, or sulfur). In certain embodiments, Y is optionally substituted heterocyclyl, optionally substituted 6-membered heteroaryl. In certain embodiments, Y is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, Y is optionally substituted 6-membered heteroaryl, e.g., optionally substituted pyridyl.

In some embodiments, Y is of formula:

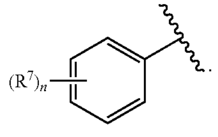

In certain embodiments, Y is of formula:

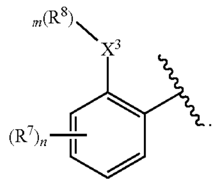

In some embodiments, Y is of formula:

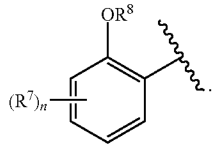

In certain embodiments, Y is of formula:

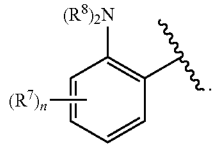

In certain embodiments, Y is of formula:

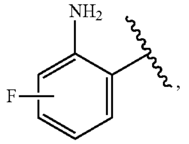

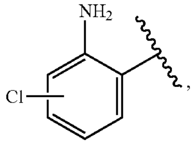

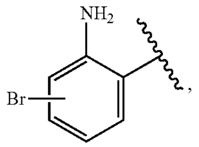

or

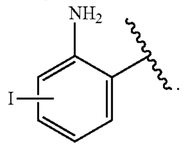

In some embodiments, Y is of formula:
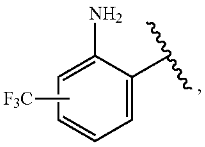, 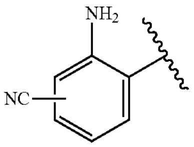, or
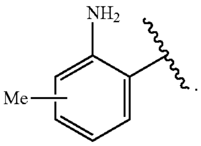.
In certain embodiments, Y is of formula:
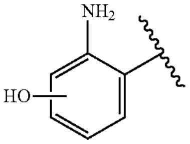 or 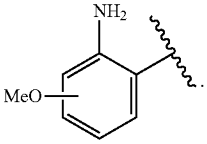.
In some embodiments, Y is of formula:
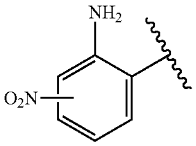 or 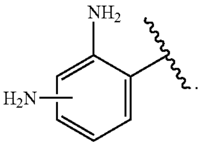.
In certain embodiments, Y is of formula:
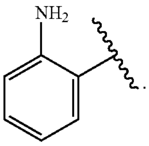 [SMILES: *c1ccccc1N].
In some embodiments, Y is of formula:
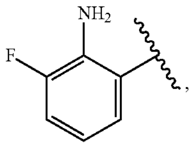, 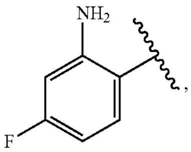,
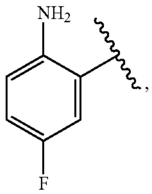, 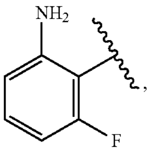, 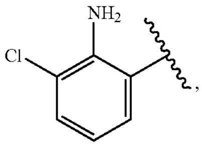,
-continued
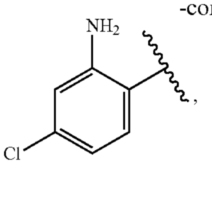, 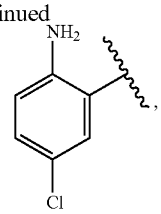, or
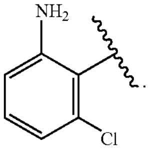.
In certain embodiments, Y is of formula:
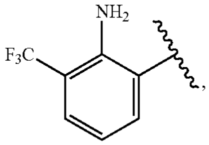, 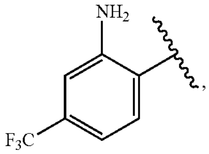,
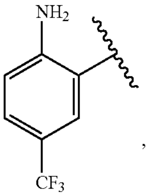, or 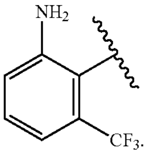.
In some embodiments, Y is of formula:
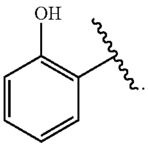.
In certain embodiments, Y is of formula:
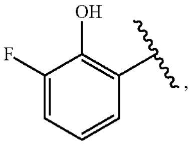, 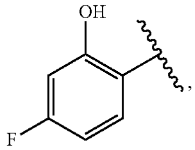, 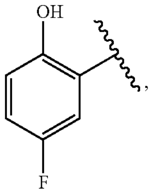,
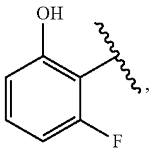, 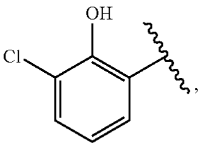, 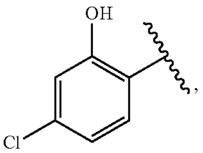,
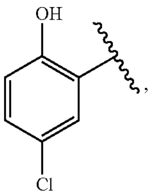, or 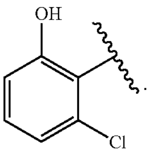.

In certain embodiments, Y is of formula:

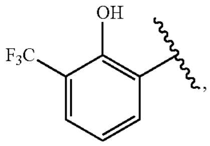, 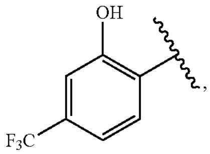, 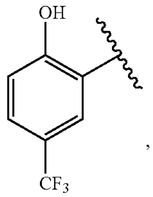, or 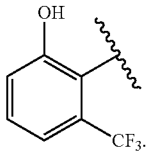.

In certain embodiments, Y is of formula:

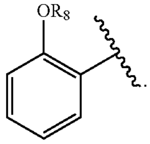.

In certain embodiments, Y is of formula:

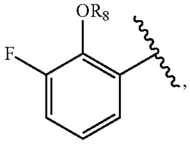, 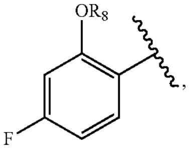, 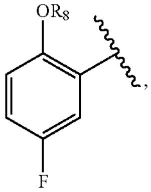, 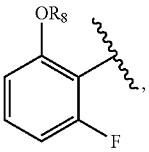, 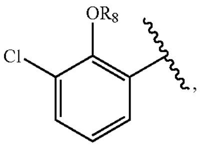, 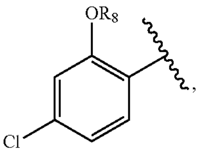, 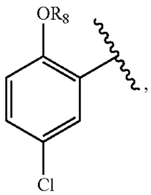, or 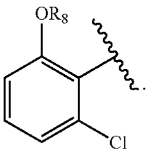.

In certain embodiments, Y is of formula:

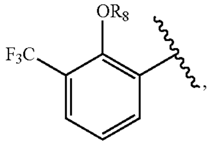, 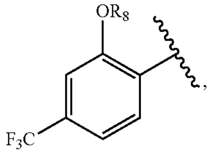,

-continued

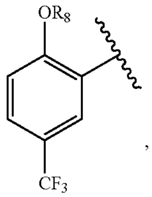, or 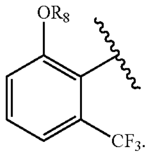.

In some embodiments, Y is of formula:

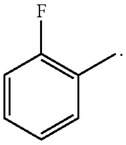.

In certain embodiments, Y is of formula:

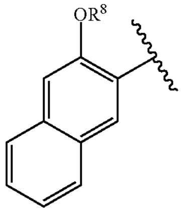 or 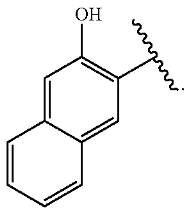.

In some embodiments, Y is of formula:

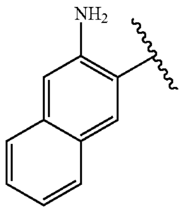 or 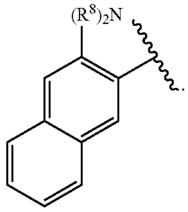.

In certain embodiments, Y is of formula:

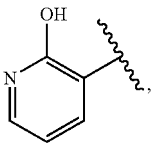, 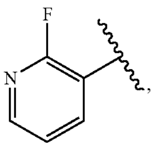, or 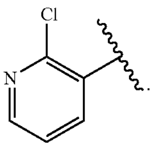.

In certain embodiments, Y is of formula:

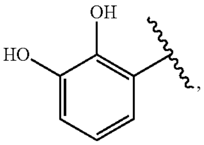, 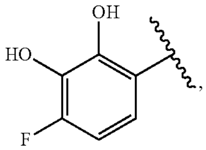,

-continued

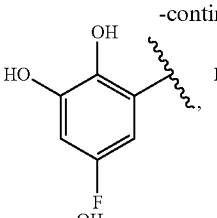,
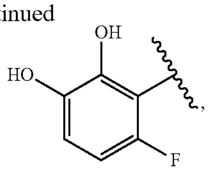,
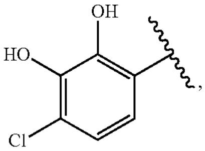,
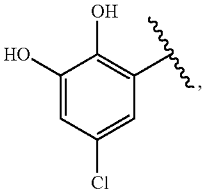, or
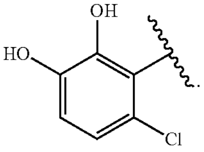.

In certain embodiments, Y is of formula:

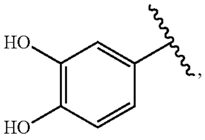,
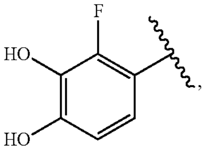,
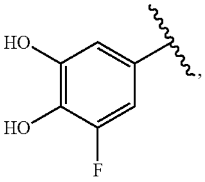,
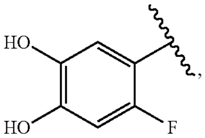,
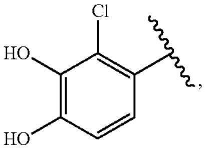,
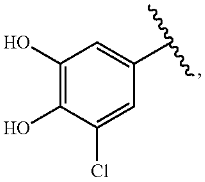, or
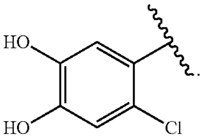.

In certain embodiments, Z is optionally substituted alkyl (e.g., optionally substituted $C_{1-6}$ alkyl), optionally substituted alkenyl (e.g., optionally substituted $C_{1-6}$ alkenyl), or optionally substituted alkynyl (e.g., optionally substituted $C_{1-6}$ alkynyl). In certain embodiments, Z is optionally substituted heteroalkyl (e.g., optionally substituted $C_{1-6}$ heteroalkyl), optionally substituted heteroalkenyl (e.g., optionally substituted $C_{1-6}$ heteroalkenyl), or optionally substituted heteroalkynyl (e.g., optionally substituted $C_{1-6}$ heteroalkynyl). In certain embodiments, Z is optionally substituted alkoxy (e.g., optionally substituted $C_{1-6}$ alkoxy), optionally substituted amino, —$OR^e$, or —$N(R^e)_2$. In certain embodiments, Z is optionally substituted carbocyclyl (e.g., optionally substituted monocyclic 3- to 7-membered carbocyclyl). In certain embodiments, Z is optionally substituted aryl (e.g., optionally substituted 6- to 14-membered aryl, e.g., optionally substituted phenyl). In certain embodiments, Z is optionally substituted heteroaryl (e.g., optionally substituted monocyclic 5- or 6-membered heteroaryl, wherein 1, 2, 3, or 4 atoms in the heteroaryl ring system are independently oxygen, nitrogen, or sulfur). In certain embodiments, Z is optionally substituted heterocyclyl, optionally substituted 6-membered heteroaryl. In certain embodiments, Z is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl. In certain embodiments, Z is optionally substituted 6-membered heteroaryl, e.g., optionally substituted pyridyl.

In some embodiments, Z is of formula:

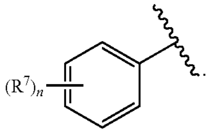.

In certain embodiments, Z is of formula:

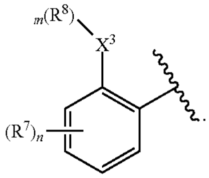.

In some embodiments, Z is of formula:

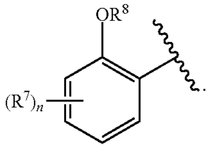.

In certain embodiments, Z is of formula:

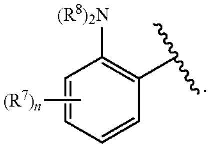.

In certain embodiments, Z is of formula:

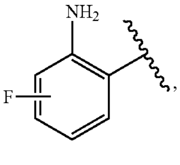,
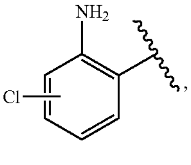,

-continued
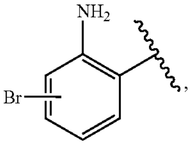
or
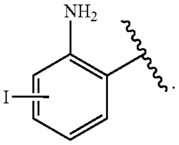
In some embodiments, Z is of formula:
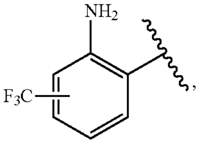
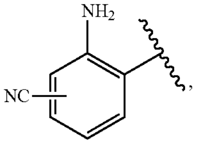
or
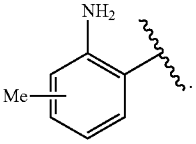
In certain embodiments, Z is of formula:
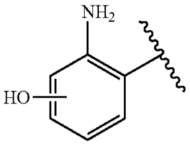
or
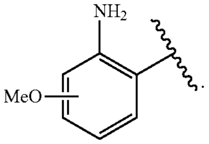
In some embodiments, Z is of formula:
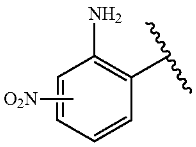
or
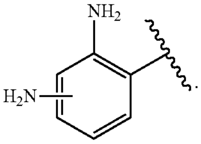
In certain embodiments, Z is of formula:
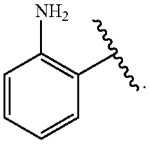 [SMILES: *c1ccccc1N]
In some embodiments, Z is of formula:
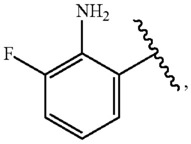
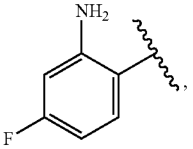
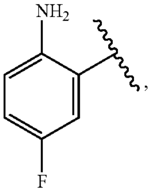
-continued
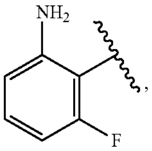
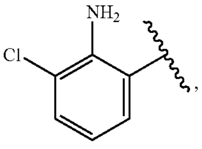
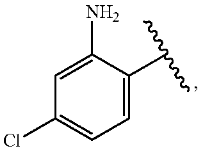
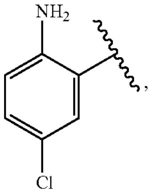
or
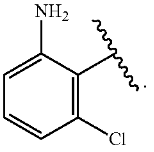
In certain embodiments, Z is of formula:
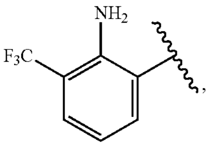
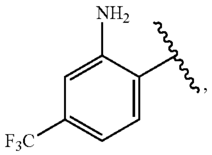
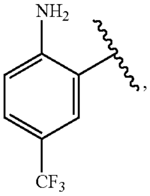
or
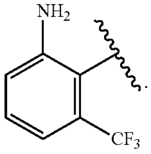
In some embodiments, Z is of formula:
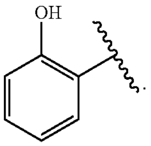
In certain embodiments, Z is of formula:
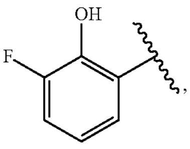
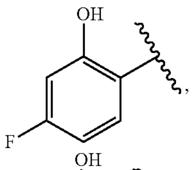
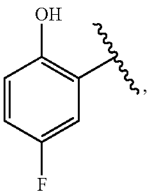
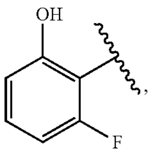
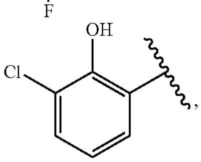
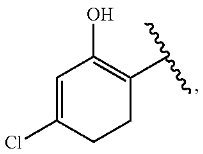

-continued
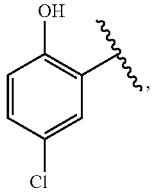
or
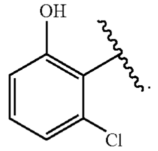
In some embodiments, Z is of formula:
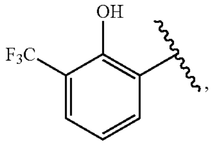
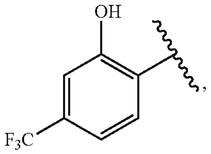
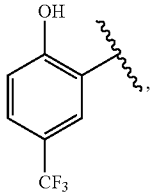
or
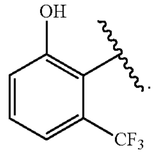
In certain embodiments, Z is of formula:
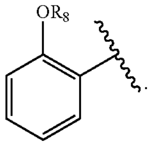
In some embodiments, Z is of formula:
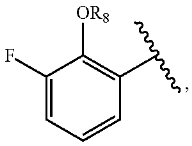
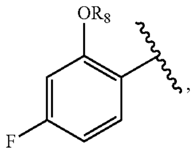
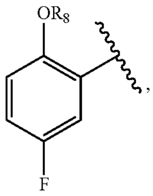
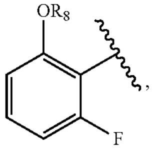
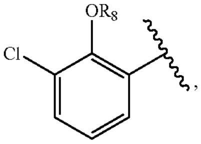
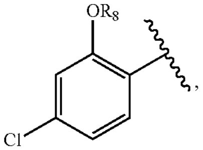
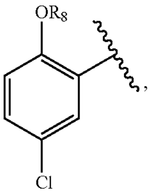
or
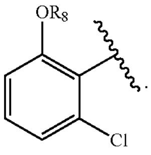
In some embodiments, Z is of formula:
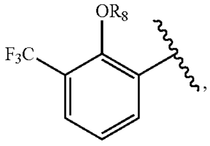
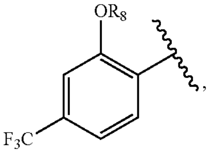
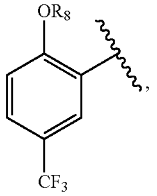
or
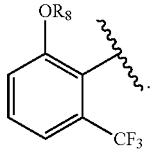
In certain embodiments, Z is of formula:
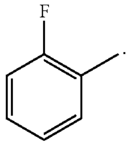
In certain embodiments, Z is of formula:
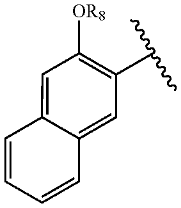
or
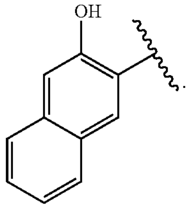
In some embodiments, Z is of formula:
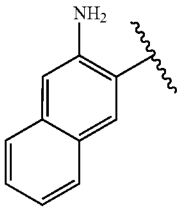
or
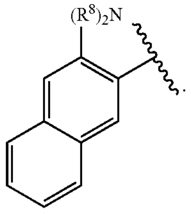
In certain embodiments, Z is of formula:
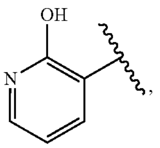
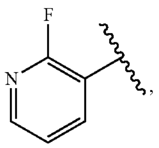
or
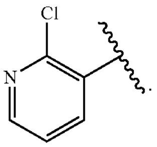

In some embodiments, Z is of formula:

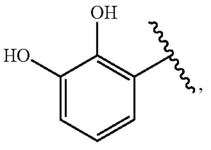

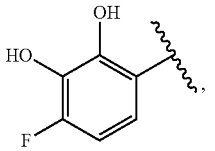

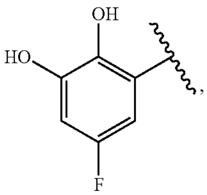

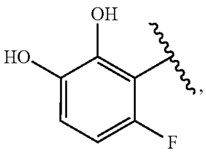

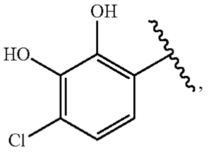

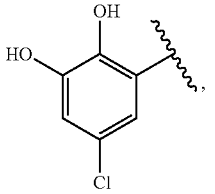

or

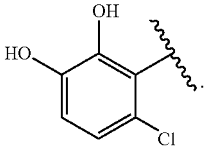

In certain embodiments, Z is of formula:

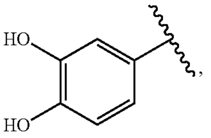

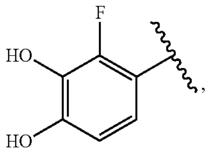

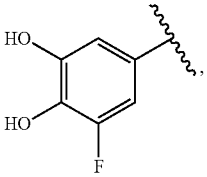

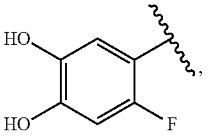

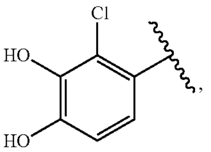

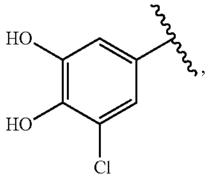

or

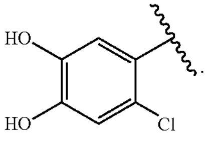

As generally defined herein, each of $R^{6a}$ and $R^{6b}$ is independently hydrogen, halogen, optionally substituted $C_{1-6}$ alkyl, —$OR^e$, or —$N(R^e)_2$. The carbon to which $R^{6a}$ and $R^{6b}$ is attached may be in either the (R) or (S) configuration. In certain embodiments, at least one of $R^{6a}$ and $R^{6b}$ is hydrogen. In certain embodiments, at least one of $R^{6a}$ and $R^{6b}$ is halogen. In some embodiments, at least one of $R^{6a}$ and $R^{6b}$ is —F. In some embodiments, at least one of $R^{6a}$ and $R^{6b}$ is —Cl, —Br, or —I. In certain embodiments, at least one of $R^{6a}$ and $R^{6b}$ is optionally substituted $C_{1-6}$ alkyl. In certain embodiments, at least one of $R^{6a}$ and $R^{6b}$ is unsubstituted $C_{1-6}$ alkyl. In certain embodiments, at least one of $R^{6a}$ and $R^{6b}$ is methyl. In certain embodiments, at least one of $R^{6a}$ and $R^{6b}$ is ethyl, propyl, or butyl.

In certain embodiments, both $R^{6a}$ and $R^{6b}$ are hydrogen. In certain embodiments, both $R^{6a}$ and $R^{6b}$ are halogen. In some embodiments, both $R^{6a}$ and $R^{6b}$ are —F. In some embodiments, both $R^{6a}$ and $R^{6b}$ are —Cl, —Br, or —I. In certain embodiments, both $R^{6a}$ and $R^{6b}$ are optionally substituted $C_{1-6}$ alkyl. In certain embodiments, both $R^{6a}$ and $R^{6b}$ are unsubstituted $C_{1-6}$ alkyl. In certain embodiments, both $R^{6a}$ and $R^{6b}$ are methyl. In certain embodiments, both $R^{6a}$ and $R^{6b}$ are ethyl, propyl, or butyl.

In certain embodiments, $R^{6a}$ is hydrogen. In certain embodiments, $R^{6a}$ is halogen. In some embodiments, $R^{6a}$ is —F. In some embodiments, at least one of $R^{68}$ is —Cl, —Br, or —I. In certain embodiments, $R^{6a}$ is optionally substituted $C_{1-6}$ alkyl. In certain embodiments, $R^{6a}$ is unsubstituted $C_{1-6}$ alkyl. In certain embodiments, $R^{6a}$ is methyl. In certain embodiments, $R^{6a}$ is ethyl, propyl, or butyl. In certain embodiments, $R^{6a}$ is —$OR^e$, e.g., —OH. In certain embodiments, $R^{6a}$ is —$N(R^e)_2$. In certain embodiments, $R^{6a}$ is —$NHR^e$, e.g., —$NH_2$.

In certain embodiments, $R^{6b}$ is hydrogen. In certain embodiments, $R^{6b}$ is halogen. In some embodiments, $R^{6b}$ is —F. In some embodiments, at least one of $R^{6b}$ is —Cl, —Br, or —I. In certain embodiments, $R^{6b}$ is optionally substituted $C_{1-6}$ alkyl. In certain embodiments, $R^{6b}$ is unsubstituted $C_{1-6}$ alkyl. In certain embodiments, $R^{6b}$ is methyl. In certain embodiments, $R^{6b}$ is ethyl, propyl, or butyl. In certain embodiments, $R^{6b}$ is —$OR^e$, e.g., —OH. In certain embodiments, $R^{6b}$ is —$N(R^e)_2$. In certain embodiments, $R^{6b}$ is —$NHR^e$. e.g., —$NH_2$.

In certain embodiments, $R^{6c}$ is hydrogen. In certain embodiments, $R^{6c}$ is halogen. In some embodiments, $R^{6c}$ is —F. In some embodiments, at least one of $R^{6c}$ is —Cl, —Br, or —I. In certain embodiments, $R^{6c}$ is optionally substituted $C_{1-6}$ alkyl. In certain embodiments, $R^{6c}$ is unsubstituted $C_{1-6}$ alkyl. In certain embodiments, $R^{6c}$ is methyl. In certain embodiments, $R^{6c}$ is ethyl, propyl, or butyl. In certain embodiments, $R^{6c}$ is —$OR^e$, e.g., —OH. In certain embodiments, $R^{6c}$ is —$N(R^e)_2$. In certain embodiments, $R^{6c}$ is —$NHR^e$, e.g., —$NH_2$.

In certain embodiments, there are no instances of $R^e$. In certain embodiments, there is a single instance of $R^e$. In certain embodiments, there are multiple instances of $R^e$. In certain embodiments, each instance of $R^e$ is independently selected, wherein all instances of $R^e$ are different. In certain embodiments, each instance of $R^e$ is independently selected, wherein some instances of $R^e$ are different. In certain embodiments, all instances of $R^e$ are the same.

In certain embodiments, at least one instance of $R^e$ is hydrogen. In certain embodiments, each instance of $R^e$ is hydrogen. In certain embodiments, $R^e$ is optionally substituted acyl (e.g., —$C(=O)CH_3$, —$C(=O)CH_2CH_3$, —$C(=O)CF_3$). In certain embodiments, at least one instance of $R^e$ is optionally substituted $C_1$-$C_6$ alkyl (e.g., optionally substituted methyl (e.g., trifluoromethyl), optionally substituted ethyl, optionally substituted propyl). In certain embodiments, $R^e$ is optionally substituted alkenyl (e.g., optionally substituted vinylene). In certain embodiments, $R^e$ is optionally substituted alkynyl (e.g., optionally substituted ethynyl). In certain embodiments, $R^e$ is optionally substituted $C_3$-$C_6$ carbocyclyl ring (e.g., cyclopropyl, cyclopentyl, cyclohexyl). In certain embodiments, $R^e$ is an optionally substituted $C_3$-$C_6$ heterocyclyl ring (e.g., piperidinyl, piperizinyl, morpholinyl, pyrrolidinyl). In certain embodiments, $R^e$ is an optionally substituted aryl (e.g., phenyl, naphthyl). In certain embodiments, $R^e$ is an optionally substituted heteroaryl (e.g., pyridinyl, pyrimidinyl, isoquinolinyl, thienopyrimidinyl). In certain embodiments, Reis a nitrogen protecting group, oxygen protecting group, or sulfur protecting group.

In certain embodiments, two $R^e$ groups are joined to form an optionally substituted carbocyclic ring. In certain embodiments, two $R^e$ groups are joined to form an optionally substituted $C_3$-$C_6$ carbocyclyl ring (e.g., cyclopropyl, cyclobutyl, cyclopentyl, cyclohexyl). In certain embodiments, two $R^e$ groups are joined to form an optionally substituted aryl ring. In certain embodiments, two $R^e$ groups form an optionally substituted phenyl. In certain embodiments, two $R^e$ groups form an optionally substituted naphthalenyl.

In certain embodiments, two $R^e$ groups are joined to form an optionally substituted heterocyclic ring. In certain embodiments, two $R^e$ groups are joined to form an optionally substituted $C_3$-$C_6$ heterocyclyl ring (e.g., piperidinyl, piperizinyl, morpholinyl, pyrrolidinyl). In certain embodiments, two $R^e$ groups are joined to form an optionally substituted heteroaryl ring. In certain embodiments, two $R^e$ groups form an optionally substituted pyridinyl. In certain embodiments, two R groups form an optionally substituted pyrimidinyl. In certain embodiments, two $R^e$ groups form an optionally substituted isoquinolinyl. In certain embodiments, two $R^e$ groups form an optionally substituted thienopyrimidinyl.

In certain embodiments, ⎓ is a single bond (—). In some embodiments, ⎓ is a double bond (=).

In certain embodiments, a compound is of the formula:

(II)

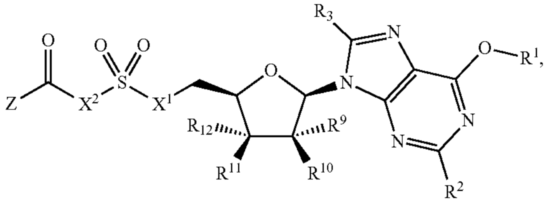

or a pharmaceutically acceptable salt, stereoisomer, or tautomer thereof.

In some embodiments, a compound is of one of the following formulae:

(II-A)

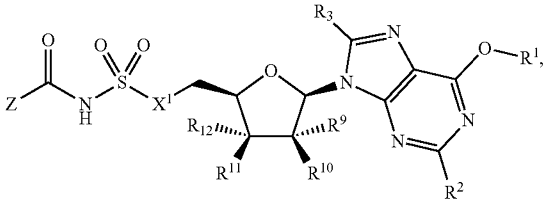

-continued (II-B)

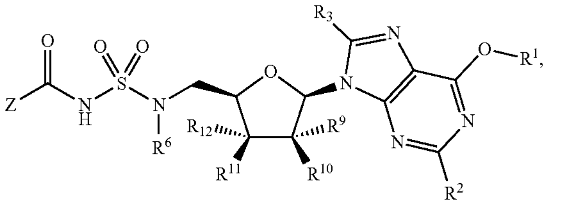

(II-C)

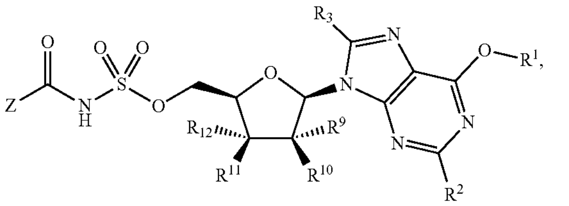

or a pharmaceutically acceptable salt, stereoisomer, or tautomer thereof.

In certain embodiments, a compound is of one of the following formulae:

(II-D)

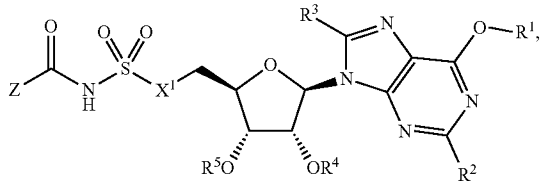

(II-E)

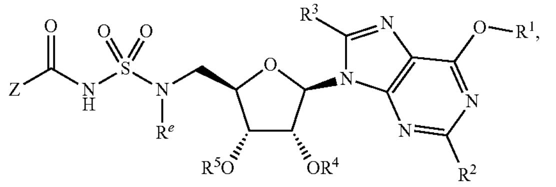

(II-F)

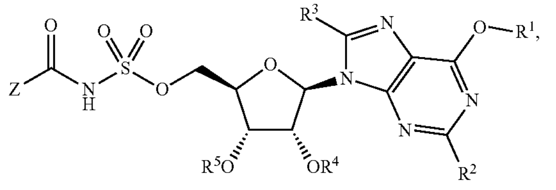

or a pharmaceutically acceptable salt, stereoisomer, or tautomer thereof.

In some aspects, the compound of Formula (I) is Formula (III):

(III)

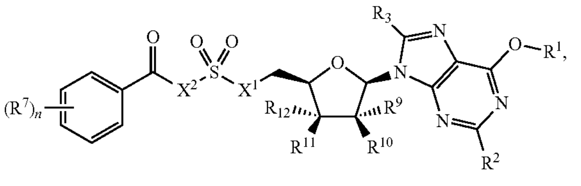

or a pharmaceutically acceptable salt, stereoisomer, or tautomer thereof, wherein:

each occurrence of $R^7$ is independently is halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, —$NO_2$, —CN, —$OR^e$, or —$N(R^e)_2$, or two $R^7$ are joined to form an optionally substituted aryl or optionally substituted heteroaryl ring; and n is 0, 1, 2, 3, 4, or 5.

In certain embodiments, there are no instances of $R^7$. In certain embodiments, there is a single instance of $R^7$. In certain embodiments, there are multiple instances of $R^7$. In certain embodiments, each instance of $R^1$ is independently selected, and all instances of $R^7$ are different. In certain embodiments, each instance of $R^7$ is independently selected, and some instances of $R^1$ are different. In certain embodiments, all instances of $R^7$ are the same.

In some embodiments, $R^7$ is —Cl, —Br, or —I. In some embodiments, $R^1$ is —F. In certain embodiments, $R^7$ is optionally substituted alkyl. In certain embodiments, $R^7$ is unsubstituted $C_{1-6}$ alkyl. In certain embodiments, $R^7$ is methyl. In certain embodiments, $R^7$ is ethyl, propyl, or butyl. In certain embodiments, $R^7$ is —$CF_3$. In certain embodiments, $R^1$ is optionally substituted alkenyl, e.g., optionally substituted $C_{2-6}$ alkenyl. In certain embodiments, $R^7$ is vinyl, allyl, or prenyl. In certain embodiments, $R^7$ is optionally substituted alkynyl, e.g., $C_{2-6}$ alkynyl.

In certain embodiments, $R^7$ is optionally substituted carbocyclyl, e.g., optionally substituted $C_{3-6}$ carbocyclyl, optionally substituted $C_{3-4}$ carbocyclyl, optionally substituted $C_{4-5}$ carbocyclyl, or optionally substituted $C_{5-6}$ carbocyclyl. In certain embodiments $R^7$ is optionally substituted heterocyclyl, e.g., optionally substituted 3-6 membered heterocyclyl, optionally substituted 3-4 membered heterocyclyl, optionally substituted 4-5 membered heterocyclyl, or optionally substituted 5-6 membered heterocyclyl.

In certain embodiments, $R^7$ is optionally substituted aryl, e.g., optionally substituted phenyl. In certain embodiments, $R^7$ is optionally substituted heteroaryl, e.g., optionally substituted 5-6 membered heteroaryl, or optionally substituted 9-10 membered bicyclic heteroaryl. In certain embodiments, $R^7$ is optionally substituted aralkyl, e.g., optionally substituted benzyl. In certain embodiments, $R^7$ is optionally substituted heteroaralkyl, e.g., methyl substituted with a 5-6-membered heteroaryl ring.

In certain embodiments, $R^7$ is —$NO_2$. In certain embodiments, $R^7$ is —CN. In certain embodiments, $R^7$ is —OR (e.g., —OH, —OMe, —O($C_{1-6}$ alkyl)). In certain embodiments, $R^7$ is —$OR^e$, and $R^e$ is an oxygen protecting group. In certain embodiments, $R^7$ is —$N(R^e)_2$ (e.g., —$NH_2$, —$NMe_2$, or —NH($C_{1-6}$ alkyl)). In certain embodiments, $R^7$ is —N($R^e$, and $R^e$ is a nitrogen protecting group. In certain embodiments, $R^7$ is optionally substituted acyl (e.g., —C(=O)($R^e$), —C(=O)O($R^e$), —C(=O)NH($R^e$), —C(=O)$N(R^e)_2$). In some embodiments, $R^7$ is —C(=O)OMe. In some embodiments, $R^7$ is —C(=O)OH.

In certain embodiments, n is 0. In some embodiments, n is 1. In certain embodiments, n is 2. In some embodiments, n is 3, 4, or 5.

In some embodiments, a compound is of one of the following formulae:

(III-A)

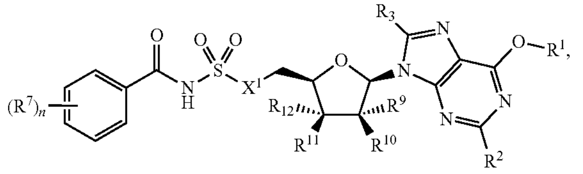

(III-B)

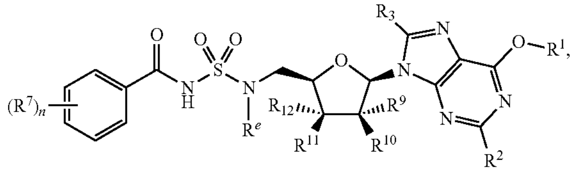

(III-C)

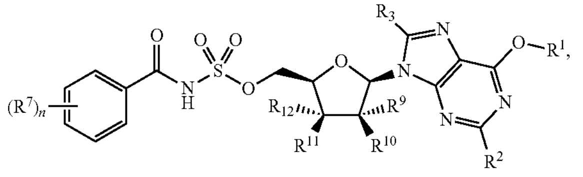

or a pharmaceutically acceptable salt, stereoisomer, or tautomer thereof.

In certain embodiments, a compound is of one of the following formulae:

(III-D)

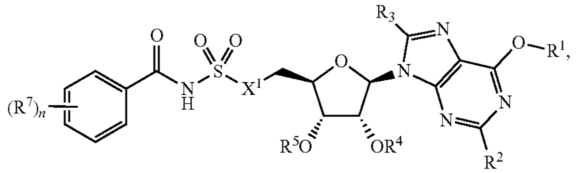

(III-E)

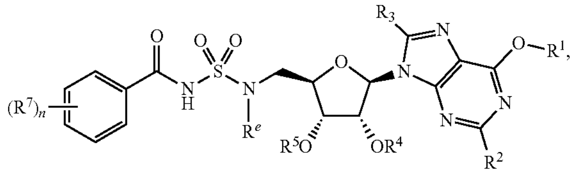

(III-F)

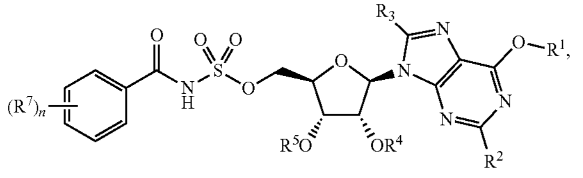

or a pharmaceutically acceptable salt, stereoisomer, or tautomer thereof.

In some aspects, the compound of Formula (I) is of Formula (IV):

(IV)

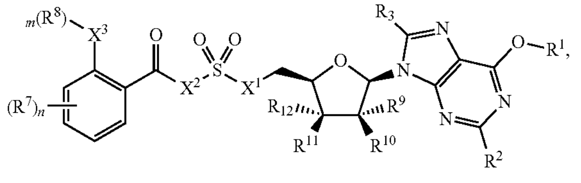

or a pharmaceutically acceptable salt, stereoisomer, or tautomer thereof, wherein:

- $X^1$ is a bond, —O—, —C—, —$(CH_2)_p$—, or —N—;
- each occurrence of $R^8$ is independently hydrogen, optionally substituted alkyl, optionally, optionally substituted carbocyclyl, optionally substituted heterocyclyl, optionally substituted aryl, optionally substituted heteroaryl, optionally substituted acyl, oxygen protecting group, or a nitrogen protecting group, or two $R^8$ are joined to form an optionally substituted carbocyclyl, optionally substituted heterocyclyl, optionally substituted aryl, or optionally substituted heteroaryl ring; and
- m is 1, 2, or 3.

In certain embodiments, $X^3$ is —O—. In some embodiments, $X^1$ is —C—. In certain embodiments, $X^3$ is —N—. In some embodiments, $X^3$ is —$(CH_2)_p$—. In certain embodiments, $X^3$ is —$CH_2$— where p is 1. In some embodiments, $X^1$ is —$(CH_2)_2$— where p is 2. In some embodiments, $X^3$ is —$(CH_2)_3$— where p is 3.

In some embodiments, p is 1, In certain embodiments, p is 2. In certain embodiments, p is 3.

In certain embodiments, there are no instances of $R^8$. In certain embodiments, there is a single instance of $R^8$. In certain embodiments, there are multiple instances of $R^8$. In certain embodiments, each instance of $R^8$ is independently selected, wherein all instances of $R^8$ are different. In certain embodiments, each instance of $R^8$ is independently selected, wherein some instances of $R^8$ are different. In certain embodiments, all instances of $R^8$ are the same.

In certain embodiments, at least one instance of $R^8$ is hydrogen. In certain embodiments, each instance of $R^8$ is hydrogen. In certain embodiments, $R^8$ is optionally substituted acyl (e.g., —C(═O)$CH_3$, —C(═O)$CH_2CH_3$, —C(═O)$CF_3$). In certain embodiments, at least one instance of $R^8$ is optionally substituted $C_1$-$C_6$ alkyl (e.g., optionally substituted methyl (e.g., trifluoromethyl), optionally substituted ethyl, optionally substituted propyl). In certain embodiments, $R^8$ is optionally substituted alkenyl (e.g., optionally substituted vinylene). In certain embodiments, $R^8$ is optionally substituted alkynyl (e.g., optionally substituted ethynyl). In certain embodiments, $R^8$ is optionally substituted $C_3$-$C_6$ carbocyclyl ring (e.g., cyclopropyl, cyclopentyl, cyclohexyl). In certain embodiments, $R^8$ is an optionally substituted $C_3$-$C_6$ heterocyclyl ring (e.g., piperidinyl, piperizinyl, morpholinyl, pyrrolidinyl). In certain embodiments, $R^8$ is an optionally substituted aryl (e.g., phenyl, naphthyl). In certain embodiments, $R^8$ is an optionally substituted heteroaryl (e.g., pyridinyl, pyrimidinyl, isoquinolinyl, thienopyrimidinyl). In certain embodiments, $R^8$ is a nitrogen protecting group, oxygen protecting group, or sulfur protecting group.

In certain embodiments, two $R^8$ groups are joined to form an optionally substituted carbocyclyl. In certain embodiments, two $R^8$ groups are joined to form an optionally substituted $C_3$-$C_6$ carbocyclyl (e.g., cyclopropyl, cyclobutyl, cyclopentyl, cyclohexyl). In certain embodiments, two $R^8$ groups are joined to form an optionally substituted heterocyclyl. In certain embodiments, two $R^8$ groups are joined to form an optionally substituted $C_3$-$C_6$ heterocyclyl (e.g., piperidinyl, piperizinyl, morpholinyl, pyrrolidinyl). In certain embodiments, two $R^8$ groups are joined to form an optionally substituted aryl. In certain embodiments, two $R^8$ groups are joined to form an optionally substituted aryl (e.g., phenyl, naphthyl). In certain embodiments, two $R^8$ groups are joined to form an optionally substituted heteroaryl ring. In certain embodiments, two $R^8$ groups form an optionally substituted pyridinyl. In certain embodiments, two $R^8$ groups form an optionally substituted pyrimidinyl. In certain embodiments, two $R^8$ groups form an optionally substituted isoquinolinyl. In certain embodiments, two $R^8$ groups form an optionally substituted thienopyrimidinyl.

In certain embodiments, m is 1. In some embodiments, m is 2. In certain embodiments m is 3.

In some embodiments, a compound is of one of the following formulae:

(IV-A)

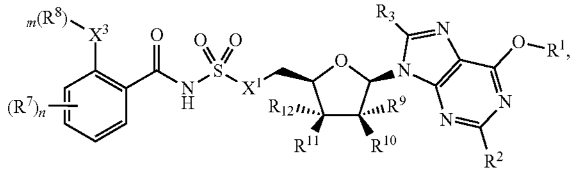

(IV-B)

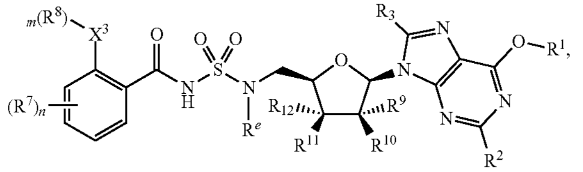

(IV-C)

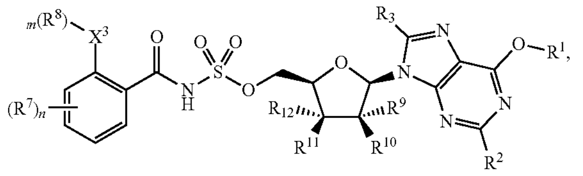

or a pharmaceutically acceptable salt, stereoisomer, or tautomer thereof.

In some embodiments, a compound is of one of the following formulae:

(IV-D)

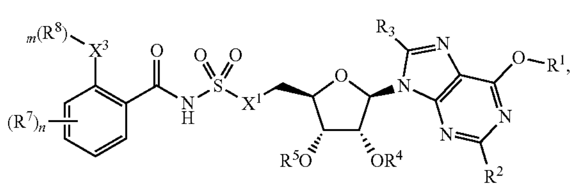

-continued (IV-E)

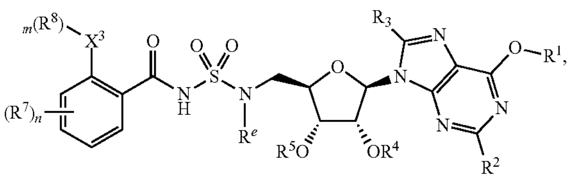

(IV-F)

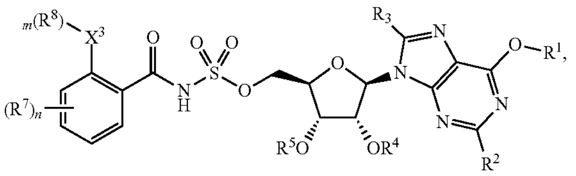

or a pharmaceutically acceptable salt, stereoisomer, or tautomer thereof.

In some embodiments, a compound is of one of the following formulae:

(IV-G)

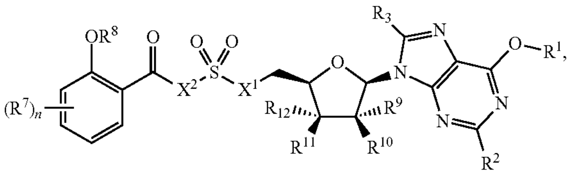

(IV-H)

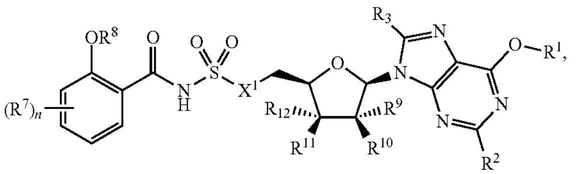

(IV-I)

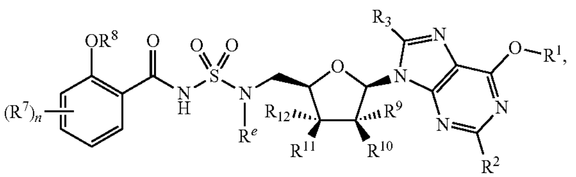

(IV-J)

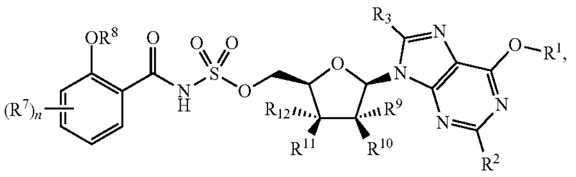

or a pharmaceutically acceptable salt, stereoisomer, or tautomer thereof.

In some embodiments, a compound is of one of the following formulae:

(IV-K)

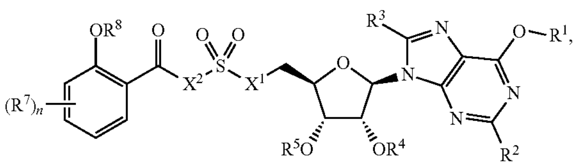

(IV-L)

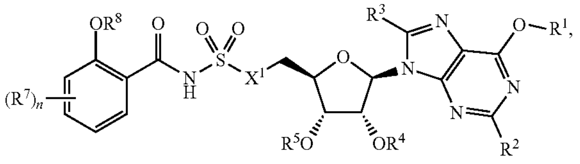

(IV-M)

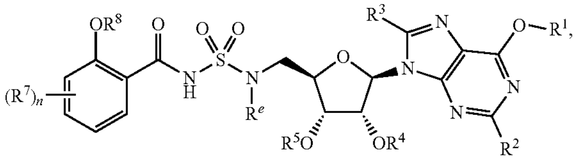

(IV-N)

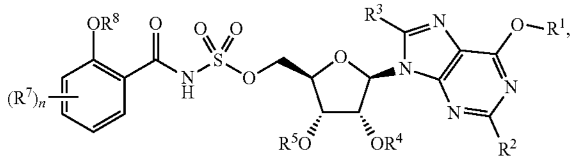

or a pharmaceutically acceptable salt, stereoisomer, or tautomer thereof.

In some embodiments, a compound is of one of the following formulae:

(IV-O)

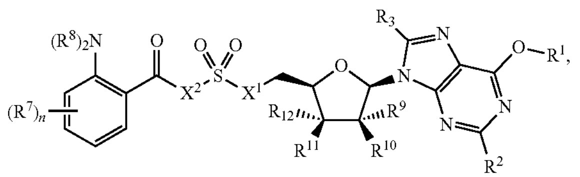

(IV-P)

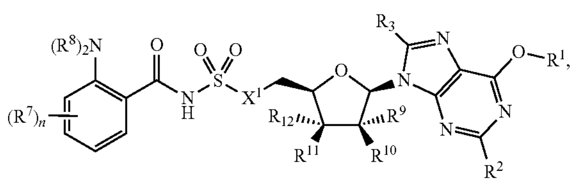

(IV-Q)

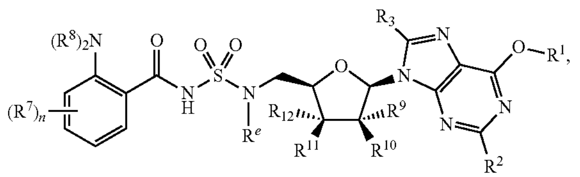

-continued (IV-R)

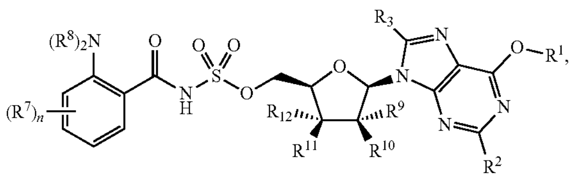

or a pharmaceutically acceptable salt, stereoisomer, or tautomer thereof.

In some embodiments, a compound is of one of the following formulae:

(IV-S)

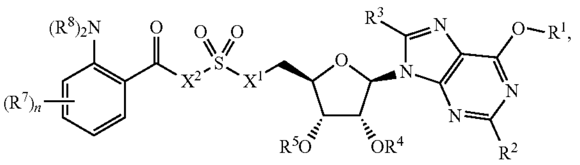

(IV-T)

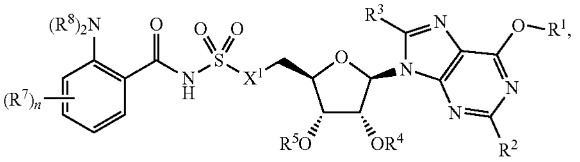

(IV-U)

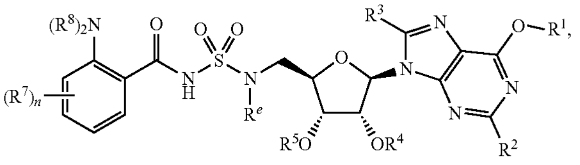

(IV-V)

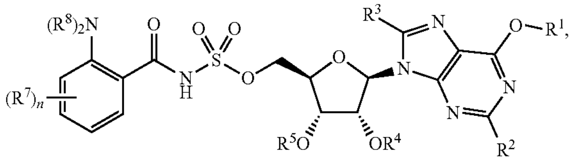

or a pharmaceutically acceptable salt, stereoisomer, or tautomer thereof.

In some embodiments, a compound is of the formula:

(V)

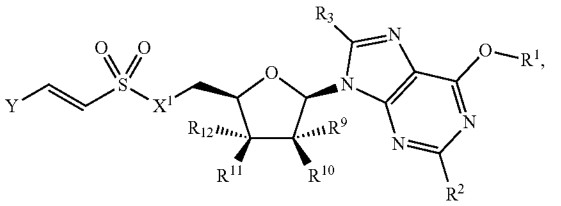

or a pharmaceutically acceptable salt, stereoisomer, or tautomer thereof.

In some embodiments, a compound is one of the following formulae:

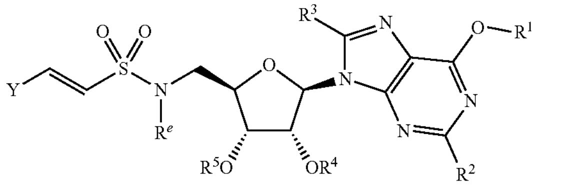

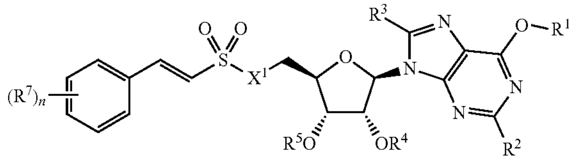

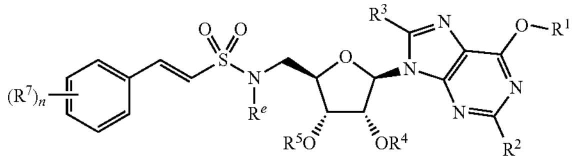

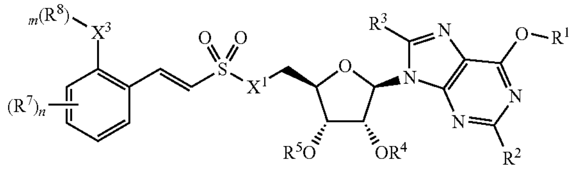

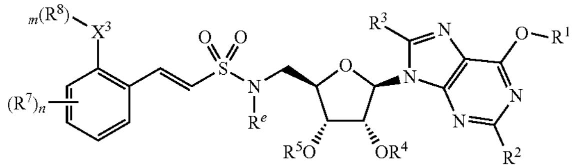

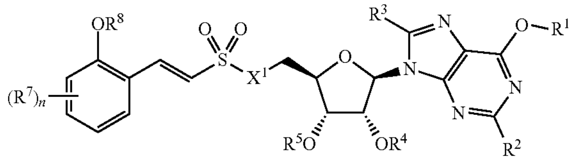

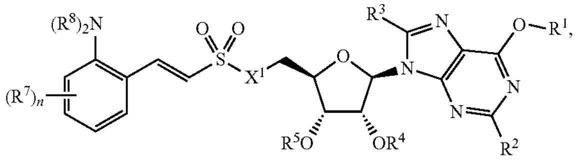

or a pharmaceutically acceptable salt, stereoisomer, or tautomer thereof.

In certain embodiments, a compound is of the formula:

(VI)

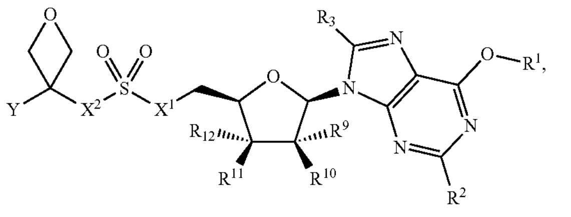

or a pharmaceutically acceptable salt, stereoisomer, or tautomer thereof.

In certain embodiments, a compound is one of the following formulae:

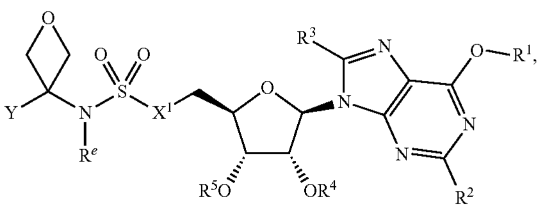
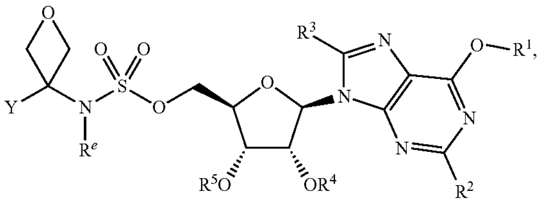
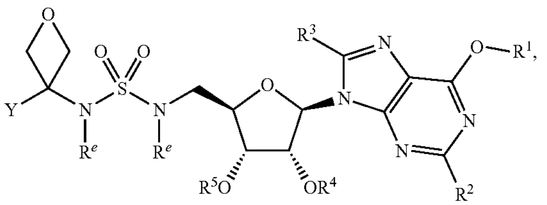
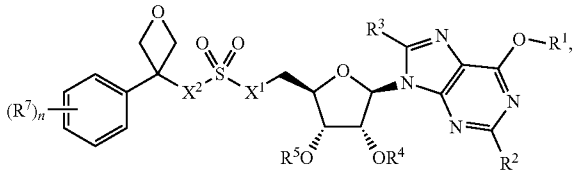
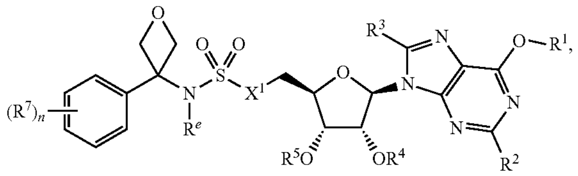
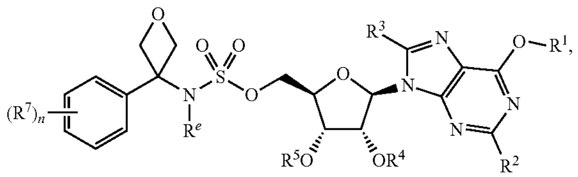
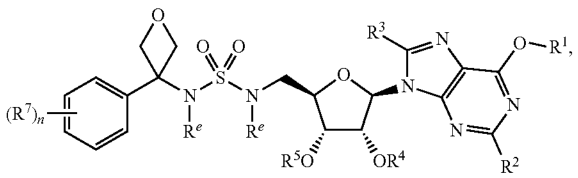
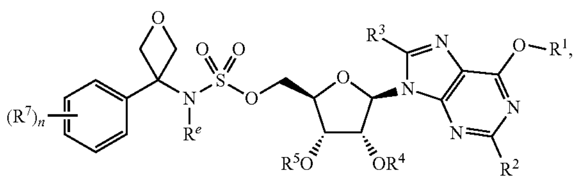
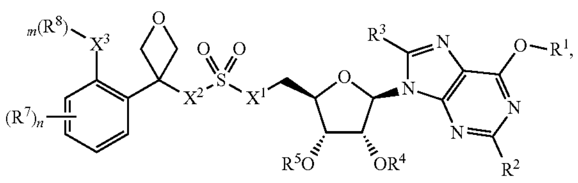
-continued
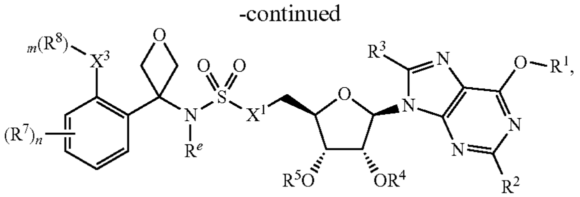
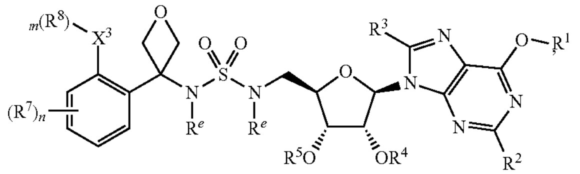
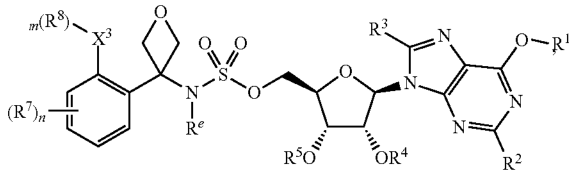
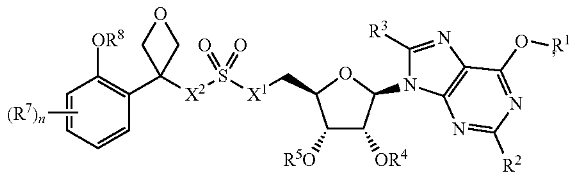
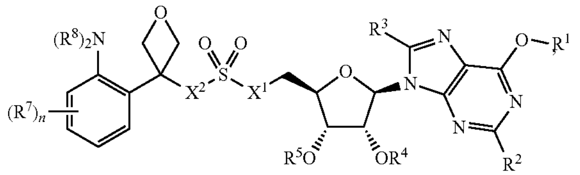
or a pharmaceutically acceptable salt, stereoisomer, or tautomer thereof.
In certain embodiments, the compound of Formula (I) is:
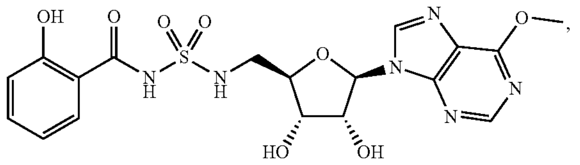
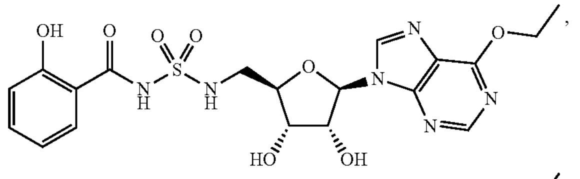
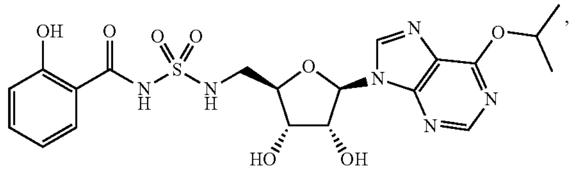
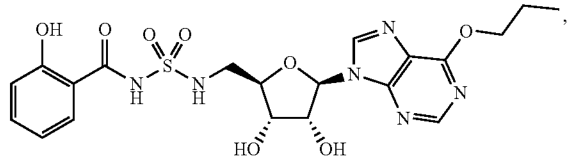

-continued
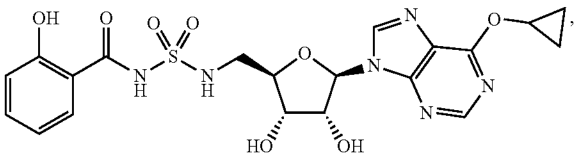,
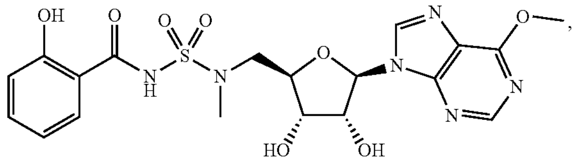,
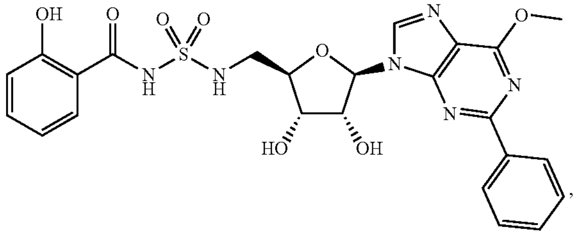,
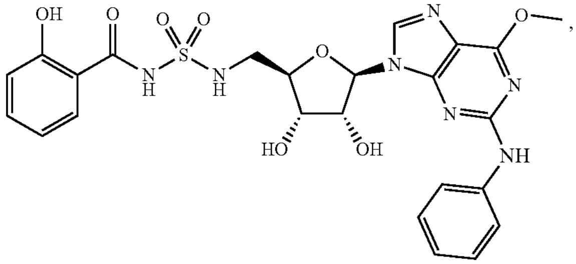,
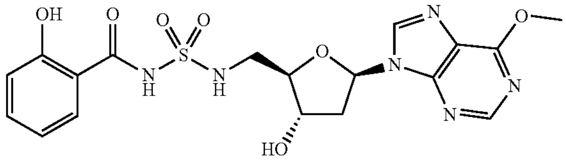,
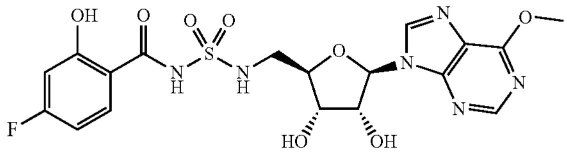,
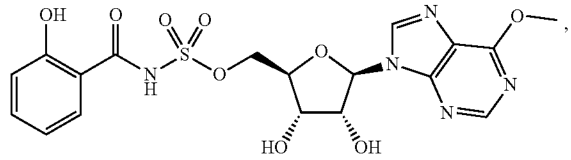,
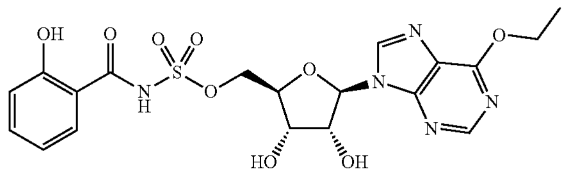,
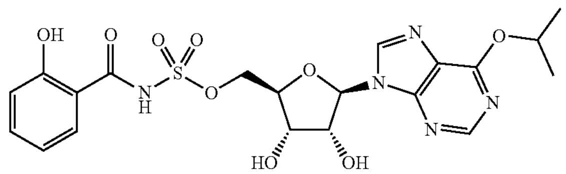,
-continued
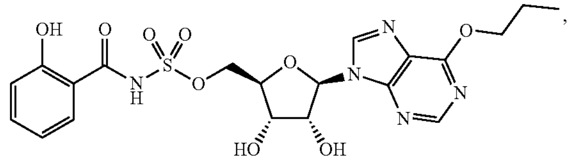,
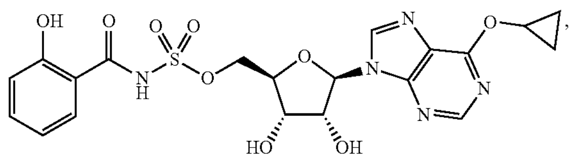,
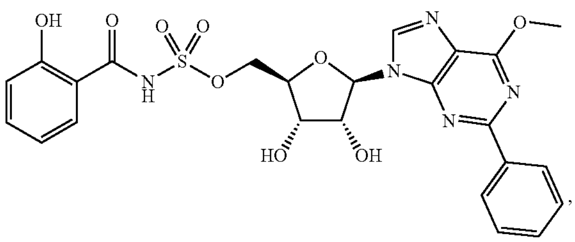,
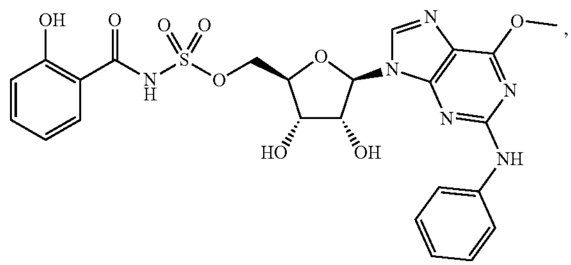,
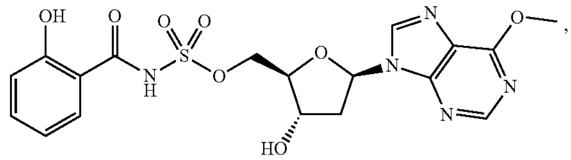,
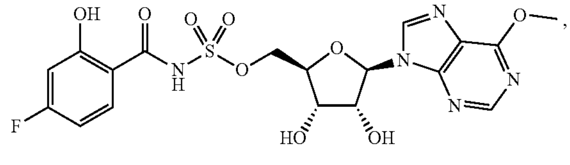,
or a pharmaceutically acceptable salt, stereoisomer, or tautomer thereof.
In certain embodiments, a compound of Formula (I) may contain the moieties expressed in Tables A, B, C, and D below. Non-limiting examples of moieties appear in Tables A to D.

TABLE A
| Exemplary Purine and Heterocycle Moieties |
| --- |
| 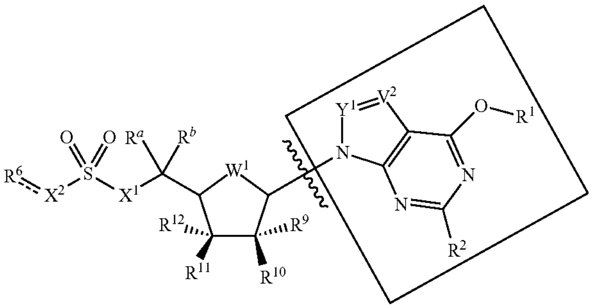 |
| 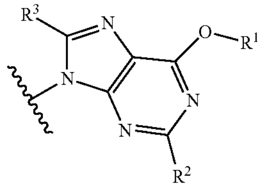 |
| 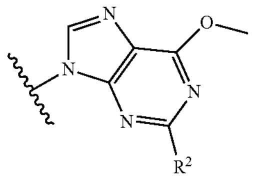 |
| 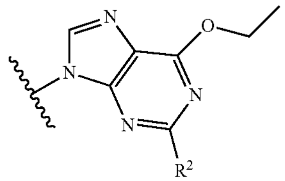 |
| 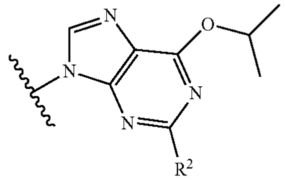 |
| 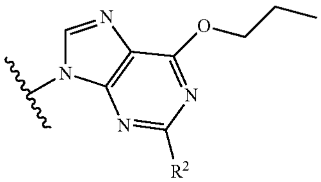 |
| 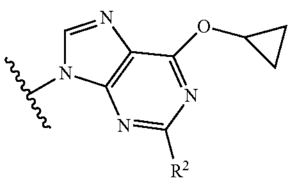 |
TABLE A-continued
| Exemplary Purine and Heterocycle Moieties |
| --- |
| 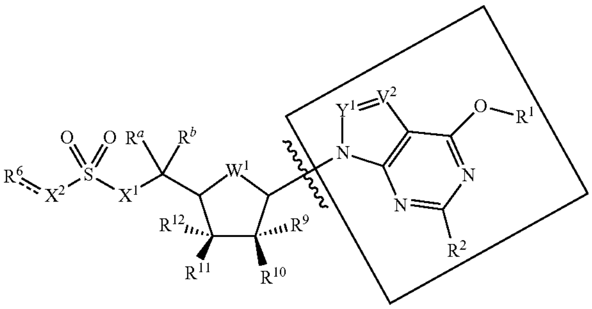 |
| 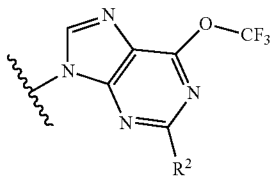 |
| 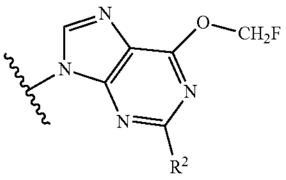 |
| 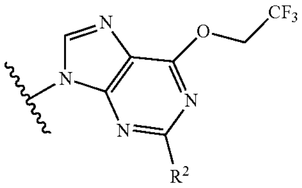 |
| 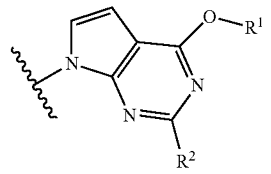 |
| 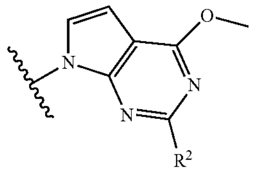 |
| 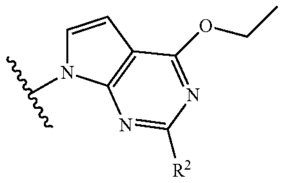 |

TABLE A-continued
Exemplary Purine and Heterocycle Moieties
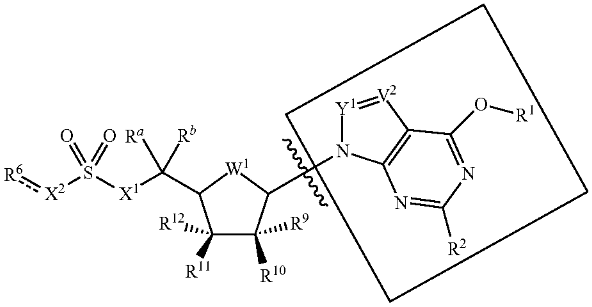
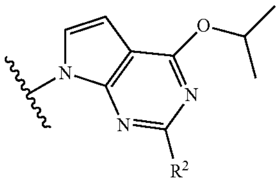
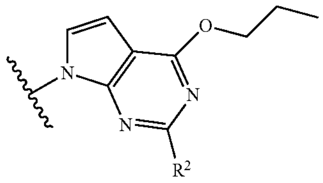
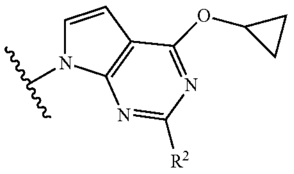
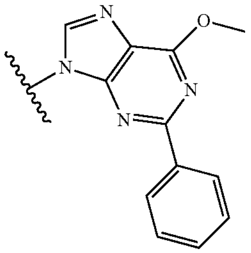 [SMILES: *n1cnc2c(OC)nc(-c3ccccc3)nc21]
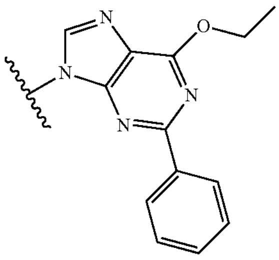 [SMILES: *n1cnc2c(OCC)nc(-c3ccccc3)nc21]
TABLE A-continued
Exemplary Purine and Heterocycle Moieties
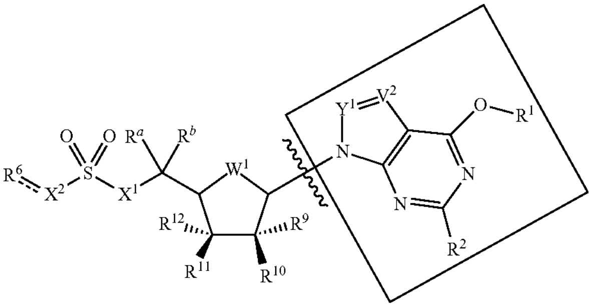
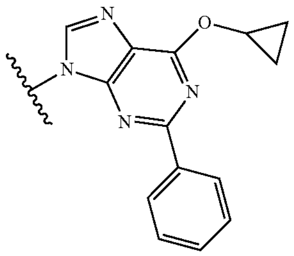 [SMILES: *n1cnc2c(OC3CC3)nc(-c3ccccc3)nc21]
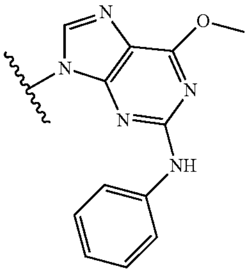 [SMILES: *n1cnc2c(OC)nc(Nc3ccccc3)nc21]
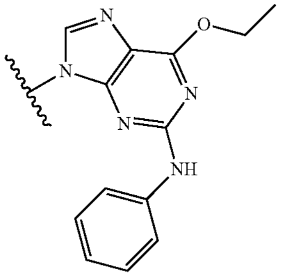 [SMILES: *n1cnc2c(OCC)nc(Nc3ccccc3)nc21]
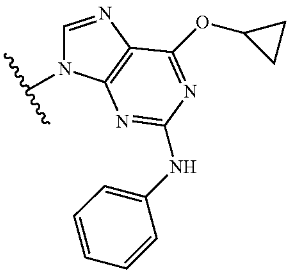 [SMILES: *n1cnc2c(OC3CC3)nc(Nc3ccccc3)nc21]

TABLE A-continued
Exemplary Purine and Heterocycle Moieties
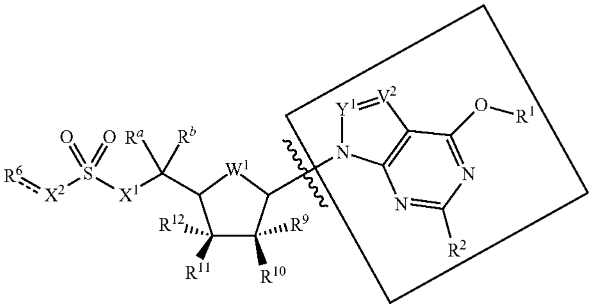
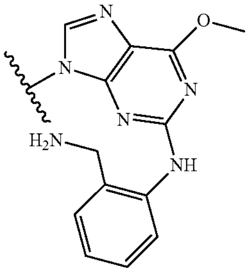 [SMILES: *n1cnc2c(OC)nc(Nc3ccccc3CN)nc21]
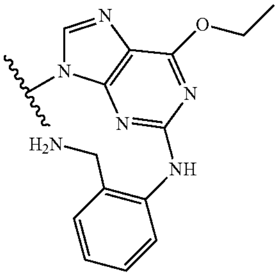 [SMILES: *n1cnc2c(OCC)nc(Nc3ccccc3CN)nc21]
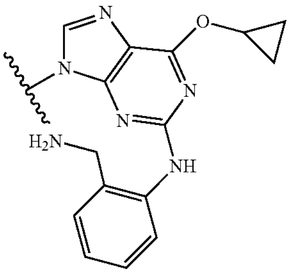 [SMILES: *n1cnc2c(OC3CC3)nc(Nc3ccccc3CN)nc21]
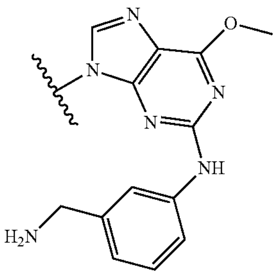 [SMILES: *n1cnc2c(OC)nc(Nc3cccc(CN)c3)nc21]
TABLE A-continued
Exemplary Purine and Heterocycle Moieties
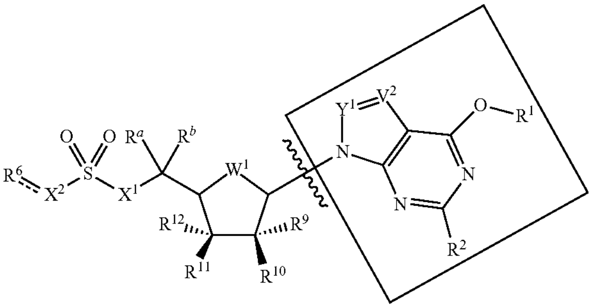
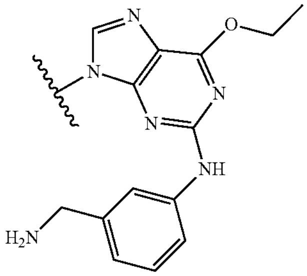 [SMILES: *n1cnc2c(OCC)nc(Nc3cccc(CN)c3)nc21]
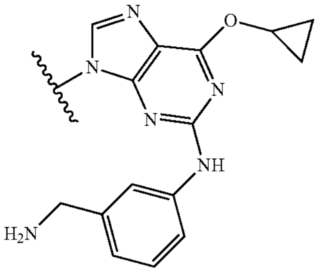 [SMILES: *n1cnc2c(OC3CC3)nc(Nc3cccc(CN)c3)nc21]
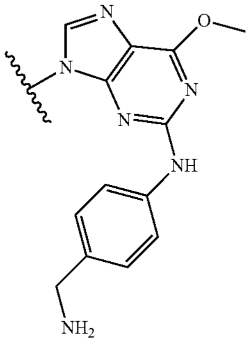 [SMILES: *n1cnc2c(OC)nc(Nc3ccc(CN)cc3)nc21]
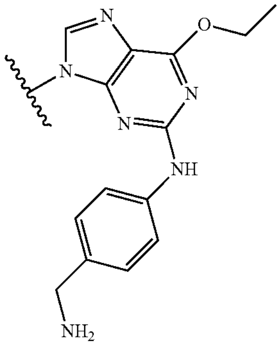 [SMILES: *n1cnc2c(OCC)nc(Nc3ccc(CN)cc3)nc21]

TABLE A-continued
Exemplary Purine and Heterocycle Moieties
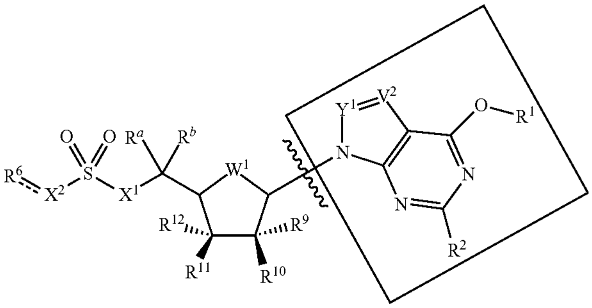
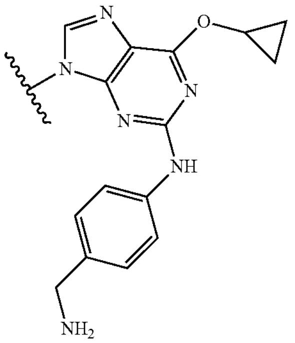 [SMILES: *n1cnc2c(OC3CC3)nc(Nc3ccc(CN)cc3)nc21]
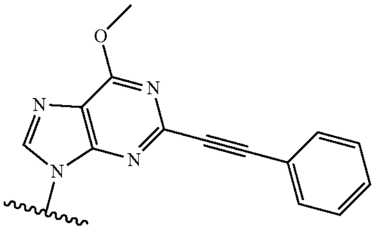 [SMILES: *n1cnc2c(OC)nc(C#Cc3ccccc3)nc21]
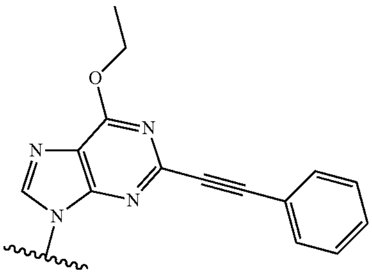 [SMILES: *n1cnc2c(OCC)nc(C#Cc3ccccc3)nc21]
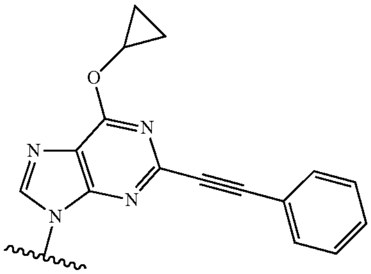 [SMILES: *n1cnc2c(OC3CC3)nc(C#Cc3ccccc3)nc21]
TABLE B
Exemplary Ribose and Heterocyclic Moieties
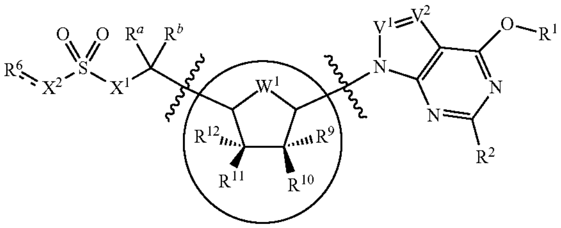
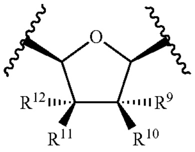
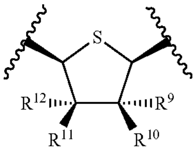
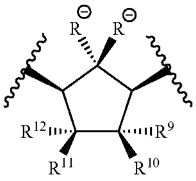
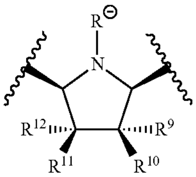
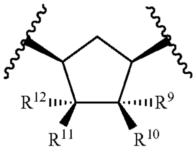
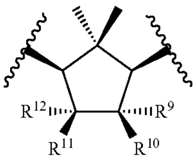
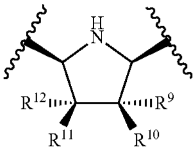

TABLE B-continued
| Exemplary Ribose and Heterocyclic Moieties |
|---|
| 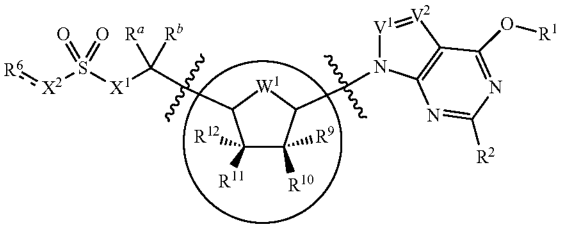 |
| 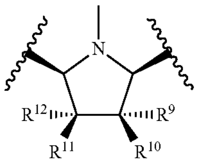 |
| 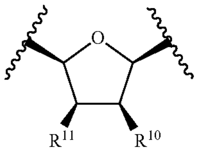 |
| 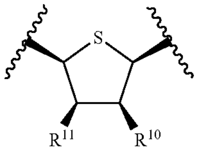 |
| 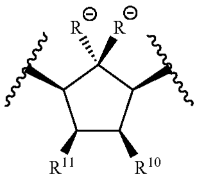 |
| 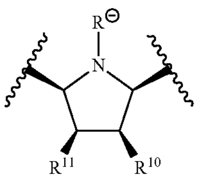 |
| 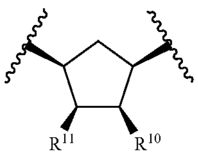 |
| 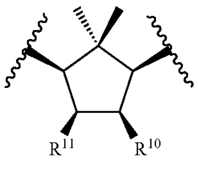 |
TABLE B-continued
| Exemplary Ribose and Heterocyclic Moieties |
|---|
| 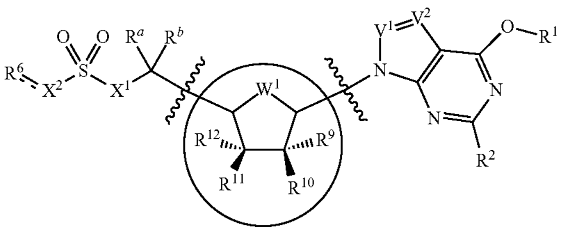 |
| 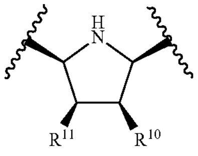 |
| 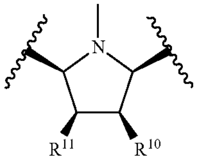 |
| 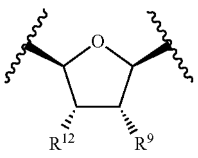 |
| 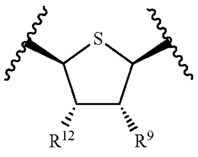 |
| 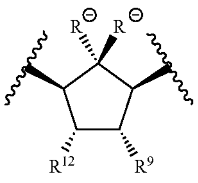 |
| 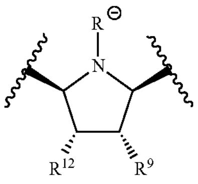 |
| 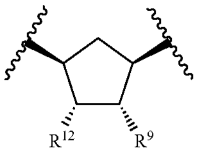 |

TABLE B-continued
Exemplary Ribose and Heterocyclic Moieties
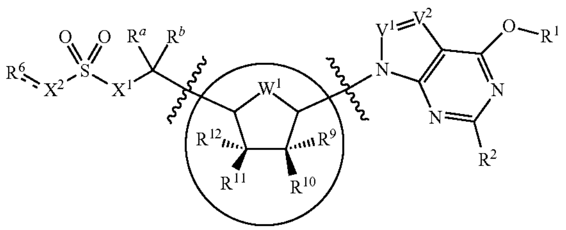
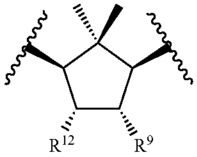
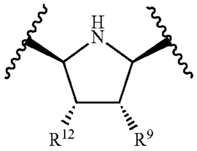
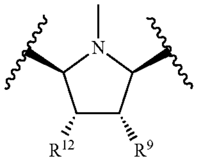
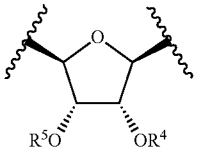
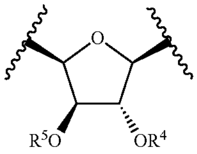
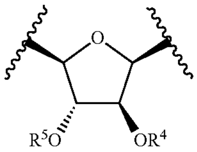
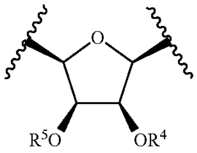
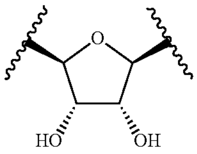 [SMILES: *[C@@H]1O[C@H](*)[C@@H](O)[C@H]1O]
TABLE B-continued
Exemplary Ribose and Heterocyclic Moieties
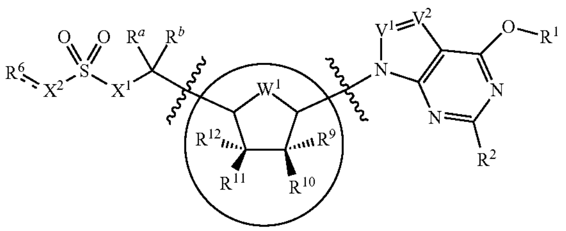
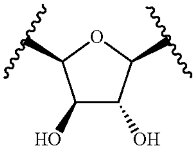 [SMILES: *[C@@H]1O[C@H](*)[C@H](O)[C@H]1O]
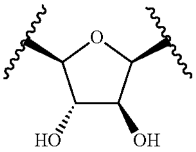 [SMILES: *[C@@H]1O[C@H](*)[C@@H](O)[C@@H]1O]
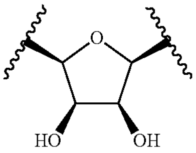 [SMILES: *[C@@H]1O[C@H](*)[C@H](O)[C@@H]1O]
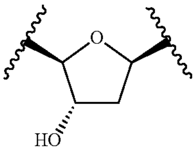 [SMILES: *[C@H]1C[C@H](O)[C@@H](*)O1]
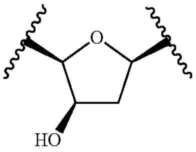 [SMILES: *[C@H]1C[C@@H](O)[C@@H](*)O1]
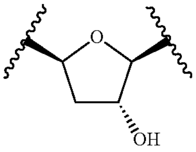 [SMILES: *[C@@H]1C[C@@H](O)[C@H](*)O1]
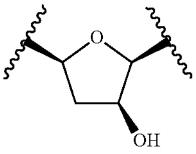 [SMILES: *[C@@H]1C[C@H](O)[C@H](*)O1]
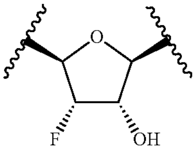 [SMILES: *[C@@H]1O[C@H](*)[C@@H](F)[C@H]1O]

TABLE B-continued
| Exemplary Ribose and Heterocyclic Moieties |
| --- |
| 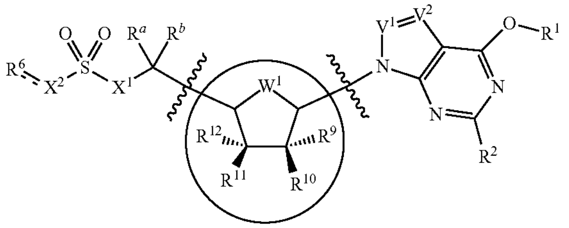 |
| 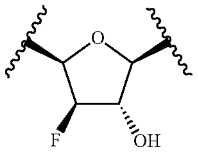 [SMILES: *[C@@H]1O[C@H](*)[C@H](F)[C@H]1O] |
| 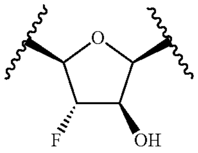 [SMILES: *[C@@H]1O[C@H](*)[C@@H](F)[C@@H]1O] |
| 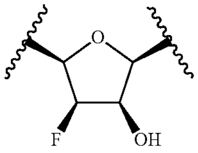 [SMILES: *[C@@H]1O[C@H](*)[C@H](F)[C@@H]1O] |
| 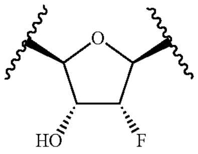 [SMILES: *[C@@H]1O[C@H](*)[C@@H](O)[C@H]1F] |
| 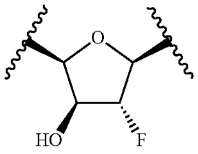 [SMILES: *[C@@H]1O[C@H](*)[C@H](O)[C@H]1F] |
| 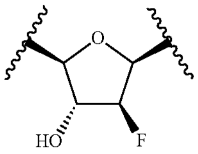 [SMILES: *[C@@H]1O[C@H](*)[C@@H](O)[C@@H]1F] |
| 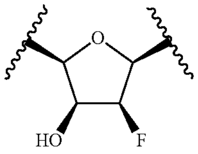 [SMILES: *[C@@H]1O[C@H](*)[C@H](O)[C@@H]1F] |
| 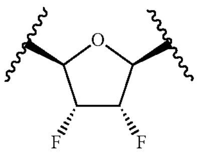 [SMILES: *[C@@H]1O[C@H](*)[C@@H](F)[C@H]1F] |
TABLE B-continued
| Exemplary Ribose and Heterocyclic Moieties |
| --- |
| 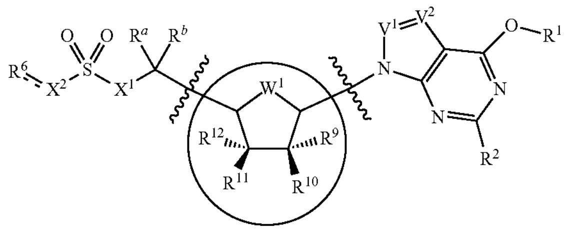 |
| 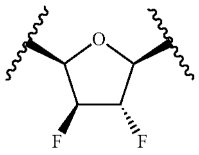 [SMILES: *[C@@H]1O[C@H](*)[C@H](F)[C@H]1F] |
| 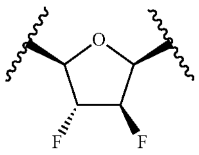 [SMILES: *[C@@H]1O[C@H](*)[C@@H](F)[C@@H]1F] |
| 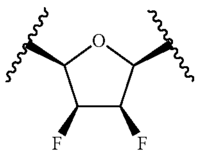 [SMILES: *[C@@H]1O[C@H](*)[C@H](F)[C@@H]1F] |
| 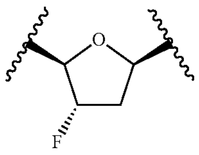 [SMILES: *[C@H]1C[C@H](F)[C@@H](*)O1] |
| 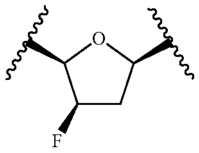 [SMILES: *[C@H]1C[C@@H](F)[C@@H](*)O1] |
| 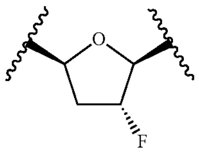 [SMILES: *[C@@H]1C[C@@H](F)[C@H](*)O1] |
| 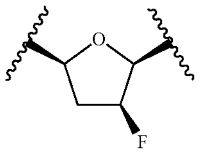 [SMILES: *[C@@H]1C[C@H](F)[C@H](*)O1] |

TABLE B-continued
| Exemplary Ribose and Heterocyclic Moieties |
| --- |
| 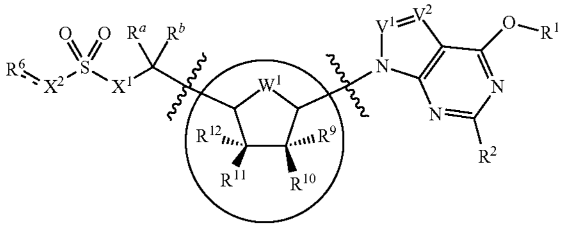 |
| 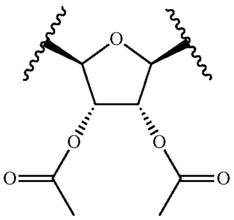 [SMILES: *[C@@H]1O[C@H](*)[C@@H](OC(C)=O)[C@H]1OC(C)=O] |
| 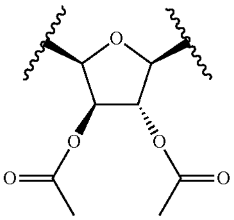 [SMILES: *[C@@H]1O[C@H](*)[C@H](OC(C)=O)[C@H]1OC(C)=O] |
| 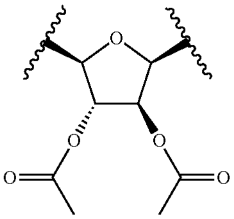 [SMILES: *[C@@H]1O[C@H](*)[C@@H](OC(C)=O)[C@@H]1OC(C)=O] |
| 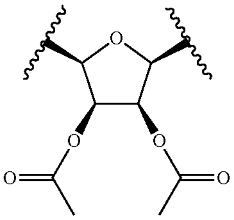 [SMILES: *[C@@H]1O[C@H](*)[C@H](OC(C)=O)[C@@H]1OC(C)=O] |
| 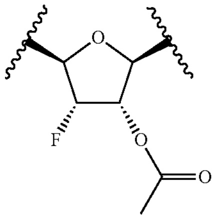 [SMILES: *[C@@H]1O[C@H](*)[C@@H](F)[C@H]1OC(C)=O] |
| 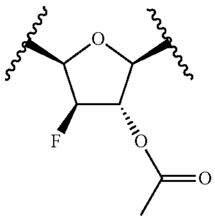 [SMILES: *[C@@H]1O[C@H](*)[C@H](F)[C@H]1OC(C)=O] |
TABLE B-continued
| Exemplary Ribose and Heterocyclic Moieties |
| --- |
| 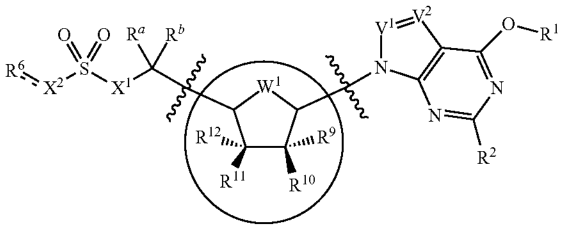 |
| 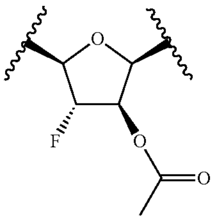 [SMILES: *[C@@H]1O[C@H](*)[C@@H](F)[C@@H]1OC(C)=O] |
| 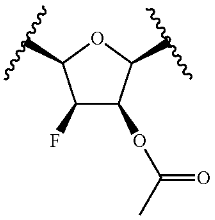 [SMILES: *[C@@H]1O[C@H](*)[C@H](F)[C@@H]1OC(C)=O] |
| 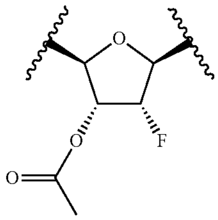 [SMILES: *[C@@H]1O[C@H](*)[C@@H](OC(C)=O)[C@H]1F] |
| 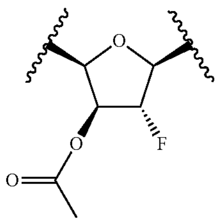 [SMILES: *[C@@H]1O[C@H](*)[C@H](OC(C)=O)[C@H]1F] |
| 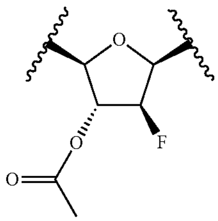 [SMILES: *[C@@H]1O[C@H](*)[C@@H](OC(C)=O)[C@@H]1F] |

TABLE B-continued
| Exemplary Ribose and Heterocyclic Moieties |
|---|
| 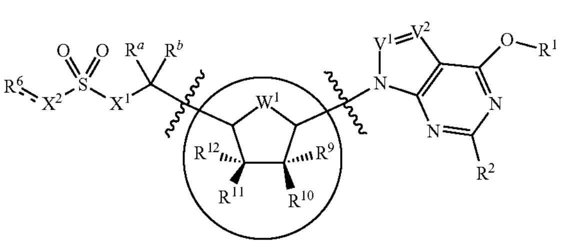 |
| 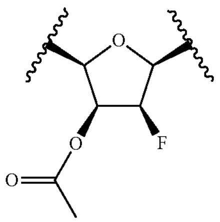 [SMILES: *[C@@H]1O[C@H](*)[C@H](OC(C)=O)[C@@H]1F] |
| 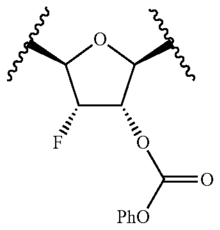 [SMILES: *[C@@H]1O[C@H](*)[C@@H](F)[C@H]1OC(=O)Oc1ccccc1] |
| 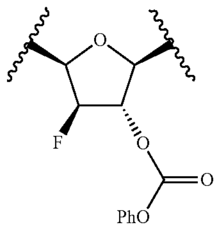 [SMILES: *[C@@H]1O[C@H](*)[C@H](F)[C@H]1OC(=O)Oc1ccccc1] |
| 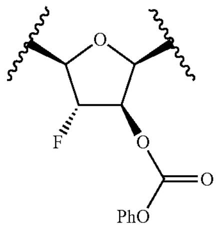 [SMILES: *[C@@H]1O[C@H](*)[C@@H](F)[C@@H]1OC(=O)Oc1ccccc1] |
| 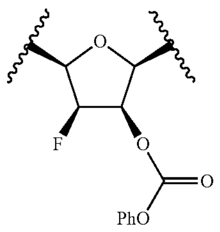 [SMILES: *[C@@H]1O[C@H](*)[C@H](F)[C@@H]1OC(=O)Oc1ccccc1] |
TABLE B-continued
| Exemplary Ribose and Heterocyclic Moieties |
|---|
| 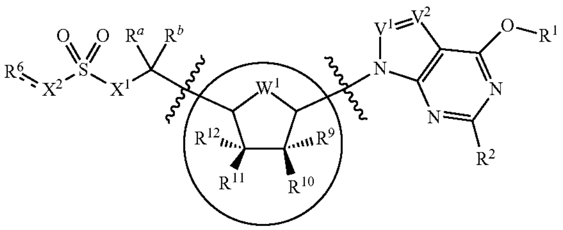 |
| 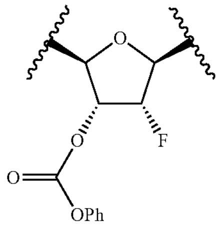 [SMILES: *[C@@H]1O[C@H](*)[C@@H](OC(=O)Oc2ccccc2)[C@H]1F] |
| 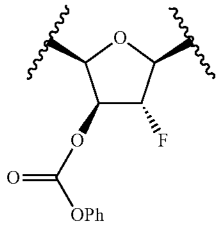 [SMILES: *[C@@H]1O[C@H](*)[C@H](OC(=O)Oc2ccccc2)[C@H]1F] |
| 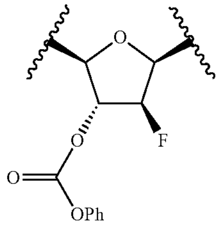 [SMILES: *[C@@H]1O[C@H](*)[C@@H](OC(=O)Oc2ccccc2)[C@@H]1F] |
| 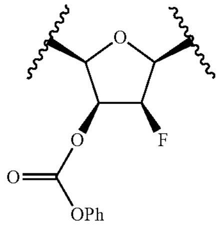 [SMILES: *[C@@H]1O[C@H](*)[C@H](OC(=O)Oc2ccccc2)[C@@H]1F] |
| 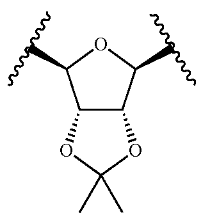 [SMILES: *[C@@H]1O[C@H](*)[C@H]2OC(C)(C)O[C@H]21] |

TABLE B-continued
| Exemplary Ribose and Heterocyclic Moieties |
| --- |
| 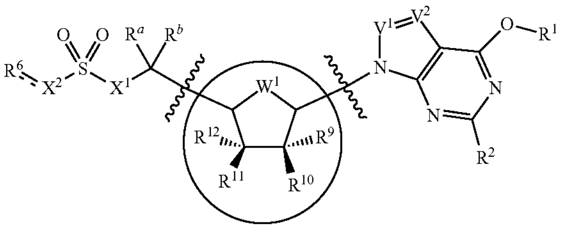 |
| 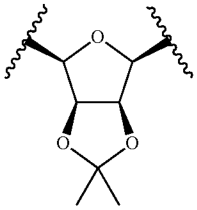 [SMILES: *[C@@H]1O[C@H](*)[C@@H]2OC(C)(C)O[C@@H]21] |
| 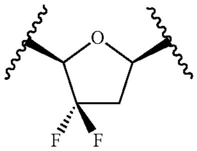 |
| 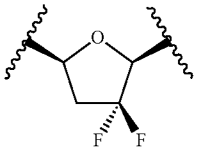 |
| 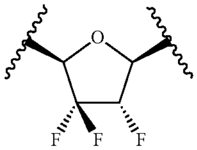 |
| 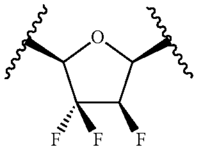 |
| 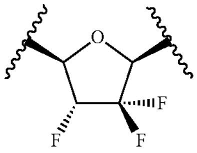 |
| 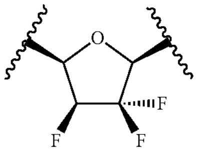 |
TABLE C
| Exemplary Linker Moieties |
| --- |
| 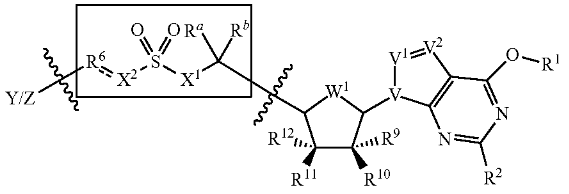 |
| 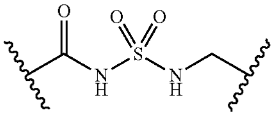 [SMILES: *CNS(=O)(=O)NC(*)=O] |
| 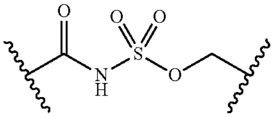 [SMILES: *COS(=O)(=O)NC(*)=O] |
| 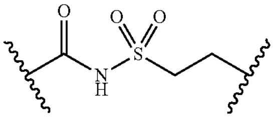 [SMILES: *CCS(=O)(=O)NC(*)=O] |
| 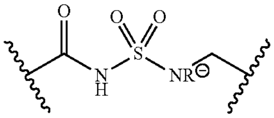 |
| 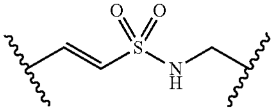 [SMILES: */C=C/S(=O)(=O)NC*] |
| 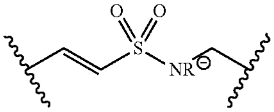 |
| 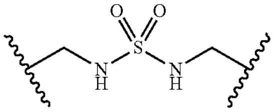 [SMILES: *CNS(=O)(=O)NC*] |
| 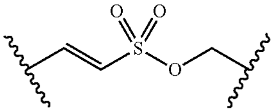 [SMILES: */C=C/S(=O)(=O)OC*] |
| 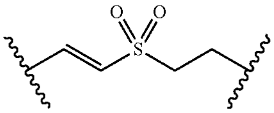 [SMILES: */C=C/S(=O)(=O)CC*] |
| 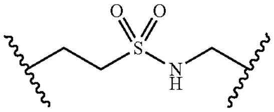 [SMILES: *CCS(=O)(=O)NC*]

TABLE C-continued
| Exemplary Linker Moieties |
|---|
| 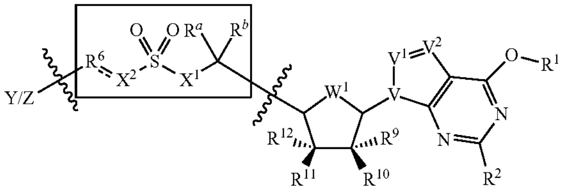 |
| 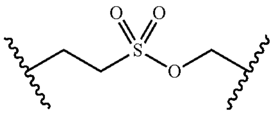 [SMILES: *CCS(=O)(=O)OC*] |
| 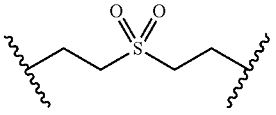 [SMILES: *CCS(=O)(=O)CC*] |
| 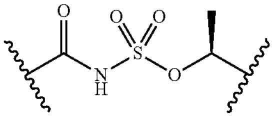 [SMILES: *C(=O)NS(=O)(=O)O[C@H](*)C] |
| 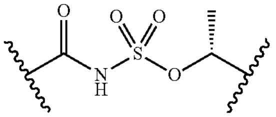 [SMILES: *C(=O)NS(=O)(=O)O[C@@H](*)C] |
| 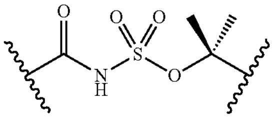 |
| 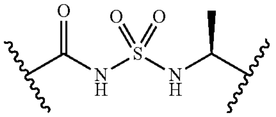 [SMILES: *C(=O)NS(=O)(=O)N[C@H](*)C] |
| 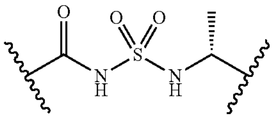 [SMILES: *C(=O)NS(=O)(=O)N[C@@H](*)C] |
| 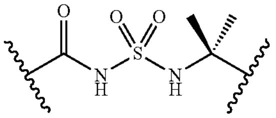 |
| 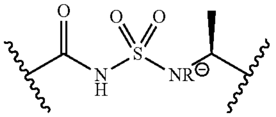 |
| 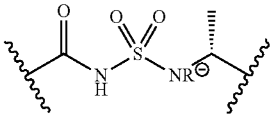 |
TABLE C-continued
| Exemplary Linker Moieties |
|---|
| 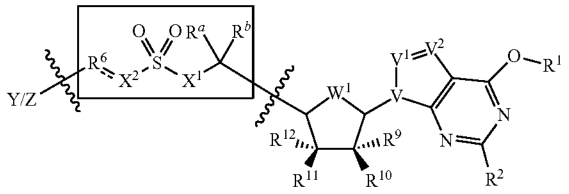 |
| 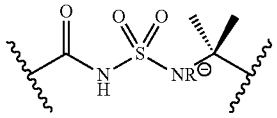 |
| 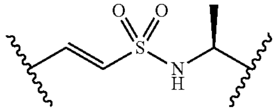 [SMILES: */C=C/S(=O)(=O)N[C@H](*)C] |
| 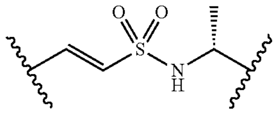 [SMILES: */C=C/S(=O)(=O)N[C@@H](*)C] |
| 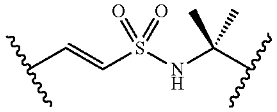 |
| 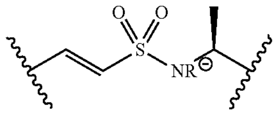 |
| 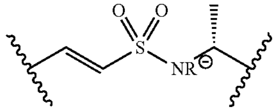 |
| 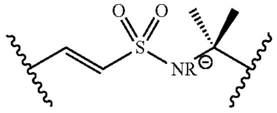 |
| 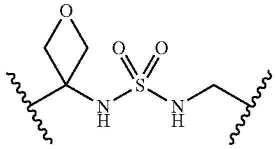 [SMILES: *CNS(=O)(=O)NC1(*)COC1] |
| 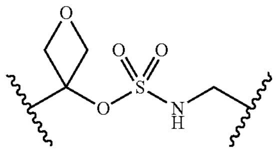 [SMILES: *CNS(=O)(=O)OC1(*)COC1] |
| 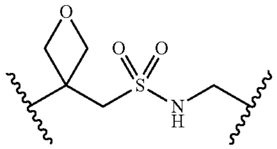 [SMILES: *CNS(=O)(=O)CC1(*)COC1] |

TABLE C-continued
| Exemplary Linker Moieties |
|---|
| 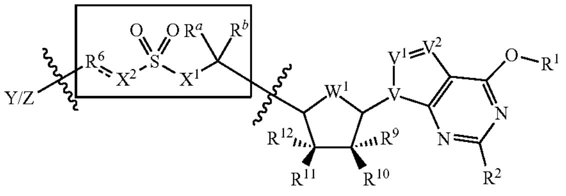 |
| 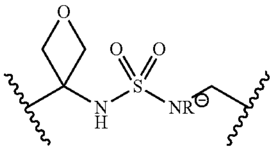 |
| 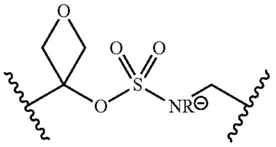 |
| 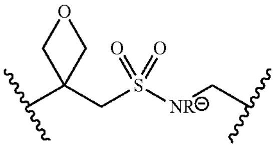 |
| 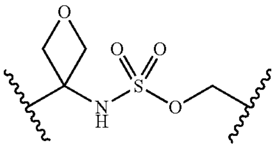 [SMILES: *COS(=O)(=O)NC1(*)COC1] |
| 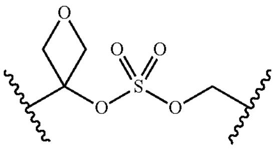 [SMILES: *COS(=O)(=O)OC1(*)COC1] |
| 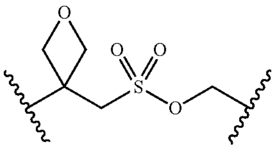 [SMILES: *COS(=O)(=O)CC1(*)COC1] |
| 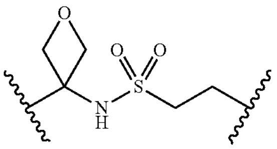 [SMILES: *CCS(=O)(=O)NC1(*)COC1] |
| 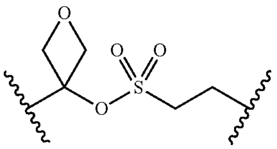 [SMILES: *CCS(=O)(=O)OC1(*)COC1] |
TABLE C-continued
| Exemplary Linker Moieties |
|---|
| 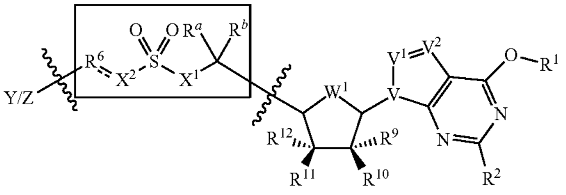 |
| 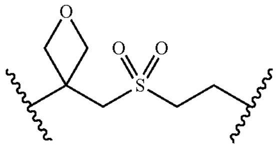 [SMILES: *CCS(=O)(=O)CC1(*)COC1] |
| 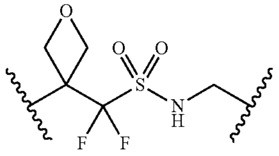 [SMILES: *CNS(=O)(=O)C(F)(F)C1(*)COC1] |
| 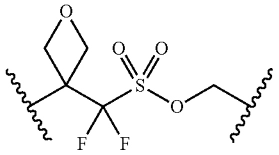 [SMILES: *COS(=O)(=O)C(F)(F)C1(*)COC1] |
| 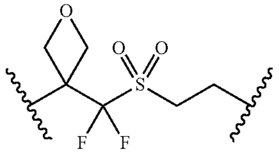 [SMILES: *CCS(=O)(=O)C(F)(F)C1(*)COC1] |
| 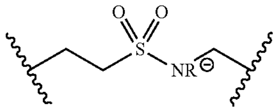 |
| 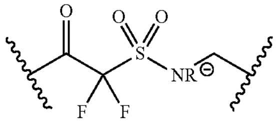 |
| 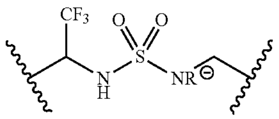 |
| 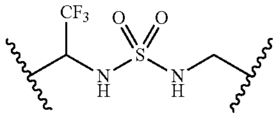 [SMILES: *CNS(=O)(=O)NC(*)C(F)(F)F] |
| 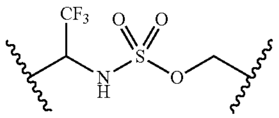 [SMILES: *COS(=O)(=O)NC(*)C(F)(F)F] |

TABLE C-continued
Exemplary Linker Moieties
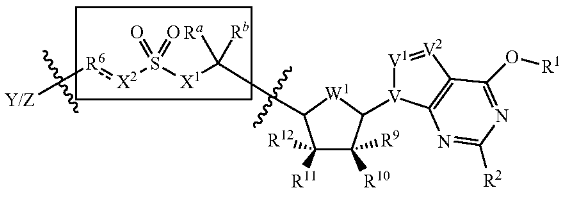
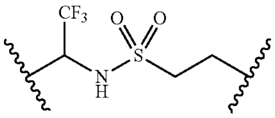 [SMILES: *CCS(=O)(=O)NC(*)C(F)(F)F]
TABLE D
Exemplary R[6] Moieties
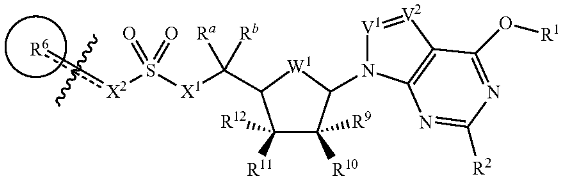
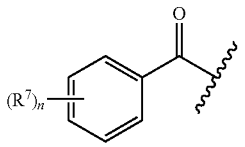
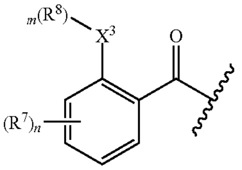
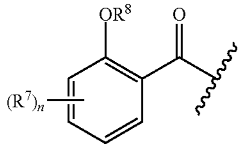
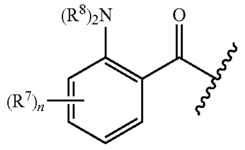
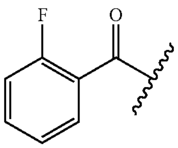 [SMILES: *C(=O)c1ccccc1F]
TABLE D-continued
Exemplary R[6] Moieties
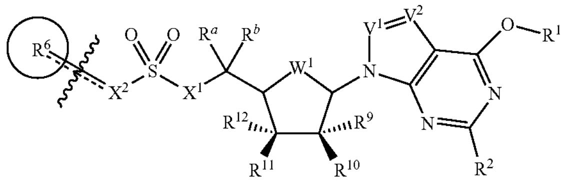
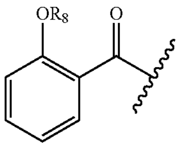
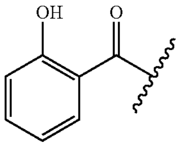 [SMILES: *C(=O)c1ccccc1O]
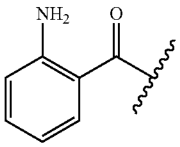 [SMILES: *C(=O)c1ccccc1N]
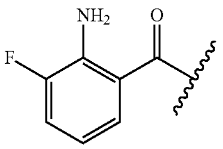 [SMILES: *C(=O)c1cccc(F)c1N]
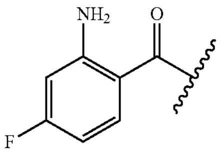 [SMILES: *C(=O)c1ccc(F)cc1N]
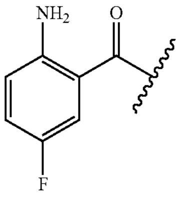 [SMILES: *C(=O)c1cc(F)ccc1N]
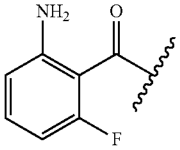 [SMILES: *C(=O)c1c(N)cccc1F]
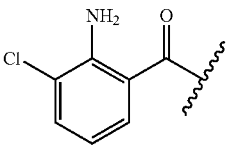 [SMILES: *C(=O)c1cccc(Cl)c1N]

TABLE D-continued
| Exemplary $R^6$ Moieties |
|---|
| 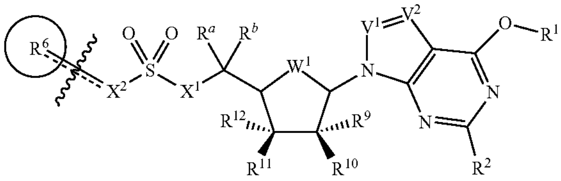 |
| 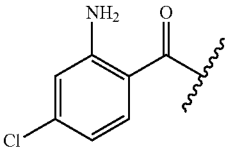 [SMILES: *C(=O)c1ccc(Cl)cc1N] |
| 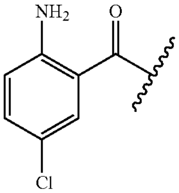 [SMILES: *C(=O)c1cc(Cl)ccc1N] |
| 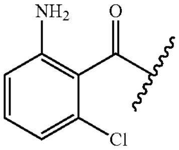 [SMILES: *C(=O)c1c(N)cccc1Cl] |
| 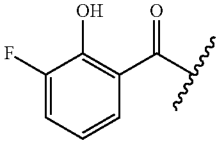 [SMILES: *C(=O)c1cccc(F)c1O] |
| 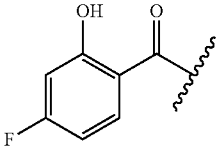 [SMILES: *C(=O)c1ccc(F)cc1O] |
| 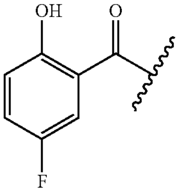 [SMILES: *C(=O)c1cc(F)ccc1O] |
| 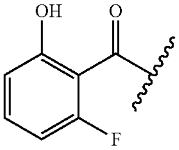 [SMILES: *C(=O)c1c(O)cccc1F] |
| 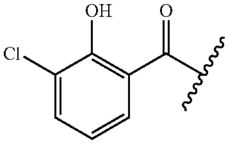 [SMILES: *C(=O)c1cccc(Cl)c1O] |
TABLE D-continued
| Exemplary $R^6$ Moieties |
|---|
| 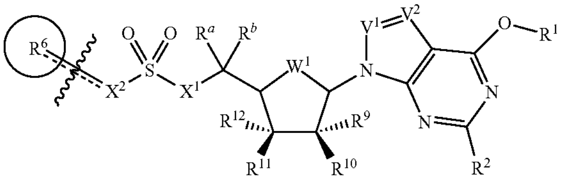 |
| 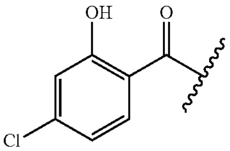 [SMILES: *C(=O)c1ccc(Cl)cc1O] |
| 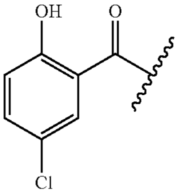 [SMILES: *C(=O)c1cc(Cl)ccc1O] |
| 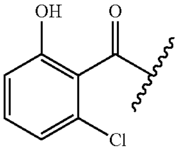 [SMILES: *C(=O)c1c(O)cccc1Cl] |
| 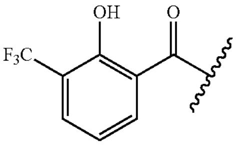 [SMILES: *C(=O)c1cccc(C(F)(F)F)c1O] |
| 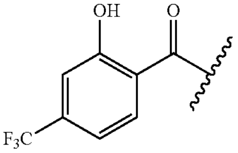 |
| 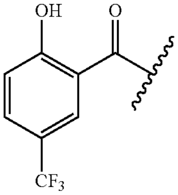 [SMILES: *C(=O)c1cc(C(F)(F)F)ccc1O] |
| 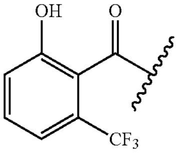 [SMILES: *C(=O)c1c(O)cccc1C(F)(F)F] |
| 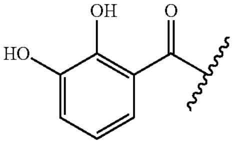 [SMILES: *C(=O)c1cccc(O)c1O] |

TABLE D-continued
Exemplary $R^6$ Moieties
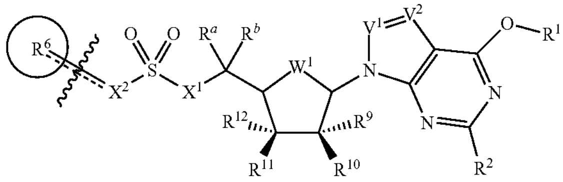
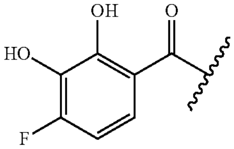 [SMILES: *C(=O)c1ccc(F)c(O)c1O]
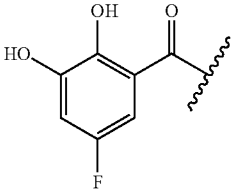 [SMILES: *C(=O)c1cc(F)cc(O)c1O]
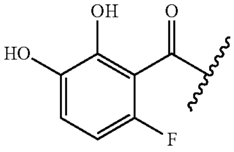 [SMILES: *C(=O)c1c(F)ccc(O)c1O]
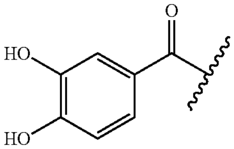 [SMILES: *C(=O)c1ccc(O)c(O)c1]
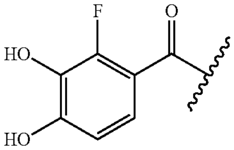 [SMILES: *C(=O)c1ccc(O)c(O)c1F]
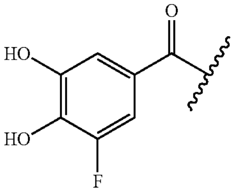 [SMILES: *C(=O)c1cc(O)c(O)c(F)c1]
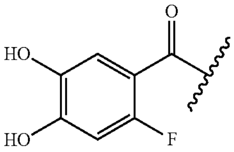 [SMILES: *C(=O)c1cc(O)c(O)cc1F]
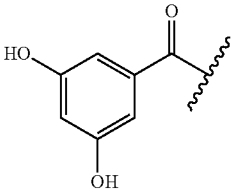 [SMILES: *C(=O)c1cc(O)cc(O)c1]
TABLE D-continued
Exemplary $R^6$ Moieties
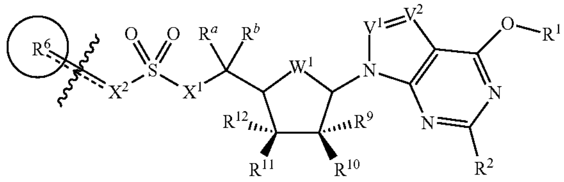
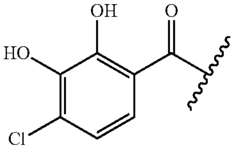 [SMILES: *C(=O)c1ccc(Cl)c(O)c1O]
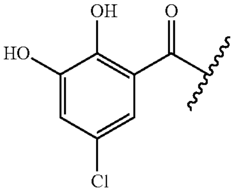 [SMILES: *C(=O)c1cc(Cl)cc(O)c1O]
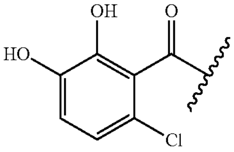 [SMILES: *C(=O)c1c(Cl)ccc(O)c1O]
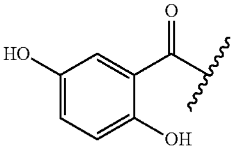 [SMILES: *C(=O)c1cc(O)ccc1O]
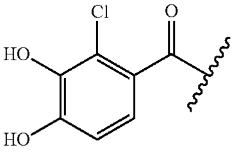 [SMILES: *C(=O)c1ccc(O)c(O)c1Cl]
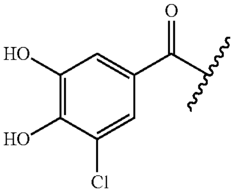 [SMILES: *C(=O)c1cc(O)c(O)c(Cl)c1]
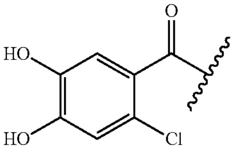 [SMILES: *C(=O)c1cc(O)c(O)cc1Cl]
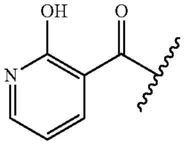 [SMILES: *C(=O)c1cccnc1O]

TABLE D-continued

| Exemplary $R^6$ Moieties |
| --- |
| 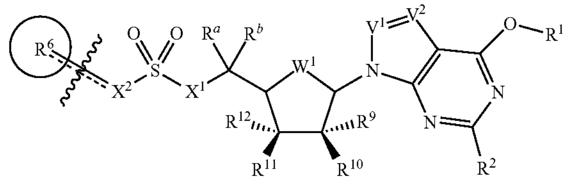 |
| 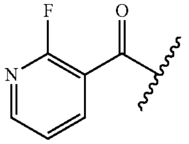 [SMILES: *C(=O)c1cccnc1F] |
| 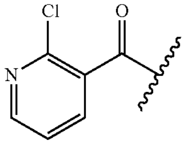 [SMILES: *C(=O)c1cccnc1Cl] |
| 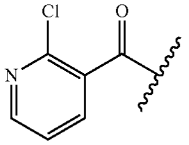 [SMILES: *C(=O)c1cccnc1Cl] |
| 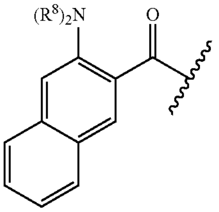 |
| 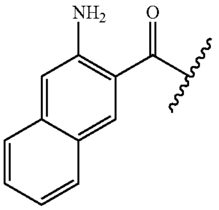 [SMILES: *C(=O)c1cc2ccccc2cc1N] |
| 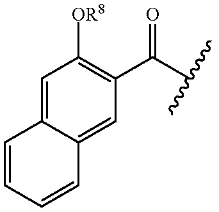 |
| 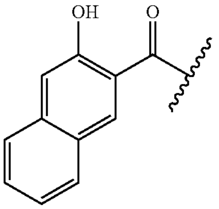 [SMILES: *C(=O)c1cc2ccccc2cc1O] |

Pharmaceutical Compositions and Administration

The present disclosure also provides pharmaceutical compositions comprising a compound described herein (e.g., a compound of Formula (I)), or a pharmaceutically acceptable or tautomer thereof, and optionally a pharmaceutically acceptable excipient. In some embodiments, the pharmaceutical compositions comprising a compound described herein (e.g., a compound of Formula (I)), or a pharmaceutically acceptable salt, solvate, hydrate, polymorph, co-crystal, tautomer, stereoisomer, or prodrug thereof, and optionally a pharmaceutically acceptable excipient. In certain embodiments, the present disclosure also provides pharmaceutical compositions comprising a compound described herein (e.g., a compound of Formula (I)), or a pharmaceutically acceptable or tautomer thereof, and optionally a pharmaceutically acceptable excipient, and further comprising an additional pharmaceutical agent (e.g., antibiotic).

In certain embodiments, the pharmaceutical composition described herein comprises a compound of Formula (I), or a pharmaceutically acceptable salt, stereoisomer, or tautomer thereof, and a pharmaceutically acceptable excipient. In certain embodiments, the pharmaceutical composition described herein comprises a compound of Formula (I), or a pharmaceutically acceptable salt, stereoisomer, or tautomer thereof, a pharmaceutically acceptable excipient, and a pharmaceutical agent. In certain embodiments, the composition is useful for and/or preventing a disease. In certain embodiments, the composition useful for treating a bacterial infection (e.g. *Mycobacterium tuberculosis* infection). In certain embodiments, the composition useful for treating tuberculosis.

In certain embodiments, the compound described herein is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for and/or preventing an infectious disease (e.g., bacterial infection (e.g., *Mycobacterium tuberculosis* infection)) in a subject in need thereof. In certain embodiments, the effective amount is an amount effective for preventing an infectious disease (e.g., bacterial infection (e.g., *Mycobacterium tuberculosis* infection)) in a subject in need thereof. In certain embodiments, the effective amount is an amount effective for reducing the risk of developing an infectious disease (e.g., bacterial infection (e.g., *Mycobacterium tuberculosis* infection)) in a subject in need thereof.

In certain embodiments, the effective amount is an amount effective for inhibiting siderophore (e.g., mycobactin, yersiniabactin, pyochelin, enterobactin, bacillibactin, vibriobactin, petrobactin) biosynthesis in an infection in a subject. In certain embodiments, the effective amount is an amount effective for inhibiting MBT biosynthesis in an infection in a subject. In certain embodiments, the effective amount is an amount effective for inhibiting $MbtA_{tb}$ in an infection in a subject. In certain embodiments, the effective amount is an amount effective for inhibiting $MbtA_{tb}$ in an infectious microorganism. In certain embodiments, the effective amount is an amount effective for inhibiting PQS biosynthesis (e.g., inhibiting anthranilate-CoA synthetase (PqsA)) in an infection in a subject. In certain embodiments, the effective amount is an amount effective for inhibiting the biosynthesis of virulence factors (e.g., pyocyanin) in an infection in a subject. In certain embodiments, the effective amount is an amount effective for inhibiting menaquinone biosynthesis (e.g., inhibiting anthranilate-CoA ligase (PqsA)) in an infectious microorganism. In certain embodiments, the effective amount is an amount effective for inhibiting the biosynthesis of virulence factors (e.g., pyocyanin) in an infectious microorganism. In certain embodiments, the effective amount is an amount effective for inhibiting yersiniabactin biosynthesis (e.g., inhibiting YbtE) in an infection in a subject. In certain embodiments, the effective amount is an amount effective for inhibiting the biosynthesis of virulence factors (e.g., yersiniabactin) in an infection in a subject. In certain embodiments, the effective amount is an amount effective for inhibiting yersiniabactin biosynthesis (e.g., inhibiting YbtE) in an infectious microorganism. In certain embodiments, the effective amount is an amount effective for inhibiting the biosynthesis of virulence factors (e.g., yersiniabactin) in an infectious microorganism.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inhibiting siderophore (e.g., mycobactin, yersiniabactin, pyochelin, enterobactin, bacillibactin, vibriobactin, petrobactin) biosynthesis by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting siderophore (e.g., mycobactin, yersiniabactin, pyochelin, enterobactin, bacillibactin, vibriobactin, petrobactin) biosynthesis by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting MBT biosynthesis by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting MBT biosynthesis by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting $MbtA_{tb}$ by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting $MbtA_{tb}$ by not more than 10%, not more than 20%, not more than 30%, not more than 40%, not more than 50%, not more than 60%, not more than 70%, not more than 80% not more than 90%, not more than 95%, or not more than 98%. In certain embodiments, the effective amount is an amount effective for inhibiting PQS biosynthesis by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting menaquinone biosynthesis by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting an adenylate-forming enzyme (e.g., an acyl-CoA synthetase) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting adenylate-forming enzyme (e.g., an acyl-CoA synthetase) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting anthranilate-CoA synthetase (PqsA) by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting anthranilate-CoA synthetase (PqsA) by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for inhibiting YbtE by at least about 10%, at least about 20%, at least about 30%, at least about 40%, at least about 50%, at least about 60%, at least about 70%, at least about 80%, at least about 90%, at least about 95%, or at least about 98%. In certain embodiments, the effective amount is an amount effective for inhibiting YbtE by not more than 10%, not more than 20%, not more than 30%, not more than 40%, not more than 50%, not more than 60%, not more than 70%, not more than 80%, not more than 90%, not more than 95%, or not more than 98%. In certain embodiments, the effective amount is an amount effective for a range of inhibition between a percentage described in this paragraph and another percentage described in this paragraph, inclusive.

Pharmaceutical compositions described herein can be prepared by any method known in the art of pharmacology. In general, such preparatory methods include bringing the compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben. Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizng agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin. (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the infectious disease being treated and/or prevented, as well as the severity of the disorder; the activity of the specific active ingredient employed; the specific composition employed; the age, body weight, general health, sex, and diet of the subject; the time of administration, route of administration, and rate of excretion of the specific active ingredient employed: the duration of the treatment and/or prevention; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a compound described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell.

In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating an infectious disease in a subject in need thereof (e.g., tuberculosis), in preventing an infectious disease in a subject in need thereof, and/or in reducing the risk to develop an infectious disease in a subject in need thereof), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a compound described herein and an additional pharmaceutical agent shows a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., infectious disease (e.g., tuberculosis), proliferative disease, hematological disease, or painful condition). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, anti-diabetic agents, anti-proliferative agents, anti-cancer agents, anti-angiogenesis agents, anti-inflammatory agents, anti-bacterial agents, anti-viral agents, cardiovascular agents, and pain-relieving agents.

In certain embodiments, the additional pharmaceutical agent inhibits siderophore biosynthesis (e.g., mycobactin (*M. tuberculosis*), yersiniabactin (*Yersinia pestis* and *E. coli*), pyochelin (*P. aeruginosa*), enterobactin (*E. coli*), bacillibactin (*Bacillus subtilis, Bacillus* anthraces), vibriobactin (*Vibrio cholerae*), petrobactin (*B. anthracis*)). In certain embodiments, the additional pharmaceutical agent inhibits the biosynthesis of MBT. In certain embodiments, the additional pharmaceutical agent is a binder or inhibitor of $MbtA_{tb}$. In certain embodiments, the additional pharmaceutical agent is a binder or inhibitor of an AMP-producing synthetase. In certain embodiments, the additional pharmaceutical agent is a binder or inhibitor of anthranilate-CoA synthetase (PqsA). In certain embodiments, the additional pharmaceutical agent is a binder or inhibitor of YbtE. In certain embodiments, the additional pharmaceutical agent inhibits cellular respiration. In certain embodiments, the additional pharmaceutical agent inhibits biosynthesis of a virulence factor. In certain embodiments, the additional pharmaceutical agent inhibits biosynthesis of pyocyanin. In some embodiments, the additional pharmaceutical agent inhibits biosynthesis of yersiniabactin. In certain embodiments, the additional pharmaceutical agent inhibits biosynthesis of PQS, PqsE, lectin, HCN, yersiniabactin, or a rhamnolipid. In certain embodiments, the additional pharmaceutical agent inhibits protein synthesis. In certain embodiments, the additional pharmaceutical agent down-regulates expression of PqsABCDE, PqsR, PqsH, or PhnAB. In certain embodiments, the additional pharmaceutical agent binds a ribosome. In certain embodiments, the additional pharmaceutical agent is an antibiotic. In certain embodiments, the additional pharmaceutical agent is an anti-bacterial agent.

In some embodiments, the additional pharmaceutical agent is an antibiotic. Exemplary antibiotics include, but are not limited to gentamicin, amikacin, tobramycin, ciprofloxacin, levofloxacin, ceflazidimine, cefepime, cefoperazone, cefpirome, ceftobiprole, carbenicllin, ticarcillin, mezlocillin, azlocillin, piperacillin, meropenem, imipenem, doripenem, polymyxin B, colistin, aztreonam, isoniazid, rifampicin (also called rifampin), pyrazinamide, ethambutol, streptomycin, moxifloxacin, gatifloxacin, amikacin, capremycin, kanamycin, ethionamide, prothionamide, cycloserine, terizidone, linezolide, clofazimine, pretomanid, bedaquiline, delamanid, or rifamycins. In certain embodiments, the additional pharmaceutical agent is isoniazid, rifampicin (also called rifampin), pyrazinamide, ethambutol, or streptomycin. In some embodiments, the additional pharmaceutical agent is levofloxacin, moxifloxacin, gatifloxacin, amikacin, capremycin, kanamycin, ethionamide, prothionamide, cycloserine, terizidone, linezolide, or clofazimine.

In certain embodiments, the additional pharmaceutical agent is a β-lactam antibiotic. Exemplary β-lactam antibiotics include, but are not limited to: β-lactamase inhibitors (e.g., avibactam, clavulanic acid, tazobactam, sulbactam); carbacephems (e.g., loracarbef); carbapenems (e.g., doripenem, imipenem, ertapenem, meropenem); cephalosporins ($1^{st}$ generation) (e.g., cefacetrile, cefadroxil, cefalexin, cefaloglycin, cefalonium, cefaloridine, cefalotin, cefapirin, cefatrizine, cefazaflur, cefazedone, cefazolin, cefradine, cefroxadine, ceftezole, cephalosporin C); cephalosporins ($2^{nd}$ generation) (e.g., cefaclor, cefamandole, cefbuperzone, cefmetazole, cefonicid, ceforanide, cefotetan, cefotiam, cefoxitin, cefminox, cefprozil, cefuroxime, cefuzonam); cephalosporins ($3^{rd}$ generation) (e.g., cefcapene, cefdaloxime, cefdinir, cefditorin, cefetamet, cefixime, cefmenoxime, cefodizime, cefoperazone, cefotaxime, cefovecin, cefpimizole, cefpiramide, cefpodoxime, ceflamere, ceftazidime, cefleram, ceftibuten, cefliofur, cefliolene, ceftizoxime, ceftriaxone, latamoxef); cephalosporins ($4^{th}$ generation) (e.g., cefepime, cefluprenam, cefoselis, cefozopran, cefpirome, cefquinome, flomoxef); cephalosporins ($5^{th}$ generation) (e.g., ceftaroline fosamil, ceftobiprole, ceftolozane); cephems (e.g., cefaloram, cefaparole, cefcanel, cefedrolor, cefempidone, cefetrizole, cefivitril, cefmepidium cefoxazole, cefrotil, cefsulodin, cefsumide, ceftioline, ceftioxime, cefuracetime, nitrocefin); monobactams (e.g., aztreonam, carumonam, norcadicin A, tabtoxinine β-lactam, tigemonam); penicillins/penams (e.g., amoxicillin, amoxicillin/clavulanate, ampicillin, ampicillin/flucloxacillin, ampicillin/sulbactam, azidocillin, azlocillin, bacampacillin, benzathine benzylpenicillin, benzathine phenoxymethylpenicillin, carbenicillin, carindacillin, clometocillin, cloxacillin, dicloxacillin, epicillin, flucloxacillin, hetacllin, mecillinam, mezlocillin, meticillin, metampiciillin, nafcillin, oxacillin, penamacillin, penicillin G, penicillin V, phenaticillin, piperacillin, piperacillin/tazobactam, pivampicillin, pivmecillinam, procaine benzylpenicillin, propicillin, sulbenicillin, talampicillin, temocllin, ticarcillin, ticarcillin/clavulanate); and penems/carbapenems (e.g., biapenem, donpenem, ertapenem, faropenem, imipenem, imipenem/cilastatin, lenapenem, meropenem, panipenem, razupenem, tebipenem, thienamycin, tomopenem).

In certain embodiments, the additional pharmaceutical agent is a non-β-lactam antibiotic. Exemplary non-β-lactam antibiotics include, but are not limited to: aminoglycosides (e.g., amikacin, dibekacin, gentamicin, kanamycin, neomycin, netilmicin, tobramycin, paromomycin, sisomicin, streptomycin, spectinomycin); ansamycins (e.g., geldanamycin, herbimycin); glycopeptides (e.g., belomycin, dalbavancin, oritavancin, ramoplanin, teicoplanin, telavancin, vancomycin); glycylcyclines (e.g., tigecycline); lincosamides (e.g., clindamycin, lincomycin): lipopeptides (e.g., anidulafungin, caspofungin, cilofungin, daptomycin, echinocandin B, micafungin, mycosubtilin); macrolides (e.g., azithromycin, carbomycin A, clarithromycin, dirithromycin, erythromycin, josmycin, kitasamycin, midecamycin, oleandomycin, roxithromycin, solithromycin, spiramycin, troleandomycin, telithromycin, tylosin): nitrofurans (e.g., furazolidone, furylfuramide, nitrofurantoin, nitrofurazone, nifuratel, nifurquinazol, nifurtoinol, nifuroxazide, nifurtimox, nifurzide, ranbezolid): nitroimidazoles (e.g., metronidazole, nimorazole, tinadazole); oxazolidinones (e.g., cycloserine, linezolid, posizolid radezolid, tedizolid); polypeptides (e.g., actinomycin, bacitracin, colistin, polymyxin B); quinolones (e.g., balofloxacin, besifloxacin, cinoxacin, ciprofloxacin, clinafloxacin, danofloxacin, delafloxacin, diflofloxacin, enoxacin, enrofloxacin, fleroxacin, flumequine, gatifloxacin, gemifloxacin, grepafloxacin, ibafloxacin, JNJ-Q2, levofloxacin, lomefloxacin, marbofloxacin, moxifloxacin, nadifloxacin, nalidixic acid, nemonoxacin, norfloxacin, ofloxacin, orbifloxacin, oxilinic acid, pazufloxacin, pefloxacin, piromidic acid, pipemidic acid, prulifloxacin, rosoxacin, rufloxacin, sarafloxacin, sparfloxacin, sitafloxacin, temafloxacin, tosufloxacin, trovafloxacin); rifamycins (e.g., rifamycin B, rifamycin S, rifamycin SV, rifampicin, rifabutin, rifapentine, rifalazil, rifaximin); sulfonamides (e.g., co-trimoxazole, mafenide, pediazole, sulfacetamide, sulfadiazine, silver sulfadiazine, sulfadimidine, sulfadimethoxine, sulfadoxine, sulfafurazole, sulfamethizole, sulfamethoxazole, sulfamethoxypyridazine, sulfametopyrazine, sulfametoxydiazine, sulfamoxole, sulfanilamide, sulfanitran, sulfasalazine, sulfisomidine, sulfonamidochrysoidine, trimethoprim): tetracyclines (e.g., 6-deoxytetracycline, aureomycin, chlortetracycline, demeclocycline, doxycycline, lymecycline, meclocycline, methacycline, minocycline, oxytetracycline, PTK-0796, sancycline, rolitetracycline, tetracycline, terramycin): tuberactinomycins (e.g., tuberactinomycin A, tuberactinomycin O, viomycin, enviomycin, capreomycin); arsphenamine; chioramphenicol; dalfoprisitin; fosfomycin; fusidic acid; fidaxomycin, gramicidin; lysozyme; mupirocin; platensimycin; pristinamycin; sparsomycin; quinupristin; quinupristin/dalfopristin; teixobactin; and thiamphenicol.

In certain embodiments, the additional pharmaceutical agent is isoniazid.

In certain embodiments, the additional pharmaceutical agent is rifampicin (also called rifampin).

In certain embodiments, the additional pharmaceutical agent is pyrazinamide.

In certain embodiments, the additional pharmaceutical agent is ethambutol.

In certain embodiments, the additional pharmaceutical agent is streptomycin.

In certain embodiments, the additional pharmaceutical agent is a carbapenem. In some embodiments, the additional pharmaceutical agent is doripenem, imipenem, or meropenem.

In certain embodiments, the additional pharmaceutical agent is a glycylcycline. In some embodiments, the additional pharmaceutical agent is tigecycline.

In certain embodiments, the additional pharmaceutical agent is a aminoglycoside. In some embodiments, the additional pharmaceutical agent is gentamycin, amikacin, or tobramycin.

In certain embodiments, the additional pharmaceutical agent is a quinolone. In some embodiments, the additional pharmaceutical agent is ciprofloxacin or levofloxacin.

In certain embodiments, the additional pharmaceutical agent is a cephalosporin. In some embodiments, the additional pharmaceutical agent is ceftazidime, cefepime, cefoperazone, cefpirome, ceftobirprole, or ceftaroline fosamil.

In certain embodiments, the additional pharmaceutical agent is a penicillin. In some embodiments, the additional pharmaceutical agent is an antipseudomonal penicillin or extended spectrum penicillin. In certain embodiments, the additional pharmaceutical agent is a carboxypenicillin or a ureidopenicillin. In some embodiments, the additional pharmaceutical agent is carbenicillin, ticarcillin, mezlocillin, azlocillin, piperacillin, or mecillinam.

In certain embodiments, the additional pharmaceutical agent is a polymyxin. In some embodiments, the additional pharmaceutical agent is polymyxin B or colistin.

In certain embodiments, the additional pharmaceutical agent is a monobactam. In some embodiments, the additional pharmaceutical agent is aztreonam.

In certain embodiments, the additional pharmaceutical agent is a β-lactamase inhibitor. In some embodiments, the additional pharmaceutical agent is sulbactam.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating an infectious disease (e.g., bacterial infection (e.g., *Mycobacterium tuberculosis* infection)) in a subject in need thereof. In certain embodiments, the kits are useful for preventing an infectious disease (e.g., bacterial infection (e.g., *Mycobacterium tuberculosis* infection)) in a subject in need thereof. In certain embodiments, the kits are useful for reducing the risk of developing an infectious disease (e.g., bacterial infection (e.g., *Mycobacterium tuberculosis* infection)) in a subject in need thereof. In certain embodiments, the kits are useful for inhibiting biosynthesis of virulence factors in an infection in a subject or in an infectious microorganism. In certain embodiments, the kits are useful for inhibiting siderophore (e.g., mycobactin, yersiniabactin, pyochelin, enterobactin, bacillibactin, vibriobactin, petrobactin) biosynthesis. In certain embodiments, the kits are useful for inhibiting MBT biosynthesis. In certain embodiments, the kits are useful for inhibiting $MbtA_{tb}$. In some embodiments, the kits are useful for inhibiting yersiniabactin biosynthesis. In some embodiments, the kits are useful for inhibiting YbtE. In certain embodiments, the kits are useful for inhibiting PQS biosynthesis (e.g., inhibiting anthranilate-CoA synthetase (PqsA)) in an infection in a subject or in an infectious microorganism. In certain embodiments, the kits are useful for treating a patient with cystic fibrosis. In certain embodiments, the kits are useful for treating a patient with tuberculosis. In certain embodiments, the kits are useful for eradication of a biofilm in a patient. In certain embodiments, the kits are useful for preventing the formation of a biofilm in a patient.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. In certain embodiments, the kits and instructions provide for treating an infectious disease (e.g., bacterial infection (e.g., *Mycobacterium tuberculosis* infection)) in a subject in need thereof. In certain embodiments, the kits and instructions provide for preventing an infectious disease (e.g., bacterial infection (e.g., *Mycobacterium tuberculosis* infection)) in a subject in need thereof. In certain embodiments, the kits and instructions provide for reducing the risk of developing an infectious disease (e.g., bacterial infection (e.g., *Mycobacterium tuberculosis* infection)) in a subject in need thereof. In certain embodiments, the kits and instructions provide for inhibiting siderophore (e.g., mycobactin, yersiniabactin, pyochelin, enterobactin, bacillibactin, vibriobactin, petrobactin) biosynthesis in an infection in a subject or in an infectious microorganism. In certain embodiments, the kits and instructions provide for inhibiting biosynthesis of MBT in an infection in a subject or in an infectious microorganism. In certain embodiments, the kits and instructions provide for inhibiting biosynthesis of virulence factors in an infection in a subject or in an infectious microorganism. In certain embodiments, the kits and instructions provide for inhibiting menaquinone biosynthesis (e.g., inhibiting anthranilate-CoA synthetase (PqsA)) in an infection in a subject or in an infectious microorganism. In certain embodiments, the kits and instructions provide for inhibiting yersiniabactin biosynthesis (e.g., inhibiting aYbtE) in an infection in a subject or in an infectious microorganism. A kit described herein may include one or more additional pharmaceutical agents described herein as a separate composition.

Methods of Treatment and Uses

The present disclosure also provides methods that may be useful for the treatment and/or prevention of a disease. In certain embodiments, the disease is an infectious disease. In certain embodiments, the infectious disease is a bacterial infection. In certain embodiments, the infectious disease is a fungal infection. In certain embodiments, the infectious disease is a parasitic infection. In certain embodiments, the infectious disease is a viral infection. In certain embodiments, the infectious disease is associated with another disease or condition, for example, in subjects with a weakened immune system as a result of HIV infection, AIDS, lupus, cancer, cystic fibrosis, or diabetes, or subjects with burns. In certain embodiments, the bacterial infection is an infection caused by Gram-positive bacteria. In certain, embodiments, the bacterial infection is an infection caused by Gram-negative bacteria. In some embodiments, the bacterial infection is caused by a member of Mycobacteriacae. In certain embodiments, the bacterial infection is an infection caused by *Mycobacterium tuberculosis*. In some embodiments, the infectious disease is tuberculosis.

Exemplary bacterial infections include, but are not limited to, infections with a Gram positive bacteria (e.g., of the phylum Actinobacteria, phylum Firmicutes, or phylum Tenericutes); Gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Nitrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacteria is a member of the phylum Firmicutes and the genus *Enterococcus*, i.e., the bacterial infection is an *Enterococcus* infection. Exemplary *Enterococci* bacteria include, but are not limited to, *E. avium, E. durans, E. faecalis, E. faecium, E. gallinarum, E. solitarius, E. casseliflavus*, and *E. raffinosus*. In certain embodiments, the bacteria is a member of the phylum Firmicutes and the genus *Staphylococcus*, i.e., the bacterial infection is a *Staphylococcus* infection. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S equorum, S. felis, S. fluroettii, S gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In certain embodiments, the *Staphylococcus* infection is a *S. aureus* infection. In certain embodiments, the bacteria is a member of the phylum Firmicutes and the genus *Bacillus*, i.e., the bacterial infection is a *Bacillus* infection. Exemplary *Bacillus* bacteria include, but are not limited to, *B. alcalophilus, B. alvei, B. aminovorans, B. amyloliquefaciens, B. aneurinolyticus, B. anthracis, B. aquaemaris, B. atrophaeus, B. boroniphilus, B. brevis, B. caldolyticus, B. centrosporus, B. cereus, B. circulars, B. coagulans, B. firmus, B. flavothermus, B. fusiformis, B. globigii, B. infernus, B. larvae, B. laterosporus, B. lentus, B. licheniformis, B. megaterium, B. mesentericus, B. mucilaginosus, B. mycoides, B. natto, B. pantothenticus, B. polymyxa, B. pseudoanthracis, B. pumilus, B. schlegelii, B. sphaericus, B. sporothermodurans, B. stearothermophilus, B. subtilis, B. thermoglucosidasius, B. thuringiensis, B. vulgatis*, and *B. weihenstephanensis*. In certain embodiments, the *Bacillus* infection is a *B. subtilis* infection. In certain embodiments, the *B. subtilis* has an efflux (e.g., mef, msr) genotype. In certain embodiments, the *B. subtilis* has a methylase (e.g., erm) genotype. In certain embodiments, the bacteria is a member of the phylum Firmicutes and the genus *Streptococcus*, i.e., the bacterial infection is a *Streptococcus* infection. Exemplary *Streptococcus* bacteria include, but are not limited to, *S. agalactiae, S. anginosus, S. bovis, S canis, S. constellatus, S. dysgalactiae, S. equinus, S. iniae, S. intermedius, S. mitis, S. mutans, S. oralis, S. parasanguinis, S. peroris, S. pneumoniae, S. pyogenes, S. ratti, S. salivarius, S. thermophilus, S. sanguinis, S. sobrinus, S. suis, S. uberis, S. vestibularis, S. viridans*, and *S. zooepidemicus*. In certain embodiments, the *Streptococcus* infection is an *S. pyogenes* infection. In certain embodiments, the *Streptococcus* infection is an *S. pneumoniae* infection. In certain embodiments, the *S. pneumoniae* has an efflux (e.g., mef, msr) genotype. In certain embodiments, the *S. pneumoniae* has a methylase (e.g., erm) genotype. In certain embodiments, the bacteria is a member of the phylum Firmicutes and the genus *Clostridium*, i.e., the bacterial infection is a *Clostridium* infection. Exemplary Clostridia bacteria include, but are not limited to, *C. botulinum, C. difficile, C. perfringens, C. tetani*, and *C. sordellii*.

In certain embodiments, the Gram negative bacteria is a bacteria of the phylum Proteobacteria and the genus *Escherichia*. i.e., the bacterial infection is an *Escherichia* infection. Exemplary *Escherichia* bacteria include, but are not limited to, *E. albertii, E. blattae, E. coli, E. fergusonii, E. hermannii*, and *E. vulneris*. In certain embodiments, the *Escherichia* infection is an *E. coli* infection. In certain embodiments, the Gram negative bacteria is a bacteria of the phylum Proteobacteria and the genus *Haemophilus*. i.e., the bacterial infection is an *Haemophilus* infection. Exemplary *Haemophilus* bacteria include, but are not limited to, *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis*, and *H. somnus*. In certain embodiments, the *Haemophilus* infection is an *H. influenzae* infection.

In certain embodiments, the Gram negative-bacteria is a bacteria of the phylum Proteobacteria and the genus *Acinetobacter*. i.e., the bacterial infection is an *Acinetobacter* infection. Exemplary *Acinetobacter* bacteria include, but are not limited to, *A. baumanii, A. haemolyticus*, and *A. lwoffii*. In certain embodiments, the *Acinetobacter* infection is an *A. baumanii* infection. In certain embodiments, the Gram-negative bacteria is a bacteria of the phylum Proteobacteria and the genus *Klebsiella*. i.e., the bacterial infection is a *Klebsiella* infection. Exemplary *Klebsiella* bacteria include, but are not limited to, *K. granulomatis, K. oxytoca, K. michiganensis, K. pneumoniae, K. quasipneumoniae*, and *K. variicola*. In certain embodiments, the *Klebsiella* infection is a *K. pneumoniae* infection. In certain embodiments, the Grain-negative bacteria is a bacteria of the phylum Proteobacteria and the genus *Pseudomonas*. i.e., the bacterial infection is a *Pseudomonas* infection. Exemplary *Pseudomonas* bacteria include, but are not limited to, *P. aeruginosa, P. oryzihabitans. P. plecoglissicida. P. syringae, P. putida*, and *P. fluoroscens*. In certain embodiments, the *Pseudomonas* infection is a *P. aeruginosa* infection. In certain embodiments, the Gram-negative bacteria is a bacteria of the phylum Bacteroidetes and the genus *Bacteroides*. i.e., the bacterial infection is a *Bacteroides* infection. Exemplary *Bacteroides* bacteria include, but are not limited to, *B. fragilis, B. distasonis, B. ovatus. B. thetaiotaomicron*, and *B. vulgates*. In certain embodiments, the *Bacteroides* infection is a *B. fragilis* infection. In certain embodiments, the Gram negative-bacteria is a bacteria of the phylum Proteobacteria and the genus *Yersinia*. i.e., the bacterial infection is an *Yersinia* infection. Exemplary *Yersinia* bacteria include, but are not limited to, *Y. pestis, Y. entercolitica*, and *Y. pseudotuberculosis*. In certain embodiments, the *Acinetobacter* infection is an *Y. pestis* infection.

In certain embodiments, the bacterial infection is caused by a bacteria of the phylum Actinobacteria. Exemplary bacteria of the phylum include, but are not limited to bacteria within Acidimicrobiaceae family, Actinomycetaceae family, Corynebacteriaceae family, Gordoniaceae family, Mycobacteriaceae family, Nocardiaceae family, Tsukamurellaceae family, Williamsiaceae family, Acidothermaceae family, Frankiaceae family, Geodermatophilaceae, Kineosporiaceae, Microsphaeraceae family, Sporichthyaceae family, Glycomycetaceae family, Beutenbergiaceae family, Bogoriellaceae family, Brevibacteriaceae family, Cellulomonadaceae family, Dermabacteraceae family, Dermatophilaceae family, Dermacoccaceae family, Intrasporangiaceae family, Jonesiaceae family, Microbacteriaceae family, Micrococcaceae family, Promicromonosporaceae family, Rarobacteraceae family, Sanguibacteraceae family, Micromonosporaceae family, Nocardioidaceae family, Propionibacteriaceae family, Actinosynnemataceae family, Pseudonocardiaceae family, Streptomycetaceae family, Nocardiopsaceae family, Streptosporangiaceae family, Iltermomonosporaceae family, Bifidobacteriaceae family, Coriobacteriaceae family, Rubrobacteraceae family, and Sphaerobacteraceae family.

In certain embodiments, the bacterial infection is a *Mycobacterium* infection, a *Staphylococcus* infection, *Pseudomonas* infection, a *Bacillus* infection, or an *Escherichia* infection. In certain, embodiments, the bacterial infection is tuberculosis. In some embodiments, the bacterial infection is a *Mycobacterium tuberculosis* infection. In certain embodiments, the bacterial infection is a *Pseudomonas* infection. In some embodiments, the bacterial infection is *Pseudomonas aeruginosa* infection. In some embodiments, the bacterial infection is *Yersinia* infection. In some embodiments the bacterial infection is *Yersinia pestis* infection. In some embodiments the bacterial infection is *E. coli* infection. In some embodiments the bacterial infection is *Bacillus subtilis* infection. In some embodiments the bacterial infection is *Bacillus anthracis* infection. In some embodiments the bacterial infection is *Vibrio cholera* infection. In some embodiments, the bacterial infection is infection of multiple species of bacterium. In some embodiments, the bacterial infection is infection of multiple species of bacterium, one of which is *P. aeruginosa*. In some embodiments, the bacterial infection is infection of multiple species of bacterium, one of which is *Mycobacterium tuberculosis*.

In some embodiments, the infectious disease is a parasitic infection. Exemplary parasites causing the parasitic infection include, but are not limited to, *Trypanosoma* spp. (e.g., *Trypanosoma cruzi, Trypansosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp. (e.g., *P. flaciparum*), *Crytosporidium* spp., *Isospora* spp., *Balantidium* spp., *Pneumocystis* spp., *Babesia, Loa loa, Ascaris lumbricoides, Dirotilaria immitis*, and *Toxoplasma* ssp. (e.g. *T. gondii*).

The present disclosure also provides methods that may be useful for the treatment and/or prevention of an infectious disease including, but not limited to pneumonic plague, septicemic plague, bubonic plague, gastroenteritis, urinary tract infections, neonatal meningitis, hemorrhagic colitis, Crohn's disease, pneumonia, septic shock, gastrointestinal infection, necrotising enterocolitis, anthrax, and tuberculosis.

The compounds described herein (e.g., compounds of Formula (I)) may exhibit inhibitory activity towards $MtbA_{tb}$, may exhibit inhibitory activity towards an adenylate-forming enzyme (e.g., an acyl-CoA synthetase), may exhibit the ability to inhibit anthranilate-CoA synthetase (PqsA), may exhibit the ability to inhibit YbtE, may exhibit the ability to inhibit the siderophore biosynthesis, may exhibit the ability to inhibit the biosynthesis of MBT, may exhibit the ability to inhibit the biosynthesis of virulence factors in an infectious microorganism, may exhibit the ability to inhibit PQS biosynthesis, may exhibit a therapeutic effect and/or preventative effect in the treatment of infectious diseases (e.g., bacterial infections), and/or may exhibit a therapeutic and/or preventative effect superior to existing agents for treatment of an infectious disease.

The compounds described herein (e.g., compounds of Formula (I)) may exhibit selective inhibition of $MtbA_{tb}$ versus inhibition of other proteins. The compounds described herein (e.g., compounds of Formula (I)) may exhibit selective inhibition of anthranilate-CoA synthetase (PqsA) versus inhibition of other proteins. The compounds described herein (e.g., compounds of Formula (I)) may exhibit selective inhibition of YbtE. In certain embodiments, the selectivity versus inhibition of another protein is between about 2 fold and about 10 fold. In certain embodiments, the selectivity is between about 10 fold and about 50 fold. In certain embodiments, the selectivity is between about 50 fold and about 100 fold. In certain embodiments, the selectivity is between about 100 fold and about 500 fold. In certain embodiments, the selectivity is between about 500 fold and about 1000 fold. In certain embodiments, the selectivity is between about 1000 fold and about 5000 fold. In certain embodiments. In certain embodiments, the selectivity is between about 5000 fold and about 10000 fold. In certain embodiments, or at least about 10000 fold.

The present disclosure provides methods that may be useful for the treatment and/or prevention of an infectious disease by administering a compound described herein, or pharmaceutically acceptable salt, solvate, hydrate, polymorph, co-crystal, tautomer, stereoisomer, or prodrug thereof, or pharmaceutical composition thereof, to a subject in need thereof. In certain embodiments, the compound is administered as a pharmaceutically acceptable salt, stereoisomer, or tautomer thereof. In certain embodiments, the compound is administered as a pharmaceutically acceptable salt of the compound. In certain embodiments, the compound is administered as a specific stereoisomer or mixture of stereoisomers of the compound. In certain embodiments, the compound is administered as a specific tautomer or mixture of tautomers of the compound. In certain embodiments, the compound is administered as a pharmaceutical composition as described herein comprising the compound.

The present disclosure also provides uses of the inventive compounds, and pharmaceutically acceptable salts, solvates, hydrates, polymorphs, co-crystals, tautomers, stereoisomers, prodrugs, and pharmaceutical compositions thereof, in the manufacture of medicaments for the treatment and prevention of diseases. In certain embodiments, the disease is an infectious disease. In certain embodiments, the infectious disease is a bacterial infection. In certain embodiments, the disease is tuberculosis. In certain embodiments, the infectious disease is a parasitic infection. In certain embodiments, the infectious disease may be associated with another disease or condition, for example, in subjects with a weakened immune system as a result of HIV infection, AIDS, lupus, cancer, cystic fibrosis, or diabetes, or subjects with burns. In certain embodiments, the infectious disease may arise as complication of another disease or condition, for example, in subjects with a weakened immune system as a result of HIV infection, AIDS, lupus, cancer, cystic fibrosis or diabetes. In certain embodiments, the bacterial infection is an infection caused by Gram-positive bacteria. In certain, embodiments, the bacterial infection is an infection caused by Gram-negative bacteria. In certain embodiments, the bacterial infection is a *Staphylococcus* infection, a *Bacillus* infection, or an *Escherichia* infection. In certain embodiments, the bacterial infection is a *Pseudomonas* infection. In some embodiments the bacterial infection is *Pseudomonas aeruginosa* infection. In some embodiments the bacterial infection is *Mycobacterium tuberculosis* infection. In some embodiments the bacterial infection is *Yersinia pestis* infection. In some embodiments the bacterial infection is *E. coli* infection. In some embodiments the bacterial infection is *Bacillus subtilis* infection. In some embodiments the bacterial infection is *Bacillus anthracis* infection. In some embodiments the bacterial infection is *Vibrio cholera* infection.

Certain methods described herein include methods of treating a bacterial infection, methods of treating an infection in a subject, preventing a bacterial infection, methods of preventing an infection in a subject, or methods of contacting an infectious microorganism with a compound described herein (e.g. a compound of Formula (I)). Any of these methods may involve a specific class of bacteria or type of bacteria. In certain embodiments, the bacterial infection is caused by Gram-positive bacteria. In certain, embodiments, the bacterial infection caused by Gram-negative bacteria. In certain embodiments the bacteria is from the genus *Yersinia, Staphylococcus, Escherichia*, or *Bacillus*. In certain embodiments the bacteria is from the genus *Pseudomonas*. In certain embodiments the bacteria is from the genus *Mycobacterium.*

In certain embodiments, the microbial infection is an infection with a bacteria, i.e., a bacterial infection. In certain embodiments, the compounds of the disclosure exhibit anti bacterial activity. For example, in certain embodiments, the compound has a mean inhibitory concentration, with respect to a particular bacterium, of less than 50 μg/mL, preferably less than 25 μg/mL, more preferably less than 5 μg/mL, and most preferably less than 1 μg/mL.

Exemplary bacteria include, but are not limited to, Gram positive bacteria (e.g., of the phylum Actinobacteria, phylum Firmicutes, or phylum Tenericutes); Gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacteria is a member of the phylum Actinobacteria and the genus *Mycobacterium*, e.g., the bacterial infection is a *Mycobacterium* infection. Exemplary *Mycobacterium* bacteria include, but are not limited to, *Mycobacterium tuberculosis, Mycobacterium leprae. Mycobacterium avium* paratuberculosis. *Mycobacterium ulcerans, Mycobacterium lepromatosis*, and *Mycobacterium marinum*. In certain embodiments, the bacteria is *Mycobacterium tuberculosis.*

In certain embodiments, the bacteria is a member of the phylum Proteobacteria and the genus *Pseudomonas*, e.g., the bacterial infection is a *Pseudomonas* infection. Exemplary *Pseudomonas* bacteria include, but are not limited to, *P. aeruginosa, P. anguilliseptica, P. agarici, P. luteola, P. oryzihabitans, P. plecoglossida, P. syringae*, and *P. tolaasii*. In certain embodiments, the bacteria is *P. aeruginosa.*

In certain embodiments, the bacteria is a member of the phylum Proteobacteria and the genus *Yersinia*, e.g., the bacterial infection is a *Yersinia* infection. Exemplary *Yersinia* bacteria include, but are not limited to, *Y. pestis, Y. entercolitica*, and *Y. pseudotuberculosis*. In certain embodiments, the *Acinetobacter* infection is an *Y. pestis* infection.

In certain embodiments, the methods of the disclosure include administering to the subject an effective amount of a compound described herein (e.g., a compound of Formula (I)), or a pharmaceutically acceptable salt, stereoisomer, or tautomer thereof, or a pharmaceutical composition thereof. In certain embodiments, the effective amount is a therapeutically effective amount. In certain embodiments, the effective amount is a prophylactically effective amount.

In another aspect, the present disclosure provides methods for inhibiting the biosynthesis of virulence factors in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting the biosynthesis of virulence factors in an infectious microorganism, by contacting the sample with a compound described herein (e.g., a compound of Formula (I)), or a pharmaceutically acceptable salt, stereoisomer, or tautomer thereof, or a pharmaceutical composition thereof.

In some embodiments, the virulence factor is pyocyanin. In some embodiments, the virulence factor is lectin, HCN, or a rhamnolipid. In some embodiments, the virulence factor is PQS. In some embodiments, the virulence factor is PqsE. In some embodiments, the virulence factor is yersiniabactin.

In another aspect, the present disclosure provides methods for inhibiting siderophore (e.g., mycobactin, yersiniabactin, pyochelin, enterobactin, bacillibactin, vibriobactin, petrobactin) biosynthesis in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting siderophore (e.g., mycobactin, yersiniabactin, pyochelin, enterobactin, bacillibactin, vibriobactin, petrobactin) biosynthesis in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting MBT biosynthesis in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting MBT biosynthesis in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting PQS biosynthesis in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting PQS biosynthesis in an infectious microorganism, by contacting the sample with a compound described herein (e.g., a compound of Formula (I)), or a pharmaceutically acceptable salt, stereoisomer, or tautomer thereof, or a pharmaceutical composition thereof.

Inhibiting PQS biosynthesis may decrease levels of one or more PQS metabolite and/or virulence factors. In some embodiments, the PQS metabolite is anthranilyl-S-CoA. In some embodiments, the PQS metabolite is 2-heptyl-4-hydroxyquinoline (HHQ). In some embodiments, the PQS metabolite is 3,4-dihydroxy-2-heptylquinoline (PQS). In some embodiments, the virulence factor is pyocyanin. In some embodiments, the virulence factor is another virulence factor described herein.

In another aspect, the present disclosure provides methods for inhibiting HHQ biosynthesis in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting HHQ biosynthesis in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting pyocyanin in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting pyocyanin biosynthesis in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting biofilm formation, in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting biofilm formation by contacting the biofilm with a compound described herein (e.g., a compound of Formula (I)), or a pharmaceutically acceptable salt, stereoisomer, or tautomer thereof: or a pharmaceutical composition thereof.

In another aspect, the present disclosure provides methods for eradicating a biofilm in a subject by administering to the subject a compound described herein (e.g., a compound of Formula (I)), or a pharmaceutically acceptable salt, stereoisomer, or tautomer thereof; or a pharmaceutical composition thereof.

In another aspect, the present disclosure provides methods for eradicating a biofilm by contacting the biofilm with a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting a mycobactin forming enzyme (e.g., $MbtA_{tb}$) in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting mycobactin forming enzyme (e.g., $MbtA_{tb}$) in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting an adenylate-forming enzyme (e.g., an acyl-CoA synthetase) in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting an adenylate-forming enzyme (e.g., an acyl-CoA synthetase) in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting bifunctional enzyme salicyl-AMP ligase ($MbtA_{tb}$) in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting bifunctional enzyme salicyl-AMP ligase ($MbtA_{tb}$) in an infectious microorganism, by contacting the sample with a compound described herein (e.g., a compound of Formula (I)), or a pharmaceutically acceptable salt, stereoisomer, or tautomer thereof: or a pharmaceutical composition thereof.

In another aspect, the present disclosure provides methods for inhibiting anthranilate-CoA synthetase (PqsA) in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting anthranilate-CoA synthetase (PqsA) in an infectious microorganism, by contacting the sample with a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting a YbtE in an infection in a subject by administering to the subject a compound described herein (e.g., a compound of Formula (I)), or a pharmaceutically acceptable salt, stereoisomer, or tautomer thereof, or a pharmaceutical composition thereof.

In another aspect, the present disclosure provides methods for inhibiting YbtE in an infectious microorganism, by contacting the sample with a compound described herein (e.g., a compound of Formula (I)), or a pharmaceutically acceptable salt, stereoisomer, or tautomer thereof, or a pharmaceutical composition thereof.

The present disclosure also provides methods of using a compound described herein (e.g., a compound of Formula (I)), or a pharmaceutically acceptable salt, solvate, hydrate, polymorph, co-crystal, tautomer, stereoisomer, or prodrug thereof, or pharmaceutical compositions thereof, in research studies in the field of disease pathology, biochemistry, cell biology, and other fields associated with infectious diseases. The compounds of the disclosure can be used to study the roles of biomolecules (e.g., $MbtA_{tb}$, MBT, anthranilate-CoA synthetase, anthranilic acid, anthranilate-AMP, anthranilyl-S-CoA, HHQ, PQS, pyocyanin, YbtE, yersiniabactin). The compounds of the disclosure can be used to study the biosynthesis of a virulence factor in a microorganism. The compounds of the disclosure can be used to study quorum sensing in a microorganism. In certain embodiments, the method comprises use of the compound or composition thereof to inhibit the biosynthesis of virulence factors, inhibit MBT biosynthesis, inhibit PQS biosynthesis, inhibit yersiniabactin biosynthesis, or disrupt quorum sensing. In certain embodiments, the method comprises use of the compound or composition thereof to inhibit $MbtA_{tb}$. In certain embodiments, the method comprises use of the compound or composition thereof to inhibit anthranilate-CoA synthetase (PqsA). In certain embodiments, the method comprises use of the compound or composition thereof to inhibit YtbE. In certain embodiments, the method comprises determining the concentration of a biomolecule in a subject or biological sample.

Certain methods described herein, may comprise administering one or more additional pharmaceutical agent in combination with the compounds described herein. The additional pharmaceutical agents include, but are not limited to, anti-diabetic agents, anti-proliferative agents, anti-cancer agents, anti-angiogenesis agents, anti-inflammatory agents, anti-bacterial agents, anti-viral agents, cardiovascular agents, and pain-relieving agents. In certain embodiments, the additional pharmaceutical agent is an antibiotic. In certain embodiments, the additional pharmaceutical agent is an anti-bacterial agent. In certain embodiments, the additional pharmaceutical agent is a binder or inhibitor of $MbtA_{tb}$. In certain embodiments, the additional pharmaceutical agent inhibits the biosynthesis of a virulence factor. In certain embodiments, the additional pharmaceutical agent inhibits siderophore (e.g., mycobactin, yersiniabactin, pyochelin, enterobactin, bacillibactin, vibriobactin, petrobactin) biosynthesis. In certain embodiments, the additional pharmaceutical agent inhibits MBT biosynthesis. In certain embodiments, the additional pharmaceutical agent is a binder or inhibitor of an AMP-producing synthetase. In certain embodiments, the additional pharmaceutical agent is a binder or inhibitor of anthranilate-CoA synthetase (PqsA). In certain embodiments, the additional pharmaceutical agent inhibits yersiniabactin biosynthesis. In certain embodiments, the additional pharmaceutical agent is a binder or inhibitor of YbtE. In certain embodiments, the additional pharmaceutical agent inhibits the biosynthesis of a virulence factor. In certain embodiments, the additional pharmaceutical agent inhibits PQS biosynthesis.

In certain embodiments, the additional pharmaceutical agent is isoniazid.

In certain embodiments, the additional pharmaceutical agent is rifampicin (also called rifampin).

In certain embodiments, the additional pharmaceutical agent is pyrazinamide.

In certain embodiments, the additional pharmaceutical agent is ethambutol.

In certain embodiments, the additional pharmaceutical agent is streptomycin.

In certain embodiments, the additional pharmaceutical agent is a carbapenem. In some embodiments, the additional pharmaceutical agent is doripenem, imipenem, or meropenem.

In certain embodiments, the additional pharmaceutical agent is a glycylcycline. In some embodiments, the additional pharmaceutical agent is tigecycline.

In certain embodiments, the additional pharmaceutical agent is a aminoglycoside. In some embodiments, the additional pharmaceutical agent is gentamycin, amikacin, or tobramycin.

In certain embodiments, the additional pharmaceutical agent is a quinolone. In some embodiments, the additional pharmaceutical agent is ciprofloxacin or levofloxacin.

In certain embodiments, the additional pharmaceutical agent is a cephalosporin. In some embodiments, the additional pharmaceutical agent is ceftazidime, cefepime, cefoperazone, cefpirome, ceftobirprole, or ceftaroline fosamil.

In certain embodiments, the additional pharmaceutical agent is a penicillin. In some embodiments, the additional pharmaceutical agent is an antipseudomonal penicillin or extended spectrum penicillin. In certain embodiments, the additional pharmaceutical agent is a carboxypenicillin or a ureidopenicillin. In some embodiments, the additional pharmaceutical agent is carbenicillin, ticarcillin, mezlocillin, azlocillin, piperacillin, or mecillinam.

In certain embodiments, the additional pharmaceutical agent is a polymyxin. In some embodiments, the additional pharmaceutical agent is polymyxin B or colistin.

In certain embodiments, the additional pharmaceutical agent is a monobactam. In some embodiments, the additional pharmaceutical agent is aztreonam.

In certain embodiments, the additional pharmaceutical agent is a β-lactamase inhibitor. In some embodiments, the additional pharmaceutical agent is sulbactam.

Codon-Optimized $MbtA_{tb}$

Figure 2:
FIG. 2 shows nucleotide sequence alignment of $MbtA_{tb}$ and $MbtA^{opt}$. Boxed nucleotides indicate changes in $mbtA^{opt}$ relative to the native $MbtA_{tb}$. The native mbtAtb (Rv2384, Quadri, L. E., et al. (1998) *Chem. Biol.* 5, 631-645) was subjected to analysis for gene optimization for protein expression in *E. coli*. The analysis assigned a 0.41 Codon Adaptation Index (CAI) rating to $MbtA_{tb}$ (CAI=1.0 is considered ideal and CAI>0.8 is good for expression in *E. coli*). The analysis identified 36% and 14% of the codons in $MbtA_{tb}$ being used <70% and <10% of the time, respectively, by *E. coli*, at least five stretches of 60+ bp with suboptimal GC content (>70%), and potentially problematic direct, inverted, and dyad repeats. The analysis recommended 341 nucleotide changes (shown) that led to a CAI rating of 0.96. The changes were incorporated in $MbtA^{opt}$.

In certain aspects, the disclosure provides a protein, $H10MbtA^{opt}$ (SEQ ID NO: 4), generated via a codon-optimized nucleotide sequence of $MbtA_{tb}$ with a His10 tag (SEQ ID NO: 3), see FIG. 2 for the original non-optimized nucleotide sequence of $MbtA_{tb}$ and the optimized nucleotide sequence of $MbtA_{tb}$). In some aspects, the protein comprises an amino acid sequence that is at least 80% identical to the amino acid sequence of SEQ ID NO: 4. In some embodiments, the amino acid sequence is at least 85%, 90%, 95%, 98%, 99%, or 99.5% identical to the amino acid sequence of SEQ ID NO: 4. In some embodiments, the disclosure provides a polynucleotide encoding a protein at least 80% identical to SEQ ID NO: 4. In some embodiments, the disclosure provides a polynucleotide encoding a protein at least 85%, 90%, 95%, 89%, 99%, or 99.5% identical to SEQ ID NO: 4. In some embodiments, the disclosure provides a vector comprising a polynucleotide of a protein at least 80% identical to SEQ ID NO: 4. In some embodiments, the disclosure provides a vector comprising a polynucleotide of a protein at least 85%, 90%, 95%, 89%, 99%, or 99.5% identical to SEQ ID NO: 4. In some embodiments, the disclosure provides a cell comprising a protein at least 80% identical to SEQ ID NO: 4. In some embodiments, the disclosure provides a cell comprising a protein at least 85%, 90%, 95%, 89%, 99%, or 99.5% identical to SEQ ID NO: 4. In certain embodiments, the disclosure provides a cell comprising the nucleic acid molecule encoding a protein at least 80% identical to SEQ ID NO: 4. In certain embodiments, the disclosure provides a cell comprising the nucleic acid molecule encoding a protein at least 85%, 90%, 95%, 89%, 99%, or 99.5% identical to SEQ ID NO: 4. In certain embodiments, the disclosure provides a kit comprising a vector for expressing a protein at least 80% identical to SEQ ID NO: 4. In certain embodiments, the disclosure provides a kit comprising a vector for expressing a protein at least 85%, 90%, 95%, 89%, 99%, or 99.5% identical to SEQ ID NO: 4.

In some embodiments, the disclosure provides a method for identifying MbtA inhibitors. In certain embodiments, the method comprises the use of a protein at least 80% identical to SEQ ID NO: 4. In certain embodiments, the method comprises the use of a protein at least 85%, 90%, 95%, 89%, 99%, or 99.5% identical to SEQ ID NO: 4. In certain embodiments, the method comprises the use of a protein at least 80% identical to SEQ ID NO: 4 and a compound. In certain embodiments, the method comprises the use of a protein at least 85%, 90°/o, 95%, 89%, 99%, or 99.5% identical to SEQ ID NO: 4 and a compound. In certain embodiments, the method comprises contacting a protein at least 80% identical to SEQ ID NO: 4 with a compound and detecting the binding of the compound to the protein. In certain embodiments, the method comprises contacting a protein at least 85%, 90%, 95%, 89%, 99%, or 99.5% identical to SEQ ID NO: 4 with a compound and detecting the binding of the compound to the protein.

In some embodiments, the disclosure provides a method for identifying MbtA inhibitors using a MesG assay. In some embodiments, the MesG assay uses MesG (7-methyl-6-thioguanosine). In certain embodiments, the method comprises the use of a protein at least 80% identical to SEQ ID NO: 4. in a MesG assay. In certain embodiments, the method comprises the use of a protein at least 85%, 90%, 95%, 89%, 99%, or 99.5% identical to SEQ ID NO: 4 in a MesG assay. In certain embodiments, the method comprises contacting a protein at least 80% identical to SEQ ID NO: 4 with a compound and detecting the phosphorolysis of MesG. In certain embodiments, the method comprises contacting a protein at least 85%, 90%, 95%, 89%, 99%, or 99.5% identical to SEQ ID NO: 4 with a compound and detecting the phosphorolysis of MesG. In certain embodiments, the method comprises contacting a protein at least 80% identical to SEQ ID NO: 4 with a compound and detecting the conversion of MesG to 2-amino-6-mercapto-7-methylpurine. In certain embodiments, the method comprises contacting a protein at least 85%, 90%, 95%, 89%, 99%, or 99.5% identical to SEQ ID NO: 4 with a compound and detecting the conversion of MesG to 2-amino-6-mercapto-7-methylpurine.

In some embodiments, the MesG assay is a hydroxylamine-7-methyl-6-thioguanosine (HA-MesG) spectrophotometric assay. In some embodiments, the disclosure provides a method for identifying MbtA inhibitors using a HA-MesG spectrophotometric assay. In certain embodiments, the method comprises contacting a protein at least 80% identical to SEQ ID NO: 4 with a compound and detecting the phosphorolysis of MesG. In certain embodiments, the method comprises contacting a protein at least 85%, 90%, 95%, 89%, 99%, or 99.5% identical to SEQ ID NO: 4 with a compound and detecting the phosphorolysis of MesG.

*Mycobacterium smegmatis*

In certain embodiments, a *Mycobacterium smegmatis* is a modified *Mycobacterium smegmatis*. In certain embodiments, a *Mycobacterium smegmatis* is a modified strain of *Mycobacterium smegmatis*. In certain embodiments, a *Mycobacterium smegmatis* is a modified version of *Mycobacterium smegmatis*. In certain embodiments, a *Mycobacterium smegmatis* has the strain designation $mc^2155$. In some embodiments, a *Mycobacterium smegmatis* has the GenBank identifier of CP000480.1. For example, a *Mycobacterium smegmatis* having the GenBank identifier of CP000480.1 is modified. In certain embodiments, a *Mycobacterium smegmatis* may be modified to remove certain amino acids. In certain embodiments, a *Mycobacterium smegmatis* may be modified to remove multiple amino acids. In certain embodiments, a *Mycobacterium smegmatis* may be modified to remove amino acid sequences. In certain embodiments, a *Mycobacterium smegmatis* may be modified to carry a plasmid. In some embodiments, a *Mycobacterium smegmatis* may be modified to carry a plasmid such as $pMbtA_{tb}$ or $pMbtA_{sm}$.

Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis,* 3rd Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, IN. 1972). The disclosure additionally encompasses compounds as individual isomers substantially free of other isomers, and alternatively, as mixtures of various isomers.

In a formula, 〰 is a single bond where the stereochemistry of the moieties immediately attached thereto is not specified - - - is absent or a single bond, ═ or ═ is a single or double bond, and ≡ is a single, double, or triple bond. If drawn in a ring, ◌ indicates that each bond of the ring is a single or double bond, valency permitting. The precise of arrangement of single and double bonds will be determined by the number, type, and substitution of atoms in the ring, and if the ring is multicyclic or polycyclic. In general, any ring atom (e.g., C or N), can have a double bond with a maximum of one adjacent atom.

Unless otherwise stated, structures depicted herein are also meant to include compounds that differ only in the presence of one or more isotopically enriched atoms. For example, compounds having the present structures except for the replacement of hydrogen by deuterium or tritium, replacement of $^{19}F$ with $^{18}F$, or the replacement of $^{12}C$ with $^{13}C$ or $^{14}C$ are within the scope of the disclosure. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic" refers to alkyl, alkenyl, alkynyl, and carbocyclic groups. Likewise, the term "heteroaliphatic" refers to heteroalkyl, heteroalkenyl, heteroalkynyl, and heterocyclic groups.

The term "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CF_3$, Bn).

The term "haloalkyl" is a substituted alkyl group, wherein one or more of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C^{1-2}$ haloalkyl"). Examples of haloalkyl groups include —$CF_3$, —$CF_2CF_3$, —$CF_2CF_2CF_3$, —$CCl_3$, —$CFCl_2$—, —$CF_2Cl$, and the like.

The term "heteroalkyl" refers to an alkyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1 or more heteroatoms within the parent chain ("hetero$C_{1-10}$ alkyl"). In some embodiments, a heteroalkyl group is a saturated group having 1 to 9 carbon atoms and 1 or more heteroatoms within the parent chain ("hetero$C_{1-9}$ alkyl"). In some embodiments, a heteroalkyl group is a saturated group having 1 to 8 carbon atoms and 1 or more heteroatoms within the parent chain ("hetero$C_{1-8}$ alkyl"). In some embodiments, a heteroalkyl group is a saturated group having 1 to 7 carbon atoms and 1 or more heteroatoms within the parent chain ("hetero$C_{1-7}$ alkyl"). In some embodiments, a heteroalkyl group is a saturated group having 1 to 6 carbon atoms and 1 or more heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

The term "alkenyl" refers to a radical of a straight-chain or branched hydrocarbon group having from 2 to 10 carbon atoms and one or more carbon-carbon double bonds (e.g., 1, 2, 3, or 4 double bonds). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl. In an alkenyl group, a C═C double bond for which the stereochemistry is not specified (e.g., —CH═$CHCH_3$ or

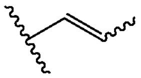

may be an (E)- or (Z)-double bond.

The term "heteroalkenyl" refers to an alkenyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and 1 or 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "alkynyl" refers to a radical of a straight-chain or branched hydrocarbon group having from 2 to 10 carbon atoms and one or more carbon-carbon triple bonds (e.g., 1, 2, 3, or 4 triple bonds) ("$C_{2-10}$alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl (C4), 2-butynyl (C4), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

The term "heteroalkynyl" refers to an alkynyl group, which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1 or more heteroatoms within the parent chain ("hetero$C_{2-10}$ alkynyl"). In some embodiments, a heteroalkynyl group has 2 to 9 carbon atoms, at least one triple bond, and 1 or more heteroatoms within the parent chain ("hetero$C_{2-9}$ alkynyl"). In some embodiments, a heteroalkynyl group has 2 to 8 carbon atoms, at least one triple bond, and 1 or more heteroatoms within the parent chain ("hetero$C_{2-8}$ alkynyl"). In some embodiments, a heteroalkynyl group has 2 to 7 carbon atoms, at least one triple bond, and 1 or more heteroatoms within the parent chain ("hetero$C_{2-7}$ alkynyl"). In some embodiments, a heteroalkynyl group has 2 to 6 carbon atoms, at least one triple bond, and 1 or more heteroatoms within the parent chain ("hetero$C_{2-6}$ alkynyl"). In some embodiments, a heteroalkynyl group has 2 to 5 carbon atoms, at least one triple bond, and 1 or 2 heteroatoms within the parent chain ("hetero$C_{2-5}$ alkynyl"). In some embodiments, a heteroalkynyl group has 2 to 4 carbon atoms, at least one triple bond, and for 2 heteroatoms within the parent chain ("hetero$C_{2-4}$ alkynyl"). In some embodiments, a heteroalkynyl group has 2 to 3 carbon atoms, at least one triple bond, and 1 heteroatom within the parent chain ("hetero$C_{2-3}$ alkynyl"). In some embodiments, a heteroalkynyl group has 2 to 6 carbon atoms, at least one triple bond, and 1 or 2 heteroatoms within the parent chain ("hetero$C_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted hetero$C_{2-10}$ alkynyl. In certain embodiments, the heteroalkynyl group is a substituted hetero$C_{2-10}$ alkynyl.

The term "carbocyclyl" or "carbocyclic" refers to a radical of a non-aromatic cyclic hydrocarbon group having from 3 to 14 ring carbon atoms ("$C_{3-14}$ carbocyclyl") and zero heteroatoms in the non-aromatic ring system. In some embodiments, a carbocyclyl group has 3 to 10 ring carbon atoms ("$C_{3-10}$ carbocyclyl"). In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 4 to 6 ring carbon atoms ("$C_{4-6}$ carbocyclyl"). In some embodiments, a carbocyclyl group has 5 to 6 ring carbon atoms ("$C_{5-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl (C7), bicyclo[2.2.2]octanyl ($C_8$), and the like. Exemplary Ciao carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or Spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

In some embodiments, "carbocyclyl" is a monocyclic, saturated carbocyclyl group having from 3 to 14 ring carbon atoms ("$C_{3-14}$ cycloalkyl"). In some embodiments, a cycloalkyl group has 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 4 to 6 ring carbon atoms ("$C_{4-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl (C3) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted $C_{3-14}$ cycloalkyl. In certain embodiments, the cycloalkyl group is a substituted $C_{3-14}$ cycloalkyl.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some %/155 embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl, and thietanyl. Exemplary κ-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 it electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group substituted by an aryl group, wherein the point of attachment is on the alkyl moiety.

The term "heteroaryl" refers to a radical of a 5-14 membered monocyclic or polycyclic (e.g., bicyclic, tricyclic) 4n+2 aromatic ring system (e.g., having 6, 10, or 14 it electrons shared in a cyclic array) having ring carbon atoms and 1-4 ring heteroatoms provided in the aromatic ring system wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group substituted by a heteroaryl group, wherein the point of attachment is on the alkyl moiety.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

A group is optionally substituted unless expressly provided otherwise. The term "optionally substituted" refers to being substituted or unsubstituted. In certain embodiments, alkyl, alkenyl, alkynyl, heteroalkyl, heteroalkenyl, heteroalkynyl, carbocyclyl, heterocyclyl, aryl, and heteroaryl groups are optionally substituted. "Optionally substituted" refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, and includes any one of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. The disclosure is not intended to be limited in any manner by the exemplary substituents described herein.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NR^{bb}C(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{bb})N(R^{bb})_2$, —$NR^{bb}C(=NR^{bb})N(R^{bb})_2$, —$C(=O)NR^{bb}SO_2R^{aa}$, —$NR^{bb}SO_2R^{aa}$, —$SO_2N(R^{bb})_2$, —$SO_2R^{aa}$, —$SO_2OR^{aa}$, —$OSO_2R^{aa}$, —$S(=O)R^{aa}$, —$OS(=O)R^{aa}$, —$Si(R^{aa})_3$, —$OSi(R^{aa})_3$—$C(=S)N(R^{bb})_2$, —$C(=O)SR^{aa}$, —$C(=S)SR^{aa}$, —$SC(=S)SR^{aa}$, —$SC(=O)SR^{aa}$, —$OC(=O)SR^{aa}$, —$SC(=O)OR^{aa}$, —$SC(=O)R^{aa}$, —$P(=O)(R^{aa})_2$, —$P(—O)(OR^{cc})_2$, —$OP(=O)(R^{aa})_2$, —$OP(=O)(OR^{cc})_2$, —$P(=O)(N(R^{bb})_2)_2$, —$OP(=O)(N(R^{bb})_2)_2$, —$NR^{bb}P(=O)(R^{aa})_2$, —$NR^{bb}P(=O)(OR^{cc})_2$, —$NR^{bb}P(=O)(N(R^{bb})_2)_2$, —$P(R^{cc})_2$, —$P(OR^{cc})_2$, —$P(R^{cc})_3^+X^-$, —$P(OR^{cc})_3^+X^-$, —$P(R^{cc})_4$, —$P(OR^{cc})_4$, —$OP(R^{cc})_2$, —$OP(R^{cc})_3^+X^-$, —$OP(OR^{cc})_2$, —$OP(OR^{cc})_3^+X^-$, —$OP(R^{cc})_4$, —$OP(OR^{cc})_1$, —$B(R^{aa})_2$, —$B(OR^{cc})_2$, —$BR^{aa}(OR^{cc})$, $C_{1-10}$ alkyl. $C_{1-10}$ perhaloalkyl, $C_{2-10}$ alkenyl, $C_{2-10}$ alkynyl, hetero$C_{1-10}$ alkyl, hetero$C_{2-10}$ alkenyl, hetero$C_{2-10}$ alkynyl, Ciao carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion; or two geminal hydrogens on a carbon atom are replaced with the group =O, =S, =$NN(R^{bb})_2$, =$NNR^{bb}C(=O)R^{aa}$, =$NNR^{bb}C(=O)OR^{aa}$, =$NNR^{bb}S(=O)_2R^{aa}$, =$NR^{bb}$, or =$NOR^{cc}$;

each instance of $R^{11}$ is, independently, selected from $C_{1-10}$ alkyl, $C_{1-10}$ perhaloalkyl, $C_{2-10}$ alkenyl, $C_{2-10}$ alkynyl, hetero$C_{1-10}$ alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; each instance of $R^{bb}$ is, independently, selected from hydrogen, —OH, —$OR^{aa}$, —$N(R^{cc})_2$, —CN, —$C(=O)R^{aa}$, —$C(=O)N(R^{cc})_2$, —$CO_2R^{aa}$, —$SO_2R^{aa}$, —$C(=NR^{cc})OR^{aa}$, —$C(=NR^{cc})N$ $(R^{cc})_2$, —$SO_2N(R^{cc})_2$, —$SO_2R^{cc}$, —$SO_2OR^{cc}$, —$SOR^{aa}$, —C(═S)$N(R^{cc})_2$, —C(═O)$SR^{cc}$, —C(═S)$SR^{cc}$, —P(═O)$(R^{aa})_2$, —P(═O)$(OR^{cc})_2$, —P(═O)$(N(R^{cc})_2)_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups: wherein $X^-$is a counterion:

each instance of $R^{cc}$ is, independently, selected from hydrogen, $C_{1-10}$ alkyl, $C_{1-10}$ perhaloalkyl, $C_{2-10}$alkenyl, $C_{2-10}$ alkynyl, hetero$C_{1-10}$ alkyl, hetero$C_{2-10}$ alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups:

each instance of $R^{dd}$ is, independently, selected from halogen, —CN. —$NO_2$, —$N_3$, —$SO_2H$, —$SO_3H$, —OH, —$OR^{ee}$, —$ON(R^{ff})_2$, —$N(R^{ff})_2$, —$N(R^{ff})_3{}^+X^-$, —$N(OR^{ee})R^{ff}$, —SH, —$SR^{ee}$, —$SSR^{ee}$, —C(═O)$R^{ee}$, —$CO_2H$, —$CO_2R^{ee}$, —OC(═O)$R^{ee}$, —$OCO_2R^{ee}$, —C(═O)$N(R^{ff})_2$, —OC(═O)$N(R^{ff})_2$, —$NR^{ff}C$(═O)$R^{ee}$, —$NR^{ff}CO_2R^{ee}$, —$NR^{ff}C$(═O)$N(R^{ff})_2$, —(═$NR^{ff}$)$OR^{ee}$, —OC(═$NR^{ff}$)$R^{ee}$, —OC(═$NR^{ff}$)$OR^{ee}$, —C(═$NR^{ff}$)$N(R^{ff})_2$, —OC(═$NR^{ff}$)$N(R^{ff})_2$, —$NR^{ff}C$(═$NR^{ff}$)$N(R^{ff})_2$, —$NR^{ff}SO_2R^{ee}$, —$SO_2N(R^{ff})_2$, —$SO_2R^{ee}$, —$SO_2OR^{ee}$, —$OSO_2R^{ee}$, —S(═O)$R^{ee}$, —$Si(R^{ee})_3$, —$OSi(R^{ee})_3$, —C(═S)$N(R^{ff})_2$, —C(═O)$SR^{ee}$, —C(═S)$SR^{ee}$, —SC(═S)$SR^{ee}$, —P(═O)$(OR^{ee})_2$, —P(═O)$(R^{ee})_2$, —OP(═O)$(R^{ee})_2$, —OP(═O)$(OR^{ee})_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form ═O or ═S; wherein X is a counterion:

each instance of $R^{ee}$ is, independently, selected from $C_{1-6}$ alkyl. $C_{1-6}$ perhaloalkyl. $C_{2-6}$ alkenyl, $C_{2-6}$ alkynyl, hetero$C_{1-6}$ alkyl, hetero$C_{2-6}$alkaryl, hetero$C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^1$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups: and each instance of $R^{gg}$ is, independently, halogen, —CN, —$NO_2$, —$N_3$, —$SO_2H$, —$SO_3H$, —OH, —$OC_{1-6}$ alkyl, —$ON(C_{1-6}$ alkyl$)_2$, —$N(C_{1-6}$ alkyl$)_2$, —$N(C_{1-6}$ alkyl$)_3{}^+X^-$, —$NH(C_{1-6}$ alkyl$)_2{}^+X^-$, —$NH_2(C_{1-6}$ alkyl$)^+X^-$, $NH_3{}^+X^-$, —$N(OC_{1-6}$ alkyl$)(C_{1-6}$ alkyl), —N(OH)$(C_{1-6}$ alkyl), —NH(OH), —SH, —$SC_{1-6}$ alkyl, —$SS(C_{1-6}$ alkyl), —C(═O)$(C_{1-6}$ alkyl), —$CO_2H$, —$CO_2(C_{1-6}$ alkyl), —OC(═O)$(C_{1-6}$ alkyl), —$OCO_2(C_{1-6}$ alkyl), —C(═O)$NH_2$, —C(═O)$N(C_{1-6}$ alkyl$)_2$, —OC(═O)$NH(C_{1-6}$ alkyl), —NHC(═O)$(C_{1-6}$ alkyl), —$N(C_{1-6}$ alkyl)C(═O)$(C_{1-6}$ alkyl), —$NHCO_2(C_{1-6}$ alkyl), —NHC(═O)$N(C_{1-6}$ alkyl$)_2$, —NHC(═O)$NH(C_{1-6}$ alkyl), —NHC(═O)$NH_2$, —C(═NH)$O(C_{1-6}$ alkyl), —OC(═NH)$(C_{1-6}$ alkyl), —OC(═NH)$OC_{1-6}$alkyl, —C(═NH)$N(C_{1-6}$ alkyl$)_2$, —C(═NH)$NH(C_{1-6}$ alkyl), —C(═NH)$NH_2$, —OC(═NH)$N(C_{1-6}$ alkyl$)_2$, —OC(NH)$NH(C_{1-6}$ alkyl), —OC(NH)$NH_2$, —NHC(NH)$N(C_{1-6}$ alkyl$)_2$,—NHC(═NH)$NH_2$, —$NHSO_2(C_{1-6}$ alkyl), —$SO_2N(C_{1-6}$ alkyl$)_2$, —$SO_2NH(C_{1-6}$ alkyl), —$SO_2NH_2$, —$SO_2C_{1-6}$ alkyl, —$SO_2OC_{1-6}$ alkyl, —$OSO_2C_{1-6}$ alkyl, —$SOC_{1-6}$ alkyl, —$Si(C_{1-6}$ alkyl$)_3$, —$OSi(C_{1-6}$ alkyl), —C(═S)$N(C_{1-6}$ alkyl$)_2$, C(═S)$NH(C_{1-6}$ alkyl), C(═S)$NH_2$, —C(═O)$S(C_{1-6}$ alkyl), —C(═S)$SC_{1-6}$ alkyl, —SC(═S)$SC_{1-6}$ alkyl, —P(═O)$(OC_{1-6}$ alkyl$)_2$, —P(═O)$(C_{1-6}$ alkyl$)_2$, —OP(═O)$(C_{1-6}$ alkyl$)_2$, —OP(═O)$(OC_{1-6}$ alkyl$)_2$, $C_{1-6}$ alkyl, $C_{1-6}$ perhaloalkyl, $C_{2-6}$ alkenyl, $C_{2-6}$ alkynyl, hetero$C_{1-6}$alkyl, hetero$C_{2-6}$alkenyl, hetero$C_{2-6}$alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form ═O or ═S; wherein $X^-$ is a counterion.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from –$OR^{aa}$, —$ON(R^{bb})_2$, —OC(═O)$SR^{aa}$, —OC(═O)$R^{aa}$, —$OCO_2R^{aa}$, —OC(═O)$N(R^{bb})_2$, —OC(═$NR^{bb}$)$R^{aa}$, —OC(═$NR^{bb}$)$OR^{aa}$, —OC(═$NR^{bb}$)$N(R^{bb})_2$, —OS(═O)$R^{aa}$, —$OSO_2R^{aa}$, —$OSi(R^{aa})_3$, —$OP(R^{cc})_2$, —$OP(R^{cc})_3{}^+X^-$, —$OP(OR^{cc})_2$, —$OP(OR^{cc})_3{}^+X^-$, —OP(═O)$(R^{aa})_2$, —OP(═O)$(OR^{cc})_2$, and —OP(═O)$(N(R^{bb}))_2$, wherein $X^-$, $R^{aa}$, $R^{bb}$, and $R^{cc}$ are as defined herein.

The term "amino" refers to the group —$NH_2$. The term "substituted amino," by extension, refers to a monosubstituted amino, a disubstituted amino, or a trisubstituted amino. In certain embodiments, the "substituted amino" is a monosubstituted amino or a disubstituted amino group.

The term "monosubstituted amino" refers to an amino group wherein the nitrogen atom directly attached to the parent molecule is substituted with one hydrogen and one group other than hydrogen, and includes groups selected from —$NH(R^{bb})$, —NHC(═O)$R^{aa}$, —$NHCO_2R^{aa}$, —NHC(═O)$N(R^{bb})_2$, —NHC(═$NR^{bb}$)$N(R^{bb})_2$, —$NHSO_2R^{aa}$, —NHP(═O)$(OR^{cc})_2$, and —NHP(═O)$(N(R^{bb})_2)_2$, wherein $R^{aa}$, $R^{bb}$ and $R^{cc}$ are as defined herein, and wherein $R^{bb}$ of the group —$NH(R^{bb})$ is not hydrogen.

The term "disubstituted amino" refers to an amino group wherein the nitrogen atom directly attached to the parent molecule is substituted with two groups other than hydrogen, and includes groups selected from —$N(R^{bb})_2$, —$NR^{bb}C$(═O)$R^{aa}$, —$NR^{bb}CO_2R^{aa}$, —$NR^{bb}C$(═O)$N(R^{bb})_2$, —$NR^{bb}C$(═$NR^{bb}$)$N(R^{bb})_2$, —$NR^{bb}SO_2R^{aa}$, —$NR^{bb}P$(═O)$(OR^{cc})_2$, and —$NR^{bb}P$(═O)$(N(R^{bb})_2)_2$, wherein $R^{aa}$, $R^{bb}$, and $R^{cc}$ are as defined herein, with the proviso that the nitrogen atom directly attached to the parent molecule is not substituted with hydrogen.

The term "trisubstituted amino" refers to an amino group wherein the nitrogen atom directly attached to the parent molecule is substituted with three groups, and includes groups selected from —N($R^{bb}$); and —N($R^{bb}$)$_3^+X^-$, wherein $R^{bb}$ and $X^-$ are as defined herein.

The term "sulfonyl" refers to a group selected from —$SO_2N(R^{bb})_2$, —$SO_2R^{aa}$, and —$SO_2OR^{aa}$, wherein $R^{aa}$ and $R^{bb}$ are as defined herein.

The term "sulfinyl" refers to the group —S(═O)$R^{aa}$, wherein $R^{aa}$ is as defined herein.

The term "acyl" refers to a group having the general formula —C(═O)$R^{X1}$, —C(═O)O$R^{X1}$, —C(═O)—O—C(═O)$R^{X1}$, —C(═O)S$R^{X1}$, —C(═O)N($R^{X1}$)$_2$, —C(═S)$R^{X1}$, —C(═S)N($R^{X1}$)$_2$, and —C(═S)S($R^{X1}$), —C(═N$R^{X1}$)$R^{X1}$, —C(═N$R^{X1}$)O$R^{X1}$, —C(═N$R^{X1}$)S$R^{X1}$, and —C(═N$R^{X1}$)N($R^{X1}$)$_2$, wherein $R^{X1}$ is hydrogen: halogen; substituted or unsubstituted hydroxyl: substituted or unsubstituted thiol: substituted or unsubstituted amino: substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl: substituted or unsubstituted alkynyl: substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^{X1}$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any one of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "carbonyl" refers a group wherein the carbon directly attached to the parent molecule is $sp^2$ hybridized, and is substituted with an oxygen, nitrogen or sulfur atom, e.g., a group selected from ketones (—C(═O)$R^{aa}$), carboxylic acids (—$CO_2H$), aldehydes (—CHO), esters (—$CO_2R^{aa}$, —C(═O)S$R^{aa}$, —C(═S)S$R^{aa}$), amides (—C(═O)N($R^{bb}$)$_2$, —C(═O)N$R^{bb}SO_2R^{aa}$, —C(═S)N($R^{bb}$)$_2$), and imines (—C(═N$R^{bb}$)$R^{aa}$, —C(═N$R^{bb}$)O$R^{aa}$), —C(═N$R^{bb}$)N($R^{bb}$)$_2$), wherein $R^{aa}$ and $R^{bb}$ are as defined herein.

The term "silyl" refers to the group —Si($R^{aa}$)$_3$, wherein $R^{aa}$ is as defined herein.

The term "oxo" refers to the group ═O, and the term "thiooxo" refers to the group ═S.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(═O)$R^{aa}$, —C(═O)N($R^{cc}$)$_2$, —$CO_2R^{aa}$, —$SO_2R^{aa}$, —C(═N$R^{bb}$)$R^{aa}$, —C(═N$R^{cc}$)O$R^{aa}$, —C(═N$R^{cc}$)N($R^{cc}$)$_2$, —$SO_2N(R^{cc})_2$, —$SO_2R^{cc}$, —$SO_2OR^{cc}$, —SO$R^{aa}$, —C(═S)N($R^{cc}$)$_2$, —C(═O)S$R^{cc}$, —C(═S)S$R^{cc}$, —P(═O)(O$R^{cc}$)$_2$, —P(═O)($R^{aa}$)$_2$, —P(═O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$alkynyl, $C_{3-10}$ carbocyclyl, 3-14 membered heterocyclyl, $C_{6-14}$ aryl, and 5-14 membered heteroaryl, or two $R^{11}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —O$R^{aa}$, —N($R^{cc}$)$_2$, —C(═O)$R^{aa}$, —C(═O)N($R^{cc}$)$_2$, —$CO_2R^{aa}$, —$SO_2R^{aa}$, —C(═N$R^{cc}$)$R^{aa}$, —C(═N$R^{cc}$)O$R^{aa}$, —C(═N$R^{cc}$)N($R^{cc}$)$_2$, —$SO_2N(R^{cc})_2$, —$SO_2R^{cc}$, —$SO_2OR^{cc}$, —SO$R^{aa}$, —C(═S)N($R^{cc}$)$_2$, —C(═O)S$R^{cc}$, —C(═S)S$R^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined herein. Nitrogen protecting groups are well known in the art and include those described in detail in *Protecting Groups in Organic Synthesis*, T. W. Greene and P. G. M. Wuts, 3rd edition, John Wiley & Sons, 1999, incorporated herein by reference.

For example, nitrogen protecting groups such as amide groups (e.g., —C(═O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(0-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(═O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1, 3dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., $—S(=O)_2R^{ee}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-olio-3-pyroolin-3-yl)amine, quaternary ammonium salts. N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl](methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentaacylchromium- or tungsten) acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, $—R^{aa}$, $—N(R^{bb})_2$, $—C(=O)SR^{aa}$, $—C(=O)R^{aa}$, $—CO_2R^{aa}$, $—C(=O)N(R^{bb})_2$, $—C(=NR^{bb})R^{aa}$, $—C(=NR^{bb})OR^{aa}$, $—C(=NR^{bb})N(R^{bb})_2$, $—S(=O)R^{aa}$, $—SO_2R^{aa}$, $—Si(R^{aa})_3$, $—P(R^{cc})_2$, $—P(R^{cc})_3^+X^-$, $—P(OR^{cc})_2$, $—P(OR^{cc})_3^+X^-$, $—P(=O)(R^{aa})_2$, $—P(=O)(OR^{cc})_2$, and $—P(=O)(N(R^{bb})_2)_2$, wherein $X^-$, $R^{aa}$, $R^{bb}$, and $R^{cc}$ are as defined herein. Oxygen protecting groups are well known in the art and include those described in detail in Protecting Groups in Organic Synthesis, T. W. Greene and P. G. M. Wuts, 3rd edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a, 4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, trip-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis (4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), 1-butyldiphenylsilyl (TBDPS), tribenzylsilyl, trip-xylylsilyl, triphenylsilyi, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio) pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2, 2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, ally) carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl) phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, March *Advanced Organic Chemistry* 6th ed. (501-502). Exemplary leaving groups include, but are not limited to, halo (e.g., chloro, bromo, iodo), $—OR^{aa}$ (when the O atom is attached to a carbonyl group, wherein $R^{aa}$ is as defined herein), $—O(C{=}O)R^{LG}$, or $—O(SO)_2R^{LG}$ (e.g., tosyl, mesyl, besyl), wherein $R^{LG}$ is optionally substituted alkyl, optionally substituted aryl, or optionally substituted heteroaryl. In some cases, the leaving group is a halogen. In some embodiments, the leaving group is I.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., $F^-$, $Cl^-$, $Br^-$, $I^-$), $NO_3^-$, $ClO_4^-$, $OH^-$, $H_2PO_4^-$, $HCO_3^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), $BF_4^-$, $PF_4^-$, $PF_6^-$, $AsF_6^-$, $SbF_6^-$, $B[3,5-(CF_3)_2C_6H_3]_4^-$, $B(C_6F_5)_4^-$, $BPh_4^-$, $Al(OC(CF_3)_3)_4^-$, and carborane anions (e.g., $CB_{11}H_{12}^-$ or $(HCB_{11}Me_5Br_6)^-$). Exemplary counterions which may be multivalent include $CO_3^{2-}$, $HPO_4^{2-}$, $PO_4^{3-}$, $B_4O_7^{2-}$, $SO_4^{2-}$, $S_2O_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and Claims. The invention is not intended to be limited in any manner by the above exemplary listing of substituents.

As used herein, the term "salt" refers to any and all salts, and encompasses pharmaceutically acceptable salts.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et at describe pharmaceutically acceptable salts in detail in *J. Pharmaceutical Sciences,* 1977, 66, 1-19, incorporated herein by reference. Pharmaceutically acceptable salts of the compounds of this disclosure include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\ alkyl)_4^-$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO. THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R.xH_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R.0.5\ H_2O$)), and polyhydrates (x is a number greater than 1. e.g., dihydrates ($R.2H_2O$) and hexahydrates ($R.6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Calm and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorph" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "co-crystal" refers to a crystalline structure composed of at least two components. In certain embodiments, a co-crystal contains a compound of the present disclosure and one or more other component, including but not limited to, atoms, ions, molecules, or solvent molecules. In certain embodiments, a co-crystal contains a compound of the present disclosure and one or more solvent molecules. In certain embodiments, a co-crystal contains a compound of the present disclosure and one or more acid or base. In certain embodiments, a co-crystal contains a compound of the present disclosure and one or more components related to said compound, including not limited to, an isomer, tautomer, salt, solvate, hydrate, synthetic precursor, synthetic derivative, fragment or impurity of said compound.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal "Disease." "disorder," and "condition" are used interchangeably herein.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term “administer,” “administering,” or “administration” refers to implanting, absorbing, ingesting, injecting, inhaling, or otherwise introducing a compound described herein, or a composition thereof, in or on a subject.

The terms “condition,” “disease,” and “disorder” are used interchangeably.

As used herein, and unless otherwise specified, the terms “treat,” “treating” and “treatment” contemplate an action that occurs while a subject is suffering from the specified disease or condition, which reduces the severity of the disease or condition, or retards or slows the progression of the disease or condition (i.e., “therapeutic treatment”), and also contemplates an action that occurs before a subject begins to suffer from the specified disease or condition (i.e., “prophylactic treatment”).

An “effective amount” of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

As used herein the term “inhibit” or “inhibition” in the context of enzymes, for example, in the context of $MbtA_{tb}$, refers to a reduction in the activity of the enzyme. In some embodiments, the term refers to a reduction of the level of enzyme activity, e.g., $MbtA_{tb}$ activity, to a level that is statistically significantly lower than an initial level, which may, for example, be a baseline level of enzyme activity. In some embodiments, the term refers to a reduction of the level of enzyme activity, e.g., $MbtA_{tb}$ activity, to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of enzyme activity.

As used herein the term “infectious microorganism” refers to a species of infectious fungi, bacteria, or protista, or to a virus. In certain embodiments, the infectious microorganism is a fungi. In certain embodiments, the infectious microorganism is a bacteria. In certain embodiments, the infectious microorganism is a protista. In certain embodiments, the infectious microorganism is a virus.

An “infection” or “infectious disease” refers to an infection with a microorganism, such as a fungus, bacteria, or virus. In certain embodiments, the infection is an infection with a fungus, i.e., a fungal infection. In certain embodiments, the infection is an infection with a virus, i.e., a viral infection. In certain embodiments, the infection is an infection with bacteria, i.e., a bacterial infection. Various infections include, but are not limited to, skin infections, GI infections, urinary tract infections, genito-urinary infections, sepsis, blood infections, and systemic infections. In some embodiments, the infectious disease is tuberculosis.

As used herein, the term “siderophore” are small, high-affinity iron-chelating compounds secreted by microorganisms such as bacteria and fungi and serving to transport iron across cell membranes. Exemplary siderophores include, but are not limited to mycobactin, yersiniabactin, pyochelin, enterobactin, bacillibactin, vibriobactin, petrobactin, aerobactin, salmochelin, pyoverdin, alcaligin, and staphyloferrin A.

As used herein, the term “bifunctional enzyme salicyl-AMP ligase” or “$MbtA_{tb}$,” refers to an enzyme converts salicylic acid to mycobactin (MBT) siderophores. $MbtA_{tb}$ may also refer to the encoding RNA and DNA sequences of the $MbtA_{tb}$ protein. In some embodiments, a $MbtA_{tb}$ inhibitor provided herein is specific for a $MbtA_{tb}$ from a species. The term $MbtA_{tb}$ further includes, in some embodiments, sequence variants and mutations (e.g., naturally occurring or synthetic $MbtA_{tb}$ sequence variants or mutations), and different $MbtA_{tb}$ isoforms. In some embodiments, the term $MbtA_{tb}$ includes protein or encoding sequences that are homologous to a $MbtA_{tb}$ protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with a $MbtA_{tb}$ sequence, for example, with a $MbtA_{tb}$ sequence provided herein. $MbtA_{tb}$ protein and encoding gene sequences are well known to those of skill in the art, and exemplary protein sequences include, but are not limited to, the following sequences. Additional $MbtA_{tb}$ sequences, e.g., $MbtA_1b$ homologues from other bacteria species, will be apparent to those of skill in the art, and the disclosure is not limited to the exemplary sequences provided herein.

(SEQ ID NO: 1)

```
MPPKAADGRRPSPDGGLGGFVPFPADRAASYRAAGYWSGRTLDTVLSDAA
RRWPDRLAVADAGDRFGHGGLSYAELDQRADRAAAALHGLGITPGDRVLL
QLPNGCQFAVALFALLRAGAIPVMCLPGHRAAELGHFAAVSAATGLVVAD
VASGFDYRPMARELVADHPTLRHVIVDGDPGPFVSWAQLCAQAGTGSPAP
PADPGSPALLLVSGGTTGMPKLIPRTHDDYVFNATASAALCRLSADDVYL
VVLAAGHNFPLACPGLLGAMTVGATAVFAPDPSPEAAFAAIERHGVTVTA
LVPALAKLWAQSCEWEPVTPKSLRLLQVGGSKLEPEDARRVRTALTPGLQ
QVFGMAEGLLNFTRIGDPPEVVEHTQGRPLCPADELRIVNADGEPVGPGE
EGELLVRGPYTLNGYFAAERDNERCFDPDGFYRSGDLVRRRDDGNLVVTG
RVKDVICRAGETIAASDLEEQLLSHPAIFSAAAVGLPDQYLGEKICAAVV
FAGAPITLAELNGYLDRRGVAAHTRPDQLVAMPALPTTPIGKIDKRAIVR
QLGIATGPVTTQRCH
```

As used herein, the term “anthranilate-CoA synthetase” or “PqsA” refers to an enzyme of the menaquinone biosynthesis pathway which converts anthranilic acid to anthranilyl-S-CoA. PqsA may also refer to the encoding RNA and DNA sequences of the PqsA protein. In some embodiments, a PqsA inhibitor provided herein is specific for a PqsA from a species, e.g., for *P. aeruginosa* PqsA. The term PqsA further includes, in some embodiments, sequence variants and mutations (e.g., naturally occurring or synthetic PqsA sequence variants or mutations), and different PqsA isoforms. In some embodiments, the term PqsA includes protein or encoding sequences that are homologous to a PqsA protein or encoding sequence, for example, a protein or encoding sequence having at least 80%, at least 85%, at least 90%, at least 91%, at least 92%, at least 93%, at least 94%, at least 95%, at least 96%, at least 97%, at least 98%, at least 99%, or at least 99.5% sequence identity with a PqsA sequence, for example, with a PqsA sequence provided herein. PqsA protein and encoding gene sequences are well known to those of skill in the art, and exemplary protein sequences include, but are not limited to, the following sequences. Additional PqsA sequences, e.g., PqsA homologues from other bacteria species, will be apparent to those of skill in the art, and the disclosure is not limited to the exemplary sequences provided herein.

(SEQ ID NO: 2)
MSTLANLTEVLFRLDFDPDTAVYHYRGQTLSRLQCRTYILSQASQLARLL

KPGDRVVLALNDSPSLACLFLACIAVGAIPAVINPKSREQALADIAADCQ

ASLVVREADAPSLSGPLAPLTLRAAAGRPLLDDFSLDALVGPADLDWSAF

HRQDPAAACFLQYTSGSTGAPKGVMHSLRNTLGFCRAFATELLALQAGDR

LYSIPKMFFGYGMGNSLFFPWFSGASALLDDTWPSPERVLENLVAFRPRV

LFGVPAIYASLRPQARELLSSVRLAFSAGSPLPRGEFEFWAAHGLEICDG

IGATEVGHVFLANRPGQARADSTGLPLPGYECRLVDREGHTIEEAGRQGV

LLVRGPGLSPGYWRASEEQQARFAGGWYRTGDLFERDESGAYRHCGREDD

LFKVNGRWVVPTQVEQAICRHLPEVSEAVLVPTCRLHDGLRPTLFVTLAT

PLDDNQILLAQRIDQHLAEQIPSHMLPSQLHVLPALPRNDNGKLARAELR

HLADTLYHDNLPEERAC

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

General Materials and Methods

Reagents were obtained from Aldrich Chemical (www.sigma-aldrich.com) or Acros Organics (www.fishersci.com) and used without further purification. Optima or HPLC grade solvents were obtained from Fisher Scientific (www.fishersci.com), degassed with Ar, and purified on a solvent drying system as described.1 All reactions were performed in flame-dried glassware under positive Ar pressure with magnetic stirring unless otherwise noted. Liquid reagents and solutions were transferred thru rubber septa via syringes flushed with Ar prior to use. TLC was performed on 0.25 mm E. Merck silica gel 60 F254 plates and visualized under UV light (254 nm). Silica flash chromatography was performed on E. Merck 230-400 mesh silica gel 60. Lyophilization of samples was performed using a Labconco Freezone 2.5 instrument.

IR spectra were recorded on a Broker Optics Tensor 27 FTIR spectrometer using an attenuated total reflection (ATR) attachment with peaks reported in cm-1. NMR spectra were recorded on a Bruker UltraShield Plus 500 MHz Avance III NMR or UltraShield Plus 600 MHz Avance III NMR with DCH CryoProbe at 24° C. Chemical shifts are expressed in ppm relative to TMS (1H, 0 ppm) or solvent signals: CDCl3 (1H, 7.24 ppm; 13C, 77.23 ppm), or CD3OD (1H, 3.31 ppm; 13C, 49.15 ppm); coupling constants are expressed in Hz. NMR spectra were processed using Bruker TopSpin, Mnova (www.mestrelab.com/software/mnova-nmr), software. High resolution mass spectra were obtained at the MSKCC Analytical Core Facility on a Waters Acuity Premiere XE TOF LC-MS by electrospray ionization (ESI).

Compound Salicyl-AMS (1) was synthesized by WuXi AppTec (Ferreras, J. A., et al. (2005) *Nat. Chem. Biol.* 1, 29-32) and salicyl-AMSN (4a) was synthesized according to published literatures procedures (Somu, R. V., et at (2006) *J. Med. Chem.* 49, 31-34). Salicyl-AMSN (4a) was converted to the sodium salt by ion exchange as described for salicyl-AMSNMe (4b) below.

Example 1A: Synthesis of salicyl-AMSNMe (4b)

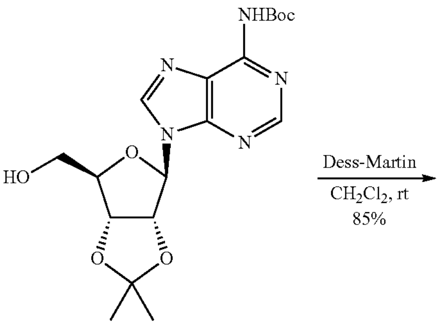

S1

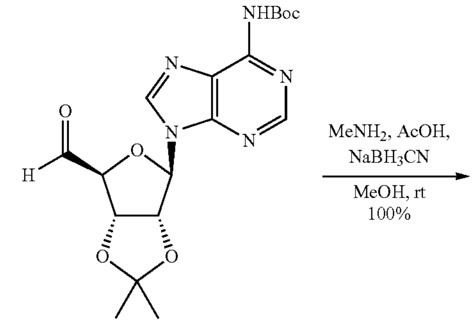

S2

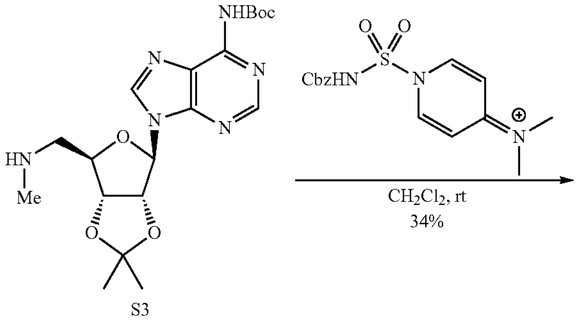

S3

-continued

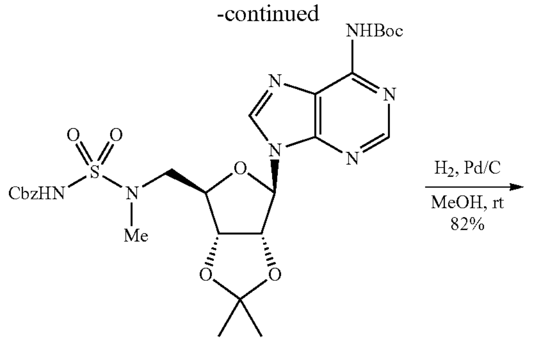

S4

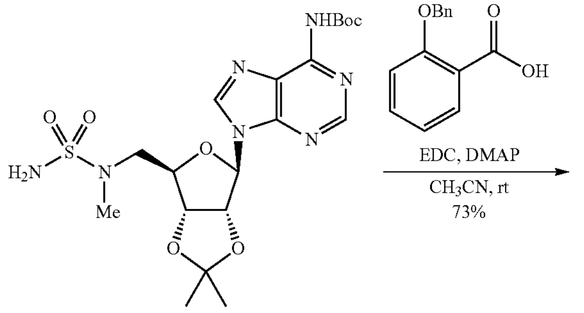

S5

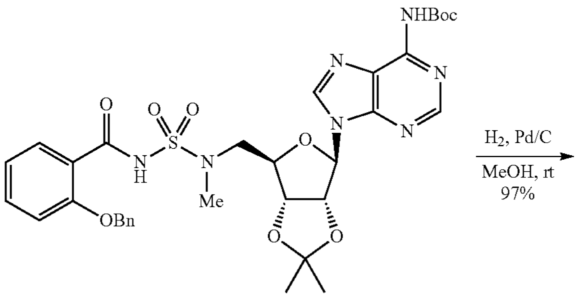

S6

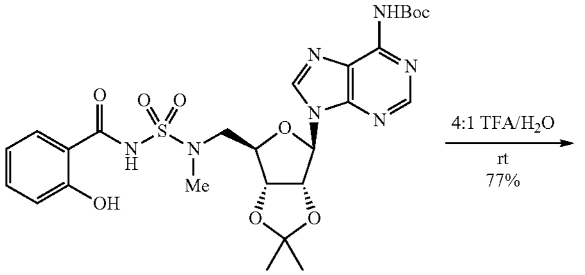

S7

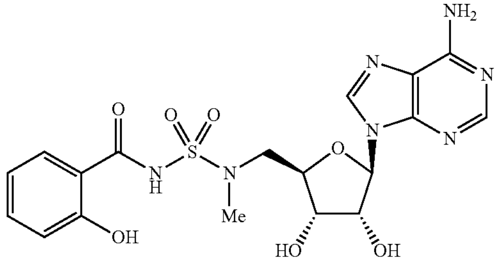

4b, salicyl-AMSNMe

Cbz=benzyloxycarbonyl; DIAD=diisopropyl azo-di-carboxyl-ate; DMAP=4-dimethylaminopyridine; DPPA=diphenylphosphoryl azide; EDC=1-ethyl-3-(3-di-methyl-amino-propyl)-carbodiimide hydrochloride; TFA=2,2,2-trifluoroacetic acid.

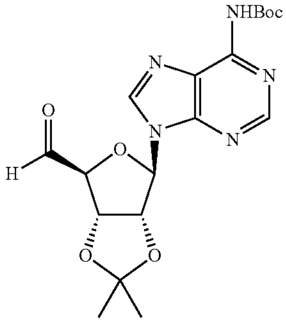 [SMILES: CC(C)(C)OC(=O)Nc1ncnc2c1ncn2[C@@H]1O[C@H](C=O)[C@H]2OC(C)(C)O[C@H]21]

tert-Butyl (9-((3aR,4R,6S,6aS)-6-formyl-2,2-dimethyltetrahydrofuro[3,4-d][1,3]dioxol-4-yl)-9H-purin-6-yl)carbamate (S2)

In a 100-mL roundbottom flask, $N^6$-Boc-2',3'-O-isopropylideneadenosine (S1)[22] (1.34 g, 3.29 mmol, 1.0 equiv.) was dissolved in $CH_2Cl_2$ (30 mL). Dess-Martin periodinane (1.67 g, 3.95 mmol, 1.2 equiv.) was added and the mixture was stirred at room temperature for 1.5 h. A mixture of saturated aqueous $NaHCO_3$ (30 mL) and saturated aqueous $Na_2S_2O_3$ (30 mL) was added and the mixture was stirred for 20 min. The organic layer was separated, washed with brine (30 mL), dried ($Na_2SO_4$), filtered, and concentrated by rotary evaporation to afford aldehyde S2 (1.14 g, 85%) as a white solid, which was used without further purification.

TLC: R/0.26 (1:19 MeOH/$CH_2Cl_2$). $^1$H-NMR (600 MHz, $CDCl_3$) δ 9.24 (s, 1H), 8.40 (s, 1H), 8.01 (s, 1H), 6.18 (s, 1H), 5.48 (dd, J=6.1, 1.8 Hz, 1H), 5.27 (d, J=6.1 Hz, 1H), 4.62 (d, J=1.8 Hz, 1H), 1.53 (s, 3H), 1.49 (s, 9H), 1.33 (s, 3H). $^{13}$C-NMR (151 MHz): δ 199.4, 152.9, 150.4, 149.7, 149.6, 142.0, 122.3, 114.5, 93.1, 92.3, 84.7, 83.6, 82.5, 53.5, 28.1, 26.6, 25.0. IR (ATR): 2982, 2936, 1750, 1611, 1590, 1525, 1370, 1329, 1144, 1077, 854, 731. HRMS calculated for $C_{18}H_{26}N_5O_7$ ($[M+H_2O+H]^+$) 424.1827, found 424.1841.

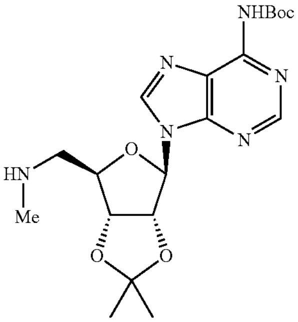 [SMILES: CNC[C@H]1O[C@@H](n2cnc3c(NC(=O)OC(C)(C)C)ncnc32)[C@@H]2OC(C)(C)O[C@@H]21]

tert-Butyl (9-((3aR,4R,6R,6aR)-2,2-dimethyl-6((methylamino)methyl)tetrahydrofuro[3,4-d][1,3]dioxol-4-yl)-9H-purin-6-yl)carbamate (S3)

In a 100-mL roundbottom flask, aldehyde S2 (1.02 g, 2.51 mmol, 1.0 equiv.) was dissolved in MeOH (30 mL). Methylamine (2 M in THF, 6.28 mL, 12.57 mmol, 5.0 equiv.) and acetic acid (287 ELL, 5.02 mmol, 2.0 equiv.) were added, followed by solid sodium cyanoborohydride (316 mg, 5.02 mmol, 2.0 equiv.). The mixture was stirred at room temperature for 16 h. The solvent was removed by rotary evaporation and the residue was partitioned between $CH_2Cl_2$ (30 mL) and saturated aqueous $NaHCO_3$ (30 mL). The organic layer was washed with brine (30 mL), dried ($Na_2SO_4$), filtered, and concentrated by rotary evaporation to afford methylamine S3 (1.05 g, 100%), which was used without further purification.

TLC: $R_f$ 0.18 (1:9 MeOH/$CH_2Cl_2$). $^1$H-NMR (600 MHz, $CDCl_3$) δ 9.70 (br s, 1H), 9.53 (br s, 1H), 8.63 (s, 1H), 8.23 (s, 1H), 6.15 (d, J=2.8 Hz, 1H), 5.24 (dd, J=6.5, 2.7 Hz, 1H), 5.13 (dd, J=6.5, 3.6 Hz, 1H), 4.65 (app dt, J=10.2, 3.4 Hz, 1H), 3.82 (dd, J=13.0, 10.2 Hz, 1H), 3.46 (dd, J=13.0, 3.2 Hz, 1H), 2.88 (s, 3H), 1.62 (s, 3H), 1.59 (s, 9H), 1.37 (s, 3H). $^{13}$C-NMR (125 MHz): δ 153.0, 150.3, 150.1, 149.7, 141.8, 122.3, 114.8, 91.0, 85.1, 83.5, 82.4, 82.3, 53.1, 36.2, 28.2, 27.2, 25.4. IR (ATR): 2980, 2936, 1746, 1611, 1583, 1532, 1369, 1325, 1232, 1143, 1075, 909, 866, 773. HRMS m/z calculated for $C_{19}H_{29}N_6O_5$ ([M+H]$^+$) 421.2199, found 421.2200.

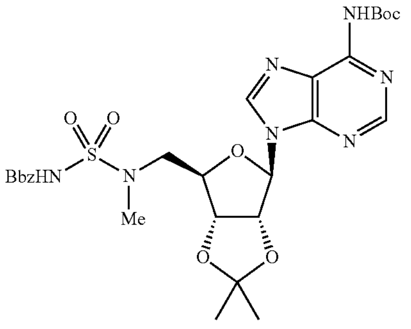

Benzyl (N-(((3aR,4R,6R,6aR)-6-(6-((tert-butoxycarbonyl)amino)-9H-purin-9-yl)-2,2-di-methyltetrahydrofuro[3,4-d][1,3]dioxol-4-yl)methyl)-N-methylsulfamoyl)carbamate (S4)

In a 100-mL roundbottom flask, crude methylamine S3 (1.05 g, 2.51 mmol, 1.0 equiv) was dissolved in $CH_2Cl_2$ (30 mL). Solid ((benzyloxy)carbonyl)((4-(dimethyliminio)pyridin-1 (4H)-yl)sulfonyl)-amide[2] (1.09 g, 3.27 mmol, 1.3 equiv) was added and the mixture was stirred at room temperature for 16 h. The mixture was diluted with $CH_2Cl_2$ (20 mL), washed with 0.2 N HCl (30 mL) and brine (30 mL), dried ($Na_2SO_4$), filtered, and concentrated by rotary evaporation. Purification by silica flash chromatography (0→3 100% EtOAc/hexanes) provided Cbz-protected sulfamide S4 (0.54 g, 34%) as a white solid.

TLC: $R_f$ 0.46 (1:9 MeOH/EtOAc). $^1$H-NMR (600 MHz, $CDCl_3$) δ 9.45 (d, J=13.3H, 1H), 8.93 (s, 1H), 8.42 (br s, 1H), 8.01 (s, 1H), 7.28-7.20 (m, 5H), 5.85 (d, J=4.9 Hz, 1H), 5.22 (dd, J=6.2, 4.9 Hz, 1H), 5.14 (d, J=12.1 Hz, 1H), 5.04-5.01 (m, 2H), 4.57 (m, 1H), 3.53-3.49 (m, 4H), 3.41 (m, 1H), 1.63 (s, 3H), 1.49 (s, 9H), 1.35 (s, 3H). $^{13}$C-NMR (151 MHz): δ 154.8, 153.4, 152.3, 151.2, 150.6, 142.1, 134.6, 128.6, 128.5, 128.3, 128.0, 114.9, 93.4, 82.7, 82.5, 82.3, 81.6, 68.2, 45.4, 35.0, 28.0, 27.5, 25.2. IR (ATR): 3242, 2987, 1712, 1583, 1455, 1420, 1358, 1221, 1156, 1091, 854, 735. HRMS m/z calculated for $C_{27}H_{36}N_7O_9S$ ([M+H]$^+$) 634.2295, found 634.2294.

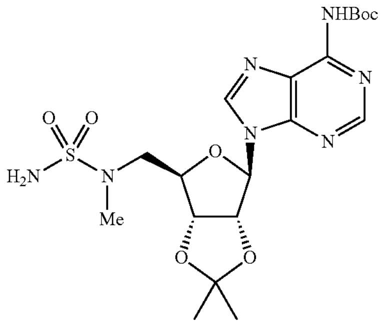 [SMILES: CN(C[C@H]1O[C@@H](n2cnc3c(NC(=O)OC(C)(C)C)ncnc32)[C@@H]2OC(C)(C)O[C@@H]21)S(N)(=O)=O]

tert-Butyl (9-((3aR,4R,6R,6aR)-2,2-dimethyl-6-((methyl(sulfamoyl)amino)methyl)-tetra-hydrofuro[3,4-d][1,3]dioxol-4-yl)-9H-purin-6-yl)carbamate (S5)

In a 50-mL roundbottom flask, Cbz-protected sulfamide S4 (540 mg, 0.85 mmol, 1.0 equiv.) was dissolved in degassed MeOH (10 mL). Solid 10% palladium on carbon (50 mg) was added and the mixture was purged with hydrogen gas and stirred at room temperature under hydrogen atmosphere (balloon) for 16 h. The catalyst was removed by filtration through Celite and the filtrate was concentrated by rotary evaporation to afford sulfamide S5 (349 mg, 82%) as a white solid, which was used without further purification.

TLC: $R_f$ 0.07 (1:4 MeOH/EtOAc). $^1$H-NMR (600 MHz, $CDCl_3$) δ 8.85 (s, 1H), 8.09 (s, 1H), 7.98 (dd, J=7.9.3.5 Hz, 1H), 5.86 (d, J=4.6 Hz), 5.29 (dd, J=6.3, 4.6 Hz, 1H), 5.11 (dd, J=6.3, 2.3 Hz, 1H), 4.81 (br s, 2H), 4.49 (m, 1H), 3.55-3.48 (m, 5H), 1.64 (s, 3H), 1.52 (s, 9H), 1.35 (s, 3H). $^{13}$C-NMR (151 MHz): δ 154.8, 153.4, 152.0, 150.9, 142.3, 128.0, 115.0, 92.9, 83.2, 82.5, 82.4, 81.4, 45.2, 35.1, 28.1, 27.4, 25.2. IR (ATR): 3266, 2984, 1714, 1581, 1456, 1419, 1356, 1320, 1216, 1154, 1091, 911, 854, 765. HRMS m/z calculated for $C_{19}H_{30}N_7O_7S$ ([M+H]$^+$) 500.1927, found 500.1904.

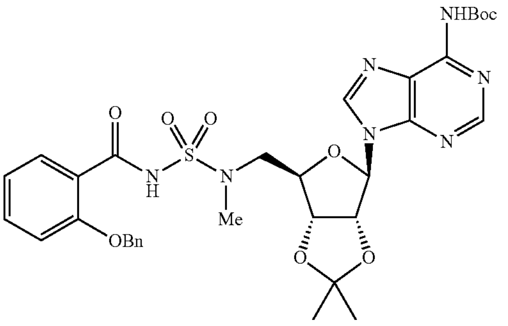 [SMILES: CN(C[C@H]1O[C@@H](n2cnc3c(NC(=O)OC(C)(C)C)ncnc32)[C@@H]2OC(C)(C)O[C@@H]21)S(=O)(=O)NC(=O)c1ccccc1OCc1ccccc1]

tert-Butyl (9-((3aR,4R,6R,6aR)-6-(((N-(2-(benzyloxy)benzoyl)sulfamoyl)(methyl)amino)-methyl)-2,2-dimethyltetrahydrofuro[3,4-d][1,3]dioxol-4-yl)-9H-purin-6-yl)carbamate (S6)

In a 25-mL roundbottom flask, sulfamide S5 (300 mg, 0.60 mmol, 1.0 equiv.) and 2-benzyloxybenzoic acid (274 mg, 1.20 mmol, 2.0 equiv.) were dissolved in $CH_3CN$ (6 mL). Solid EDC (230 mg, 1.20 mmol, 2.0 equiv.) was added, followed by DMAP (73 mg, 0.60 mmol, 1.0 equiv.). The mixture was stirred at room temperature for 16 h. The solvent was removed by rotary evaporation and the residue was partitioned between $CH_2Cl_2$ (30 mL) and saturated aqueous $NH_4Cl$ (30 mL). The organic layer was washed with brine (30 mL), dried ($Na_2SO_4$), filtered, and concentrated by rotary evaporation. Purification by silica flash chromatography (30→100% EtOAc/hexanes) afforded acyl sulfamide S6 (312 mg, 73%) as a white solid.

TLC: $R_f$ 0.36 (1:1 EtOAc/hexanes). $^1$H-NMR (600 MHz, $CDCl_3$) δ 10.17 (s, 1H), 9.32 (d, J=9.36, 1H), 8.94 (s, 1H), 8.04 (dd, J=7.8, 1.8 Hz, 1H), 7.90 (s, 1H), 7.45 (ddd, J=8.7, 7.3, 1.9 Hz, 1H), 7.42-7.37 (m, 3H), 7.37-7.34 (m, 2H), 7.01 (dt, J=8.0, 2.2 Hz, 2H), 5.75 (d, J=5.0 Hz, 1H), 5.21-5.16 (m, 3H), 4.95 (dd, J=6.1, 1.7 Hz, 1H), 4.43 (app q, J=2.3 Hz, 1H), 3.45 (s, 3H), 3.35-3.25 (m, 2H), 1.55 (s, 3H), 1.42 (s, 9H), 1.26 (s, 3H). $^{13}$C-NMR (125 MHz): δ 162.8, 157.0, 154.9, 153.5, 152.6, 150.8, 141.9, 134.8, 134.6, 132.8, 129.2, 129.1, 128.2, 127.9, 112.0, 119.4, 114.7, 113.0, 93.6, 82.8, 82.4, 82.2, 81.8, 71.9, 45.5, 35.0, 28.1, 27.6, 25.2. IR (ATR): 3300, 3075, 2984, 2935, 1713, 1684, 1456, 1421, 1357, 1316, 1219, 1156, 1126, 1091, 1044, 1022, 990, 910, 893, 855, 756, 733. HRMS m/z calculated for $C_{33}H_{39}N_7O_9S$ ($[M+H]^+$) 710.2608, found 710.2612.

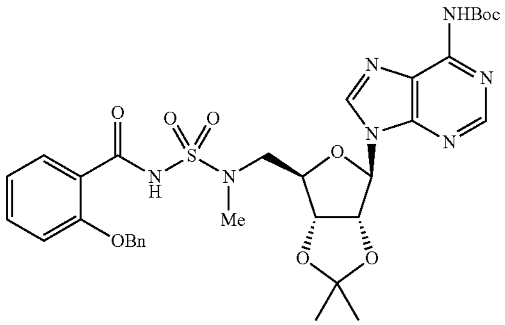 [SMILES: CN(C[C@H]1O[C@@H](n2cnc3c(NC(=O)OC(C)(C)C)ncnc32)[C@@H]2OC(C)(C)O[C@@H]21)S(=O)(=O)NC(=O)c1ccccc1OCc1ccccc1]

tert-Butyl (9-((3aR,4R,6R,6aR)-6-(((N-(2-hydroxybenzoyl)sulfamoyl)(methyl)amino)-methyl)-2,2-dimethyltetrahydrofuro[3,4d][1,3]dioxol-4-yl)-9H-purin-6-yl)carbamate (S7)

In a 100-mL roundbottom flask, acyl sulfamide S6 (780 mg, 1.10 mmol, 1.0 equiv.) was dissolved in MeOH (30 mL). Solid 10% palladium on carbon (80 mg) was added and the mixture was purged with hydrogen gas and stirred at room temperature under hydrogen atmosphere (balloon) for 16 h. The catalyst was removed by filtration through Celite and the filtrate was concentrated by rotary evaporation to afford salicyl sulfamide S7 (662 mg, 97%) as a white solid, which was used without further purification.

TLC: $R_f$ 0.50 (1:9 MeOH/$CH_2Cl_2$). $^1$H-NMR (600 MHz, $CDCl_3$) δ 8.90 (s, 1H), 7.86 (br s, 1H), 7.51 (app d, J=8.0 Hz, 1H), 7.35 (app t, J=7.9 Hz, 1H), 6.87 (app d, J=8.4 Hz, 1H), 6.79 (app t, J=7.9 Hz, 1H), 5.80 (d, J=2.0 Hz, 1H), 5.22 (dd, J=6.4, 2.0 Hz, 1H), 4.47 (dd, J=6.4, 3.3 Hz, 1H), 3.58 (m, 1H), 3.46-3.42 (m, 4H), 1.54 (s, 3H), 1.46 (s, 9H), 1.28 (s, 3H). $^{13}$C-NMR (151 MHz): δ 167.6, 160.7, 154.5, 153.8, 152.4, 150.9, 142.3, 135.7, 128.0, 127.9, 119.6, 118.6, 114.9, 93.0, 83.6, 82.9, 82.8, 81.8, 45.8, 35.3, 28.2, 27.4, 25.2. IR (ATR): 3258, 3109, 2984, 2395,1716, 1653, 1582, 1461, 1420, 1358, 1216, 1158, 1091, 854, 758. HRMS m/z calculated for $C_{26}H_{33}N_7O_9S$ ($[M+H]^+$) 620.2139, found 620.2113.

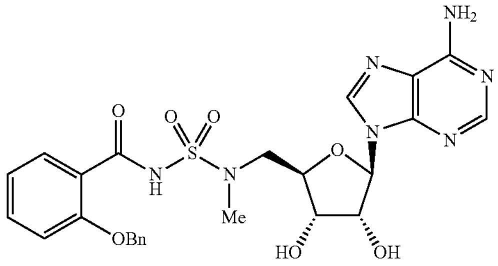 [SMILES: CN(C[C@H]1O[C@@H](n2cnc3c(N)ncnc32)[C@H](O)[C@@H]1O)S(=O)(=O)NC(=O)c1ccccc1OCc1ccccc1]

N—(N-(((2R,3S,4R,5R)-5-(6-Amino-9H-purin-9-yl)-3,4-dihydroxytetrahydrofuran-2-yl)-methyl)-N-methylsulfamoyl)-2-hydroxybenzamide (salicyl-AMSNMe, 4b)

In a 25-mL roundbottom flask, salicyl sulfamide S7 (600 mg, 0.97 mmol, 1.0 equiv.) was dissolved in 10 mL 4:1 TFA/water and stirred at room temperature for 16 h. The solvent was removed by rotary evaporation and the oily residue was purified by silica flash chromatography (0→100% MeOH/EtOAc) to provide salicyl-AMSNMe (4b) (357 mg, 77%) as a white solid. This compound was converted to its corresponding sodium salt by ion exchange as follows. A Dowex 50WX8 (200-400 mesh, H+ form) cation exchange column was prepared by sequentially washing with 5 column volumes each of water, MeOH, water, then 1 N NaOH to generate the sodium salt form of the resin. The resin was flushed with water until the eluent reached pH 7. In a 4 mL scintillation vial, the compound was dissolved in a minimal amount of a water/$CH_3CN$ (1 M, 1:1 water/$CH_3CN$) and cooled to 0° C. Triethylamine (1.1 equiv) was added dropwise and the reaction was stirred for 10 minutes. The resulting mixture was flash frozen with liquid nitrogen, and concentrated by lyophilization to obtain the triethylammonium salt of the compound as a white solid. The triethylammonium salt was dissolved in a minimal amount of water (1 M) and loaded onto the Dowex column, then incubated with the resin for 10 min before eluting with water. Appropriate fractions were combined and flash frozen with liquid nitrogen, and concentrated by lyophilization to obtain the sodium salt the analogue as a white solid. The sodium salt was purified by preparative HPLC (5%→65% $CH_3CN$ in H2O with 0.1% TFA). Appropriate fractions were combined and flash frozen with liquid nitrogen, and concentrated by lyophilization to yielded pure sodium salt of the compound as a white solid.

TLC: $R_f$ 0.35 (3:7 methanol/ethyl acetate). $^1$H-NMR (600 MHz, $CD_3OD$) δ 8.40 (s, 1H), 8.23 (s, 1H), 7.96 (dd, J=7.9, 1.8 Hz, 1H), 7.30 (ddd, J=8.7, 7.2, 1.8 Hz, 1H), 6.85-6.67 (m, 2H), 6.07 (d, J=5.2 Hz, 1H), 4.78 (t, J=5.2 Hz, 1H), 4.59 (brs, 2H), 4.51 (t, J=4.8 Hz, 1H), 4.28 (app q, J=5.1 Hz, 1H), 3.65 (dd, J=14.8, 5.0 Hz, 1H), 3.58 (dd, J=14.8, 5.6 Hz, 1H), 2.87 (s, 3H). $^{13}$C-NMR (151 MHz, $CD_3OD$) δ 174.2, 161.8, 157.3, 154.0, 150.8, 141.3, 134.1, 131.2, 121.0, 120.4, 119.2, 117.8, 89.7, 85.2, 75.0, 73.0, 54.3, 38.3. IR (ATR): 3204, 1685, 1608, 1559, 1541, 1507, 1465, 1355, 1202, 1150, 977, 897, 848, 800, 759, 724. HRMS m/z calculated for $C_{18}H_{22}N_7O_7S$ ($[M+H]^+$) 480.1296, found 480.1267.

Example 1B. Synthesis of salicyl-6-MeO-AMSN(6)
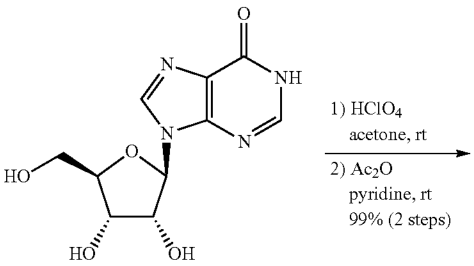
S8
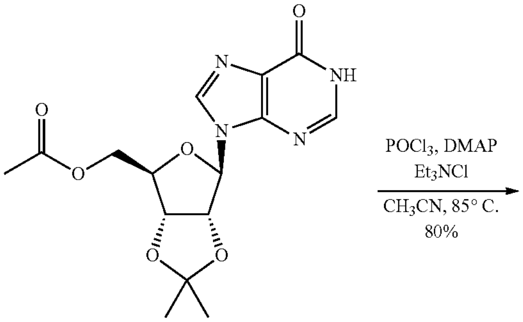
S9
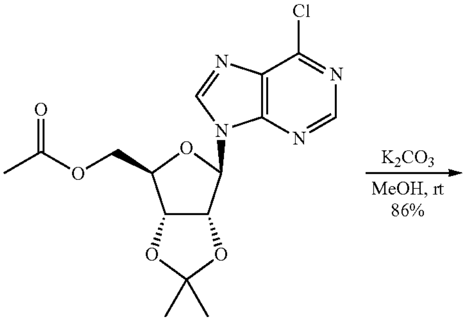
S10
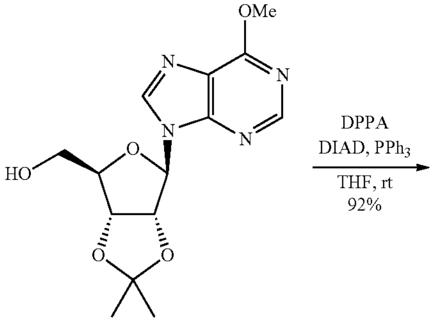
S11
-continued
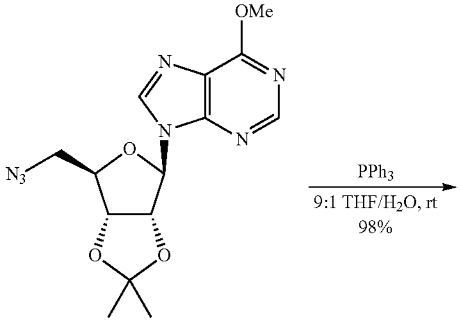
S12
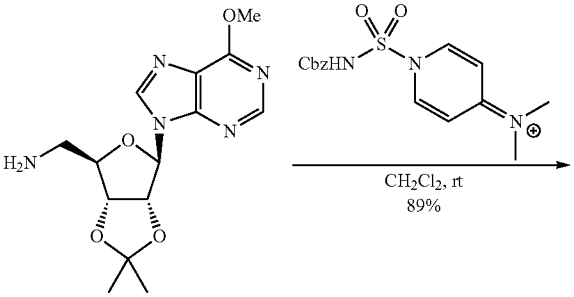
S13
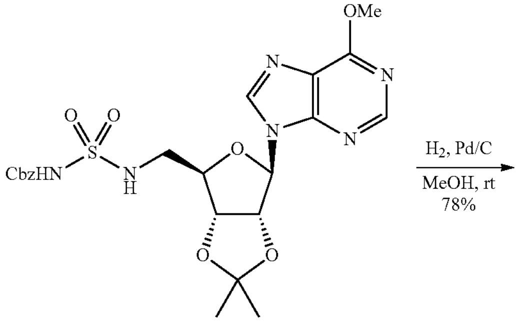
S14
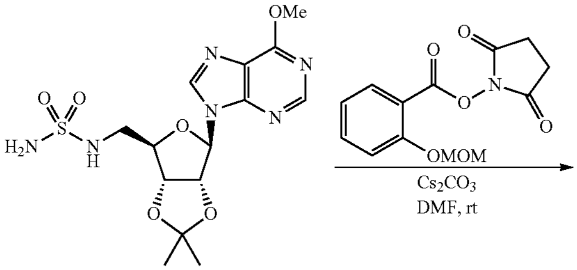
S15
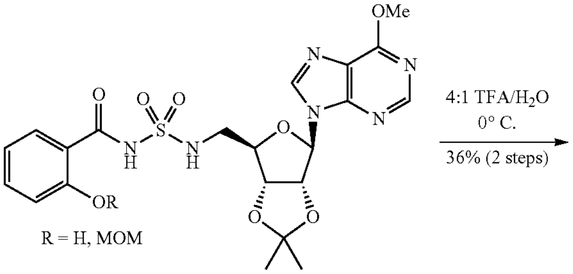
S16

-continued

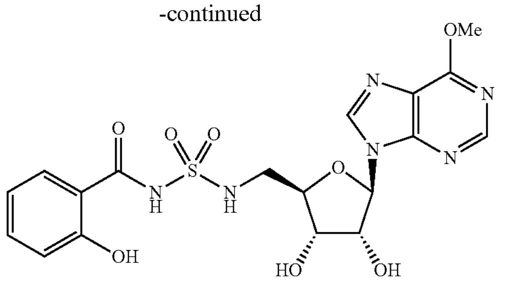

6

Cbz = benzyloxycarbonyl; DIAD = diisopropyl azo-di-carboxyl-ate; DMAP = 4-dimethylaminopyridine; DPPA = diphenylphosphoryl azide; TFA = 2,2,2-tri-fluoro-acetic acid.

Compound 6 lacks a C6-substituent hydrogen-bond donor but also maintains the adenine tautomeric form (NI lone pair). Notably, initial attempts to synthesize the corresponding sulfamate analogue, salicyl-6-MeO-AMS (not shown), were thwarted by product instability, necessitating replacement with the more stable sulfamide in 6 (Somu JMC 2006, 49, 31). Thus, salicyl-6-MeO-AMSN (6) was synthesized.

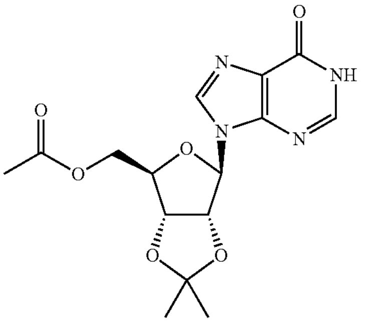 [SMILES: CC(=O)OC[C@H]1O[C@@H](n2cnc3c(=O)[nH]cnc32)[C@@H]2OC(C)(C)O[C@@H]21]

((3aR,4R,6R,6aR)-2,2-Dimethyl-6-(6-oxo-1,6-dihydro-9H-purin-9-yl)tetrahydrofuro[3,4-d][1,3]dioxol-4-yl)methyl acetate (5'-acetyl-2',3'-O-isopropylideneinosine, S9)

In a 500-mL roundbottom flask, inosine (S8) (10.0 g, 37.4 mmol, 1.0 equiv.) was suspended in acetone (370 mL) and cooled to 0° C. A solution of 70% perchloric acid (5.5 mL) was added dropwise over a period of 5 min. The reaction was stirred at room temperature for 3.5 h, then neutralized to pH 7 with concentrated $NH_4OH$. The resulting gel was vigorously stirred at room temperature for 12 h until a solid white precipitate formed. The solvent was removed by rotary evaporation and the crude mixture was dissolved 50 mL pyridine. Neat acetic anhydride (73 mL) was added and the reaction was stirred at room temperature for 25 min. The mixture was diluted with 20 mL toluene and concentrated by rotary evaporation to afford a brown oil, which was redissolved in 20 mL ethanol and concentrated by rotary evaporation. Purification by silica flash chromatography (0→10% $MeOH/CH_2Cl_2$) afforded protected inosine S9 (13.84 g, 99%) as a white solid.

TLC: $R_f$ 0.40 (1:9 $MeOH/CH_2Cl_2$). $^1$H-NMR (500 MHz, $CD_3OD$): δ 8.20 (s, 1H), 8.10 (s, 1H), 6.20 (d, J=2.3 Hz, 1H), 5.42 (dd, J=6.3, 2.3 Hz, 1H), 5.04 (dd, J=6.3, 3.2 Hz, 1H), 4.45 (ddd, J=5.9, 4.6, 3.2 Hz, 1H), 4.26 (m, 2H), 1.97 (s, 3H), 1.58 (s, 3H), 1.37 (s, 3H). $^{13}$C-NMR (125 MHz): δ 172.4, 159.0, 149.6, 147.1, 141.1, 126.2, 115.7, 92.2, 86.3, 85.9, 83.1, 65.3, 27.6, 25.6, 20.7. IR (ATR): 3434, 3116, 2990, 2074, 1742, 1699, 1588, 1549, 1419, 1215, 1157, 1105, 1076, 868. HELMS m/z calculated for $C_{15}H_{18}N_4O_6$ ($[M+H]^+$) 351.1305; found 351.1297.

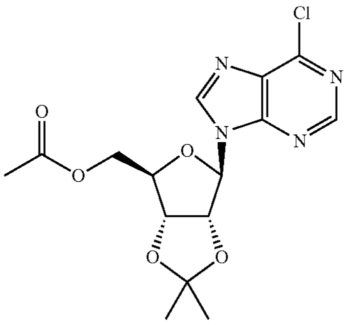 [SMILES: CC(=O)OC[C@H]1O[C@@H](n2cnc3c(Cl)ncnc32)[C@@H]2OC(C)(C)O[C@@H]21]

((3aR,4R,6R,6aR)-6-(6-Chloro-9H-purin-9-yl)-2,2-dimethyltetrahydrofuro[3,4-d][1,3]-dioxol-4-yl) methyl acetate (S10)

In a 100 mL flask fitted with a reflux condenser, protected inosine S9 (3.69 g, 10.52 mmol, 1.0 equiv.) and tetraethylammonium chloride (3.49 g, 21.04 mmol, 2.0 equiv.) were dissolved in $CH_3CN$ (21 mL). Neat N,N-dimethylaniline (1.33 mL, 10.52 mmol, 1.0 equiv.) and phosphorus oxychloride (5.87 mL, 63.10 mmol, 6.0 equiv.) were added and the reaction was heated to reflux in a sand bath for 20 min. The reaction was cooled to room temperature and concentrated by rotary evaporation to afford a yellow oil. The crude mixture was dissolved in 60 mL $CH_2Cl_2$ and quenched by vigorous stirring with ~30 g crushed ice for 15 min. The aqueous layer was extracted with $CH_2Cl_2$ (5×60 mL), and the combined organic extracts were washed with saturated aqueous $NaHCO_3$ (2×60 mL), dried ($MgSO_4$), filtered, and concentrated by rotary evaporation. Purification by silica flash chromatography (0→5% $MeOH/CH_2Cl_2$) afforded chloride S10 (3.06 g, 80%) as a light brown foam.

TLC: $R_f$ 0.68 (1:9 MeOH/EtOAc). $^1$H-NMR (500 MHz, $CDCl_3$): δ 8.59 (s, 1H), 8.18 (s, 1H), 6.07 (d, 1H, J=2.2 Hz), 5.29 (dd, 1H, J=6.3, 2.2 Hz), 4.88 (1H, dd, J=6.3, 3.4 Hz), 4.36 (m, 1H), 4.16 (dd, 1H, J=12.0, 4.2 Hz), 4.06 (dd, 1H, J=12.0, 5.8 Hz), 1.80 (s, 3H), 1.45 (s, 3H), 1.22 (s, 3H). $^{13}$C-NMR (125 MHz): δ 170.0, 151.9, 151.1, 150.8, 144.3, 132.2, 114.7, 91.2, 84.8, 84.0, 81.3, 63.7, 27.0, 25.2, 20.5. IR (ATR): 3405, 2999, 2941, 1744, 1592, 1562, 1493, 1439, 1384, 1339, 1215, 1158, 1138, 1104, 1078937, 863. HRMS m/z calculated for $C_{15}H_{17}N_4O_5Cl$ ($[M+H]^+$) 369.0966, found 369.0956.

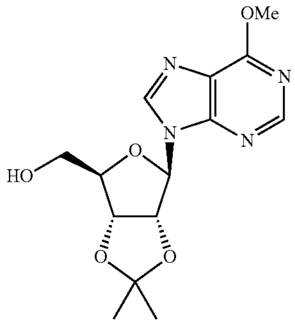 [SMILES: COc1ncnc2c1ncn2[C@@H]1O[C@H](CO)[C@H]2OC(C)(C)O[C@H]21]

((3aR,4R,6R,6aR)-6-(6-Methoxy-9H-purin-9-yl)-2,2-dimethyltetrahydrofuro[3,4-d][1,3]-dioxol-4-yl) methanol (S11)

In a 25-mL roundbottom flask, chloride S10 (104 mg, 0.28 mmol, 1.0 equiv.) was dissolved in MeOH (5 mL). Solid $K_2CO_3$ (78 mg, 0.56 mmol, 2.0 equiv.) was added and the mixture was stirred at room temperature for 20 min. The solution was diluted with 20 mL $CHCl_3$, filtered through Celite, and concentrated by rotary evaporation. Purification by silica flash chromatography (0→10% MeOH/$CH_2Cl_2$) afforded protected 6-O-methylinosine S11 (78 mg, 86%) as a white powder.

TLC: $R_f$ 0.46 (1:9 MeOH/$CH_2Cl_2$). $^1$H-NMR (500 MHz, $CD_3OD$): δ 8.52 (s, 1H), 8.48 (s, 1H), 6.25 (d, 1H, J=3.2 Hz), 5.34 (dd, 1H, J=6.1, 3.2 Hz), 5.08 (dd, 1H, J=6.1, 2.5 Hz), 4.41 (m, 1H), 4.18 (s, 3H), 3.81 (dd, 1H, J=12.0, 3.7 Hz), 3.75 (dd, 1H, J=12.0, 4.2 Hz), 1.64 (s, 3H), 1.40 (s, 3H). $^{13}$C-NMR (125 MHz): δ 162.3, 153.3, 152.3, 143.7, 122.5, 115.3, 92.8, 88.5, 85.6, 83.0, 63.5, 55.0, 27.6, 25.7. IR (ATR): 2360, 2341, 1599, 1479, 1350, 1319, 1214, 1157, 1110, 1074, 952, 851, 800. HRMS m/z calculated for $C_{14}H_{19}N_4O_5$ ([M+H]$^+$) 323.1255: found 323.1357.

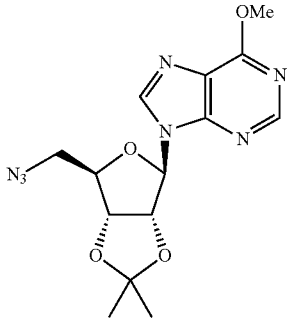 [SMILES: COc1ncnc2c1ncn2[C@@H]1O[C@H](CN=[N+]=[N-])[C@H]2OC(C)(C)O[C@H]21]

9-((3aR,4R,6R,6aR)-6-(Azidomethyl)-2,2-dimethyltetrahydrofuro[3,4-d][1,3]dioxol-4-yl)-6-methoxy-9H-purine (S12)

In a 250-mL roundbottom flask, DIAD (0.71 mL, 3.63 mmol, 1.5 equiv.) was dissolved in THE (62 mL) and cooled to 0° C. A solution of triphenylphosphine (952 mg, 3.63 mmol, 1.5 equiv.) in 12 mL THE was added and the resulting solution was stirred at 0° C. for 10 min. A solution of alcohol S11 (780 mg, 2.42 mmol, 1.0 equiv.) in 12 mL THE was added and the reaction mixture was stirred at 0° C. for an additional 10 min. Neat DPPA was added (1.04 mL, 4.84 mmol, 2.0 equiv.) and the reaction was stirred at 0° C. for 10 min. The reaction mixture was warmed to room temperature and stirred for an additional 1.5 h. The solvent was removed by rotary evaporation. Purification by silica flash chromatography (20→9 40% EtOAc/$CH_2Cl_2$) yielded azide S12 (770 mg, 92%) as an off-white chalky solid.

TLC: $R_f$ 0.35 (3:7 EtOAc/$CH_2Cl_2$). $^1$H-NMR (600 Hz, $CDCl_3$): δ 8.59 (s, 1H), 8.10 (s, 1H), 6.18 (d, J=2.4 Hz, 1H), 5.46 (dd, J=6.4, 2.3 Hz, 1H), 5.09 (dd, J=6.4, 3.5 Hz), 4.42 (dt, J=5.5, 3.5 Hz, 1H), 4.23 (s, 3H), 3.62 (d, J=5.5 Hz, 2H), 1.65 (s, 3H), 1.42 (s, 3H). $^{13}$C-NMR (151 MHz): δ 161.3, 152.5, 151.0, 141.4, 122.2, 115.0, 90.7, 85.5, 84.1, 81.9, 54.4, 52.3, 27.2, 25.3. IR (ATR): 2988, 2941, 2100, 1725, 1597, 1578, 1478, 1415, 1315, 1211, 1156, 867, 730. HRMS calculated for $C_{14}H_{17}N_7O_4$ ([M+H]$^+$) 348.1420, found 348.1415.

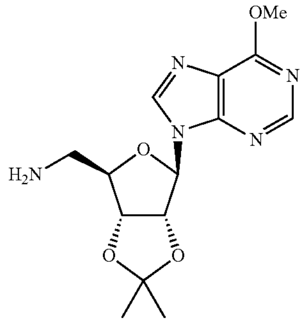 [SMILES: COc1ncnc2c1ncn2[C@@H]1O[C@H](CN)[C@H]2OC(C)(C)O[C@H]21]

((3aR,4R,6R,6aR)-6-(6-Methoxy-9H-purin-9-yl)-2,2-dimethyltetrahydrofuro[3,4-d][1,3]-dioxol-4-yl) methanamine (S13)

In a 25-mL roundbottom flask, azide S12 (280 mg, 0.81 mmol, 1.0 equiv.) was dissolved in 9:1 THE/water (2.4 mL). Solid triphenylphosphine (423 mg, 1.61 mmol, 2.0 equiv.) was added and the reaction mixture was stirred at room temperature for 15 h. The crude mixture was concentrated by rotary evaporation. Purification by silica flash chromatography (EtOAc, then 20→25% MeOH/EtOAc) and filtration through Celite afforded amine S13 (253 mg, 98%) as a white solid.

TLC: $R_f$ 0.18 (1:9 MeOH/$CH_2Cl_2$). $^1$H-NMR (600 MHz, $CDCl_3$): δ 8.48 (s, 1H), 7.99 (s, 1H), 6.01 (d, J=3.1), 5.39 (dd, J=6.5, 3.1 Hz, 1H), 4.96 (dd, J=6.5, 3.5 Hz, 1H), 4.20 (m, 1H), 4.12 (s, 3H), 2.96 (dd, J=13.4, 4.4 Hz, 1H), 2.88 (dd, J=13.4, 6.0 Hz, 1H), 1.56 (s, 3H), 1.33 (s, 6H). $^{13}$C-NMR (125 MHz): δ 161.2, 152.3, 151.3, 141.5, 122.4, 114.7, 90.7, 87.6, 83.7, 81.8, 54.3, 43.9, 27.3, 25.4. IR (ATR): 3370, 2990, 2942, 1601,1579, 1480, 1385, 1349, 1319, 1214, 1076, 869. HRMS m/z calculated for $C_{14}H_{19}N_5O_4$ ([M+H]$^+$) 322.1515. found 322.1521.

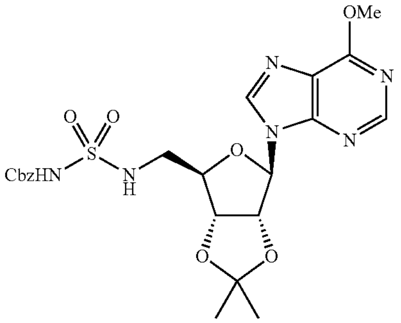 [SMILES: COc1ncnc2c1ncn2[C@@H]1O[C@H](CNS(=O)(=O)NC(=O)OCc2ccccc2)[C@H]2OC(C)(C)O[C@H]21]

Benzyl (N-(((3aR,4R,6R,6aR)-6-(6-methoxy-9N-purin-9-yl)-2,2-dimethyltetrahydrofuro-[3,4-d][1,3]dioxol-4-yl)methyl)sulfamoyl)carbamate (S14)

In a 250-mL roundbottom flask, amine S13 (500 mg, 1.56 mmol, 1.0 equiv.) was dissolved in $CH_2Cl_2$ (100 mL). Solid ((benzyloxy)carbonyl)((4-(dimethyliminio)pyridin-1 (4H)-yl)sulfonyl)amide[2] (678 mg, 2.02 mmol, 1.3 equiv.) was added and the reaction was stirred at room temperature for 16. The crude mixture was concentrated by rotary evaporation, dissolved in EtOAc, filtered through Celite, and purified by silica flash chromatography (0→5% MeOH/EtOAc) to afford Cbz-protected sulfamide S14 (740 mg, 89% yield) as a white solid.

TLC: $R_f$ 0.36 (1:9 MeOH/$CH_2Cl_2$) $^1$H-NMR (60 (1 MHz, $CDCl_3$): δ 9.66 (d, J=9.7 Hz, 1H), 8.75 (s, 1H), 8.55 (br s, 1H), 7.95 (s, 1H), 7.28-7.20 (m, 5H), 5.85 (d, J=4.9 Hz), 5.21 (dd, J=6.2, 4.9 Hz, 1H), 5.16 (d, J=12.1 Hz, 1H), 5.04 (m, 1H), 4.58 (dd, J=2.3, 2.2 Hz, 1H), 4.17 (s, 3H), 3.54 (ddd, J=12.5, 9.7.2.4 Hz, 1H), 3.43 (m, 1H), 1.64 (s, 3H), 1.36 (s, 3H). $^{13}$C-NMR (151 MHz): δ 161.5, 153.0, 151.2, 150.1, 141.7, 134.6, 128.6, 128.5, 128.2, 122.8, 114.9, 93.4, 82.8, 82.6, 81.7, 68.2, 54.5, 45.5, 27.5, 25.2. IR (ATR): 3066, 2870, 1742, 1600, 1479, 1455, 1418, 1375, 1355, 1318, 1263, 1216, 1156, 1124, 1068, 991, 909, 852, 799, 771, 727, 698. HRMS m/z calculated for $C_{22}H_{27}N_6O_8S$ ([M+H]$^+$) 535.1611, found 535.1596.

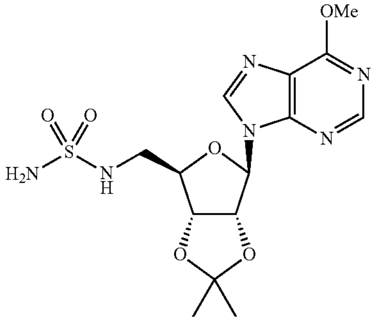 [SMILES: COc1ncnc2c1ncn2[C@@H]1O[C@H](CNS(N)(=O)=O)[C@H]2OC(C)(C)O[C@H]21]

((3aR,4R,6R,6aR)-6-(6-Methoxy-9H-purin-9-yl)-2, 2-dimethyltetrahydrofuro[3,4-d][1,3]-dioxol-4-yl) methyl)sulfamide (S15)

In a 250-mL roundbottom flask, Cbz-protected sulfamide S13 (740 mg, 1.39 mmol, 1.0 equiv.) was dissolved in degassed methanol (47 mL). Solid 10% palladium on carbon (110 mg) was added and the reaction mixture was purged with hydrogen for 10 min, then stirred for 18 h under hydrogen atmosphere (balloon). The reaction mixture was filtered through Celite and concentrated by rotary evaporation. Purification by silica flash chromatography (1:19 MeOH/EtOAc) afforded sulfamide S15 (430 mg, 78%) as a fluffy white solid.

TLC: $R_f$ 0.48 (1:9 MeOH/$CH_2Cl_2$)$^1$H-NMR (600 MHz, $CDCl_3$): δ 8.68 (s, 1H), 7.98 (s, 1H), 5.87 (d, J=4.7 Hz, 1H), 5.29 (dd, J=6.3, 4.7 Hz, 1H), 5.15 (dd, J=6.4, 2.2 Hz, 1H), 4.60 (m, 1H), 4.22 (s, 3H), 3.58 (m, 2H), 1.66 (s, 3H), 1.39 (s, 3H). $^{13}$C-NMR (151 MHz): δ 161.7, 152.7, 150.3, 141.7, 123.0, 115.0, 93.1, 83.0, 82.6, 81.4, 54.6, 45.2, 27.5, 25.2. IR (ATR): 3261, 3110, 2935, 1662, 1602, 1583, 1481, 1418, 1387, 1320, 1221, 1157, 1093, 856, 800. HRMS m/z calculated for $C_{14}H_{20}N_6O_6S$ ([M+H]$^+$) 401.1243, found 401.1227.

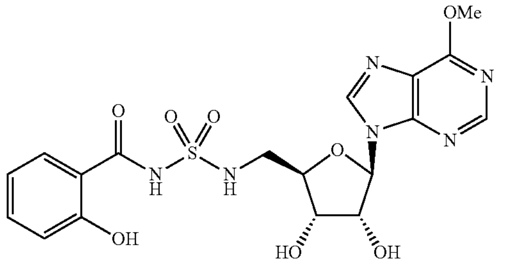 [SMILES: COc1ncnc2c1ncn2[C@@H]1O[C@H](CNS(=O)(=O)NC(=O)c2ccccc2O)[C@@H](O)[C@H]1O]

N—(N-(((2R,3S,4R,5R)-3,4-Dihydroxy-5-(6-methoxy-9H-purin-9-yl)tetrahydrofuran-2-yl) methyl)sulfamoyl)-2-hydroxybenzamide (salicyl-6-MeO-AMSN, 6)

In a 10-mL roundbottom flask, sulfamide S15 (20 mg, 50.0 μmol, 1.0 equiv.) was dissolved in DMF (1.7 mL) and cooled to 0° C. O-MOM-protected salicyl-NHS ester[23] (42 mg, 150 μmol, 3.0 equiv.) was added, followed by $Cs_2CO_3$ (24.4 mg, 74.9 μmol, 1.5 equiv.). The reaction mixture was stirred at room temperature for 3 h. The solution was diluted with EtOAc, filtered through Celite, and the filtrate was concentrated by rotary evaporation to afford a clear oil. The crude mixture contained both MOM-protected (R=MOM) and MOM-deprotected (R═H) acyl sulfamides S16. The mixture was partially purified by silica flash chromatography (1:19 MeOH/EtOAc), and all fractions containing either MOM-protected (R=MOM) or MOM-deprotected (R═H) acyl sulfamides S16 were combined. In a 25-mL roundbottom flask, the acyl sulfamides S16 were cooled to 0° C. ice bath, then dissolved in 4:1 TFA/water (1.2 mL). The reaction mixture was stirred at 0° C. for 1 h. TFA was removed by rotary evaporation (12° C. water bath). The crude mixture was diluted with water (5 mL), flash frozen with liquid nitrogen, and concentrated by lyophilization. Purification by silica flash chromatography (12% MeOH/EtOAc) afforded salicyl-6-MeO-AMSN 6 (8 mg, 36%) as a white solid.

TLC: $R^1$ 0.15 (1:9 MeOH/EtOAc). $^1$H-NMR (600 MHz, $CD_3OD$): δ 8.73 (s, 1H), 8.40 (s, 1H), 7.83 (dd, 1H, J=8.3, 1.7 Hz), 7.43 (app dt, J=8.3, 1.7 Hz, 1H), 6.94-6.92 (m, 2H), 5.93 (d, 1H, J=6.9 Hz), 4.91 (dd, J=6.9, 1.7 Hz, 1H), 4.33 (dd, J=5.4, 2.9 Hz, 1H), 4.30 (app q, J=3.1 Hz, 1H), 4.21 (s, 3H), 3.51 (dd, 1H, J=13.6, 3.7 Hz, 1H), 3.37 (dd, J=13.6, 3.1 Hz). $^{13}$C-NMR (151 MHz): δ 167.8, 162.5, 160.0, 153.9, 152.1, 144.6, 136.3, 131.0, 123.1, 121.0, 116.8, 115.8, 91.9, 86.0, 74.4, 73.3, 55.0, 46.6. IR (ATR): 2076, 1681, 1609, 1484, 1352, 1207, 1073, 980, 725. HRMS m/z calculated for $C_{18}H_6O_8S$ ([M+H]$^+$) 481.1142, found 481.1126.

The structure of compound 6 as well as other relevant compounds used herein appear in Table 1.

TABLE 1

| Salicyl-AMS Compounds |
| --- |
| 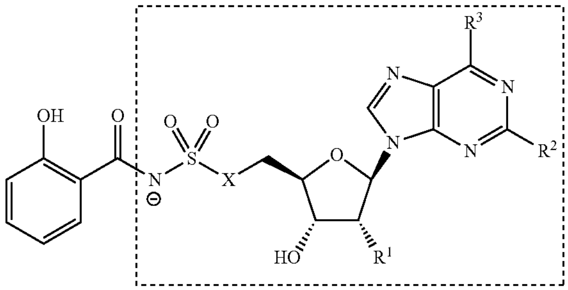 |

TABLE 1-continued

| Cmpd. | X | $R^1$ | $R^2$ | $R^3$ |
|---|---|---|---|---|
| 1 | O | OH | H | $NH_2$ |
| 4a | N | OH | H | $NH_2$ |
| 4b | N—Me | OH | H | $NH_2$ |
| 6 | N | OH | H | O—Me |

Example 2. Overexpression and Purification of $H_{10}MbtA^{opt}$

The gene $mbtA_{tb}$ was subjected to analysis for codon optimization for protein expression in *E. coli* using GenScript OptimumGene™. Nucleotide changes suggested by this analysis were introduced into a synthetic $mbtA_{tb}$ (GenScript Corp.). The synthetic DNA (1,707 bp) included a 5'-end NdeI site that contained $mbtA^{opt}$'s start codon and a 3'-end BamHI site following the stop codon. The synthetic DNA was cloned into pET15b linearized by NdeI-BamHI digestion to generate $pH_6MbtA^{opt}$, which expresses N-terminally $His_6$-tagged MbtAopt ($H_6MbtA^{opt}$). To construct the remaining nine pET15b derivatives, the mbtAopt segment of $pH6MbtA^{opt}$ was PCR amplified with specific primer pairs (Table 6) to generate nine alternative $MbtA^{opt}$-polyhistidine tag fusions. The primers incorporated the appropriate tag, a stop codon when needed, and flanking NcoI and BamHI sites. Each of the amplicons was first cloned into pCR2.1-Topo, then excised from the pCR2.1 Topo construct using NcoI and BamHI, and recloned into pET15b linearized by NcoI-BamHI digestion to generate the protein-expression plasmids.

Mtb MbtA (UniProtKB P71716), codon-optimized for expression in *E. coli* with an N-terminal $His_{10}$ tag ($H_{10}MbtA^{opt}$, SEQ ID NO: 3 and SEQ ID NO: 4) was overproduced in *E. coli* BL21(DE3)pLysS carrying plasmid $pH_{10}MbtA^{opt}$ (strains and plasmids used in this study are shown in Table 2A and Table 2B respectively). The strain was cultured in Luria-Bertani broth (Sambrook, J., et al. (2001) *Molecular cloning: A laboratory manual,* $3^{rd}$ ed., Cold Spring Harbor Pres, Cold Spring Harbor, NY) in Fernsbach baffled flasks (wide-mouth, 2.8-L capacity) under rotary agitation (220 rpm) at 25° C. to $OD_{600}$=0.3. The temperature was then reduced to 20° C. and incubation was continued. Protein overproduction was induced by addition of 1 mM IPTG (isopropyl β-D-1-thiogalactopyranoside) at $OD_{600}$≈0.6. After 16 h of additional incubation, the cultures were chilled on ice and the cells were harvested by centrifugation. The cells were resuspended in 20 mL of lysis buffer per liter of culture (50 mM Tris·HCl, pH 8; 10 mM imidazole, 0.5 M NaCl; 20% sucrose: 1 mM β-mercaptoethanol; 1 mM PMSF; 0.1% IGEPAL). Lysozyme (300 μg/ml), DNase I (100 μg/ml), and $MgCl_2$ (25 mM) were added to the cell suspension, which was then incubated at 0° C. for 30 min and subsequently subjected to a freeze/thaw cycle for lysis. The lysate was then sonicated (Branson Ultrasonics Digital Sonifier; 2×30 sec, 90% intensity), diluted 1.3 times in lysis buffer, subjected to high-speed centrifugation (1 h, 20,000 g), filtered (2.7-μm pore size Whatman filter paper), and degassed under reduced pressure. $H_{10}MbtA^{opt}$ was purified from the cleared lysate by $Ni^{2+}$-column chromatography using Ni-NTA Superflow resin according to the manufacturer's instructions (Qiagen) and an ÄKTA Purifier UPC 10 FPLC System (GE Healthcare). The loaded column (7 mL) was washed with 5 column volumes of wash buffer (75 mM Tris-HCl, pH 8; 20 mM imidazole, 0.5 M NaCl; 5% glycerol) and proteins were eluted using an imidazole gradient [solvent A: wash buffer; solvent B: elution buffer (75 mM Tris·HCl, pH 8; 0.8 M imidazole; 0.2 M NaCl; 5% glycerol)]. $H_{10}MbtA_{opt}$ eluted at ≈0.36 M imidazole. Fractions containing $H_{10}MbtA^{opt}$ were then dialyzed (Slide-A-Lyzer Dialysis cassettes; Pierce) into dialysis buffer (25 mM Tris·HCl, pH 8; 0.2 M NaCl; 2 mM DTT; 5% glycerol), aliquoted, flash-frozen, and stored at −80° C. Protein fraction quality and protein concentration were determined by SDS-PAGE (sodium dodecyl sulfate polyacrylamide gel electrophoresis) analysis (Sambrook, J., et al. (2001) *Molecular cloning: A laboratory manual,* $3^{rd}$ ed., Cold Spring Harbor Pres, Cold Spring Harbor, NY) and Bio-Rad Protein Assay (Bio-Rad Laboratories, Inc.), respectively.

(SEQ ID NO: 3)

```
ATGGGCAGCAGCCATCATCATCATCATCATCATCATCATCACAGCAGCGG
CCTGGTGCCGCGCGGCAGCCATATGCCGCCGAAAGCGGCGGATGGTCGTC
GTCCGAGCCCGGATGGTGGTCTGGGTGGTTTTGTGCCGTTCCCGGCGGAT
CGTGCGGCGAGCTACCGTGCGGCGGGTTATTGGAGCGGCCGTACCCTGGA
CACCGTGCTGAGCGATGCGGCGCGTCGTTGGCCGGATCGTCTGGCGGTTG
CGGATGCGGGTGATCGTCCGGGCCACGGTGGCCTGAGCTACGCGGAACTG
GACCAGCGTGCGGATCGTGCTGCGGCGGCGCTGCACGGTCTGGGTATCAC
CCCGGGCGATCGTGTGCTGCTGCAGCTGCCGAACGGTTGCCAATTCGCGG
TTGCGCTGTTTGCGCTGCTGCGTGCGGGTGCGATTCCGGTGATGTGCCTG
CCGGGTCATCGTGCGGCGGAACTGGGTCACTTTGCGGCGGTGAGCGCGGC
GACCGGCCTGGTGGTTGCGGATGTTGCGAGCGGTTTTGATTATCGTCCGA
TGGCGCGTGAGCTGGTTGCGGACCACCCGACCCTGCGTCACGTGATCGTT
GACGGTGATCCGGGTCCGTTTGTTAGCTGGGCGCAGCTGTGCGCGCAAGC
GGGCACCGGCAGCCCGGCTCCGCCGGCGGACCCGGGCAGCCCGGCGCTGC
TGCTGGTTAGCGGTGGCACCACCGGTATGCCGAAGCTGATTCCGCGTACC
CACGACGATTATGTGTTTAACGCGACCGCGAGCGCGGCGCTGTGCCGTCT
GAGCGCGGACGATGTTTATCTGGTGGTTCTGGCGGCGGGTCACAACTTTC
CGCTGGCGTGCCCGGGTCTGCTGGGTGCGATGACCGTGGGTGCGACCGCG
GTTTTTGCGCCGGACCCGAGCCCGGAGGCGGCGTTTGCGGCGATTGAACG
TCACGGTGTTACCGTTACCGCGCTGGTGCCGGCGCTGGCGAAACTGTGGG
CGCAGAGCTGCGAGTGGGAACCGGTGACCCCGAAGAGCCTGCGTCTGCTG
CAAGTTGGTGGCAGCAAACTGGAGCCGGAAGATGCGCGTCGTGTGCGTAC
CGCGCTGACCCCGGGCCTGCAGCAAGTTTTCGGTATGGCGGAAGGCCTGC
TGAACTTTACCCGTATCGGTGACCCGCCGGAAGTGGTTGAACACACCCAA
GGTCGTCCGCTGTGCCCGGCGGACGAGCTGCGTATTGTGAACGCGGATGG
TGAACCGGTTGGTCCGGGCGAGGAAGGTGAACTGCTGGTGCGTGGCCCGT
ACACCCTGAACGGTTATTTCGCGGCGGAGCGTGACAACGAACGTTGCTTC
GACCCGGATGGTTTTTACCGTAGCGGCGATCTGGTTCGTCGTCGTGACGA
TGGCAACCTGGTGGTTACCGGTCGTGTGAAGGACGTTATCTGCCGTGCGG
GTGAAACCATTGCGGCGAGCGATCTGGAGGAACAGCTGCTGAGCCATCCG
```

-continued

GCGATTTTCAGCGCTGCGGCGGTTGGCCTGCCGGACCAATACCTGGGTGA

AAAAATCTGCGCGGCGGTGGTTTTTGCGGGTGCGCCGATTACCCTGGCGG

AGCTGAACGGCTATCTGGACCGTCGTGGTGTGGCGGCGCACACCCGTCCG

GATCAACTGGTTGCGATGCCGGCGCTGCCGACCACCCCGATCGGCAAGAT

TGATAAACCTGCGATTGTTCGTCAACTGGGTATTGCGACCGGCCCGGTTA

CCACCCAACGCTGCCACTAA (SEQ ID NO: 4)

MGSSHHHHHHHHHHSSGLVPRGSHMPPKAADGRRPSPDGGLGGFVPFPAD

RAASYRAAGYWSGRTLDTVLSDAARRWPDRLAVADAGDRPGHGGLSYAEL

DQRADRAAAALHGLGITPGDRVLLQLPNGCQFAVALFALLRAGAIPVMCL

PGHRAAELGHFAAVSAATGLVVADVASGFDYRPMARELVADHPTLRHVIV

DGDPGPFVSWAQLCAQAGTGSPAPPADPGSPALLLVSGGTTGMPKLIPRT

HDDYVFNATASAALCRLSADDVYLVVLAAGHNFPLACPGLLGAMTVGATA

VFAPDPSPEAAFAAIERHGVTVTALVPALAKLWAQSCEWEPVTPKSLRLL

QVGGSKLEPEDARRVRTALTPGLQQVFGMAEGLLNFTRIGDPPEVVEHTQ

GRPLCPADELRIVNADGEPVGPGEEGELLVRGPYTLNGYFAAERDNERCF

DPDGFYRSGDLVRRRDDGNLVVTGRVKDVICRAGETIAASDLEEQLLSHP

AIFSAAAVGLPDQYLGEKICAAVVFAGAPITLAELNGYLDRRGVAAHTRP

Figure 1B:
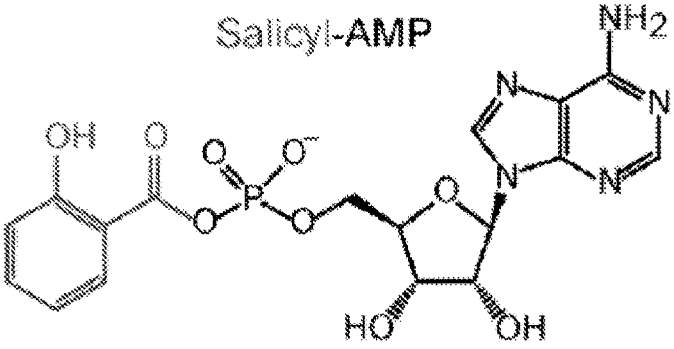
FIG. 1B shows the salicyl-AMP intermediate synthesized by the salicylate adenylation enzyme activity of $MbtA_{tb}$.
Figure 1C:
FIG. 1C shows reactions catalyzed by $MbtA_{tb}$ during mycobactin (MBT) biosynthesis. $MbtA_{tb}$ catalyzes formation of the first covalent acyl-enzyme intermediate during MBT acyl-chain assembly through a mechanism involving two-half reactions. The first half reaction is the ATP-dependent adenylation of salicylic acid to generate a salicyl-AMP intermediate that remains non-covalently bound to the active site. The second half-reaction is the transfer of the salicyl moiety of the adenylate onto the phosphopantetheinyl group of the carrier protein domain of the peptide synthetase MbtB.
Figure 3A:
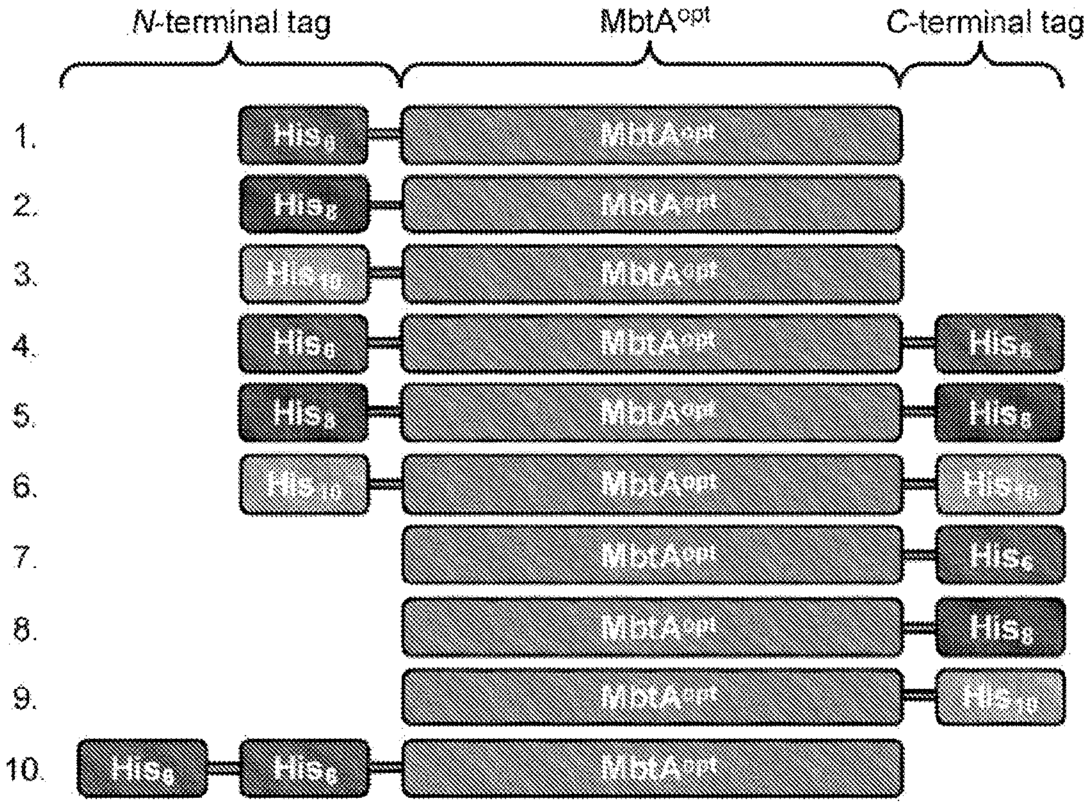
FIG. 3A shows different polyhistidine tag strategies evaluated with $MbtA^{opt}$.
Figure 3B:
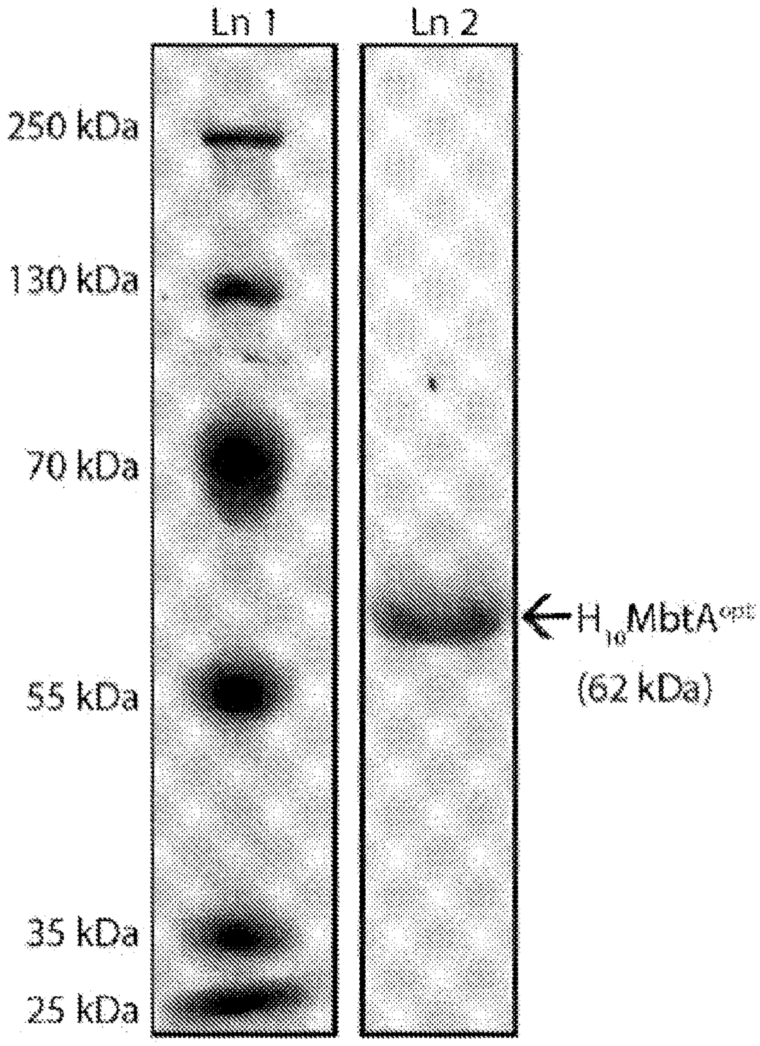
FIG. 3B shows sodium dodecyl sulfate polyacrylamide gel electrophoresis analysis. Lane 1, molecular marker standards. Lane 2, purified $H_{10}MbtA^{opt}$ (77 μg loaded). The gel (12.5%) was stained with GelCode Blue Stain Reagent (Thermo Fisher Scientific) for protein visualization.

DQLVAMPALPTTPIGKIDKRAIVRQLGIATGPVTTQRCH $MbtA_{tb}$ catalyzes formation of the first covalent acyl-enzyme intermediate during MBT aryl-chain assembly (Quadri, L. E., et al. (1998) *Chem. Biol.* 5, 631-645) and is the molecular target of the antibacterial lead compound salicyl-AMS (1) (Ferreras, J. A., et al. (2005) *Nat. Chem. Biol.* 1, 29-32) (FIGS. 1A-C). Previous approaches for purification of recombinant $MbtA_{tb}$ expressed in *E. coli* have been characterized by low yields (0.1-2 mg/L) due to low expression, poor solubility, inefficient affinity tag removal, and/or the need of multiple purification steps (Ferreras, J. A., et al. (2005) *Nat. Chem. Biol.* 1, 29-32; Quadri, L. E., et al. (1998) *Chem. Biol.* 5, 631-645; Somu, R. V., et al. (2006) *J. Med. Chem.* 49, 7623-7635). Codon optimization, alternative polyhistidine-tag fusion strategies, and changes in expression and purification conditions were explored. Codon optimization was carried out, which led to changes in 322 of the 566 codons of $mbtA_{tb}$ (FIG. 2). Then ten different polyhistidine affinity tag strategies (vis. alternative tag lengths and locations, double tags, and a tandem tag) for the codon-optimized $MbtA_{tb}$ ($MbtA^{opt}$) were evaluated (FIG. 3A). This included unconventional tags that have been shown to be advantageous with other problematic recombinant proteins (Khan, F., et al. (2006) *Anal. Chem.* 78, 3072-3079; Lee, J., et al. (2009) *Protein. Expr. Purif.* 63, 58-61). Pilot experiments for assessment of protein expression, solubility, and binding to $Ni^{2+}$-charged resin revealed that N-terminal deca-His tagged $MbtA^{opt}$ ($H_{10}MbtA^{opt}$) had the best properties overall (not shown). Thus, $H_{10}MbtA^{opt}$ was advanced to larger-scale overproduction and purification experiments that ultimately led to the final methodology used to obtain the enzyme for the biochemical and inhibition studies described herein. Overall, the optimizations and methodological improvements shortened the purification protocol by eliminating the need for tag cleavage and size exclusion chromatography, rendered purified $H_{10}MbtA^{opt}$ with purity levels comparable to those reported for other recombinant $MbtA_{tb}$ variants (FIG. 3B), and permitted final yields of up to ≈8 mg/L. This represents a 4-fold increase relative to the highest yield previously reported for $MbtA_{tb}$ (Somu, R. V., et al. (2006) *J. Med Chem.* 49, 7623-7635).

TABLE 2A

Bacterial Strains

| Strain | Characteristics | Source or Reference |
|---|---|---|
| Msm $mc^2155$ | Wild-type laboratory strain; $EXO^+$ $MBT^+$ | Snapper, S., et al. (1990) *Mol. Microbiol. 4*, 1911-1919 |
| Msm ΔE | Msm $mc^2155$ with an in-frame, unmarked MSMG_0019 deletion; $EXO^-$ $MBT^+$ | This study |
| Msm ΔM | Msm $mc^2155$ with an in-frame, unmarked mbtA deletion; $EXO^+$ $MBT^-$ | Chavadi, S. S., et al. (2011) *J. Bacterial. 193*, 5905-5913 |
| Msm ΔEM | Msm $mc^2155$ with an in-frame, unmarked MSMG_0019 and mbtA deletions; $EXO^-$ $MBT^+$ | This study |
| Msm ΔEM-p$MbtA_{tb}$ | Msm ΔEM carrying plasmid p$MbtA_{tb}$; $EXO^-$ $MBT^+$ | This study |
| Msm ΔEM-p$MbtA_{sm}$ | Msm ΔEM carrying plasmid p$MbtA_{sm}$; $EXO^-$ $MBT^+$ | This study |
| *E. coli* DH5α | Strain used for general cloning and subcloning applications | Sambrook, J., et al. (2001) *Molecular cloning: A laboratory manual*, 3rd ed., Cold Spring Harbor Pres, Cold Spring Harbor, NY |
| *E. coli* BL21(DE3)pLysS | Strain used for high-efficienev recombinant protein overproduction | Thermo Fisher Scientific Inc. |

TABLE 2B

| Plasmids | | |
|---|---|---|
| Plasmid | Characteristics | Source or Reference |
| pCR2.1-TOPO | *E. coli* cloning vector | Thermo Fisher Scientific Inc. |
| pET15b | *E. coli* gene expression vector | Millipore Sigma |
| pCP0 | Mycobacterial expression vector | Ferreras, J. A., et al. (2008). *Chem. Biol. 15*, 51-61 |
| p2NIL | Mycobacterial mutagenesis vector | Parish, T., et al. (2000) Microbiology 146, 1969-1975 |
| pGOAL19 | Mycobacterial mutagenesis vector | Parish, T., et al. (2000) *Microbiology 146*, 1969-1975 |
| $pH_{10}MbtA^{opt}$ | pET15b derivative expressing N-terminally $His_{10}$-tagged $MbtA^{opt}$ | This study |
| $pH_8MbEA^{opt}$ | pET15b derivative expressing N-terminally $His_8$-tagged $MbtA^{opt}$ | This study |
| $pH_6MbtA^{opt}$ | pET15b derivative expressing-N-terminally $His_6$-tagged $MbtA^{opt}$ | This study |
| $pMbtA^{opt}H_{10}$ | pET15b derivative expressing C-terminally $His_{10}$-tagged $MbtA^{opt}$ | This study |
| $pMbtA^{opt}H_8$ | pET15b derivative expressing C-terminally $His_8$-tagged $MbtA^{opt}$ | This study |
| $pMbtA^{opt}H_6$ | pET15b derivative expressing C-terminally $His_6$-tagged $MbtA^{opt}$ | This study |
| $pH_6MbEA^{opt}H_6$ | pET15b derivative expressing C- and N-terminally $His_6$-tagged $MbtA^{opt}$ | This study |
| $pH_8MbtA^{opt}H_8$ | pET15b derivative expressing C- and (N-terminally $His_8$-tagged $MbtA^{opt}$ | This study |
| $pH_{10}MbtA^{opt}H_{10}$ | pET15b derivative expressing C- and N-terminally $His_{10}$-tagged $MbtA^{opt}$ | This study |
| $pH_{6\times2}MbtA^{opt}$ | pET15b derivative expressing $MbtA^{opt}$ with an N-terminal $His_6$-linker-$His_6$ tag | This study |
| $pMbtA_{tb}$ | pCP0 derivative expressing $mbtA_{tb}$ | This study |
| $pMbtA_{ms}$ | pCP0 derivative expressing $mbtA_{ms}$ | Chavadi, S. S., et al. (2011) *J. Bacterial. 193*, 5905-5913 |
| p2NILΔ0019 | p2NIL derivative carrying a MSMEG_0019 deletion cassette | Tins study |
| pΔ0019 | p2NILΔ0019-pGOAL19; MSMEG_0019 deletion cassette-delivery, suicide plasmid | This study |

Example 3. Assay or $MbtA_{tb}$ Activity and Inhibition

The adenylation activity of $H_{10}MbtA^{opt}$ and its inhibition were evaluated using a $H_{10}MbtA^{opt}$-optimized variation of the hydroxylamine-7-methyl-6-thioguanosine (HA-MesG) spectrophotometric assay (Wilson, D. J., et al. (2010) *Anal. Biochem.* 404, 56-63). The assay was carried out in a 96-well plate format as previously reported (Davis, T. D., et al. (2016) *Bioorg. Med. Chem. Lett.* 26, 5340-5345). The assay reaction mixture was optimized for $H_{10}MbtA_{opt}$ activity. Optimization experiments included evaluation of various concentrations of Tris·HCl (and pH), hydroxylamine, MesG, ATP, NaCl, $MgCl_2$, glycerol, reducing agents (DTT and TCEP), and detergent (IGEPAL, CHAPS, and Triton-X100). Unless otherwise indicated for specific experiments, the optimized assay reaction mixture contained the following: 50 mM Tris·HCl, pH 8.0; 3 mM $MgCl_2$; 0.5 mM DTT; 0.1 U purine nucleoside phosphorylase (PNP); 0.04 U inorganic pyrophosphatase (PPT); 450 mM hydroxylamine; 0.4 mM MesG; 1 mM ATP; 300 µM salicylic acid; 0.01% CHAPS buffer; 7.5% ultrapure glycerol; and $H_{10}MbtA^{opt}$ at concentrations noted for specific experiments. When needed, MbtA inhibitors were added from 10% DMSO stock solutions, with a final DMSO concentration of 1% in both inhibitor-containing reactions and control reactions (no inhibitor). Reactions were preincubated for 10 min at 25° C. before being initiated by the addition of either salicylic acid for steady state kinetic analysis or $H_{10}MbtA^{opt}$ for progress curve analysis. The phosphorolysis of MesG was measured continuously at either regular 1-min intervals (for steady state kinetic analysis) or 25-sec intervals (for progress curves analysis) for up to 45 min, at 360 nm and 25° C. in a DTX 880 multimode detector microplate reader (Beckman Coulter, Inc.). The concentration of active $H_{10}MbtA^{opt}$ was validated by active-site titration (Copeland, R. A. (2013) *Evaluation of enzyme inhibitors in drug discovery*, pp 245-285, John Wiley & Sons, Inc.) using salicyl-AMS (1) as the reference inhibitor. The calculated concentration of total $H_{10}MbtA^{opt}$ used in the assays was essentially indistinguishable from the concentration of active $H_{10}MbtA^{opt}$ determined by active-site titration (not shown).

Figure 1D:
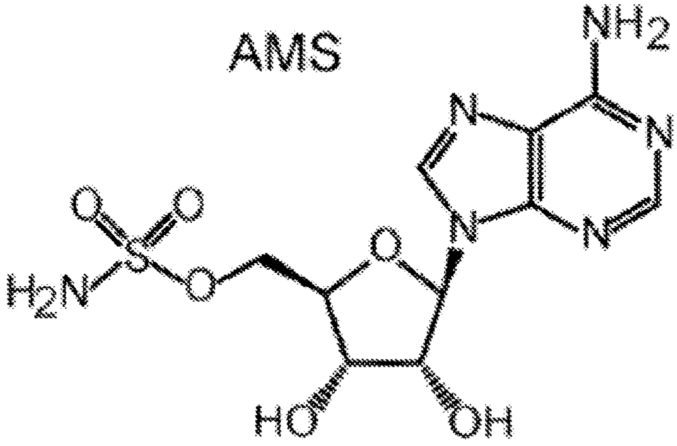
FIG. 1D shows the compound 5'-O-sulfamoyladenosine (AMS).
Figure 1E:
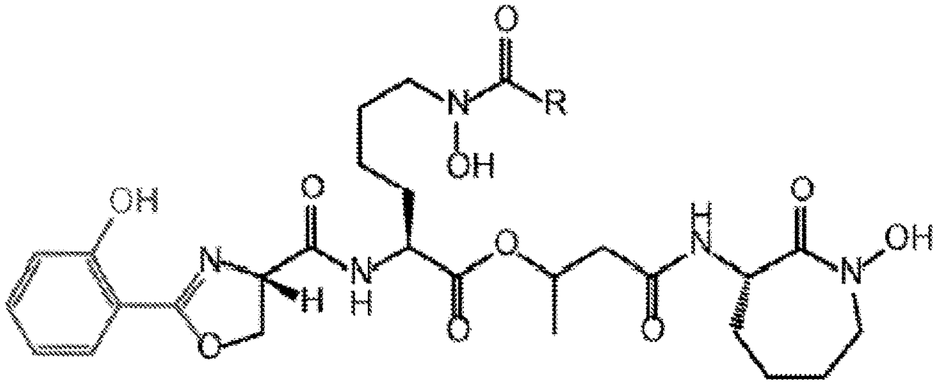
FIG. 1E shows a representative genus of mycobactin siderophores of *M. tuberculosis*. R represents variable fatty acyl groups (mycobactin variants) or acyl substituents terminating in a carboxylate or a methyl ester (carboxymycobactin variants). All these variants are collectively referred herein to as MBTs.
Figure 4A:
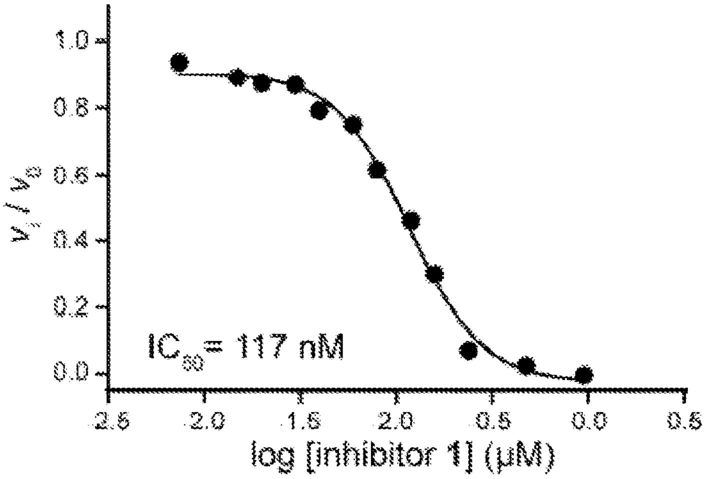
FIG. 4A shows a preliminary dose-response experiment ($v_i/v_o$ vs. log[inhibitor]) demonstrating inhibition of $H_{10}MbtA^{opt}$ by compound 1 wherein $IC_{50}$=117 nM.

The results of the first assessment of the activity of $H_{10}MbtA^{opt}$ and its inhibition by salicyl-AMS (1) using the HA-MesG assay demonstrated enzyme activity and the expected TBI behavior for 1 (i.e. $IC_{50}$≈½ [E]) (FIG. 4A). Out of an abundance of caution, it was determined whether salicyl-AMS (1) had any inhibitory effect on the PPT-PNP coupling system of the HA-MesG assay. Four salicyl-AMS fragments that could possibly result from hydrolytic degradation of salicyl-AMS compounds and/or be present as trace contaminants were also tested (i.e., AMS (7, FIG. 1D), salicyl-sulfamate (8), salicylamide (9), and $N^3$-5'-cycloadenosine (10); Table 3) had a negative impact on the HA-MesG assay. It was found that salicyl-AMS compounds did not affect the PPT-PNP coupling system when tested at up to 40 µM (10 times the maximum concentration of 1 used in the HA-MesG assay), and salicyl-sulfamate (8) depressed the $H_{10}MbtA^{opt}$-dependent signal in the HA-MesG assay, and only to a negligible extend ($IC_{50}$≈1 mM) (Table 3). Therefore, inhibition by an off-target effect of salicyl-AMS compounds or by potential trace amounts of fragments 7-10 is not an assay confounder.

TABLE 3

Off-Target effect and nonspecific inhibition controls

| Inhibitor | Effect of MbtA inhibitors on the activity of the PPT/PNP coupling system of the HA-MesG assay[a] Fractional velocity $v_1/v_0$ [inhibitor] = 4 μM | Fractional velocity $v_1/v_0$ [inhibitor] = 40 UM |
|---|---|---|
| 1 | 0.96 | 1.01 |
| 4a | 0.94 | 0.96 |
| 4b | 0.95 | 0.89 |
| 6 | 1.00 | 1.00 |

| Compound | Effect of compounds shown on the $MbtA_{tb}$-dependent signal in the HA-MesG assay[b] Structure | $IC_{50}$ (mM) |
|---|---|---|
| 7 | 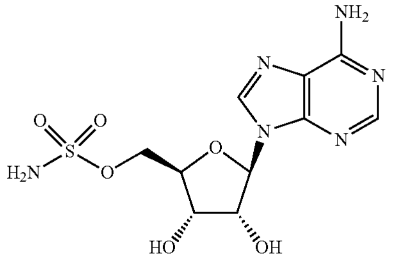 [SMILES: Nc1ncnc2c1ncn2[C@@H]1O[C@H](COS(N)(=O)=O)[C@@H](O)[C@H]1O] | >1 |
| 8 | 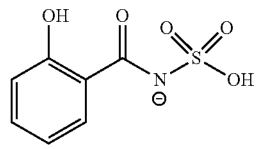 [SMILES: O=C([N-]S(=O)(=O)O)c1ccccc1O] | ≈1 |
| 9 | 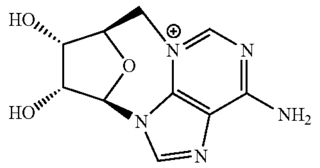 [SMILES: Nc1nc[n+]2c3c1ncn3[C@@H]1O[C@H](C2)[C@@H](O)[C@H]1O] | >1 |
| 10 | 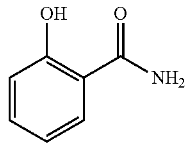 | >1 |

Example 4. $IC_{50}$ Values

Figure 4B:
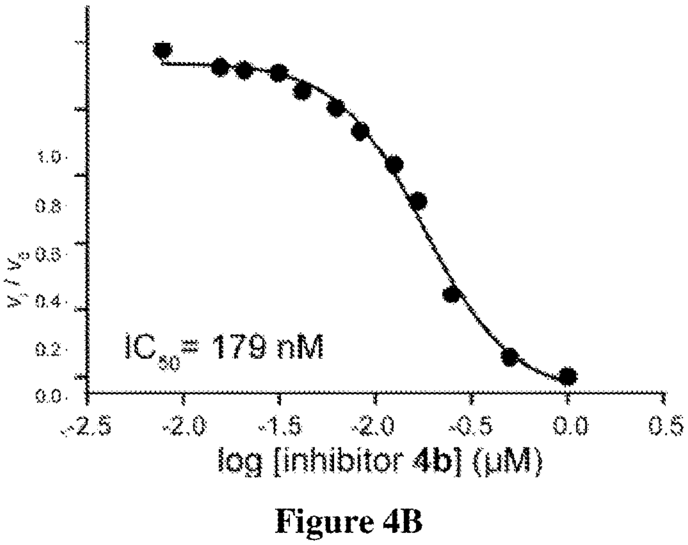
FIG. 4B shows preliminary dose-response experiment ($v_i/v_o$ vs. log [inhibitor]) demonstrating inhibition of $H_{10}MbtA^{opt}$ by compound 4b wherein $IC_{50}$=179 nM.
Figure 4C:
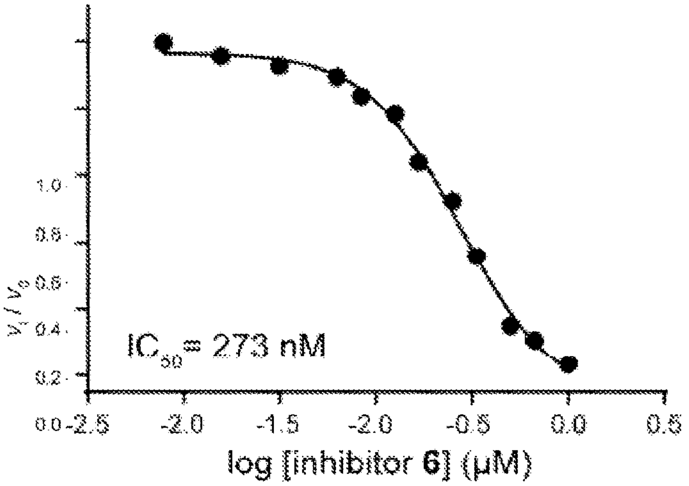
FIG. 4C shows preliminary dose-response experiment ($v_i/v_o$ vs. log [inhibitor]) demonstrating inhibition of $H_{10}MbtA^{opt}$ by compound 6 wherein $IC_{50}$=273 nM.

The $IC_{50}$ values were calculated by fitting the dose-response datasets ($v_i/v_0$ vs [inhibitor]; see FIGS. 4A-C for an exemplary graph resulting from a single experiment) to the sigmoidal equation $v_i/v_0=b+a-b/1+([I]/IC_{50})^s$, where $v_i$ and $v_0$ are initial reaction velocities of inhibitor-containing reactions and DMSO-containing reaction controls (no inhibitor), respectively, a and b are the top and bottom of the sigmoidal curve (solid line; $R^2$ values ≥0.988), respectively, and s is the Hill coefficient. The data shown for each inhibitor (indicated in the label of the x axis) is derived from one of two independent dose-response experiments using $H_{10}MbtA^{opt}$ at 250 nM. Resulting $IC_{50}$ values are shown in Table 4.

Pilot experiments were carried out to assess whether the tight-binding inhibitor behavior of the previously reported analogues (1, 4a) as per the ATP-PPi assay (Neres, J., et al. (2008) *J Med. Chem.* 51, 5349-5370; Somu, R. V., et al. (2006) *J. Med. Chem.* 49, 31-34; Somu, R. V., et al. (2006) *J. Med. Chem.* 49, 7623-7635; Vannada, J., et al. (2006) *Org. Lett.* 8, 4707-4710) was recapitulated under the conditions of the HA-MesG assay and whether the novel analogues salicyl-AMSNMe (4b) and salicyl-6-MeO-AMSN (6) were also a tight-binding inhibitor. Encouragingly, 6 displayed $IC_{50}$ values ≈½ [E], thus indicating tight-binding inhibitor behavior.

TABLE 4

$IC_{50}$ values

| Compound | $IC_{50}$ (nM) |
|---|---|
| 1 | 117.2 ± 0.3 |
| 4a | 245.6 ± 2.9 |
| 4b | 174.6 ± 4.3 |
| 6 | 288.9 ± 16.4 |

Example 5. Progress Curves and Determination of Kinetic Parameters $K_i^{App}$, $k_{on}^{App}$, $k_{off}$, and $t_R$ Reactions were pre-incubated for 10 min before being initiated by the addition of $H_{10}MbtA^{opt}$ (1 μM). The concentration range at which each inhibitor was tested was selected empirically by pilot experiments. The ranges were as follows: 4,000-1,041 nM range (1.4-fold dilution series) for 1, 4a, 4b, and 6. As done in similar studies, (Sikora, A. L., et al. (2010) *Biochemistry* 49, 3648-3657; McClerren, A. L., et al. (2005) *Biochemistry* 44, 16574-16583) the background-corrected spectrophotometric data were fitted to Eq. 2 (Morrison, J. F., et al. (1988) *Adv. Enzymol. Relat. Areas Mol. Biol.* 61, 201-301). In Eq. 2, A is the absorbance at time t, $v_{ps}$ is the pre-steady state initial velocity, $v_s$ is the steady-state velocity at equilibrium, and $k_{obs}$ is the rate constant for progression to steady state. The datasets of $v_s$ vs. [I] derived from the progress curves were fitted to Eq. 1 to calculate the $K_i^{app}$ values. The $k_{obs}$ values were determined with Eq. 2 for each inhibitor concentration. Each kinetic parameter reported is the average derived from a minimum of five independent experiments. Pearson correlation analysis between kinetic parameters was carried out using the statistical analysis package in Prism v6.01. Pearson correlation coefficients (PCCs) with Student's t-test p values ≤0.05 were considered statistically significant. Results are shown in Table 5 ($K_i^{app}$) and FIGS. 5A-6C.

Figure 5A:
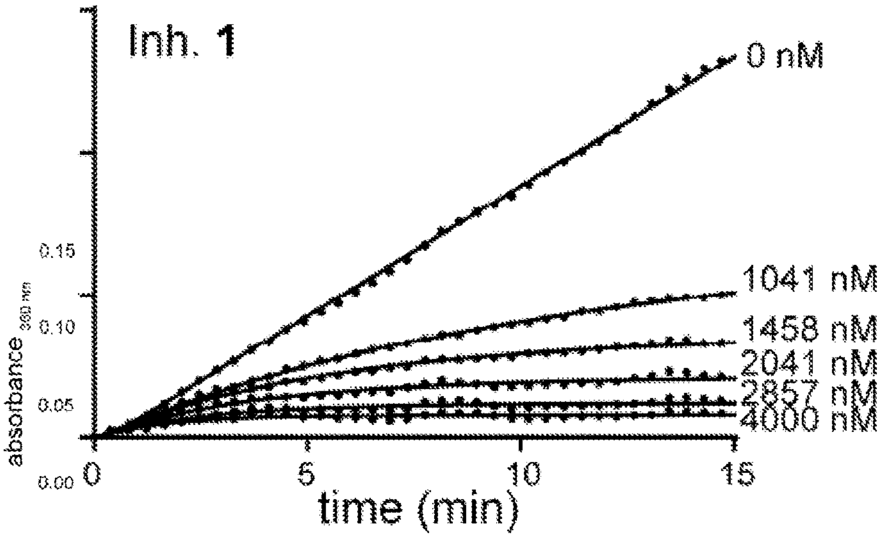
FIG. 5A shows a Progress curve for $MbtA_{tb}$ inhibition at different concentrations of compound 1 (0 nM, 1041 nM, 1458 nM, 2041 nM, 2857 nM, and 4000 nM).
Figure 5B:
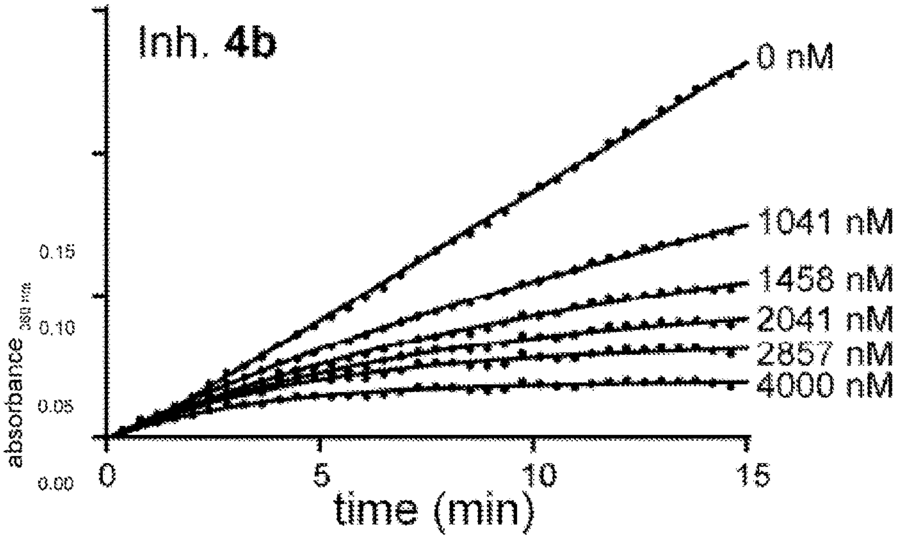
FIG. 5B shows a Progress curve for $MbtA_{tb}$ inhibition at different concentrations of compound 4b (0 nM, 1041 nM, 1458 nM, 2041 nM, 2857 nM, and 400 nM).
Figure 5C:
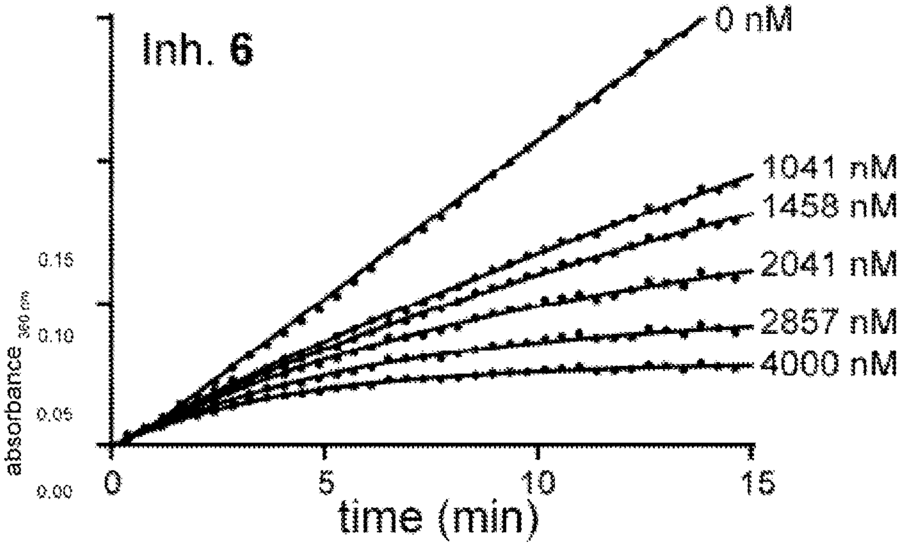
FIG. 5C shows a Progress curve for $MbtA_{tb}$ inhibition at different concentrations of compound 6 (0 nM, 1041 nM, 1458 nM, 2041 nM, 2857 nM, and 4000 nM).
Figure 6A:
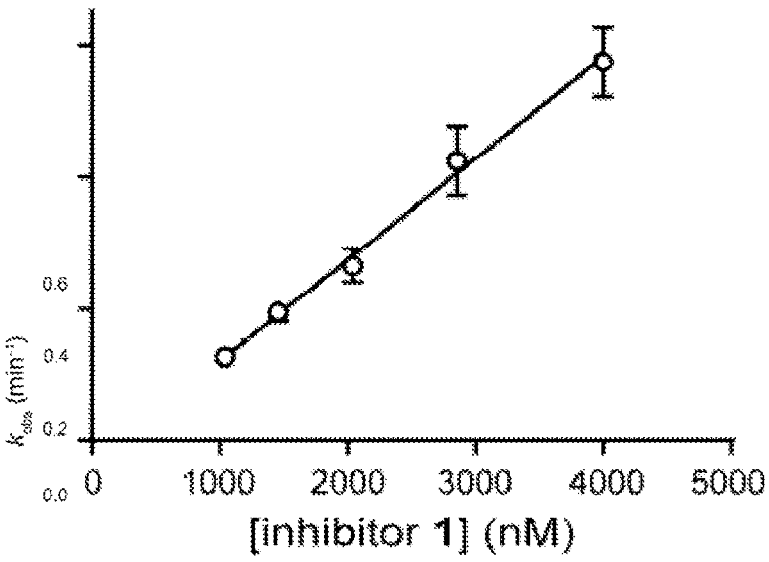
FIG. 6A shows the dependence of the $k_{obs}$ on the concentration of compound 1.
Figure 6B:
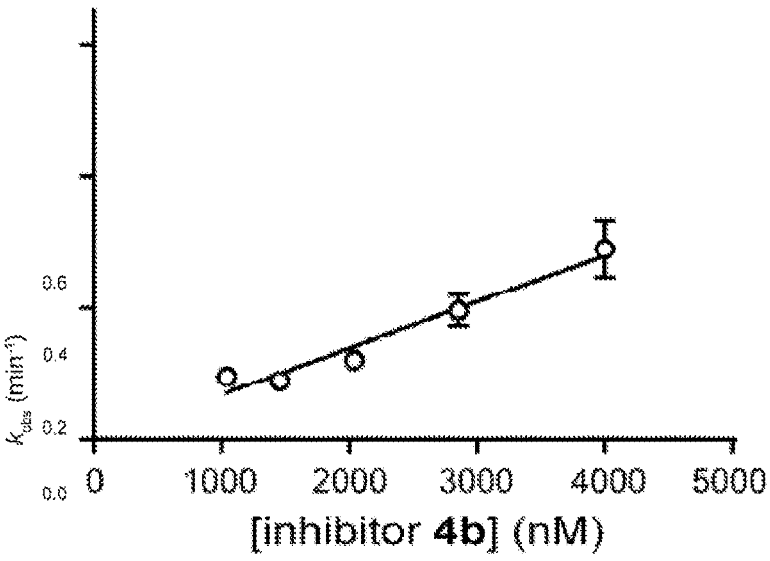
FIG. 6B shows the dependence of the $k_{obs}$ on the concentration of compound 4b.
Figure 6C:
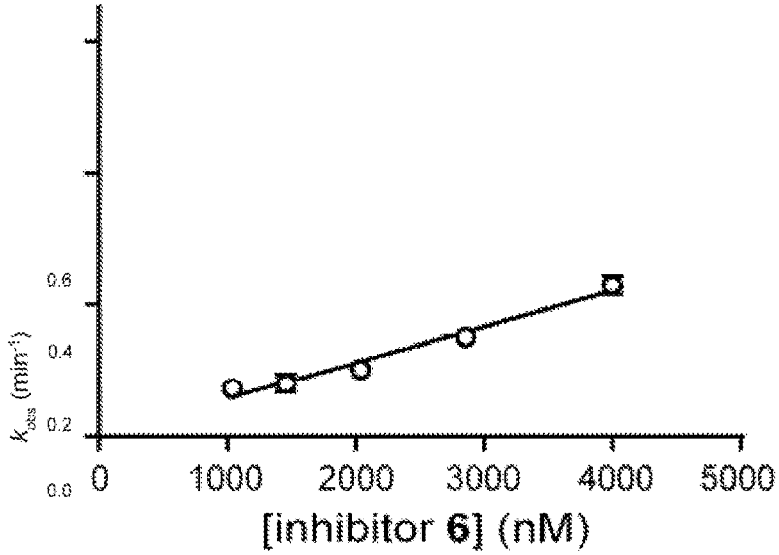
FIG. 6C shows the dependence of the $k_{obs}$ on the concentration of compound 6.

For each compound, the progress curves displayed a nonlinear profile of $H_{10}MbtA^{opt}$ inhibition with the characteristic three phases of a time-dependent, slow-onset mechanism of inhibition (FIGS. 5A-C); i.e., an initial linear phase that extrapolates to a slope corresponding to a pre-equilibrium initial velocity (vps) at t=0; a final linear phase with a slope representing the equilibrium, steady-state velocity (vs): and an exponential phase that connects the two linear phases with a pseudo-first order rate constant (kobs) for the approach to the steady state (Morrison. J. F., et al. (1988) *Adv. Enzymol. Relat. Areas Mol. Biol.* 61, 201-301; Copeland, R. A. (2013) *Evaluation of enzyme inhibitors in drug discovery*, pp 203-244, John Wiley & Sons, Inc.). In contrast, the progress curves for uninhibited reactions (DMSO controls) showed the expected linear profile of the steady-state kinetics (FIGS. 5A-C). Thus, the results demonstrated that salicyl-AMS (1) and its analogs including salicyl-6-MeO-AMSN (6) are slow-onset inhibitors of H10MbtAopt. Encouragingly, the results also provided the first indication of the potent activity of salicyl-AMSNMe (4b) and salicyl-6-MeO-AMSN (6) against $MbtA_{tb}$.

Interestingly, salicyl-6-MeO-AMSN (6) remains a fairly potent inhibitor of $MbtA_{tb}$, despite the lack of a hydrogen-bond donor on the C6-substituent and the presence of the sulfamide linker. This result was unexpected based on previous SAR studies (Neres, J., et al. (2008) *J. Med. Chem.* 51, 5349-5370), and is not readily rationalized based on protein structure analysis (May, J. J., et al. (2002) *Proc. Natl. Acad. Sci.* 99, 12120-12125; Labello, N. P., et al. (2008) *J. Med. Chem.* 51, 7154-7160). Nonetheless, it opens the door to further investigation of such C6-substituents.

$$\frac{v_i}{v_0} = 1 - \frac{([E] + [I] + K_i^{app}) - \sqrt{([E] + [I] + K_i^{app})^2 - 4\,[E]\,[I]}}{2\,[E]} \quad \text{Eq. 1}$$

$$A = v_s\, t + \frac{v_{ps} - v_s}{k_{obs}}\,[1 - e^{(-k_{obs} t)}] \quad \text{Eq. 2}$$

TABLE 5

| $K_i^{app}$ values | |
|---|---|
| Compound | $K_i^{app}$ (nM) |
| 1 | 26.6 ± 2.5 |
| 4a | 295.3 ± 23.9 |
| 4b | 158.5 ± 8.1 |
| 6 | 277.1 ± 12.2 |

Example 6. Bacterial Culturing and Recombinant DNA Manipulations

Msm $mc^2155$ (ATCC 700084) (Snapper, S. B., et al. (1990) *Mol. Microbiol.* 4, 1911-1919) and its derivatives were regularly cultured under standard conditions in Middlebrook 7H9 or 7H11 (Difco) supplemented as reported (Chavadi, S. S., et al. (2011) *J. Bacterial.* 193, 5905-5913). Msm strains were cultured in Fe-limiting GASTD medium or GASTD supplemented with 100 μM FeCl3 (GASTD+Fe medium) (Ferreras, J. A., et al. (2005) *Nat. Chem. Biol.* 1, 29-32; Ferreras, J. A., et al. (2011) *Bioorg. Med. Chem. Lett.* 21, 6533-6537) for specific experiments as noted below. Routine culturing of *E. coli* strains was done under standard conditions in Luria-Bertani media (Sambrook, J., et al. (2001) *Molecular cloning: A laboratory manual,* 3rd ed., Cold Spring Harbor Pres, Cold Spring Harbor, NY). When required, kanamycin (30 μg/ml), chloramphenicol (34 μg/ml), ampicillin (100 μg/ml), sucrose (2%), and/or 5-bromo-4-chloro-3-indolyl-β-D-galactopyranoside (X-gal, 70 μg/ml) were added to the growth media. DNA manipulations were carried out using established protocols and *E. coli* DH5α. as the primary cloning host (Sambrook, J., et al. (2001) *Molecular cloning: A laboratory manual,* 3rd ed., Cold Spring Harbor Pres, Cold Spring Harbor, NY). PCR-generated DNA fragments used in plasmid constructions were sequenced to verify fidelity. The oligonucleotides used in this study are shown in Table 6. Genomic DNA isolation, plasmid electroporation into Msm, and selection of Msm transformants were carried out as reported (Ferreras, J. A., et al. (2005) *Nat. Chem. Biol.* 1, 29-32.). Unless otherwise indicated, molecular biology, biochemical, and microbiology reagents were purchased from Sigma-Aldrich, Invitrogen, New England Biolabs, QIAGEN, or IDT.

TABLE 6

| Oligonucleotides | | |
|---|---|---|
| Name | Sequence (5' → 3') | Comments |
| OF0019<br>IR0019soe | ACTTTGGTCGTCGGATTCCTGCTGGTGCG<br>CTATCCAGAAGCCACATCCGCGGTCACGTGCGAGCGTCC | Primers used for amplification of the 5' fragment for the MSMEG_0019 deletion cassette |
| OR0019<br>IF0019soe | ACATTGGCTTCGCGCCATGGCACCGATTTT<br>CACGTGACCGCGGATGTGGCTTCTGGATAGTGGCCGGAA | Primers used for amplification of the 3' fragment for the MSMEG_0019 deletion cassette |
| IF0019<br>IR0019 | ATCTTCTGAACACGCTCAAGGC<br>AGGTAGTTGAACAGCAGTTGCG | Primers used for amplification of internal segment of MSMEG_0019 |
| $mbtA_{tb}F1$<br>$mbtA_{tb}R1$ | TAGTTAACGAGGAAACCCACATGCCACCGA<br>TAGCTAGCTCAATGGCAGCGCTGGGTCGTCA | Primers used for generation of RBS-$mbtA_{tb}$ amplicon |
| mbtAopt-F | TACCATGGGCATGCCGCCGAAAGCGGCGGAT | $mbtA^{opt}$ amplification; introduction of 5'-end NcoI site |
| mbtAopt-H6F | TACCATGGGCAGCAGCCATCATCATCATCATCACAGC | $mbtA^{opt}$ amplification; addition of N-terminal $His_6$ tag and 5'-end NcoI site |
| mbtAopt-H8F | TACCATGGGCAGCAGCCATCATCATCATCATCATCATCA<br>CAGCAGCGGCC | $mbtA^{opt}$ amplification; addition of N-terminal $His_8$ tag and 5'-end NcoI site |
| mbtAopt-H10F | TACCATGGGCAGCAGCCATCATCATCATCATCATCATCA<br>TCATCACAGCAGCGGCC | $mbtA^{opt}$ amplification; addition of N-terminal $His_{10}$ tag and 5'-end NcoI site |
| mbtAopt-H6X2F | TACCATGGGCAGCAGCCATCATCATCATCATCACAGCCG<br>TGCGTGGCGTCATCCGCAGTTTGGCGGTCATCATCATCAT<br>CATCACAGCAGCGGCC | $mbtA^{opt}$ amplification; addition of N-terminal $His_{6x2}$ tag and 5'-end NcoI site |
| mbtAopt-R | CCGGATCCTTAGTGGCAGCGTTG | $mbtA^{opt}$ amplification; introduction of 3'-end BamHI site |
| mbtAopt-H6R | CCGGATCCTTAGTGGTGGTGGTGGTGGTGCAGGCCGCTG<br>CTGTGGCAGCGTTGGGTGGTAAC | $mbtA^{opt}$ amplification; addition of C-terminal $His_6$ tag and 3'-end BamHI site |

TABLE 6-continued

| Oligonucleotides | | |
|---|---|---|
| Name | Sequence (5' → 3') | Comments |
| mbtAopt-H8R | CCGGATCCTTAGTGGTGGTGGTGGTGGTGGTGGTGCAGG CCGCTGCTGTGGCAGCGTTGGGTGGTAAC | mbtA$^{opt}$ amplification; addition of C-terminal His$_8$ tag and 3'-end BamHI site |
| mbtAopt-H10R | CCGGATCCTTAGTGGTGGTGGTGGTGGTGGTGGTGGTGG TGCAGGCCGCTGCTGTGGCAGCGTTGGGTGGTAAC | mbtA$^{opt}$ amplification; addition of C-terminal His$_{10}$ tag and 3'-end BamHI site |

Example 7. Generation of *M. smegmatis* Mutants ΔE, ΔEM, and ΔEM pMbtA$_{tb}$ Mutants were generated using the p2NIL/pGOAL 19-based flexible cassette method (Parish, T., et al. (2000) *Microbiology* 146, 1969-1975) as reported (Chavadi, S. S., et al. (2011) *J. Bacteriol.* 193, 5905-5913). Exochelin (EXO)-deficient Msm ΔE carried an unmarked, in-frame deletion of MSMEG_0019 (SEQ ID NO: 5), encoding the peptide synthetase (7,523 amino acids, the largest protein in Msm (Mohan, A., et al. (2015) *Genome Announc.* 3) required for biosynthesis of EXO siderophores (Fiss, E. H., et al. (1994) *Mol. Microbiol.* 14, 557-569; Yu, S., et al. (1998) *J. Bacteriol.* 180, 4676-4685; Zhu, W., et al. (1998) *Mol. Microbiol.* 29, 629-639). A MSMEG_0019 deletion cassette-delivery, suicide plasmid (pΔ0019) was used to generate the chromosomal deletion, which eliminated codons 5 through 7,519 of the gene. The deletion cassette contained from 5'- to 3'-end: the 984-bp segment upstream of the gene, the gene's first 4 codons, the gene's last 4 codons, the stop codon, and the 1,029-bp segment downstream of the gene. To generate the cassette, primer pair OF0019 and IR0019soe and primer pair IF0019soe and OR0019 were first used to generate the 5' fragment (1,011 bp) and the 3' fragment (1,059 bp) for the cassette, respectively, from genomic DNA template. The fragments, which had a 30-bp overlap at the splice site embedded in IF0019soe and IR0019soe, were then used together as a template for PCR with primers OF0019 and OR0019 to fuse the fragments. The PCR-generated cassette was cloned into pCR2.1Topo (TOPO TA Cloning Kit, Invitrogen, Thermo Fisher Scientific Inc.), then excised from the pCR2.1Topo construct using HindIII and EcoRV, and religated into p2NIL (Parish, T., et al. (2000) *Microbiology* 146, 1969-1975) linearized by HindIII-PmlI digestion. The resulting plasmid (p2NILΔ0019) and pGOAL19 (Parish, T., et al. (2000) *Microbiology* 146, 1969-1975) were digested with PacI, and then the PacI marker cassette of pGOAL19 was ligated to the linearized p2NILΔ0019 to create pΔ0019. Electroporation of pΔ0019 into Msm wild-type (WT) and selection of potential single- and double-crossover mutants were conducted as reported (Chavadi, S. S., et al. (2011) *J. Bacterial.* 193, 5905-5913). The MSMEG_0019 deletion was screened for and confirmed by PCR using two primer pairs (OF0019 and OR0019: yielding an undetectable 24,585-bp amplicon for WT and a 2,040-bp amplicon for mutant: IF0019 and IR0019: yielding a 148-bp amplicon for WT and no amplicon for mutant) (not shown).

(SEQ ID NO: 5)

MTADSLDIAELLELWNNHSTPERTSTVPTLFAAQCALTPDEVAVVDGERRLTYRHLETHVAQ

LAHAVRVAAGEGPEPIVAIGVPRSAEMVVCVLAAMMAGVAFVPLDPSWPAHRRRQVLADSGA

VATFITREDESDWGVPGLRVDLGAWQFTAESPVLPQADVHPAQLAYVIFTSGSTGKPKGAMI

RHDAIAERLQWQRDHILHFGKHDHTDASLFKAPLSFDISVNEILLPLVSGGRVVVAVPDGEK

DPEYLLELIRTEQVTFVYLVSSMLDTLLELDRLATADGAPSSLASLRHVWCGGEVLTPGLFA

RFRKQLTTTLYHGYGPAEATIGVSHVIYRDTAERIATSIGRPNPHTQLYVLDEYLRPVPPGV

GGELYAAGFLLGRGYVNAPSLTASRFVANPFDGNGSRMYRTGDLARWTEDGSLEFLGRADNQ

VKIGGRRVELEEIESQLADHPAVRHAVVDVHRQGGADVLVGYLVAADGVRNDAAWHAEVADW

ARTRLPEYMVPKAFVALDQVPLTANGKTDRRALPAPDLERSGTVKPPRTPRETVLCQVFADA

LDIDAVGVDEDFFALGGDSIVAIRVVSRLRAAGYTLRPRDMFAHRTVEALAPLLGDSDVRDT

GPAVDPTGAATPTPILRWLDEVGTAGSVLNGFHQGMSLVTPADADENTLRAAIAATVRRHHV

LWAPPGRTASDIDIPGTPPETRLLIADASDGIPAQAEKVARQLVSLLDTARIAFGWIRRPAA

PGRLVVIADHTVIDGVSLRILAEDIATAYGLIAEGRAVELPTPHTSWRAWAQRLADTAAAGG

FDADLEHWQQVCATTETPWGDRALDPAIDTVATESRLTVELPSAVTDAILTTVPDRIHGHVN

DALVAALYLALRRWLHTRGVGADTLLVEMEGHGREGHLVDSDTAGLDLSNTVGWFTTLYPVA

LRDAEFDWQAAVSGGPQLGAAVRSVKDQLRSVPSHGFSYGALRYLRDGTSGLEAAPQVLFNY

LGRFGTADRPWALANDTTAVLEDRDPGMPLPRLLEVNAEAVTTADGSVLRATFSWPAHAVAE

-continued

VDVRTLAGMWTDLLTAIASSDDVRGHSASDFDRVSVTADDVAELERRYPGLTDLLPLTPTQQ

GIYFHSTFSRDRDPYVVQQIVDITGPLDTERFQRATESVAARHRALGAVFTTLSDGTPVAVH

AATVAPDFDVLDARHAADPSTVVAQRARWERERRFDLAAAPLTRYTLVRRRDDLHTMIETVH

HIVADGWSVPIVLDDLLTAYAGDDFDGPAPEFARFVDWLEQRDTDSDRAAWAPALEDITEPT

RLAAADGARGRTTGSGFGTRTVTLQSRSAVADAANGAAVTVGTLLHTAWGLALGRLTGRDDV

VFGTVVSGRGADVHGIESMVGLLVNTVPVRVAWSADDTGADVAGRLAAVESTLLEHHHLPLT

EAHRLAGVGELFDTLVVIENLGATTHTRGDLTLGDIGVIEAPHYPLTLMISVRDTITVTVTN

DREHVSDVLADTAVAAFTEVLTALTADPGVSPGDIALPAPQATAPPTQAPQTVTDLIAAAIA

EHRDDIALVVGETEWTYGQLGARAGELAAALAEAGVRRGDIVALATARSADLVAAIWAIIAA

GAAYLPVDLAYPRTRIEYMLRHARPTAVIADGVGAHVVSGALPADTIVVSTTATHAAVPFTP

VPVDGADAVSVLYTSGSTGEPKAVVGTHAALANRLAWAVEAWPAATRIAKSPLSFIDGTTEL

LAGLAAGARTVLAGDETARDGRRLAQLVAAHGVEQLLAVPSLAAVLADERTEDVAELNRWIV

SGEALSPRHLHALRTACPTAEIVNSYGSSEVAGDVLAGVQDDAGITLGAAVPGAGIRILDSR

LRQLPAGVIGEIYVTGGQLARGYLGRPGQTATRFVAAPGGERMYRTGDLGALLPGGRVVFAG

RADDQLKINGHRVEPGEIESVLARQPGVREAAVIGTGTQLAAFVVLESDAPGAGDLLTAVSA

ELPGHLVPSSLRPVDAIPLLPNGKRDNNALRSLLVPGESTGTAPTNDVERAVLDVMTGVLGR

DPLGADDDFFAVGGDSISAIRVTSRLARAGYHIATEDVFRGRTAAGVAALVDTVESLAHDAA

IEPFATVRLSPQTIDRIRESGQVEDIWAMSPLQLGVYYQSTLADAGPTYIAQNVFEFDRRID

VDAMRRAFTALLRRHPQLRAGFRTVEHAEPEPAPDATPVVQVVVTDPPSDLTVVDLTDQDDP

AAAQHIVDTDRTAPFDVATPPLLRLTVIRLPGGRDRMLFTYHFLLFDGWSRELVLRDLFALY

DSDAQHGAIAPHGDLVVRHLQWLATDGDFQASGARDAWRDLLAGLTEPTLASGVSPDHPDAR

PGTEPGRIVVRVPEDVTTQLHTCATAHGATLNSVVTAAVALVTGYHAGTTDVVIGTTVAGRP

GHLVGIDETIGLFLNTVPVRVDMSPTRSVAAAMASIGEQRVAMMRHDHLGLGQIQRAAGDSG

SALFDSLLVLQNFLDDDTFTDLESRHGIVDVSYKDTTHFPLTWVLTPGRELAIKLEHRVVDD

ARATEMVEQLVTVLRTIAAEPDTAVGAVDLIGADRRAQLERRWSSTERPLEPVTIAELLARR

AEQNPDDVALVFGAQSVTYREFDDRVSQFARHLRARGAAPETFVALALPRSIDMVVALFAVL

RAGAAYLPLELDLPIDRLRTIIDNAEPVLLVTTTDRTELIGHARARGADVIALDDAETAATL

ADTPAHPLTAGELGAFASDSTRLNHPAYLIYTSGSTGRPKGVLTGYAGLTNMYFNHREAIFA

PTVARAGSAEQLRIAHTVSFSFDMSWEELFWLVEGHQVHVCDEELRRDAPALVAYCHRHRID

VINVTPTYAHHLFDAGLLDDGAHTPPLVLLGGEAVGDGVWSALRDHPDSAGYNLYGPTEYTI

NTLGGGTDDSDTPTVGQPIWNTRGYILDAALRPVPDGAVGELYIAGTGLALGYHRRAGLTAA

TMVADPYVPGGRMYRTGDLVRRRPGSAELLDYLGRVDDQVKIRGYRVELGEIESVLTRADGV

ARCAVVARATGANPPVKTLAAYVIPDRWPAEDAAFITGLRDHLARVLPGYMVPTRYGIVDTL

PLTINGKLDVAALPEPIAATSGTGRTPRTDREATLLEIVASVLGIDGIGVDDDFFTLGGDSI

SSISVCGRARKAGLNITPRDVFRRRTIAALAASADTTQTPESGPDTGTGAITATPMLAETAQ

ANTPLTNFYQAMVLATPAGITAHEVQRVLQTVVDAHAMLRARLVTTATGWTLTVPDQTAAIG

LTVRSGALTSDCVEAEKAAAAAELDPRAGNMVRAVWFDAPEASGQLLLVIHHLVIDGVSWRI

LSEDLSRAWNDLAAGRDVAADAVPTSFHTWANALAQRTFDDESEYWADVLATPDPDLGSRPP

DPAIDTADTVRSHEVTLASDVTEALLTSVPAAMHGGVNDVLLTGLAVALAQWRADRGHSQNT

AAVISLEGHGRESDLVAADLDLSRTVGWFTSIYPVRIDPGPLEWDTVRSAGAELAAAAKAVK

EQLRAVPNRGLGYGVLRHLHGALDGTPPQILFNYLGRFTGGSGNDWRPVAGIGALTEGVDPS

-continued

NPAMSLEINALAEERPDGTVLSMTLAWPGGLLDADDVSELGSMWADVLVALTRCDALRGHTP

SDFGLVTVSQDDIDGWDRLGEVEEVLPLLPLQEGMYFHSMFGDPATDTYRVQQIAQLSGPVD

PEVLRTSLTVVMRRHQALRASFNELTDGRVAQVIWSDVPVQLTVVDTDDLESIAAEELARPF

NLAEAPLVRYMLVRLGDDDHRLVQTMHHIIADGWSYPVLFGDIVDHYNAAIGVGSAPQPITV

TLRDHIETVTDRDRGAARQAWEQALAGAEPTALVPRPDGAPVGEHRSVVRRLDSARTAAVGR

AARVHGVTVGTVLHGAWGLMLGRLLGRNRVVFGSTVSGRGGDLAGTESIVGLLINTIPVPMS

WEPHATLASALIDLQDQQSALLDAQQMGLAELARLAGVREFFDTMVIVENFPSTSSAEHTDP

RAVAFRGFTGTDSPHYPVSFVAYADDQLTVEIKYDAGVVTPEQAERYAERVERILTAFAETP

DLPVSRIDLRTNAERQFTAGHASRPGPGRTLGASFAEVAATYPDAVAVSCGDTRLTYRELDD

RAAAVAATLAERGVGAESRVAIALPRSADLIVAVLAVIKAGGTYVPIDIGAPAARVQHILAD

SAPVCLLTDTAERFTGVPHVILAEAAQNPARPQAPTVSPDHAAYVIYTSGSTGVPKGVEVTH

RNVAALFAGTTSGLYDFGPDDVWTMFHSAAFDFSVWELWGPLLHGGRLVVVEHDVARDPERF

VDLLARERVTVLNQTPSAFYPLLEADARLRRQLALRYVIFGGEALDVRRLAPWYANHESHSP

RLVNMYGITETCVHVSHRALDTADTGAAGSVIGGPLPGLRIHLLDNNLQPVPAGVVGEMYIA

GGQVARGYTGRPGLTATRFVANPFDGAGERLYRSGDLAMWTDAGELVYLGRSDAQVKVRGYR

IELGEVEAALVTLPGVTNAAADVRHDDTGRARLIGYVVGDALDIGALRSTLAERLPDYMVPS

VLLRLDVLPLTVNGKLDRAALPDPEPVEQAPAPVAGTGTASLLAGLCTEILGTTVGVEDDFF

TAGGDSIIAIQLVNRARREGVRITPQQVFVHRTPAALASVLDTGSVAAPDATPDEDAGPDLG

EVMLTPIVQRLAELGGTVTRFNQSELLRTPAGATVARLETAINAVIARHDALRIRLHRPAPM

LWSLETTAAAPVSITRIDAHGFDDEQLRTVIATESDAAADRLDPENGVVVVAVWFDRGTDTQ

GRLLLVVHHLAVDGVSWRILLDDLAEAYRQALSGQRVAPAPVTTSLRQYARTVNENAQHSSR

LTEFEHWTEVLAPGGELVATADVVTLTVGATRDHEIRLSTEDTAPLLTTVPAAANADVTETL

VAALHLAVSRWRAARGEAADAPLVLSLERHGRDGWPDDVDLSRTVGWFTSIAPVRLPAPGED

LLNTLKAVKESLRAAPDGGLGFGQLRYCNPRTSAVLARLGTPQLLFNYLGRWAADACDDWAS

APEVDALRTEPNPDLGTPYLVEVNAICDDTVDGPRLRATLTYADGELDEPSVAELGELWVAA

LRELGSLATGGDAALTPSDLPLVTLTQEHIDRVTGAVPGNVETIWPLSPLQEGVYLQARYAT

AAVYIVQNVFDFAEPVDTTALRTAYSAVMARNPVLRSAFWADDLPQPVAAIVADPVCEPRVV

DLGGLPATQVERRVEEITADDRQQTFDLAAAPLARMTVLRTPDRDRLIFSYHFLLLDGWSRE

QLLRELFAEYTAARGGAVAQLPAPTADFTDYLRWLARQDRDVSAREWSEALRDLEAPTLLVP

DAVGTDPTLALRLEFLLSEADTAALTAAARSAGVTLNALISTALAMVLAYETGRDDVVFGST

VAGRPTDLDGIDSVIGLFLNTVPTRVRLAPHRTVADTMRAVQSDRLRLMDHEYLGLGDIQRA

VSTGGGPLFDSLYVLQNFLDDDTFTDMEAQYGIVGHDSIDASHYPLTWVASPGRRLWMKLEY

RPDVVERDRAQGLLDRLRQVLLQVGTGVERPSAALTLPLPAEADHKRTRDAATEHDLPHASV

LDLLAERAVQSGDLTALVCGGEFVDYAELLARVNRLAWVLRSRGIGPEDTVALAVPRSIDAV

VALFAVLRAGAAYLPLELDYPDERLAVMLGDAEPVRVLVTGATAQRIARVASAPLTVLDAPD

TCDELARARSDWDGYSPHPDQPAYVIYTSGSTGKPKGVVTPHRGLTNMHLNHREAIFAPTIA

RAHGRRLKIAHTVSFSFDMSWEELLWLIEGHEVHICDEVLRRDATSLVRYCHDHRIDVINVT

PTYAALLFEEGLLEQAGHPPVLVLLGGEAVSTTVWNRLRDSERWYGYNLYGPTEYTINTLGG

GTDDSATPTVGTPIWNTRAHILDNWLRPVPDGVPGELYIAGAGLARGYLGQPGLTASRFVAN

PFEPGRMYRTGDLVVRRADDNIDFLGRTDDQVKIRGYRVELGDIEAALVSHPGVSQAAVIAR

-continued

PDTAGSSRLVAYVVPTTENPDVLDDLRMHLTATLPAYMVPTAMATLTEIPLTDNGKLDTRAL

PDVAPIGRHGAGRAPQGAVEATLCSVFAEVLGLDGPDGLSVDDDFFDLGGHSLLTIRLISRI

RSELGAELTLGDVFNSRTVAALARHVTADEGDNRRPRLVAGPRPQHIPASPAQRRMLMLDRL

GETGSAYNYPLVFRVRGALDVDALRDALTAVVDRHEALRTVFDDRDGVYHQRILPRGTQPPL

HVSDCPEHELATRADALVEHRFDLTGEIPLRVDVLRSGPEDHTVVMLLHHIAIDEWSDAVFL

ADLDAAYAAHRAGTAAPLPEPVVQYADHTLWQRDVLAQLGDRQREFWRTALAGAPDELALPA

DRPRPARPTGAGGTLDVEITAETASALRRLAADKQVSMLMVLHAAVAVLIHRLGAGDDIVVG

TPVAGRDDAALDDVVGLFVNTVVLRADLAGNPTFTELLDRVRTADLAAFAHQDLPFDHLVEE

LNPPRVAGRNPLFNLFVGYHLRSGTDSDMFGLPTEWTEPAVSAAMFDLGFTLVDHGGDESAS

ITAEYAADLFDASTVHTLARRLVALLDHVVADAETRIGALDLLAPGEHDTLVVEHNATEHPL

EPITLGALVSRQATSTPHATALRYEESELSYRDLDGWSDRLAAHLSARGAAPGTVVGVSLPR

SVELVVALVAVAKSGAAFLPLDPEYPRERLEYMVSDARPITVLDDPDAVRRSRGEPDGELPR

IDPAAWAYVLYTSGSTGRPKGVAVAHAGIVNRIACLQHAYPLGTDDRMLVKTPISFDTSVWE

VFWPLSVGATLVVARPGGHREPAYLAAMIAEQCVTAVDFVPSMLEVFLDEVAGTCASLTRVT

VGGEALTTELAARFAEAFPGVPLHNLYGPTEAAVDVLGWTADGGPVALGVPGWNVRAYVLDD

YLNPVPAGAPGELYLAGIQLADGYLHRGALTAARFVASPFDQGARMYRTGDVVRWRADGQLE

YLGRSDDQIKLRGVRIEPGEIETVLATHPAVSSVRVIARGGRLMAYYVPAGVEASAGELRDE

LREHAAAALPSHMVPSGFVALTEFPLTPSGKLDRRALPEFAGATAGVPGRAPTTERQHRLCE

LFSDVLGLEVTGIDDDFFVLGGHSLLLVRLAAALRREFSVDVPVADLMVSPTVADIDQRLDA

AGSSVDSLAPVLPFRASGTDAPLFCVHPASGLSWQFAGLKRHLPRQIPIYGLQSPLFTGTPL

PESIAELTARYADTIVAVAPSGPVRLLGWSFGGSMALLIAQELSRRGREVTFVGMLDARTDT

ADPNAGFDPEAVLAGLLREMGFGVDPQARMTVADAVALVRDTDDAITVLDDEQIALVIENYV

AAERLTADADYGRYDGDVFFVDATILEMDLAGVASRGWHDHVGGRLKVAELDCRHSELMDAE

VLERLGPLIAAELRGGDVASG

EXO/MBT-deficient Msm ΔEM carried the MSMEG_0019 deletion noted above and an unmarked, in-frame deletion of $mbtA_{sm}$, encoding the salicyl-AMP ligase essential for MBT biosynthesis (Chavadi, S. S., et al. (2011) *J. Bacteriol.* 193, 5905-5913). The $mbtA_{sm}$ deletion (MSMEG_4516, SEQ ID NO: 6) left behind only the gene's start codon followed by the stop codon, and it was created in Msm ΔE with the same approach reported for generation of the identical $mbtA_{sm}$ deletion in Msm WT to generate the mutant referred hereafter to as Msm ΔM (Chavadi, S. S., et al. (2011) *J. Bacteriol.* 193, 5905-5913).

(SEQ ID NO: 6)

MTLTTPHPRPEQSESAAQSSLLAGFTPFPAERAQAYRAAGYWRDQLLDS

VLRTAARTWPDHIAVIDADHRHTYAELDRLADRAAAGIAGLGIRPGDRV

LVQLPNTAEFAVALFGLLRAGAVPVMCLPGHRLAELTHFAEVSSAVALV

VADTAGGFDHRDLARELVRSHPDVRHVLVDGDAAEFLSWAEVTRAAPGP

VPEIAPDPAAPALLLVSGGTTGAPKLIPRTHQDYVYNATASAELCRLTA

DDVYLVALPAAHNFPLACPGLLGAMTVGATTVFTTDPSPEAAFAAIDEH

GVTATALVPALAKLWAQACAWEPLAPKTLRLLQVGGAKLAAPDAALVRG

ALTPGLQQVFGMAEGLLNYTRIGDPPEVLENTQGRPLSPDDEIRIVDEV

-continued

GNEVPPGAEGELLVRGPYTLNGYFNAEAANERSFSPDGFYRSGDRVRRF

ADGPLAGYLEVTGRIKDVIVRGGENVSALDLEEHLLTHPSVWAAAAVAL

PDEFLGEKICAVVVFNGPPVSLAELHAHLEQRGVAAHSRPDALVPMPSL

PTTAVGKIDKKAIVRQLGG

A strain complemented with Mtb MBT, Msm ΔEM-$pMbtA_{tb}$ was generated by transformation of Msm ΔEM with $pMbtA_{tb}$ (expressing $mbtA_1b$). To construct $pMbtA_{tb}$, a DNA fragment encompassing mbtA of Mtb ($mbtA_{tb}$, Rv2384, (Chavadi, S. S., et al. (2011) *J. Bacteriol.* 193, 5905-5913)) was generated by PCR from genomic DNA template using primer pair $mbtA_{tb}F1$ and $mbtA_{tb}R1$. The PCR product, which included an optimized ribosome-binding site (Ma, J., et al. (2002) *J. Bacteriol.* 184, 5733-5745) upstream of $mbtA_tb$ introduced by primer mbtAtbF1, was cloned into pCR2.1Topo. Subsequently, the insert was recovered from the pCR2.1Topo construct as a HpaI-NheI fragment and subcloned into the mycobacterial, low-copy number plasmid pCP0 (Ferreras, J. A., et al. (2008). *Chem. Biol.* 15, 51-61) linearized by HpaI-NheI digestion. This subcloning created $pMbtA_{tb}$, in which $mbtA_{tb}$ is under the control of the constitutive mycobacterial hsp60 promoter located in pCP0.

Figure 7:
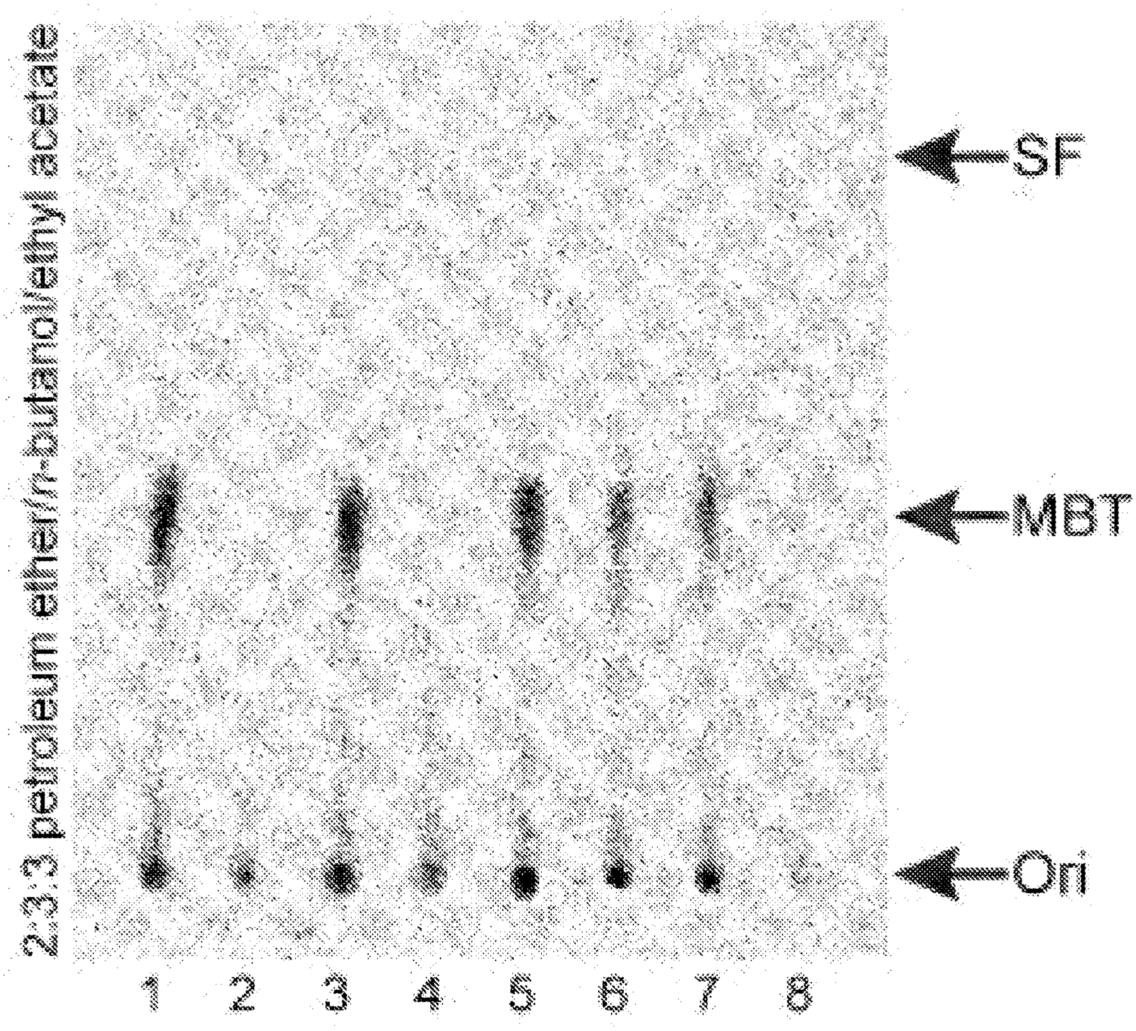
FIG. 7 shows phenotypes and salicyl-AMS susceptibility of Msm strains via radio-thin layer chromatography (TLC) analysis of $^{14}C$-labeled MBTs. Lanes: 1=Msm wild-type; 2=Msm ΔM; 3=Msm ΔE; 4=Msm ΔEM; 5=Msm ΔEM-$pMbtA_{sm}$: 6=Msm ΔEM-$pMbtA_{tb}$; 7, Msm ΔEM-$pMbtA_{tb}$ with DMSO treatment (control); 8, Msm ΔEM-$pMbtA_{tb}$ with inhibitor compound 1 treatment. The Msm ΔM strain represents a no MBT production control (Chavadi. S. S., et al. (2011) *J. Bacteriol.* 193, 5905-5913). The image shows the entire TLC plate wherein Ori refers to origin and SF refers to solvent front. The solvent system used was 2:3:3 petroleum ether:n-butanol:ethyl acetate.

The study of the antimicrobial properties of tuberculosis lead compounds using Mtb is challenging due to the need for biosafety level 3 procedures and the bacterium's slow growth rate. Thus, to simplify the analysis of the antimicrobial properties of $MbtA_{tb}$ inhibitors, it was desired use the nonpathogenic, fast-replicating Msm model system. Msm has the MBT siderophore system, and we have shown that the $MbtA_{tb}$ orthologue in Msm ($MbtA_{sm}$) (71% sequence identity) is essential for MBT biosynthesis (Chavadi, S. S., et al. (2011) *J. Bacterial.* 193, 5905-5913). However, Msm also has a second siderophore system that accounts for 90-95% of siderophore activity in the bacterium (i.e. the EXO system) (Ratledge, C., et al. (1996) *Microbiology* 142, 2207-2212; Sharman, G. J., et al. (1995) *Biochem. J.* 305, 187-196). It was hypothesized that production of EXOs would render Msm resistant to salicyl-AMS compounds, thus impeding the use of Msm for evaluation of MbtA inhibitors. To explore this hypothesis, the susceptibility of mutant strains Msm WT, Msm ΔE ($EXO^-$), and Msm ΔM (MBT, FIG. 7) to salicyl-AMS compounds in Fe-limiting and Fe-rich growth media were investigated (Table 7). Next, the possibility of developing a Msm $EXO^-$ strain that is dependent upon $MbtA_{tb}$, the primary intended target of salicyl-AMS compounds was explored. Transformation of Msm ΔEM double mutant with $pMbtA_{tb}$ to enable heterologous expression of $mbtA_{tb}$ was carried out. The complemented transformant (Msm ΔEM-$pMbtA_{tb}$) regained MBT production (FIG. 7) and had the same pattern of susceptibility to salicyl-AMS (1) seen for Msm ΔE (Table 7). Moreover, compound 1 inhibited MBT production in Msm ΔEM-$pMbtA_{tb}$ (FIG. 7), a result paralleling that seen with Mtb (Ferreras, J. A., et al. (2005) *Nat. Chem. Biol.* 1, 29-32). Taken together, these results established that Msm ΔEM-$pMbtA_{tb}$ has high, $MbtA_{tb}$-dependent salicyl-AMS susceptibility, and thus the strain represents a convenient model system to assess and compare the antimycobacterial properties of the $MbtA_{tb}$ inhibitors.

TABLE 7

Susceptibility of M. smegmatis strains to salicyl-AMS

| | MIC (μg/ml)[b] | |
|---|---|---|
| Msm strain (EXO/MET)[a] | GASTD medium | GASTD + Fe medium |
| Msm WT (+/+) | >1000 | >1000 |
| Msm ΔE (−/+) | 0.5-1.0 | >1000 |
| Msm ΔM (+/−) | >1000 | >1000 |
| Msm ΔEM (−/−) | no growth | >1000 |
| Msm ΔEM-$pMbtA_{tb}$ (−/+) | 0.5-1.0 | >1000 |

Example 8. Growth Inhibition Assays for Msm Strains

Dose-response experiments using microdilution assays in a 96-well plate platform were performed as reported (Ferreras, J. A., et al. (2011) *Bioorg. Med. Chem. Lett.* 21, 6533-6537; Stirrett, K. L., et al. (2008) *Bioorg. Med Chem. Lett.* 18, 2662-2668). Msm strains were grown in GASTD or GASTD+Fe media. Cultures (200 μL/well) were started at $OD_{600}$=0.0005 (≈$9\times10^4$ CFU/well) from culture stocks prepared in GASTD medium as reported (Ferreras, J. A., et al. (2005) *Nat. Chem. Biol.* 1, 29-32.). Growth was assessed as ODD after 4 days of incubation (37° C., 170 rpm) using the DTX 880 microplate reader. Unless otherwise indicated in specific experiments, compounds were typically evaluated using a 0.031-64 μg/ml range (2-fold dilution series format). Inhibitors were added from 10% DMSO stock solutions, with a final DMSO concentration of 0.5% in both inhibitor-treated cultures and DMSO controls (no inhibitor). Minimum inhibitory concentration (MIC) values were calculated as the lowest concentration tested that inhibited growth by ≥95% relative to DMSO controls. Data presented are derived from three independent experiments. Results are shown in Table 8.

The results demonstrated potent antimicrobial activity for the novel salicyl-6-MeO-AMSN (6). Notably, (6) did not reach MIC when tested at up 64 μg/mL in Fe-rich medium (Table 8). This selectivity is consistent with their expected mechanism of action in inhibition of MBT siderophore biosynthesis, and revealed that the structural features of the analogues setting them apart from the lead compound 1 did not lead to unintended off-target effects of significance in Msm.

TABLE 8

Antimicrobial activity of $MbtA_{tb}$, inhibitors in M. smegmatis ΔEM-$pMbtA_{tb}$

| | MIC (μg/ml)[a] | | |
|---|---|---|---|
| | GASTB medium | | GASTD + Fe |
| Cmpd | range | mean | medium |
| 1 | 0.5-1.0[b] | 0.83 ± 8.17 | >64 |
| 4a | 1.0 | 1.00 ± 0 | >64 |
| 4b | 0.5-1.0 | 0.83 ± 0.17 | >64 |
| 6 | 4.0-8.0 | 5.33 ± 1.33* | >64 |

Example 9. Post-Antibiotic Effect (PAE) Assays

Figure 8:
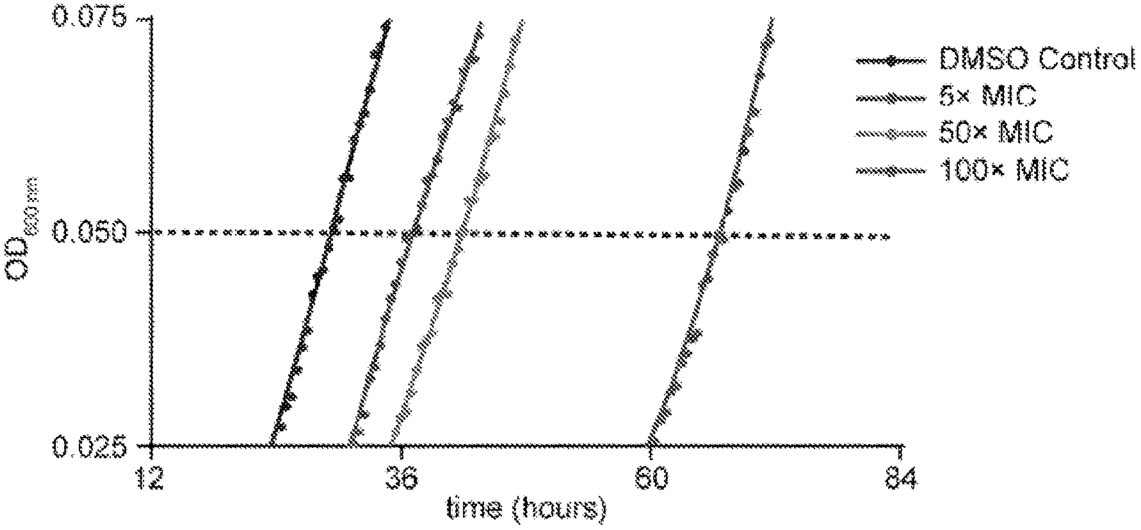
FIG. 8 shows a representative plot of post-antibiotic effect (PAE) for salicyl-AMS (1). The growth vs. time datasets were analyzed to determine the time at which cultures reached an exponential growth phase threshold of $OD_{600\ nm}$=0.05 (dotted line). The time-to-threshold data were used to calculate PAE as the difference between the time-to-threshold values of the inhibitor-exposed culture and the control cultures.

Cells from mid-log growth phase cultures of Msm ΔEM-$pMbtA_{tb}$ in GASTD medium (37° C., 170 rpm, $OD_{600}$≈0.75) were harvested by centrifugation and washed in GASTD medium (3 times with I culture volume). The washed cells were resuspended in GASTD medium and transferred to U-bottom 96-well cell culture plates (Corning, Inc.) for inhibitor exposure at a cell density corresponding to $OD_{600}$=1.0 (50 μL/well). Cells were exposed to 5×, 50×, and 100× average MIC value, in line with reported studies with other antimycobacterial compounds (Chan, C. Y., et al. (2004) *Agents Chemother.* 48, 340-343). Inhibitors were added from 10% DMSO stock solutions, with a final DMSO concentration of 1% in both inhibitor-exposed cultures and DMSO controls (no inhibitor). After the exposure period (1 h, 37° C., 170 rpm), the cultures were diluted in pre-warmed, inhibitor-free medium to $OD_{600}$=0.001 (1,000-fold dilution, bringing inhibitor concentrations to 0.005×, 0.05×, and 0.1× average MIC values) and reseeded into flat-bottom, 96-well culture plates (Corning, Inc.) at 200 μl/well. The 96-well plates were incubated for culture growth at 37° C. in a FLUOstar Optima microplate reader (BMG Labtech, Inc.), and $OD_{600}$ readings were taken every 30 min following plate shaking (5 min, 200 rpm) for 5 days. The growth vs. time datasets were analyzed to determine the time at which cultures reached an exponential growth phase threshold of $OD_{600}$=0.05 (≈5% of maximal growth) (FIG. 8). The time-to-threshold data were used to calculate PAE as the difference between the time-to-threshold values of the inhibitor-exposed culture and the control cultures (Stubbings, W. J., et al. (2004) *J. Antimicrob. Chemother.* 54, 139-143). Data presented are derived from three independent experiments.

Pearson correlation analysis between PAE and $t_R$ datasets was carried out using Prism v6.01, and PCCs with p values ≤0.05 were considered statistically significant. Results appear in Table 9.

Notably, despite the relevance of PAE information to the lead optimization and prioritization phases of antibiotic development (Craig, W. A. (2007) *Antimicrobial pharmacodynamics in theory and clinical practice,* $2^{nd}$ ed., pp 1-22, Informa Healthcare USA, Inc., New York, NY; Tonge, P. J. (2018) *ACS Chem. Neurosci.* 9, 29-39; MacKenzie, F. M., et al. (1993) *J Antimicrob Chemother* 32, 519-537), seemingly PAE studies have not been undertaken previously for salicyl-AMS (1) or any of its analogues.

Encouragingly, the assessment of the in vitro PAE using washout experiments revealed that all the inhibitors, including (6) had a substantial PAE (Table 9). A concentration-dependent PAE trend was found for the eight inhibitors tested at different concentrations, showing 0-14 h, 12-30 h, and 19-50 h ranges for the 5×, 50×, and 100× MIC exposures, respectively. These results provide the first demonstration of PAE for $MbtA_{tb}$ inhibitors. Moreover, they validate Msm ΔEM-pMbtAtb as a convenient model system for analyses of inhibitors of $MbtA_{tb}$.

TABLE 9

Post-antibiotic effect of $MbtA_{tb}$ inhibitors in M. smegmatis AEKT-$pMbtA_{tb}$

| | PAE (hours)[c] | | |
|---|---|---|---|
| Cmpd. | 5 × MIC | 50 × MIC | 100 × MIC |
| 1 | 9.4 ± 1.6 | 14.2 ± 0.9 | 34.5 ± 1.8 |
| 4a | 10.6 ± 2.7 | 18.7 ± 1.3 | 23.1 ± 3.1* |
| 4b | 13.4 ± 2.6 | 17.4 ± 4.7 | 10.4 ± 2.2** |
| 6 | 1185.3 ± 2.8* | ND | ND |

Example 10. Growth Inhibition Assays for *M. tuberculosis* H37Rv

Lab strain *Mycobacterium tuberculosis* H37Rv was grown to mid-log phase in 7H9. Cells were washed three times using GAST-D media, then re-suspended in an equal volume of GAST-D. $OD_{600}$ was measured, and an aliquot was diluted to $OD_{600}$=0.001. To set up the MIC assay plate, two-fold serial dilutions were made using a 96-well plate, ranging from 16 to 0.0313 μg/mL, in both GAST-D and GAST-D plus 100 μM of $FeCl_3$ media. 100 μl of diluted bacterial suspension was added to wells and plate was incubated for 7 days at 37° C. Alamar Blue reagent was added to all wells and incubated for 16 h. The plate was read at Ex544 nm/Em590 nm using a fluorescence plate reader and the lowest concentration that yielded at least 90% inhibition was defined as MIC. Results are presented below in Table 10.

TABLE 10

MIC Values for M. tuberculosis H37Rv

| | MIC (μg/mL) | |
|---|---|---|
| Compound | GAST-D medium | GAST-D + Fe medium |
| 1 | 0.125-0.25 | 0.5-1.0 |
| 6 | 0.125-0.25 | 0.5-1.0 |

Example 11. In Vivo Efficacy Evaluation in DBA/2 Mouse Model

Compound (1) was previously tested in an in vivo efficacy model in BABL/c mice as described in Lun, S. et al. *Antimicrob. Agents Chemother.* 2013, 57(10), 5138-40. Comparative results are generated in six-week-old female DBA/2 mice. Mice are aerosol-infected with Mtb H37Rv using an inhalation system (Glas-Col Inc., Terre Haute, IN). At day 1 post-infection, five mice are sacrificed to determine the Day 1 implantation by enumerating colony-forming-units (CFUs) in the lungs. From day 1 after infection, groups of five mice are treated with IP injection of test compound at 100 mg/kg (in biological saline), daily and 5 days a week for 4 weeks. Other controls may include Sal-AMS plus 5% AMS and Salicyl-AMS at various dose levels. Ethambutol at 100 mg/kg is administered as positive control and infected but untreated mice are used as negative controls. At Day 28 after treatment initiation, 5 mice from each treatment group are sacrificed and the lungs removed. Lungs are photographed for gross pathology. The lungs are homogenized, diluted, and plated on 7H11 selective agar plates to enumerate CFUs. Efficacy is analyzed based on CFU reduction compared with untreated control.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any one of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (I):

(III-A)

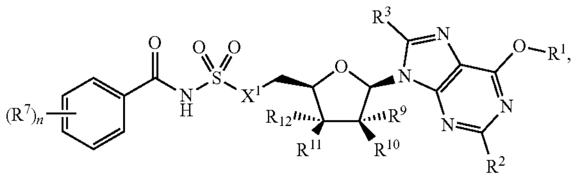

or a pharmaceutically acceptable salt, stereoisomer, or tautomer thereof, wherein:

$R^1$ is optionally substituted alkyl, optionally substituted heteroalkyl, optionally substituted carbocyclyl, optionally substituted heterocyclyl, optionally substituted aryl, optionally substituted heteroaryl, or optionally substituted acyl;

each or $R^2$ and $R^3$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-NO_2$, $-CN$, $-OR^e$, $-N(R^e)_2$, $-N_3$, $-SO_2H$, $-SO_3H$; $-SH$, $-SR^e$, $-SSR^e$, $-OC(=O)R^e$, $-OCO_2R^e$, $-OC(=O)N(R^e)_2$, $-C(=O)N(R^e)_2$, $-NC(=O)N(R^e)_2$, $-OC(=O)O(R^e)_2$, $-SO_2R^e$, $-SO_2OR^e$, $-OSO_2R^e$, $-S(=O)R^e$, or $-OS(=O)R^e$;

each of $R^9$, $R^{10}$, $R^{11}$ and $R^{12}$ is hydrogen, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-NO_2$, $-CN$, $-OR^4$, $-OR^5$, $-OR^e$, $-N(R^e)_2$, $-N_3$, $-SO_2H$, $-SO_3H$; $-SH$, $-SR^e$, $-SSR^e$, $-OC(=O)R^e$, $-OCO_2R^e$, $-OC(=O)N(R^e)_2$, $-OC(=O)N(R^e)_2$, $-C(=O)N(R^e)_2$, $-NC(=O)N(R^e)_2$, $-OC(=O)O(R^e)_2$, $-SO_2R^e$, $-SO_2OR^e$, $-OSO_2R^e$, $-S(=O)R^e$, $-OS(=O)R^e$, or two occurrences of any $R^9$, $R^{10}$, $R^{11}$ and $R^{12}$ are joined to form an optionally substituted carbocyclic ring or an optionally substituted heterocyclic ring;

each of $R^4$ and $R^5$ is independently hydrogen, optionally substituted $C_{1-6}$ alkyl, optionally substituted acyl, or an oxygen protecting group, or $R^4$ and $R^5$ are joined to form an optionally substituted heterocyclic ring;

$X^1$ is a bond, $-O-$, $-(C(R^d)_2)_q-$, or $-NR^e-$;

each occurrence of $R^d$ is independently hydrogen, halogen, optionally substituted $C_{1-6}$ alkyl, $-OR^e$, or $-N(R^e)_2$;

each occurrence of $R^e$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, an oxygen protecting group when attached to an oxygen atom, a nitrogen protecting group when attached to a nitrogen atom, or two $R^e$ are joined to form an optionally substituted carbocyclic, an optionally substituted aryl, an optionally substituted heterocyclic or optionally substituted heteroaryl ring;

q is 1, 2, or 3;

each occurrence of $R^7$ is independently halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted acyl, $-NO_2$, $-CN$, $-OR^e$, or $-N(R^e)_2$, or two $R^7$ are joined to form an optionally substituted aryl or optionally substituted heteroaryl ring; and n is 0, 1, 2, 3, 4, or 5.

2. The compound of claim 1, wherein the compound is of formula:

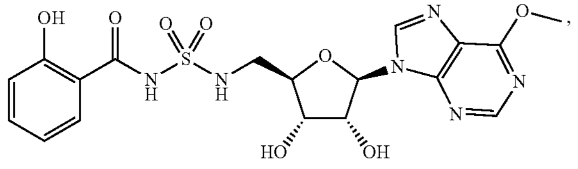

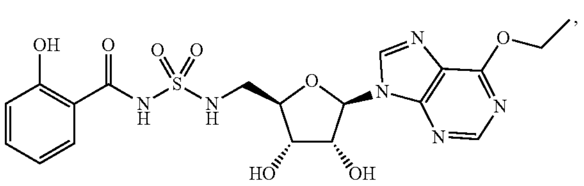

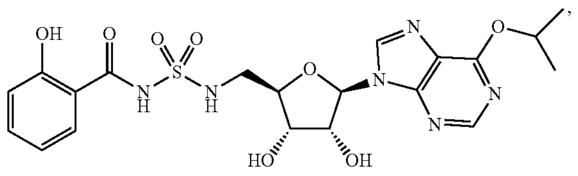

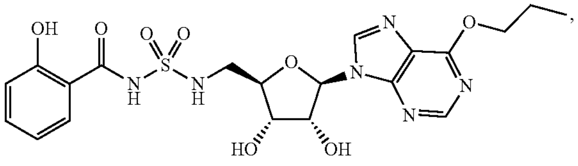

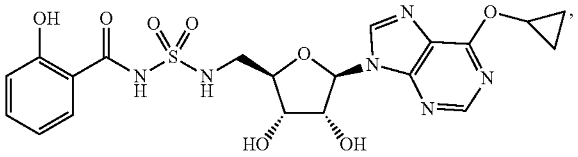

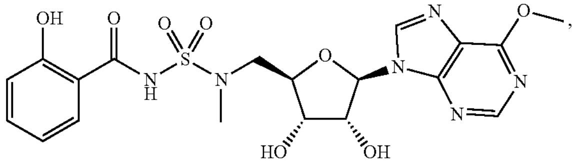

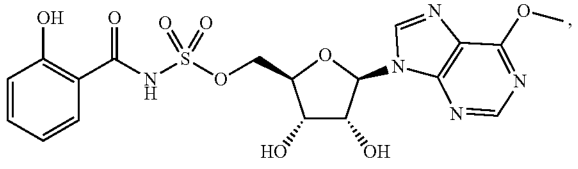

-continued

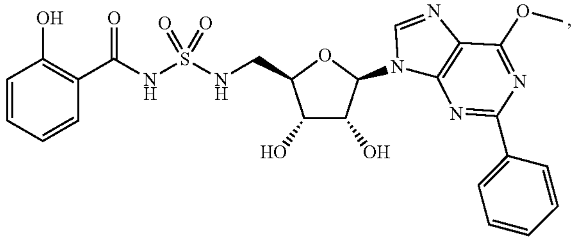

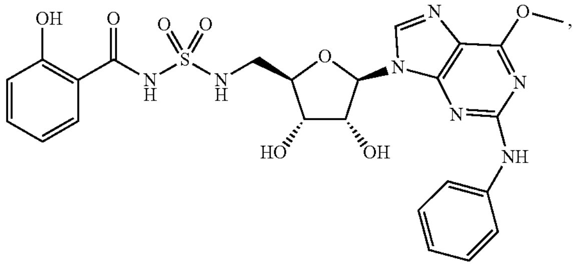

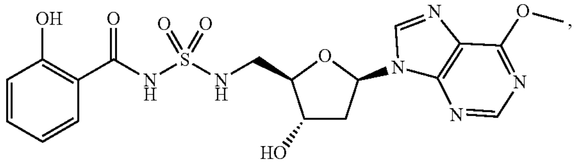

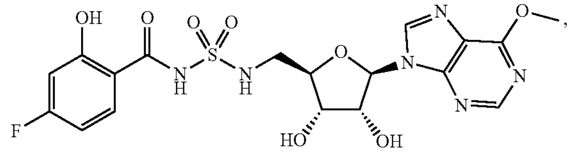

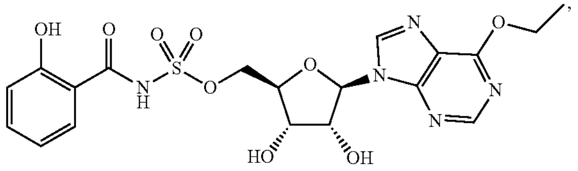

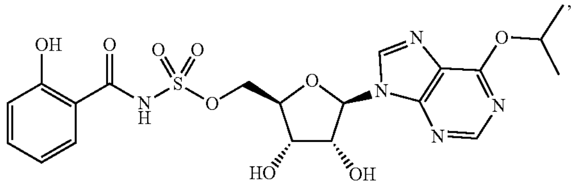

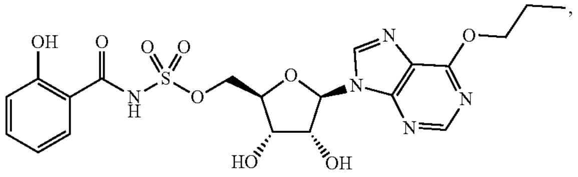

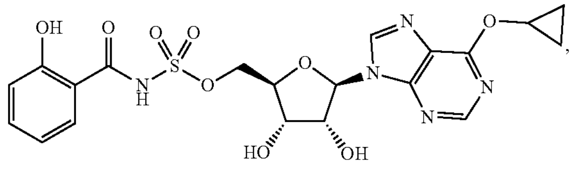

-continued

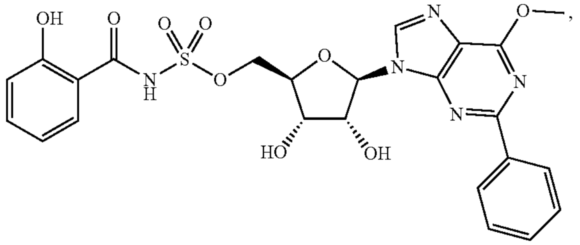

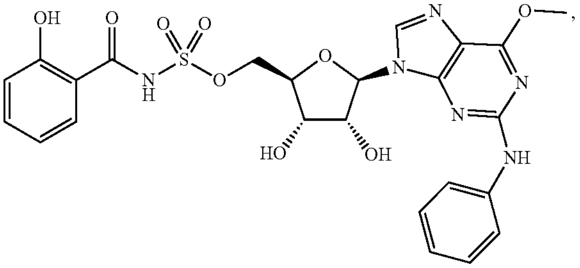

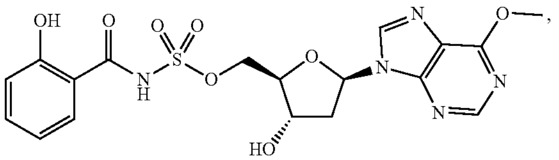

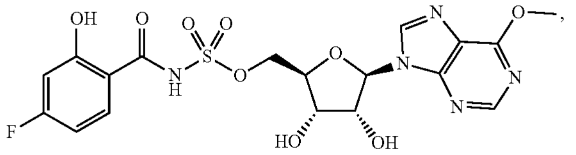

or a pharmaceutically acceptable salt, stereoisomer, or tautomer thereof.

3. A pharmaceutical composition comprising a compound of claim 1, and a pharmaceutically acceptable excipient.

4. A method of treating or preventing an infectious disease comprising administering an effective amount of a compound of claim 1 to a subject in need thereof.

5. A method of inhibiting siderophore biosynthesis in an infection in a subject, the method comprising administering to the subject a compound of claim 1.

6. A method of inhibiting siderophore biosynthesis in an infectious microorganism, the method comprising contacting the infectious microorganism with a compound of claim 1.

7. A method of inhibiting biosynthesis of a virulence factor in an infection in a subject, the method comprising administering to the subject a compound of claim 1.

8. A method of inhibiting biosynthesis of a virulence factor in an infectious microorganism, the method comprising contacting the infectious microorganism with a compound of claim 1.

9. A kit comprising:

a compound of claim 1;

and instructions for administering to a subject the compound or composition.

10. The compound of claim 1, wherein the compound is of the Formula (III-B):

(III-B)

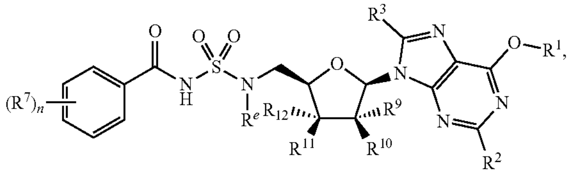

or a pharmaceutically acceptable salt, stereoisomer, or tautomer thereof.

11. The compound of claim 1, wherein the compound is of the Formula (III-C):

(III-C)

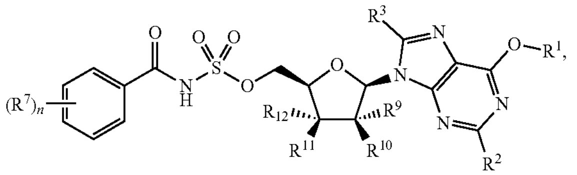

or a pharmaceutically acceptable salt, stereoisomer, or tautomer thereof.

12. The compound of claim 1, wherein the compound is of the Formula (III-D):

(III-D)

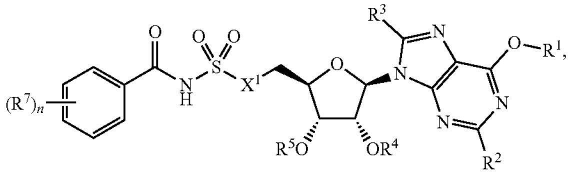

or a pharmaceutically acceptable salt, stereoisomer, or tautomer thereof.

13. The compound of claim 1, wherein the compound is of the Formula (III-E):

(III-E)

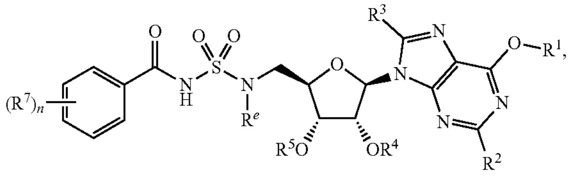

or a pharmaceutically acceptable salt, stereoisomer, or tautomer thereof.

14. The compound of claim 1, wherein the compound is of the Formula (IV-L):

(IV-L)

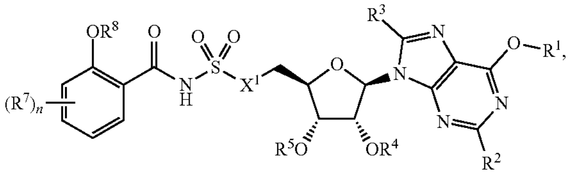

or a pharmaceutically acceptable salt, stereoisomer, or tautomer thereof, wherein:

$R^8$ is independently hydrogen, optionally substituted alkyl, optionally substituted carbocyclyl, optionally substituted heterocyclyl, optionally substituted aryl, optionally substituted heteroaryl, optionally substituted acyl, oxygen protecting group, or a nitrogen a protecting group; and n is 0, 1, 2, 3, or 4.

15. The compound of claim 1, wherein the compound is of the Formula (IV-M) or Formula (IV-N):

(IV-M)

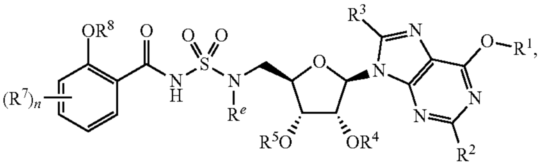

or (IV-N)

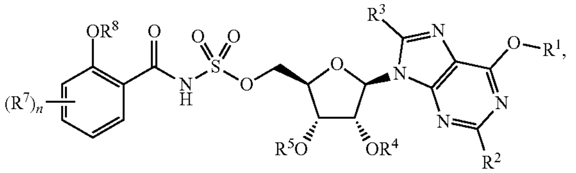

or a pharmaceutically acceptable salt, stereoisomer, or tautomer thereof, wherein:

$R^8$ is independently hydrogen, optionally substituted alkyl, optionally substituted carbocyclyl, optionally substituted heterocyclyl, optionally substituted aryl, optionally substituted heteroaryl, optionally substituted acyl, oxygen protecting group, or a nitrogen a protecting group; and n is 0, 1, 2, 3, or 4.

16. The compound of claim 1, wherein the compound is of the Formula (IV-T):

(IV-T)

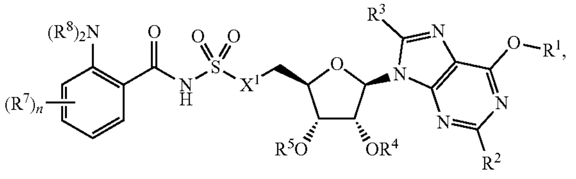

or a pharmaceutically acceptable salt, stereoisomer, or tautomer thereof, wherein:

each occurrence of $R^8$ is independently hydrogen, optionally substituted alkyl, optionally substituted carbocyclyl, optionally substituted heterocyclyl, optionally substituted aryl, optionally substituted heteroaryl, optionally substituted acyl, oxygen protecting group, or a nitrogen a protecting group, or two $R^8$ are joined to form an optionally a substituted heterocyclyl, or optionally substituted heteroaryl ring; and n is 0, 1, 2, 3, or 4.

17. The compound of claim 1, wherein the compound is of the Formula (IV-U) or Formula (IV-V):

(IV-U)

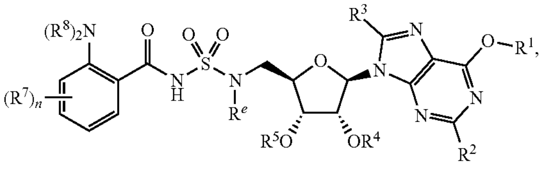

or (IV-V)

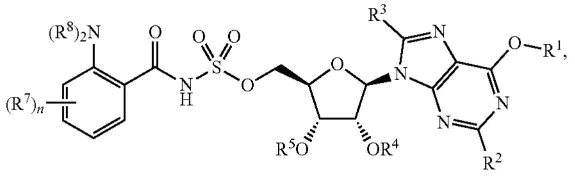

or a pharmaceutically acceptable salt, stereoisomer, or tautomer thereof, wherein:

each occurrence of $R^8$ is independently hydrogen, optionally substituted alkyl, optionally substituted carbocyclyl, optionally substituted heterocyclyl, optionally substituted aryl, optionally substituted heteroaryl, optionally substituted acyl, oxygen protecting group, or a nitrogen a protecting group, or two $R^8$ are joined to form an optionally a substituted heterocyclyl, or optionally substituted heteroaryl ring; and n is 0, 1, 2, 3, or 4.

18. The compound of claim 1, wherein $R^1$ is selected from the group consisting of methyl, ethyl, propyl, isopropyl, cyclopropyl, and trifluoromethyl.

19. The compound of claim 1, wherein each occurrence of $R^e$ is hydrogen.

20. The compound of claim 1, wherein the phenyl ring bearing $R^7$ is of formula:

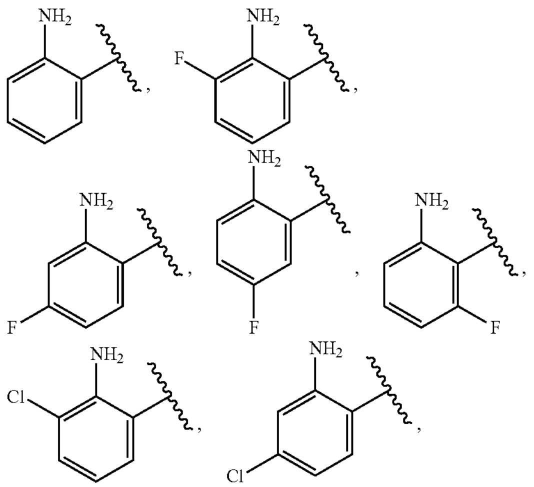

-continued
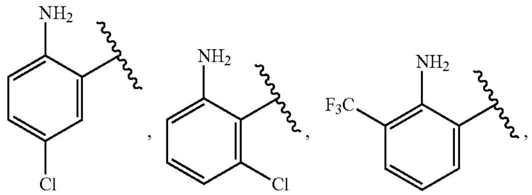,
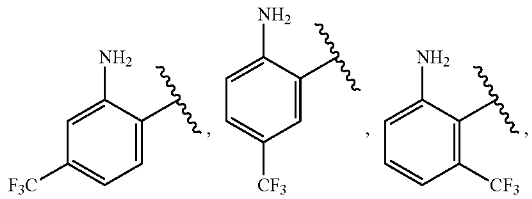,
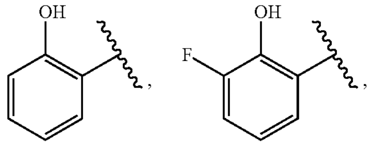
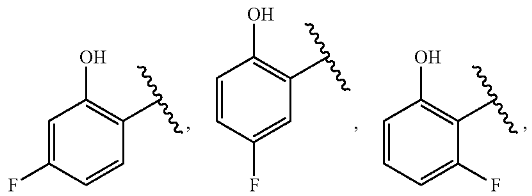,
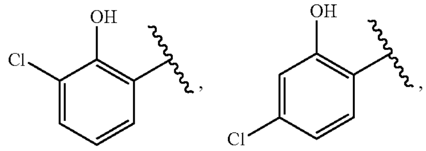,
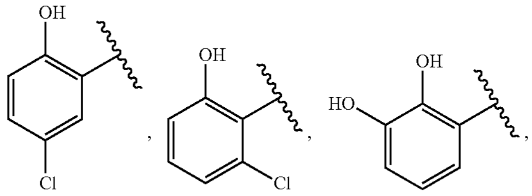,
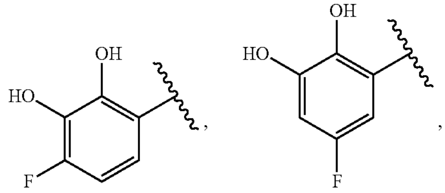,
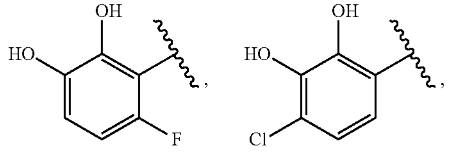,
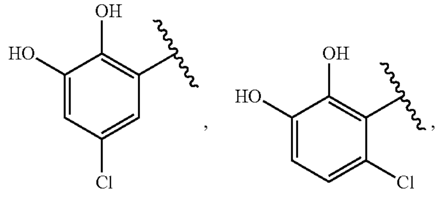
-continued
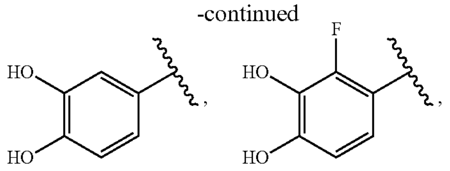,
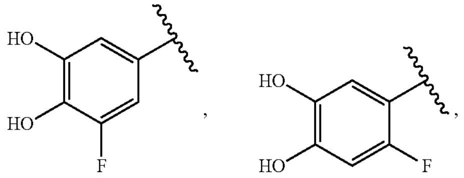,
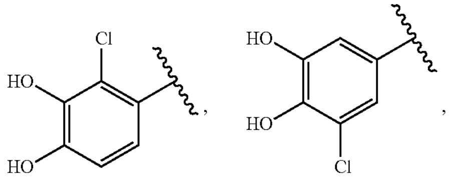,
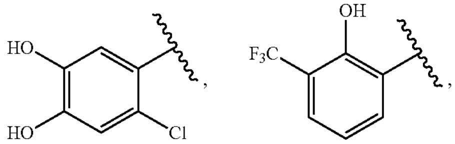,
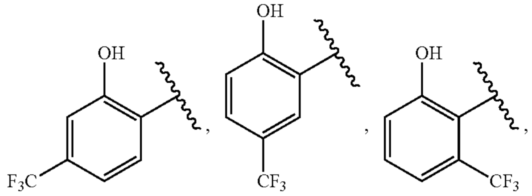,
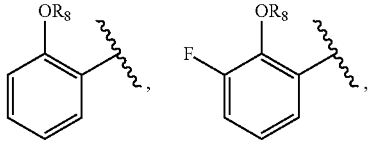,
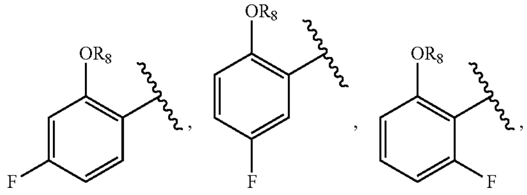,
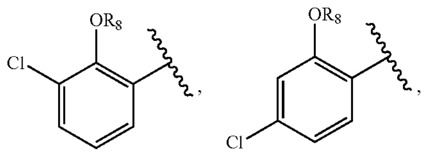,
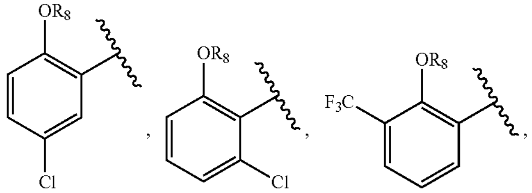,
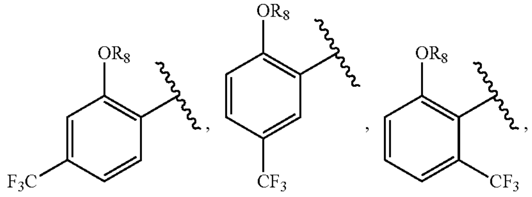

-continued
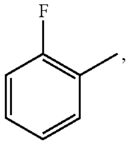, 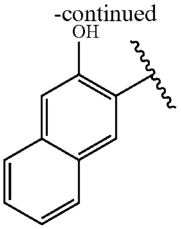, 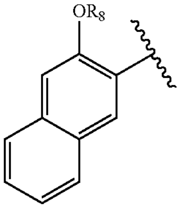,
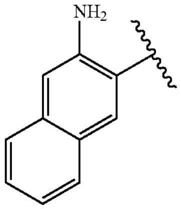, 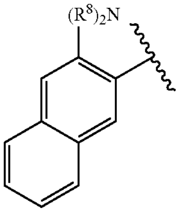,
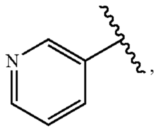, 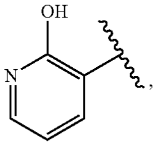, 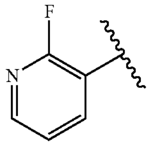, or
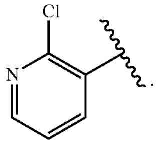.
* * * * *